(12) United States Patent
Graham et al.

(10) Patent No.: US 11,358,711 B2
(45) Date of Patent: *Jun. 14, 2022

(54) TETRACYCLIC HETEROCYCLE COMPOUNDS USEFUL AS HIV INTEGRASE INHIBITORS

(71) Applicant: Merck Sharp & Dohme Corp., Rahway, NJ (US)

(72) Inventors: Thomas H. Graham, Quincy, MA (US); Tao Yu, Edison, NJ (US); Yonglian Zhang, Metuchen, NJ (US); John A. McCauley, Maple Glen, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/025,371

(22) Filed: Sep. 18, 2020

(65) Prior Publication Data

US 2021/0009262 A1  Jan. 14, 2021

Related U.S. Application Data

(63) Continuation of application No. 16/447,421, filed on Jun. 20, 2019.

(51) Int. Cl.
| | |
|---|---|
| *A61K 31/5365* | (2006.01) |
| *B64C 27/48* | (2006.01) |
| *B64C 11/08* | (2006.01) |
| *A61P 31/18* | (2006.01) |
| *A61K 31/18* | (2006.01) |
| *A61K 31/407* | (2006.01) |
| *A61K 31/4188* | (2006.01) |
| *A61K 31/4439* | (2006.01) |
| *A61K 31/4985* | (2006.01) |
| *A61K 31/519* | (2006.01) |
| *A61K 31/553* | (2006.01) |
| *A61K 31/7076* | (2006.01) |
| *C07D 498/16* | (2006.01) |
| *C07D 498/22* | (2006.01) |
| *C12N 15/113* | (2010.01) |

(52) U.S. Cl.
CPC .............. *B64C 27/48* (2013.01); *A61K 31/18* (2013.01); *A61K 31/407* (2013.01); *A61K 31/4188* (2013.01); *A61K 31/4439* (2013.01); *A61K 31/4985* (2013.01); *A61K 31/519* (2013.01); *A61K 31/5365* (2013.01); *A61K 31/553* (2013.01); *A61K 31/7076* (2013.01); *A61P 31/18* (2018.01); *B64C 11/08* (2013.01); *C07D 498/16* (2013.01); *C07D 498/22* (2013.01); *A61K 2300/00* (2013.01); *C12N 15/1132* (2013.01); *C12N 2740/16011* (2013.01)

(58) Field of Classification Search
CPC ................ C07D 498/22; C07D 487/22; A61K 31/5365; A61K 31/553; A61K 31/4985
USPC ........... 540/546; 544/95, 247, 343; 514/243, 514/250, 211.1, 229.5
See application file for complete search history.

(56) References Cited

U.S. PATENT DOCUMENTS

| | | | |
|---|---|---|---|
| 8,188,271 B2 | 5/2012 | Yoshida et al. | |
| 9,127,013 B2 * | 9/2015 | Haas | .................... C07D 471/04 |
| 10,479,801 B2 | 11/2019 | Graham | |
| 2005/0054645 A1 | 3/2005 | Mayazaki et al. | |
| 2012/0022251 A1 | 1/2012 | Sumino | |
| 2012/0108564 A1 | 5/2012 | Miyazaki et al. | |
| 2013/0096109 A1 | 4/2013 | Hattori et al. | |
| 2017/0226128 A1 | 8/2017 | Yoshinaga et al. | |

FOREIGN PATENT DOCUMENTS

| | | |
|---|---|---|
| EP | 1544199 B1 | 10/2008 |
| EP | 1422218 B1 | 3/2012 |
| EP | 2602260 B1 | 9/2016 |

(Continued)

OTHER PUBLICATIONS

Akiyama, T.; et al, Discovery of novel HIV integrase inhibitors part 2: Selection and evaluation of anazabicyclic carbamoyl pyridone inhibitor as a preclinical candidate, 245th ACS National Meeting Poster Session, 2013, abstract, 245.

(Continued)

*Primary Examiner* — Jeffrey H Murray
(74) *Attorney, Agent, or Firm* — John C. Todaro

(57) ABSTRACT

The present invention relates to Tetracyclic Heterocycle Compounds of Formula

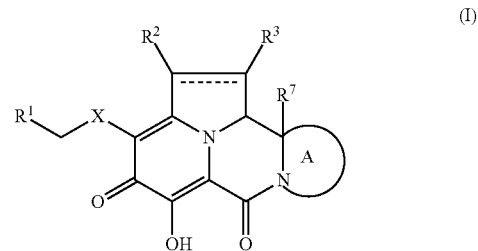

and pharmaceutically acceptable salts or prodrug thereof, wherein A, X, $R^1$, $R^2$, $R^3$ and W are as defined herein. The present invention also relates to compositions comprising at least one Tetracyclic Heterocycle Compound, and methods of using the Tetracyclic Heterocycle Compounds for treating or preventing HIV infection in a subject.

14 Claims, No Drawings

(56) References Cited

FOREIGN PATENT DOCUMENTS

| | | | |
|---|---|---|---|
| JP | 2006342115 A | 12/2006 |
| WO | 2005087766 A1 | 9/2005 |
| WO | 2006066414 A1 | 6/2006 |
| WO | 2006116764 A1 | 11/2006 |
| WO | 2007049675 A1 | 3/2007 |
| WO | 2010011816 A1 | 1/2010 |
| WO | 2010068262 A1 | 6/2010 |
| WO | 2011011483 A1 | 1/2011 |
| WO | 2011119566 A1 | 9/2011 |
| WO | 2011129095 A1 | 10/2011 |
| WO | 2012095388 A3 | 10/2012 |
| WO | 2012151361 A1 | 11/2012 |
| WO | 2013038407 A1 | 3/2013 |
| WO | 2013054862 A1 | 4/2013 |
| WO | 2014099586 A1 | 6/2014 |
| WO | 2014100323 A1 | 6/2014 |
| WO | 2014104279 A1 | 7/2014 |
| WO | 2014183532 A1 | 11/2014 |
| WO | 2014200880 A1 | 12/2014 |
| WO | 2015006731 A1 | 1/2015 |
| WO | 2015006733 A1 | 1/2015 |
| WO | 2015039348 A1 | 3/2015 |
| WO | 2015048363 A1 | 4/2015 |
| WO | 2015089847 A1 | 6/2015 |
| WO | 2016027879 A1 | 2/2016 |
| WO | 2015095258 A1 | 6/2016 |
| WO | 2016094197 A1 | 6/2016 |
| WO | 2017113288 A1 | 7/2017 |
| WO | 2017116928 A1 | 7/2017 |

OTHER PUBLICATIONS

International Search Report and Written Opinion for PCT/US2017/063831 dated Jan. 22, 2018, 15 pages.

Johns, et al, Carbamoyl Pyridone HIV-1 Integrase Inhibitors 3. A Diastereomeric Approach to Chiral Nonracemic Tricyclic Ring Systems and the Discovery of Dolutegravir (S/GSK1349572) and (S/GSK1265744), Journal of Medicinal Chemistry, 2013, 5901-5916, 56.

Kawasuji, T.; et al., Carbamoyl Pyridone HIV-1 Integrase Inhibitors. 2. Bi- and Tricyclic Derivatives Result in Superior Antiviral and Pharmacokinetic Profiles, Journal of Medicinal Chemistry, 2013, pp. 1124-1135., vol. 56, No. 3.

Taoda, Y; et al., Discovery of novel HIV integrase inhibitors part 1: Molecular design and SAR of azabicyclic carbamoyl pyridone inhibitors, 245th ACS National Meeting Poster Session, 2013, abstract, 245.

U.S. Appl. No. 16/447,421, filed Jun. 20, 2019.

\* cited by examiner

TETRACYCLIC HETEROCYCLE COMPOUNDS USEFUL AS HIV INTEGRASE INHIBITORS

CROSS-REFERENCE TO RELATED APPLICATIONS

This application is a continuation application of U.S. Ser. No. 16/447,271, filed Jun. 20, 2019, which claims priority from U.S. Ser. No. 15/826,898, filed Nov. 30, 2017, which claims priority to U.S. Provisional Application No. 62/429,470, filed Dec. 2, 2016. Each of the aforementioned US and priority applications is incorporated by reference in its entirety.

FIELD OF THE INVENTION

The present invention relates to Tetracyclic Heterocycle Compounds, compositions comprising at least one Tetracyclic Heterocycle Compound, and methods of using the Tetracyclic Heterocycle Compounds for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA and covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Tohours, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication.

The following references may be of interest as background:

International Publication Nos. WO 11/045330 and WO 11/121105 disclose macrocyclic compounds having HIV integrase inhibitory activity.

Kinzel et al., Tet. Letters 2007, 48(37): pp. 6552-6555 discloses the synthesis of tetrahydropyridopyrimidones as a scaffold for HIV-1 integrase inhibitors.

Ferrara et al., Tet. Letters 2007, 48(37), pp. 8379-8382 discloses the synthesis of a hexahydropyrimido[1,2-a]azepine-2-carboxamide derivative useful as an HIV integrase inhibitor.

Muraglia et al., J. Med. Chem. 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. Nos. 7,169,780, 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that may be useful as HIV integrase inhibitors.

U.S. Pat. Nos. 7,135,467 and 7,037,908 disclose certain pyrimidine carboxamides that may be useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that may be useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that may be useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that may be useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

U.S. Pat. Nos. 7,462,608 and 7,649,015 each disclose phosphate and phosphonate substituted heterocycles useful as HIV nNRTI inhibitors and HIV protease inhibitors, respectively.

SUMMARY OF THE INVENTION

In one aspect, the present invention provides Compounds of Formula (I):

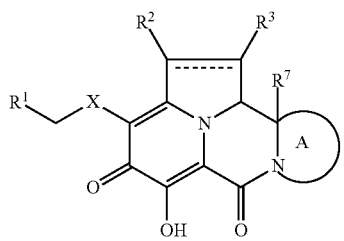

(I)

or pharmaceutically acceptable salts thereof,
wherein:
----- represents an optional double bond;
ring A, inclusive of the carbon atom and nitrogen atom to which ring A is fused, is a 5- to 8-membered monocyclic or bicyclic heterocycloalkyl group, which can be optionally and independently substituted on ring A carbon atom with a group selected from $C_1$-$C_6$ alkyl, —O—($C_1$-$C_6$ alkyl) and $C_3$-$C_7$ cycloalkyl, and which can be optionally and independently substituted on a ring nitrogen atom with a group selected from $C_1$-$C_6$ alkyl, —C(O)—($C_1$-$C_6$ alkyl) and —S(O)$_2$—($C_1$-$C_6$ alkyl);

X is selected from 5 or 6-membered monocyclic heteroaryl and —N($R^4$)C(O)—;

$R^1$ is a phenyl group which is optionally substituted with from 1 to 3 groups, each independently selected from $C_1$-$C_6$ alkyl, halo, —O—($C_1$-$C_6$ alkyl), $C_1$-$C_6$ haloalkyl, —O—($C_1$-$C_6$ haloalkyl), —CN, —NO$_2$, —N($R^4$)$_2$, —C(O)O$R^6$, —C(O)N($R^4$)$_2$ and —NHC(O)$R^6$;

$R^2$ is selected from H, $C_1$-$C_6$ alkyl, $C_3$-$C_7$ cycloalkyl, halo, $C_1$-$C_6$ haloalkyl, —O$R^5$, —N($R^4$)$_2$, —C(O)$R^5$, —C(O)N($R^4$)$_2$ and —NHC(O)$R^5$, wherein said $C_1$-$C_6$ alkyl group is optionally substituted with one or more groups, each independently selected from halo, —OH, —O($C_1$-$C_6$ alkyl) and —N($R^4$)$_2$;

$R^3$ is selected from H, $C_1$-$C_6$ alkyl and —O—($C_1$-$C_6$ alkyl), —N($R^4$)$_2$;

each occurrence of $R^4$ is independently selected from H and $C_1$-$C_6$ alkyl;

each occurrence of $R^5$ is independently selected from H, $C_1$-$C_6$ alkyl and $C_3$-$C_7$ cycloalkyl;

each occurrence of $R^6$ is independently selected from H and $C_1$-$C_6$ alkyl; and $R^7$ is selected from H and $C_1$-$C_6$ alkyl.

In another aspect, the present invention provides Compounds of Formula (I):

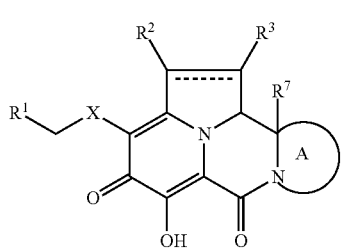

(I)

or pharmaceutically acceptable salts thereof,
wherein:
----- represents an optional double bond;
ring A, inclusive of the carbon atom and nitrogen atom to which ring A is fused, is a 5- to 7-membered monocyclic or bicyclic heterocycloalkyl group, which can be optionally and independently substituted on ring A carbon atom with a group selected from $C_1$-$C_6$ alkyl, —O—($C_1$-$C_6$ alkyl) and $C_3$-$C_7$ cycloalkyl, and which can be optionally and independently substituted on a ring nitrogen atom with a group selected from $C_1$-$C_6$ alkyl, —C(O)—($C_1$-$C_6$ alkyl) and —S(O)$_2$—($C_1$-$C_6$ alkyl);

X is selected from 5 or 6-membered monocyclic heteroaryl and —N($R^4$)C(O)—;

$R^1$ is a phenyl group which is optionally substituted with from 1 to 3 groups, each independently selected from $C_1$-$C_6$ alkyl, halo, —O—($C_1$-$C_6$ alkyl), $C_1$-$C_6$ haloalkyl, —O—($C_1$-$C_6$ haloalkyl), —CN, —NO$_2$, —N($R^4$)$_2$, —C(O)O$R^6$, —C(O)N($R^4$)$_2$ and —NHC(O)$R^6$;

$R^2$ is selected from H, $C_1$-$C_6$ alkyl, $C_3$-$C_7$ cycloalkyl, halo, $C_1$-$C_6$ haloalkyl, —O$R^5$, —N($R^4$)$_2$, —C(O)$R^5$, —C(O)N($R^4$)$_2$ and —NHC(O)$R^5$, wherein said $C_1$-$C_6$ alkyl group is optionally substituted with one or more groups, each independently selected from halo, —OH, —O($C_1$-$C_6$ alkyl) and —N($R^4$)$_2$;

$R^3$ is selected from H, $C_1$-$C_6$ alkyl and —O—($C_1$-$C_6$ alkyl), —N($R^4$)$_2$;

each occurrence of $R^4$ is independently selected from H and $C_1$-$C_6$ alkyl;

each occurrence of $R^5$ is independently selected from H, $C_1$-$C_6$ alkyl and $C_3$-$C_7$ cycloalkyl;

each occurrence of $R^6$ is independently selected from H and $C_1$-$C_6$ alkyl; and $R^7$ is selected from H and $C_1$-$C_6$ alkyl.

The Compounds of Formula (I) (also referred to herein as the "Tetracyclic Heterocycle Compounds") and pharmaceutically acceptable salts or prodrugs thereof may be useful, for example, for inhibiting HIV viral replication or replicon activity, or for treating or preventing HIV infection in a subject. Without being bound by any specific theory, it is believed that the Tetracyclic Heterocycle Compounds inhibit HIV viral replication by inhibiting HIV Integrase.

Accordingly, the present invention provides methods for treating or preventing HIV infection in a subject, comprising administering to the subject an effective amount of at least one Tetracyclic Heterocycle Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Tetracyclic Heterocycle Compounds, compositions comprising at least one Tetracyclic Heterocycle Compound, and methods of using the Tetracyclic Heterocycle Compounds for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Tetracyclic Heterocycle Compound and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)— alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "$C_1$-$C_6$ alkylene" refers to an alkylene group having from 1 to 6 carbon atoms. The term "$C_1$-$C_3$ alkylene" refers to an alkylene group having from 1 to 3 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "$C_2$-$C_6$ alkenylene" refers to an alkenylene group having from 2 to 6 carbon atoms. The term "$C_3$-$C_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group is optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group is optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

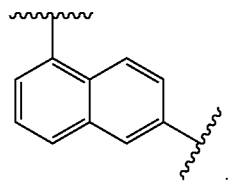 [SMILES: *c1ccc2c(*)cccc2c1]

is understood to represent both:

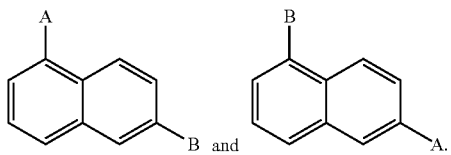

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

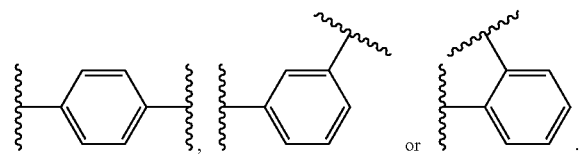

Unless otherwise indicated, an arylene group is unsubstituted.

The term "cycloalkyl," as used herein, refers to a non-aromatic mono- or multicyclic saturated ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group is optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

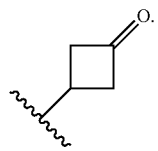

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. In another embodiment, a heteroaryl group is bicyclic and has 9 or 10 ring atoms. A heteroaryl group is optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo

[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group is optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

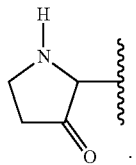

In one embodiment, a heterocycloalkyl group is a 5-membered monocyclic heterocycloalkyl. In another embodiment, a heterocycloalkyl group is a 6-membered monocyclic heterocycloalkyl. The term "4 to 7-membered monocyclic heterocycloalkyl" refers to a monocyclic heterocycloalkyl group having from 4 to 7 ring atoms. The term "5 to 8-membered monocyclic heterocycloalkyl" refers to a monocyclic heterocycloalkyl group having from 5 to 8 ring atoms. The term "8 to 11-membered bicyclic heterocycloalkyl" refers to a bicyclic heterocycloalkyl group having from 8 to 11 ring atoms. Unless otherwise indicated, a heterocycloalkyl group is unsubstituted.

The term "heterocycloalkenyl," as used herein, refers to an heterocycloalkyl group, as defined above, which is non-aromatic and contains at least one endocyclic double bond between two adjacent ring atoms. A heterocycloalkenyl group can be joined via a ring carbon, ring silicon atom or ring nitrogen atom. In one embodiment, a heterocycloalkenyl group is monocyclic and has from about 3 to about 7 ring atoms. In another embodiment, a heterocycloalkenyl group is monocyclic has from about 5 to about 8 ring atoms. In another embodiment, a heterocycloalkenyl group is bicyclic and has from about 8 to about 11 ring atoms. In still another embodiment, a heterocycloalkenyl group is monocyclic and has 5 or 6 ring atoms. In one embodiment, a heterocycloalkenyl group is monocyclic. In another embodiment, a heterocycloalkenyl group is bicyclic. There are no adjacent oxygen and/or sulfur atoms present in the ring system. Any —NH group in a heterocycloalkenyl ring may be substituted or may exist protected such as, for example, as an —N(BOC), —N(Cbz), —N(Tos) group and the like; such protected heterocycloalkenyl groups are considered part of this invention. The term "heterocycloalkenyl" also encompasses a heterocycloalkenyl group, as defined above, which is fused to an aryl (e.g., benzene) or heteroaryl ring. A heterocycloalkenyl group is optionally substituted by one or more "ring system substituents" which may be the same or different, and are as defined herein below. The nitrogen or sulfur atom of the heterocycloalkenyl can be optionally oxidized to the corresponding N-oxide, S-oxide or S,S-dioxide.

A ring carbon atom of a heterocycloalkenyl group may be functionalized as a carbonyl group. An illustrative example of such a heterocycloalkenyl group is:

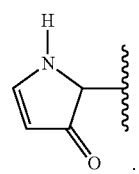 [SMILES: *C1NC=CC1=O]

In one embodiment, a heterocycloalkenyl group is a 5-membered monocyclic heterocycloalkenyl. In another embodiment, a heterocycloalkenyl group is a 6-membered monocyclic heterocycloalkenyl. The term "4 to 7-membered monocyclic heterocycloalkenyl" refers to a monocyclic heterocycloalkenyl group having from 4 to 7 ring atoms. The term "5 to 8-membered monocyclic heterocycloalkenyl" refers to a monocyclic heterocycloalkenyl group having from 5 to 8 ring atoms. The term "8 to 11-membered bicyclic heterocycloalkenyl" refers to a bicyclic heterocycloalkenyl group having from 8 to 11 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O— alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

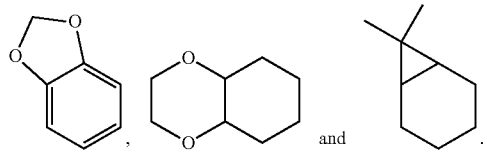

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., R$^4$ and R$^5$) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Tetracyclic Heterocycle Compound or a pharmaceutically acceptable salt of the compound. The transformation may occur by various mechanisms (e.g., by metabolic or chemical processes), such as, for example, through hydrolysis in blood. For example, if a Tetracyclic Heterocycle Compound or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as (3-dimethylaminoethyl), carbamoyl-(C$_1$-C$_2$)alkyl, N,N-di(C$_1$-C$_2$)alkylcarbamoyl-(C$_1$-C$_2$)alkyl and piperidino-, pyrrolidino- or morpholino(C$_2$-C$_3$)alkyl, and the like.

Similarly, if a Tetracyclic Heterocycle Compound contains an alcohol functional group, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylaminomethyl, succinoyl, (C$_1$-C$_6$)alkanoyl, α-amino(C$_1$-C$_4$)alkyl, α-amino(C$_1$-C$_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Tetracyclic Heterocycle Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently (C$_1$-C$_{10}$)alkyl, (C$_3$-C$_7$) cycloalkyl, benzyl, a natural α-aminoacyl, —C(OH)C(O)OY$^1$ wherein Y$^1$ is H, (C$_1$-C$_6$)alkyl or benzyl, —C(OY$^2$)Y$^3$ wherein Y$^2$ is (C$_1$-C$_4$) alkyl and Y$^3$ is (C$_1$-C$_6$)alkyl; carboxy (C$_1$-C$_6$)alkyl; amino(C$_1$-C$_4$)alkyl or mono-N— or di-N,N—(C$_1$-C$_6$)alkylaminoalkyl; —C(Y$^4$)

$Y^5$ wherein $Y^4$ is H or methyl and $Y^5$ is mono-N— or di-N,N—$(C_1$-$C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—$(C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_6$-24)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tetracyclic Heterocycle Compounds can form salts which are also within the scope of this invention. Reference to a Tetracyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tetracyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt.

In another embodiment, the salt is other than a pharmaceutically acceptable salt. Salts of the Compounds of Formula (I) may be formed, for example, by reacting a Tetracyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tetracyclic Heterocycle Compounds may be atropisomers (e.g., substituted biaryls) and are considered as part of this invention. Enantiomers can also be directly separated using chiral chromatographic techniques.

It is also possible that the Tetracyclic Heterocycle Compounds may exist in different tautomeric forms, and all such forms are embraced within the scope of the invention. For example, all keto-enol and imine-enamine forms of the compounds are included in the invention.

Unless a specific stereochemistry is indicated, the present invention is meant to comprehend all such isomeric forms of these compounds. For example, geometric isomers, optical isomers and the like of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tetracyclic Heterocycle Compound incorporates a double bond or a fused ring, both the cis- and trans-forms, as well as mixtures, are embraced within the scope of the invention.

When a substituent on a chiral carbon atom is depicted as a racemate (by using a straight line bond to a chiral center), it to be understood that both the alpha and beta configurations of said substituent group are to be considered part of the present invention. For example, the compound of the present invention, which is drawn as follows:

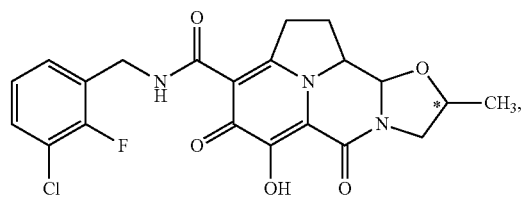 [SMILES: CC1CN2C(=O)c3c(O)c(=O)c(C(=O)NCc4cccc(Cl)c4F)c4n3C(CC4)C2O1]

is understood to encompass both diastereomers at the indicated chiral center, the structures of which are as follows:

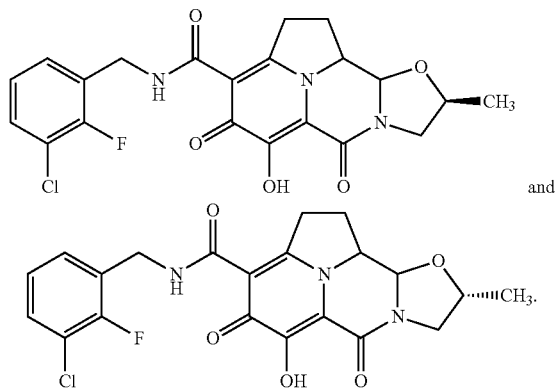

In the Examples section below, compounds of the present invention that have been purified into pure diasteromers are sometimes depicted in racemic form but identified as "enantiomer A" and "enantiomer B." In this instance, the absolute stereochemistry of each isolated diastereomer has not been determined and the A and B designations are used to represent each individual purified enantiomer.

In the Examples section, selected compounds of the invention are sometimes also designated as having cis or trans stereochemistry. This designation refers to the isomerism about the ring fusion bond indicated by the arrow below:

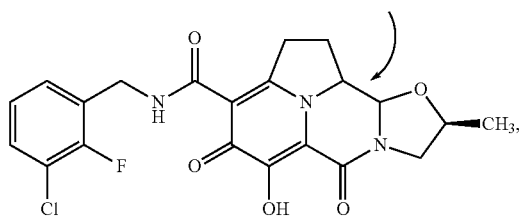 [SMILES: C[C@H]1CN2C(=O)c3c(O)c(=O)c(C(=O)NCc4cccc(Cl)c4F)c4n3C(CC4)C2O1]

wherein the following isomers have the "cis" designation:

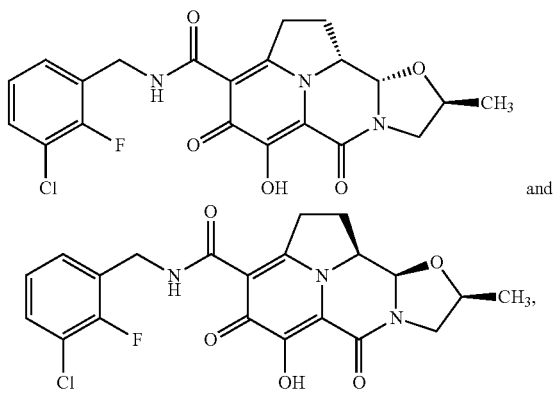

and the following isomers have the "trans" designation:

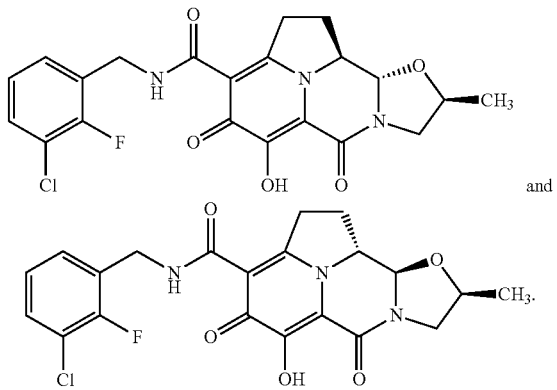

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Tetracyclic Heterocycle Compounds may be useful in human and veterinary medicine for treating or preventing HIV infection in a subject. In one embodiment, the Tetracyclic Heterocycle Compounds can be inhibitors of HIV viral replication. In a specific embodiment, the Tetracyclic Heterocycle Compounds are inhibitors of HIV-1. Accordingly, the Tetracyclic Heterocycle Compounds may be useful for treating HIV infections and AIDS. In accordance with the invention, the Tetracyclic Heterocycle Compounds can be administered to a subject in need of treatment or prevention of HIV infection.

Accordingly, in one embodiment, the invention provides methods for treating HIV infection in a subject comprising administering to the subject an effective amount of at least one Tetracyclic Heterocycle Compound or a pharmaceutically acceptable salt thereof. In a specific embodiment, the present invention provides methods for treating AIDS in a subject comprising administering to the subject an effective amount of at least one Tetracyclic Heterocycle Compound or a pharmaceutically acceptable salt thereof.

List of Abbreviations

Ac=acetyl
ACN=acetonitrile
Bn=benzyl
BnBr=benzyl bromide
Boc=tert-butoxycarbonyl
Boc$_2$O=t-butyloxycarbonate anhydride
t-BuOH=tert-butanol
DCM=dichloromethane
DEA=diethylamine
Dess-Martin reagent=1,1,1-Triacetoxy-1,1-dihydro-1,2-benziodoxol-3(1H)-one
DIBAL=diisobutylaluminum hydride
DMF=dimethylformamide
DMSO=dimethyl sulfoxide
Et=ethyl
EtOAc=ethyl acetate
EtOH=ethanol
FBS=fetal bovine serum
HCl=hydrochloric acid
HPLC=high-pressure liquid chromatography
IPA=isopropanol
KHMDS=potassium hexamethyldisilazane
LiHMDS=lithium hexamethyldisilazane
m-CPBA=meta-chloroperoxybenzoic acid
MeCN=acetonitrile
MeOH=methanol
MePh$_3$PBr=triphenylmethyl phosphonium bromide
MS=mass spectroscopy
MeI=iodomethane
Ms=methanesulfonyl ("mesyl")
MSCl=methanesulfonyl chloride
NBS=N-bromosuccinimide
NHS=normal human serum
NIS=N-iodosuccinimide
NMR=nuclear magnetic resonance spectroscopy
Pd/C=palladium on carbon
Pd(PPh$_3$)$_4$=tetrakis (triphenylphoshpine) palladium(0)
RP-HPLC=reverse-phase high performance liquid chromatography
rt=room temperature
SC—CO$_2$=supercritical carbon dioxide
SFC=supercritical fluid chromatography
SiO$_2$=silical gel
TBAF=tetra-n-butylammonium fluoride
TEMPO=2,2,6,6-tetramethylpiperidine-N-oxide
TFA=trifluoroacetic acid
THF=tetrahydrofuran
THP=tetrahydropyran
TLC=thin-layer chromatography
TMS=trimethylsilyl
TMSBr=trimethylsilyl bromide
TMSCHN$_2$=trimethylsilyl diazomethane The Compounds of Formula (I)

The present invention provides Tetracyclic Heterocycle Compounds of Formula (I):

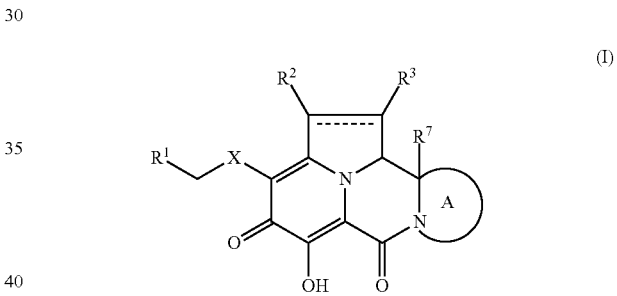

and pharmaceutically acceptable salts thereof, wherein A, X, $R^1$, $R^2$, $R^3$ and $R^7$ are defined above for the Compounds of Formula (I).

In one embodiment, the double bond represented by ---- is absent.

In another embodiment, the double bond represented by ---- is present.

In one embodiment, ring A, inclusive of the carbon atom and nitrogen atom to which ring A is fused, is selected from:

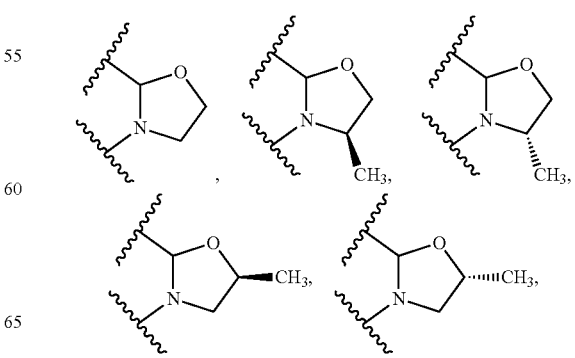

-continued

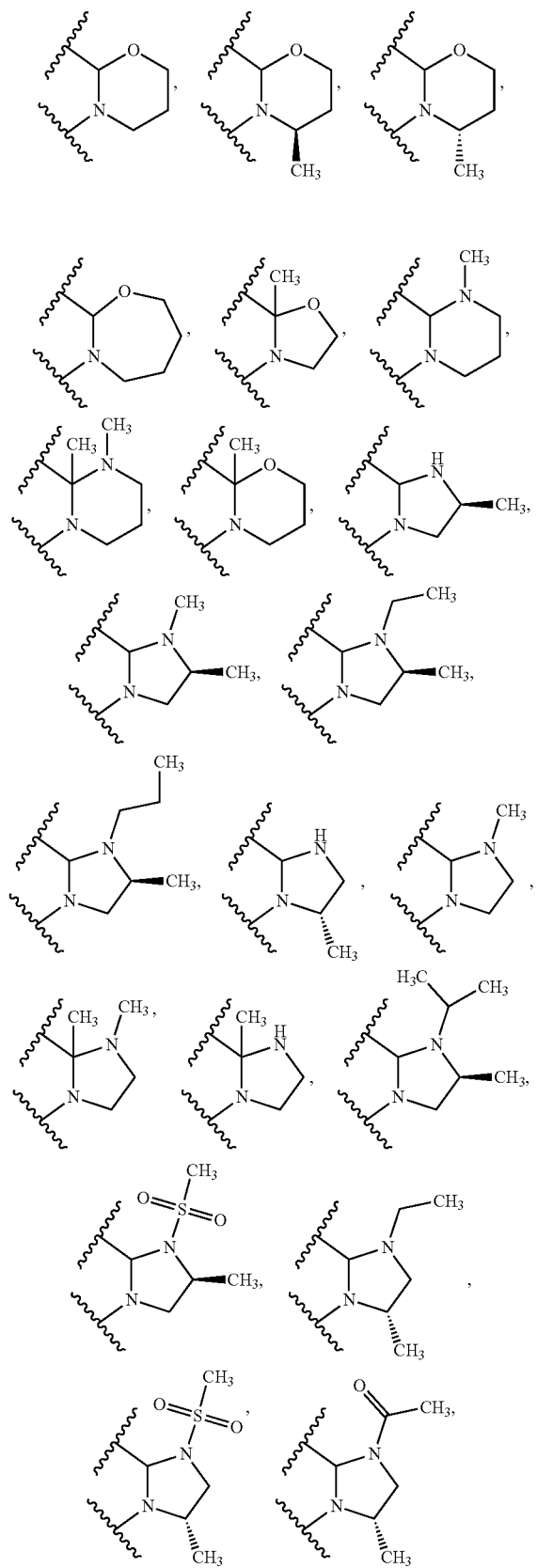

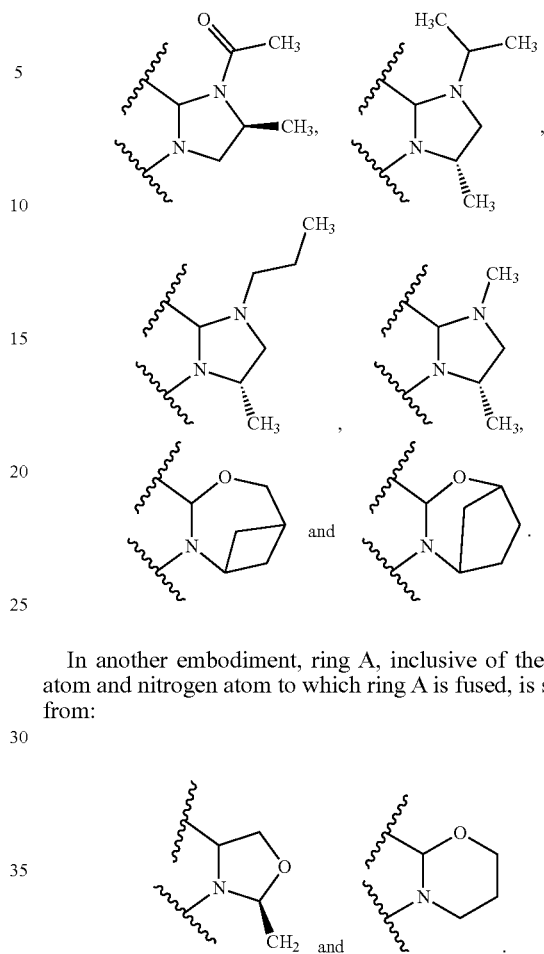

In another embodiment, ring A, inclusive of the carbon atom and nitrogen atom to which ring A is fused, is selected from:

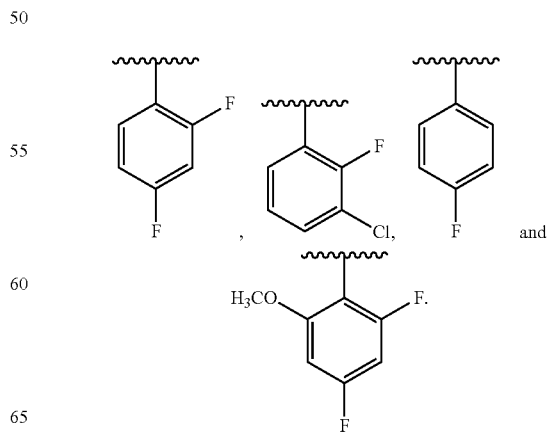

In one embodiment, X is —NHC(O)—.
In another embodiment, X is 5-membered heteroaryl.
In another embodiment, X is thiadiazolyl.
In one embodiment, $R^1$ is phenyl, which is optionally substituted with from 1 to 3 groups, each independently selected from $C_1$-$C_6$ alkyl, halo and —O—($C_1$-$C_6$ alkyl);
In one embodiment, $R^1$ is phenyl, which is substituted with 1 or 2 halo groups, each independently selected from Cl and F.
In another embodiment, $R^1$ is selected from:

In another embodiment, X is —NHC(O)— and $R^1$ is selected from:

[chemical structures: 2,4-difluorophenyl; 2-fluoro-3-chlorophenyl; 4-fluorophenyl; and 2-methoxy-4,6-difluorophenyl]

In another embodiment, X is —NHC(O)— and $R^1$ is:

[chemical structure: 2-fluoro-3-chlorophenyl]

In one embodiment, $R^2$ is H or —O—($C_1$-$C_6$ alkyl).
In another embodiment, $R^2$ is H.
In another embodiment, $R^2$ is —O—($C_1$-$C_6$ alkyl).
In still another embodiment, $R^2$ is methoxy.
In one embodiment, $R^3$ is H.
In another embodiment, $R^3$ is —O—($C_1$-$C_6$ alkyl).
In still another embodiment, $R^2$ and $R^3$ are each H.
In another embodiment, $R^2$ is methoxy and $R^3$ is H.
In one embodiment, $R^7$ is H.
In another embodiment, $R^7$ is $C_1$-$C_6$ alkyl.
In another embodiment, $R^7$ is methyl.
In still another embodiment, $R^2$ is methoxy, $R^3$ is H and $R^7$ is H.

In one embodiment, ring A, inclusive of the carbon atom and nitrogen atom to which ring A is fused, is selected from:

[multiple chemical structures of heterocyclic rings: oxazolidines, morpholines, oxazepanes, imidazolidines, piperazines with various substituents including methyl, ethyl, propyl, isopropyl, methylsulfonyl, and acetyl groups]

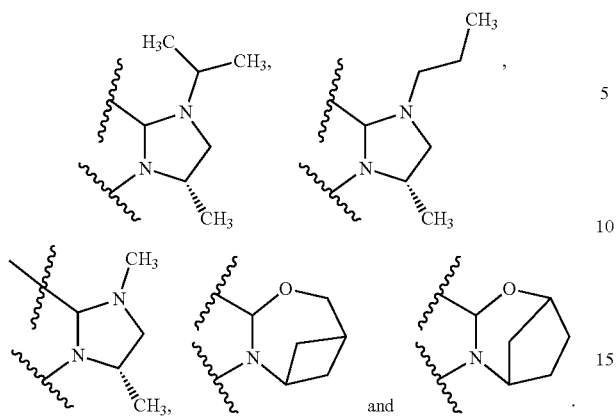
In another embodiment, ring A, inclusive of the carbon atom and nitrogen atom to which ring A is fused, is selected from:
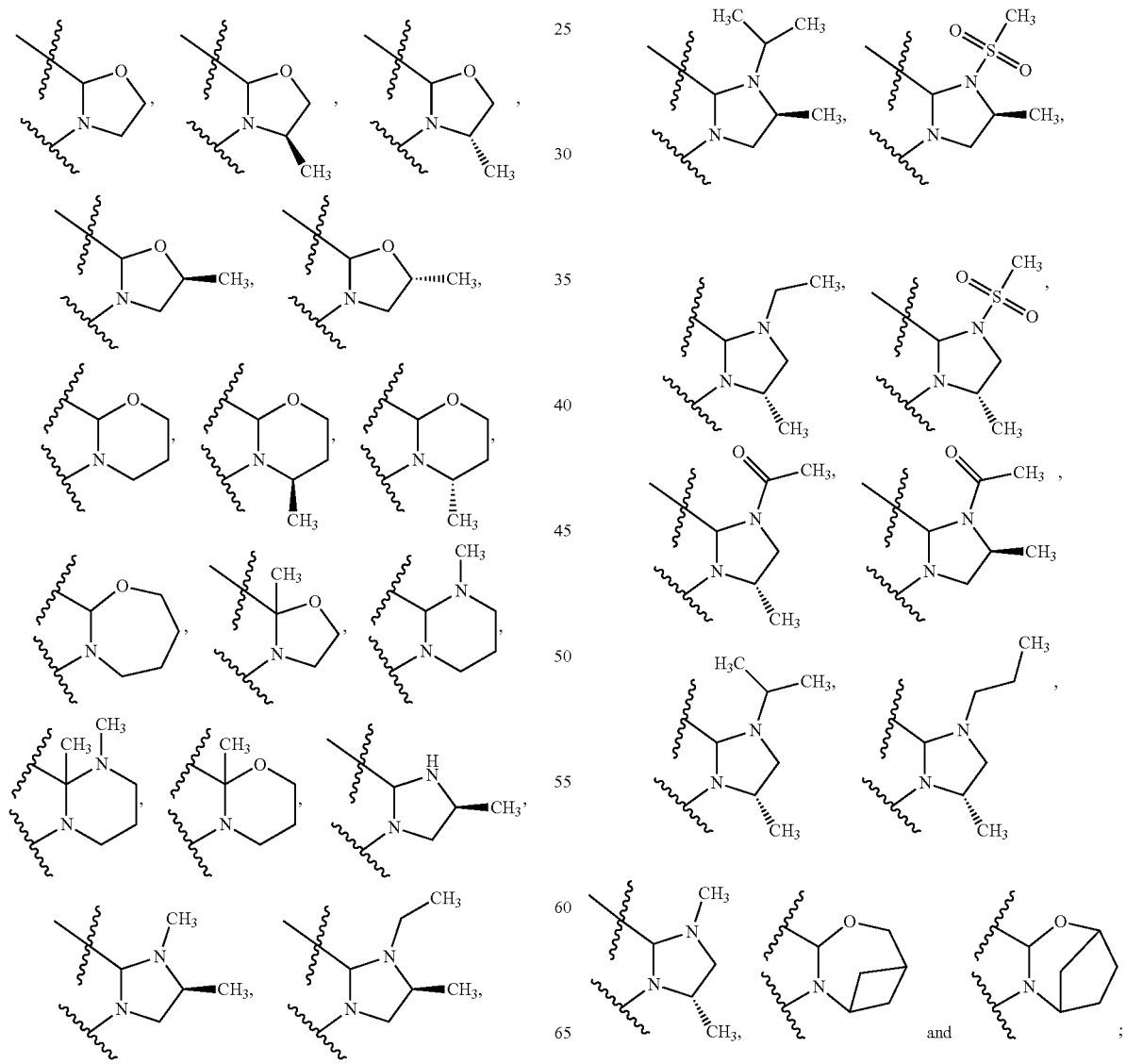

X is —NHC(O)—; and
R¹ is selected from:
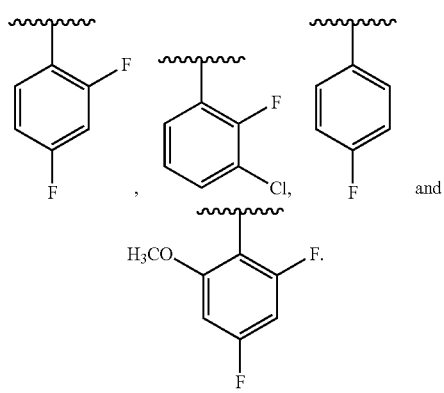
In one embodiment, the compounds of formula (I) have the formula (Ia):
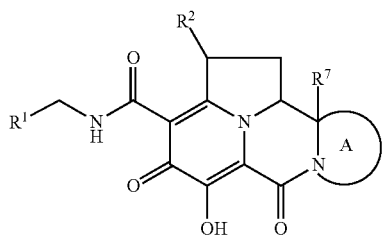
or a pharmaceutically acceptable salt thereof, wherein
ring A, inclusive of the carbon atom and nitrogen atom to which ring A is fused, is selected from:
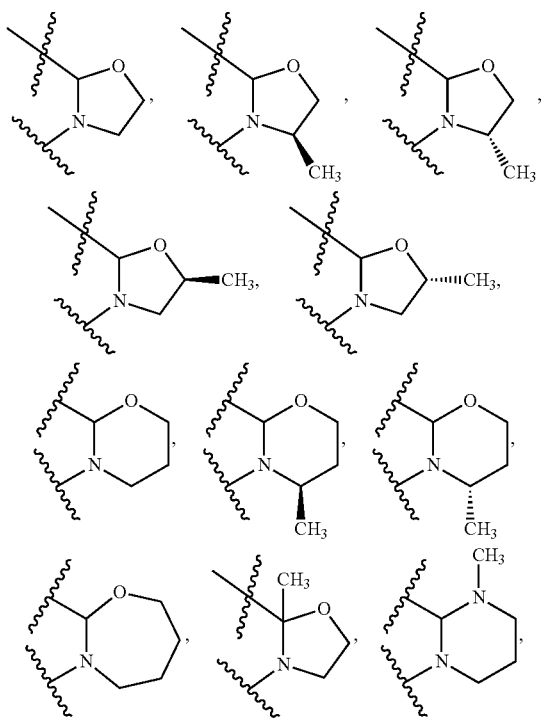
-continued
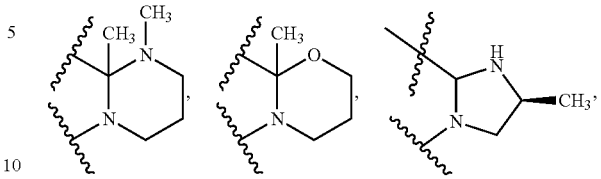
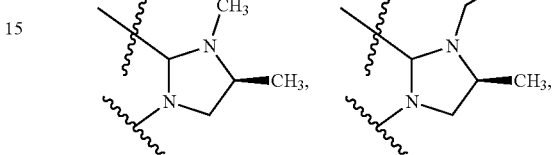
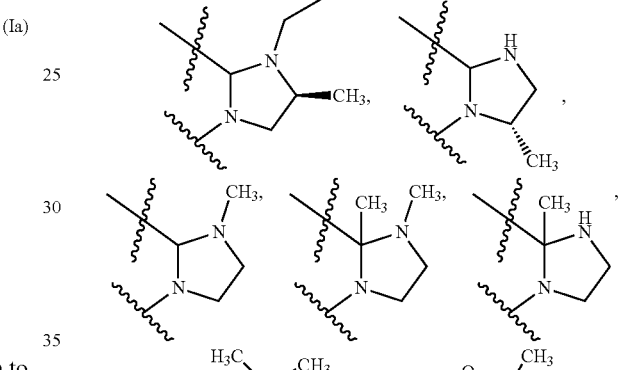
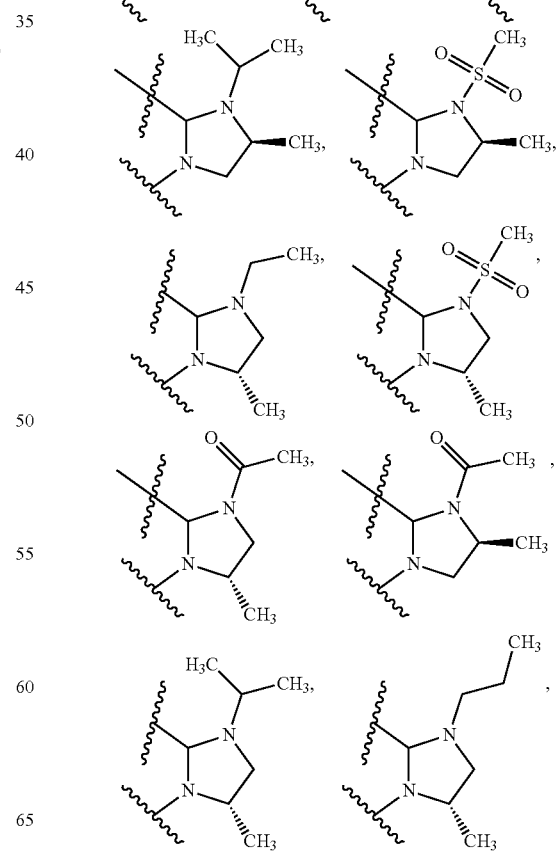

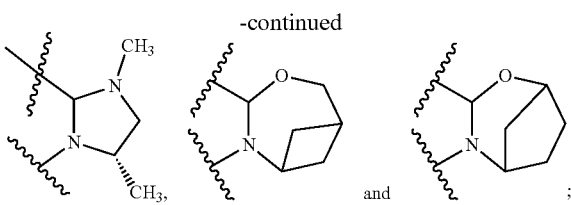

$R^1$ is a phenyl group which is optionally substituted with from 1 to 3 groups, each independently selected from $C_1$-$C_6$ alkyl, halo and —O—($C_1$-$C_6$ alkyl);

$R^2$ is selected from H and —O—($C_1$-$C_6$ alkyl); and $R^7$ is selected from H and $C_1$-$C_6$ alkyl.

In one embodiment, variables A, X, $R^1$, $R^2$, $R^3$ and $R^7$ for the Compounds of Formula (I) are selected independently of each other.

In another embodiment, the Compounds of Formula (I) are in substantially purified form.

It is to be understood that any of the aforementioned embodiments can be combined with one or more separate embodiments.

Other embodiments of the present invention include the following:

(a) A pharmaceutical composition comprising an effective amount of a Compound of Formula (I), and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors and HIV NNRTI inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors and HIV NNRTI inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula (I), and a pharmaceutically acceptable carrier.

(m) The pharmaceutical composition of (l), further comprising a second therapeutic agent selected from the group consisting of HIV antiviral agents, immunomodulators, and anti-infective agents.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula (I) and (ii) a second therapeutic agent selected from the group consisting of HIV antiviral agents, immunomodulators, and anti-infective agents; wherein the pharmaceutically acceptable salt of the Compound of Formula (I) and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula (I).

(r) A method of treating HIV infection and/or reducing the likelihood or severity of symptoms of HIV infection in a subject in need thereof which comprises administering to the subject an effective amount of a pharmaceutically acceptable salt of a Compound of Formula (I).

(s) The method of (r), wherein the pharmaceutically acceptable salt of the Compound of Formula (I) is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NS5B polymerase inhibitors.

(u) A method of inhibiting HIV replication in a subject in need thereof which comprises administering to the subject the pharmaceutical composition of (l), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (l), (m) or (n) or the combination of (o) or (p).

Further embodiments of the present invention include the following:

(w) A pharmaceutical composition comprising an effective amount of a Compound of Formula (I) or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula (I) and (ii) or a pharmaceutically acceptable salt thereof, a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula (I) or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula (I) or a pharmaceutically acceptable salt thereof.

(dd) The method of (cc), wherein the Compound of Formula (I) or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV protease inhibitors and HIV NNRTI inhibitors.

(ff) A method of inhibiting HIV replication in a subject in need thereof which comprises administering to the subject the pharmaceutical composition of (w) (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w) (x) or (y) or the combination of (z) or (aa).

The present invention also includes a compound of the present invention for use (i) in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula (I) include compounds 2-207 as set forth in the Examples below, and pharmaceutically acceptable salts thereof Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-4 below. Alternative synthetic pathways and analogous structures will be apparent to those skilled in the art of organic synthesis.

Scheme 1
Scheme 1 describes methods useful for preparing the compounds of Formula (I).

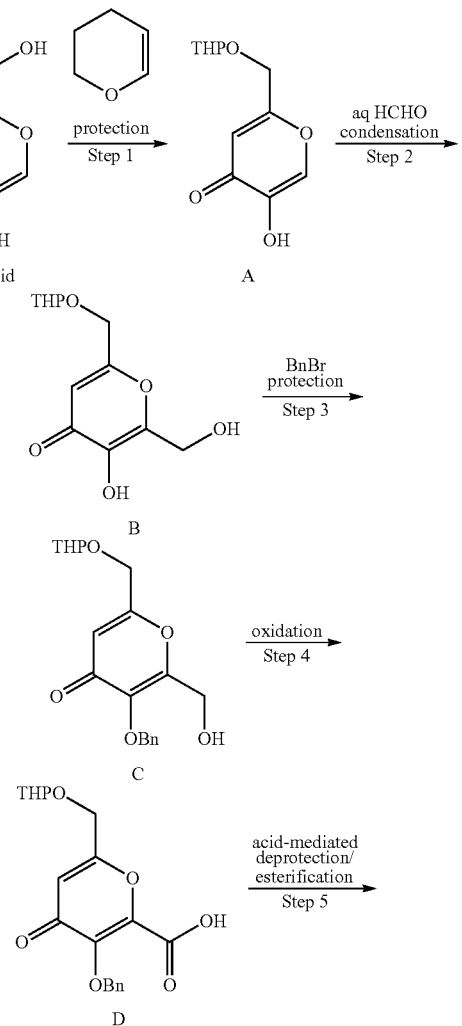

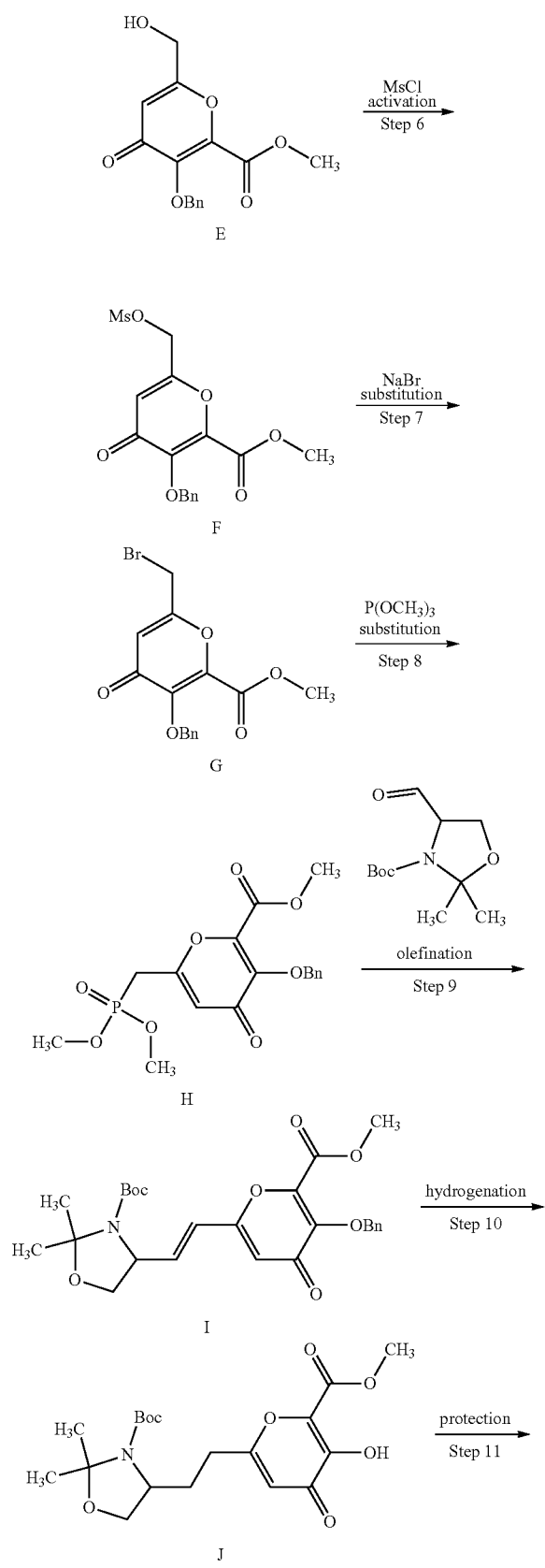
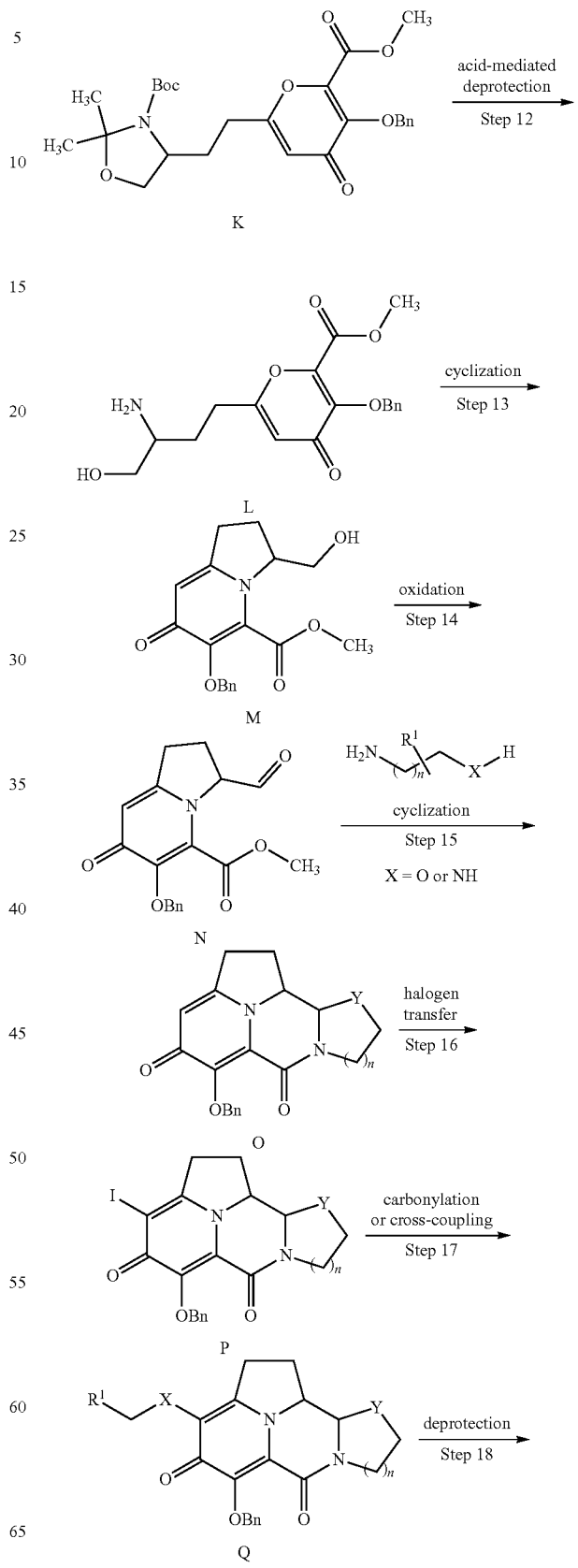

33
-continued

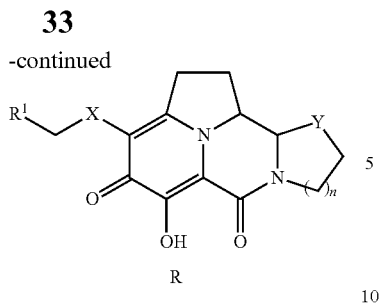

R

Wherein X and $R^1$ are as defined above for the compounds of Formula (I); n is 1, 2 or 3; and Y is O or a substituted or unsubstituted nitrogen atom.

Kojic acid is protected as the THP ether to provide compound A which is condensed with formaldehyde to provide compound B. Protection of the more acidic hydroxyl affords compound C which is oxidized to provide acid D. Removal of the THP under acidic conditions with concomitant esterification affords compound E which is activated as the mesylate F. Compound F is subjected to a series of displacement reactions to provide compound H. Olefination with the Garner aldehyde affords I which is hydrogenated to provide compound J. Re-protection of the hydroxyl followed by acid-mediated deprotection of the BOC-acetal affords compound L. Cyclization of compound L affords compound M which is oxidized to provide compound N. Condensation with a suitably functionalized diamine or amino alcohol affords compound O. Halogen transfer affords compound P which is subjected to transition metal-mediated carbonylation or cross-coupling to provide compound Q. Finally, deprotection of compound Q affords compound R.

Scheme 2 describes additional methods useful for preparing the compounds of Formula (I).

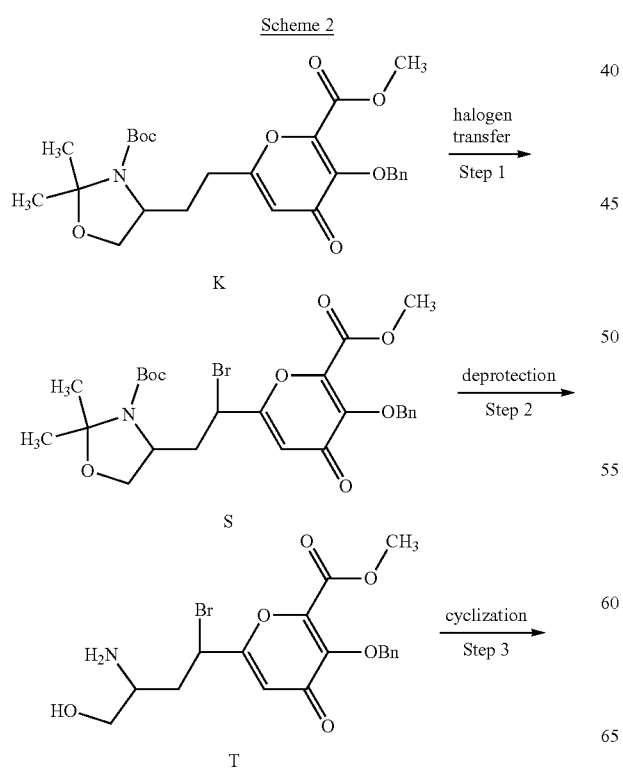

34
-continued

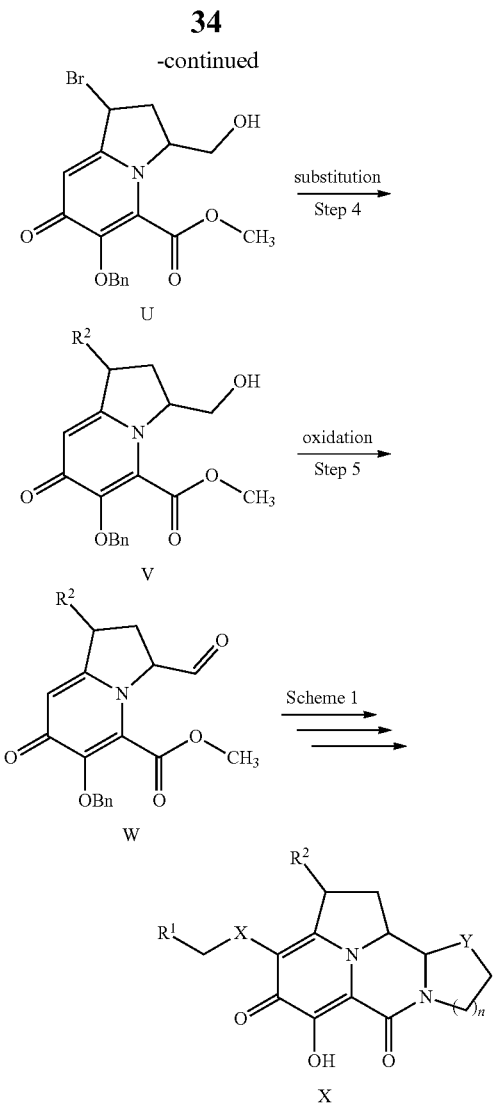

Wherein X, $R^1$ and $R^2$ are as defined above for the compounds of Formula (I); n is 1, 2 or 3; and Y is O or a substituted or unsubstituted nitrogen atom.

Compound K is subjected to halogen transfer conditions to provide compound S. Acid-mediated deprotection affords compound T which is cyclized to provide compound U. Substitution affords compound V which is oxidized to provide compound W. Compound W is then converted to the final compound X according to the methods outlined is Scheme 1.

Scheme 3 describes additional methods useful for preparing the compounds of Formula (I).

Scheme 3

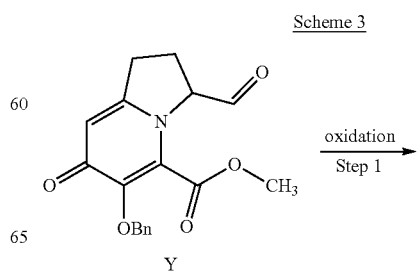

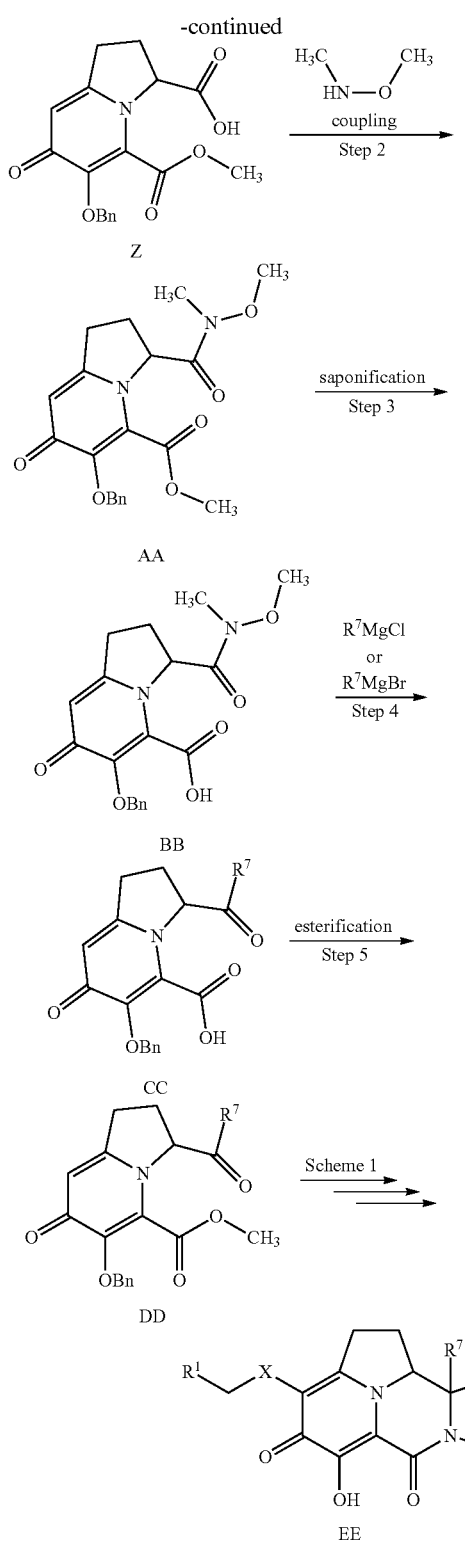

Compound Y is oxidized to provide compound Z which is coupled with N,O-dimethylhydroxylamine to provide compound AA. Saponification affords compound BB which is reacted with a suitable organometallic reagent to provide compound CC. Esterification affords compound DD. Compound DD is then converted to the final compound EE according to the methods outlined is Scheme 1.

Scheme 4 describes additional methods useful for preparing the compounds of Formula (I).

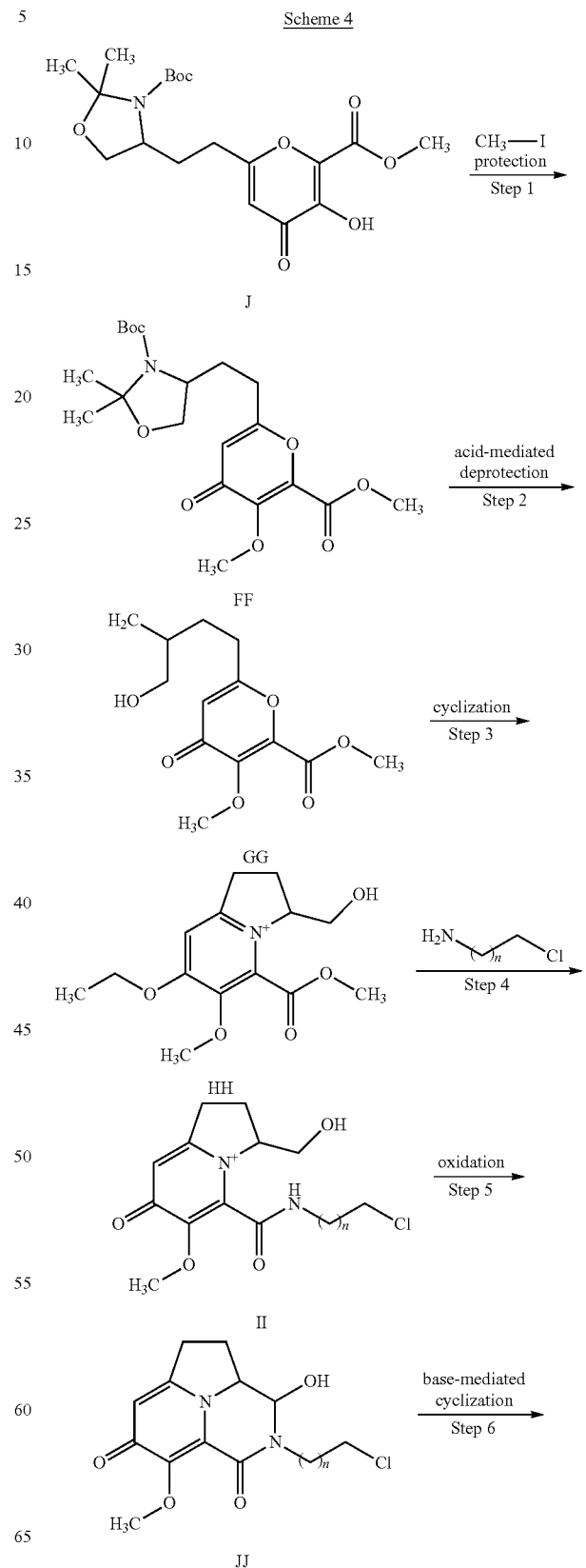

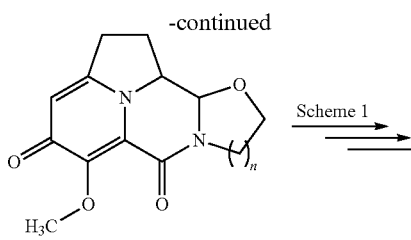

KK

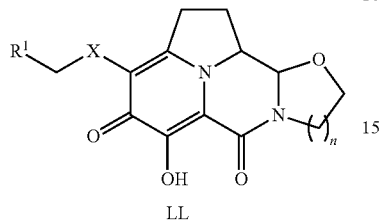

LL

Compound J is converted to the methyl ether FF. Acid-mediated deprotection affords compound GG which is cyclized to provide compound HH. Condensation with a suitably functionalized aminoalkyl halide affords compound II. Oxidation affords compound JJ which is subjected to base-mediated cyclization to provide compound KK. Compound KK is then converted to the final compound LL according to the methods outlined is Scheme 1.

EXAMPLES

General Methods

The compounds described herein can be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. Concentration refers to the removal of the volatile components at reduced pressure (e.g. rotary evaporation) unless otherwise noted. All temperatures are degrees Celsius unless otherwise noted. Mass spectra (MS) were measured by electrospray ion-mass spectroscopy (ESI) in positive ion detection mode and m/z refers to the [M+H]$^+$ ion unless otherwise noted. $^1$H NMR spectra were recorded at 400-500 MHz at ambient temperature unless otherwise noted. RP-HPLC refers to reverse-phase HPLC on C18-functionalized preparative or semi-preparative columns with gradient elution using acetonitrile and water modified with trifluoroacetic acid as eluents and fractions were lyophilized or concentrated in vacuo by rotary evaporation unless otherwise noted. Purification by column chromatography on silica gel was accomplished using a flash chromatography system (e.g. ISCO or Biotage) and commercial pre-packed silica gel columns with elution using the stated solvent systems. Compounds described herein were synthesized as the racemates unless otherwise noted in the experimental procedures and compound tables. Unless otherwise noted, for stereoisomers, enantiomer A or 1 refers to the earlier eluting enantiomer and enantiomer B or 2 refers to the later eluting enantiomer at the point of separation and this nomenclature is maintained through the remainder of a synthetic sequence for a given enantiomeric series regardless of the possibility that subsequent intermediates and final compounds may have the same or different orders of elution. Unless otherwise noted, diastereomer A or 1 refers to the earlier eluting diastereomer and diastereomer B or 2 refers to the later eluting diastereomer and this nomenclature is maintained through the remainder of a synthetic sequence for a given diastereomeric series regardless of the possibility that subsequent intermediates and final compounds may have the same or different orders of elution. The relative stereochemistry of diastereomers was assigned by using standard NMR techniques.

Example 1

Preparation of Intermediate Compound 1

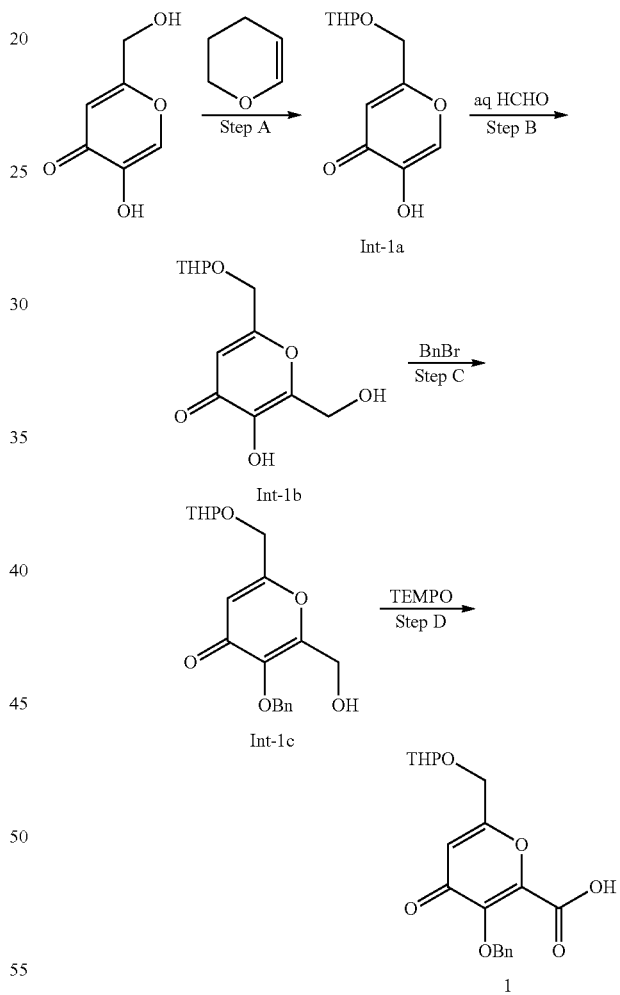

Step A—Synthesis of Intermediate Compound Int-1a

Into a 100-L reactor purged and maintained with an inert atmosphere of nitrogen, was charged a solution of 5-hydroxy-2-(hydroxymethyl)-4H-pyran-4-one (5 kg, 35.18 mol, 1.00 equiv) in dichloromethane (50 L) and 3,4-dihydro-2H-pyran (3.54 kg, 42.08 mol, 1.20 equiv). This was followed by the addition of p-toluenesulfonic acid monohydrate (60 g, 315 mmol, 0.01 equiv) in several batches at 10° C. in 20 min. The resulting solution was stirred for 3 h at room temperature. The solution was adjusted to pH 7 with sodium hydroxide (5 M). The organic phase was washed with 1×10 L of brine and concentrated in vacuo under vacuum to provide Int-1a, which was used without further purification.

Step B—Synthesis of Intermediate Compound Int-1b

Into a 50-L 4-necked round-bottom flask purged and maintained with an inert atmosphere of nitrogen, was placed a solution of Int-1a (5.5 kg, 24.31 mol, 1.00 equiv) in water (27.5 L), sodium hydroxide (973.5 g, 24.34 mol, 1.00 equiv) and formaldehyde (2.15 kg, 26.49 mol, 1.09 equiv, 37% aqueous). The resulting solution was stirred overnight at room temperature. The pH value of the solution was adjusted to pH 5 with acetic acid. The resulting solution was extracted with ethyl acetate (5×20 L) and the organic layers combined. The resulting mixture was washed with 5 L of brine. The mixture was dried over anhydrous sodium sulfate and concentrated in vacuo under vacuum to provide Int-1b, which was used without further purification.

Step C—Synthesis of Intermediate Compound Int-1c

Into a 50-L, 4-necked, round-bottom flask purged and maintained with an inert atmosphere of nitrogen, was placed a solution of Int-1b (5.6 kg, 21.85 mol, 1.00 equiv) in N,N-dimethylformamide (20 L), potassium carbonate (6.04 kg, 43.70 mol, 2.00 equiv) and benzyl bromide (3.93 kg, 22.98 mol, 1.05 equiv). The resulting solution was stirred overnight at room temperature. The reaction was then quenched by pouring into 100 L of water. The resulting solution was extracted with ethyl acetate (3×20 L) and the organic layers combined and concentrated in vacuo under vacuum to provide Int-1c, which was used without further purification.

Step D—Synthesis of Intermediate Compound 1

Into a 50-L, 4-necked, round-bottom flask, was charged a solution of Int-1c (5 kg, 14.44 mol, 1.00 equiv) in dichloromethane (25 L) followed by a solution of KBr (343.6 g, 2.89 mol, 0.20 equiv) in water (5 L), a solution of $KHCO_3$ (5.058 kg, 50.58 mol, 3.50 equiv) in water (20 L) and 2,2,6,6-tetramethylpiperidine 1-oxyl (TEMPO) (40.75 g, 0.02 equiv). This was followed by the dropwise addition of NaClO (30 kg, 32%) with stirring at 5° C. over 4 hr. The resulting solution was stirred overnight at room temperature. The resulting solution was extracted with dichloromethane (2×10 L) and the aqueous layers combined. The pH value of the combined aqueous portion was adjusted to pH 3 with aqueous hydrogen chloride (6 M). The resulting solution was extracted with ethyl acetate (3×20 L) and the organic layers combined and dried over anhydrous sodium sulfate and concentrated in vacuo under vacuum to provide compound 1. $^1$H NMR (400 MHz, $CDCl_3$) δ 7.50 (5H, m), 6.66 (1H, s), 5.65 (2H, s), 4.76 (1H, s), 4.64 (1H, m), 4.45 (1H, m), 3.82 (1H, m), 3.58 (1H, m), 1.69-1.90 (6H, m). Mass Calc'd for $C_{19}H_{20}O_7$: 360.1, found 361.1 (M+H)$^+$.

Example 2

Preparation of Compound 2

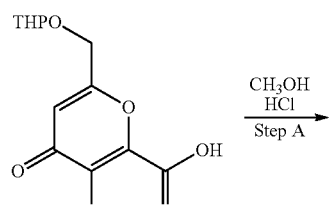

1

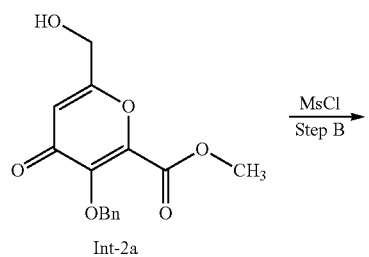

Int-2a

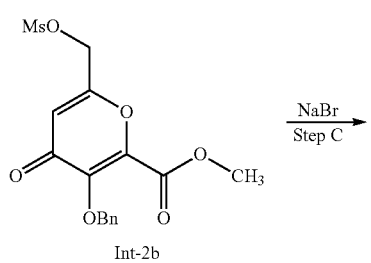

Int-2b

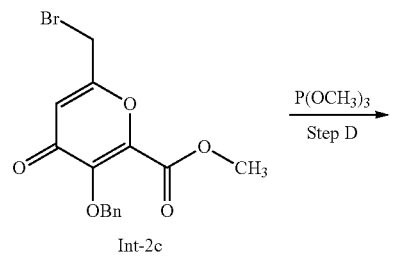

Int-2c

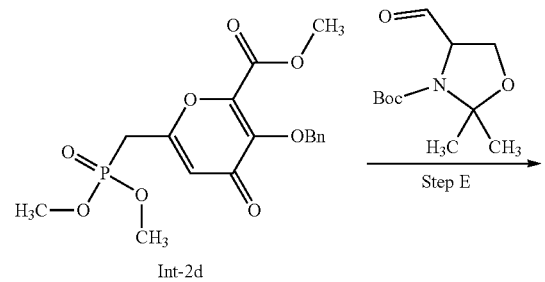

Int-2d

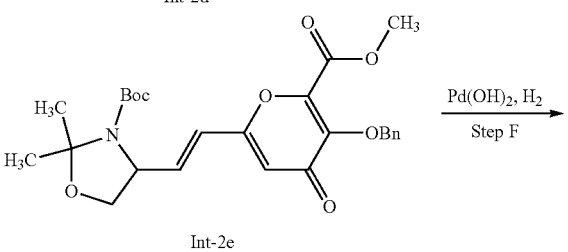

Int-2e

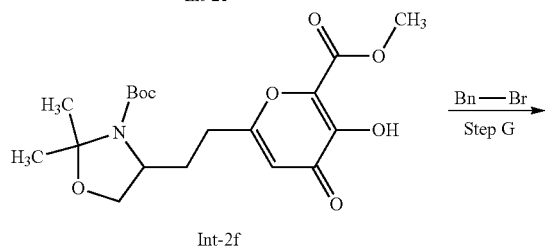

Int-2f

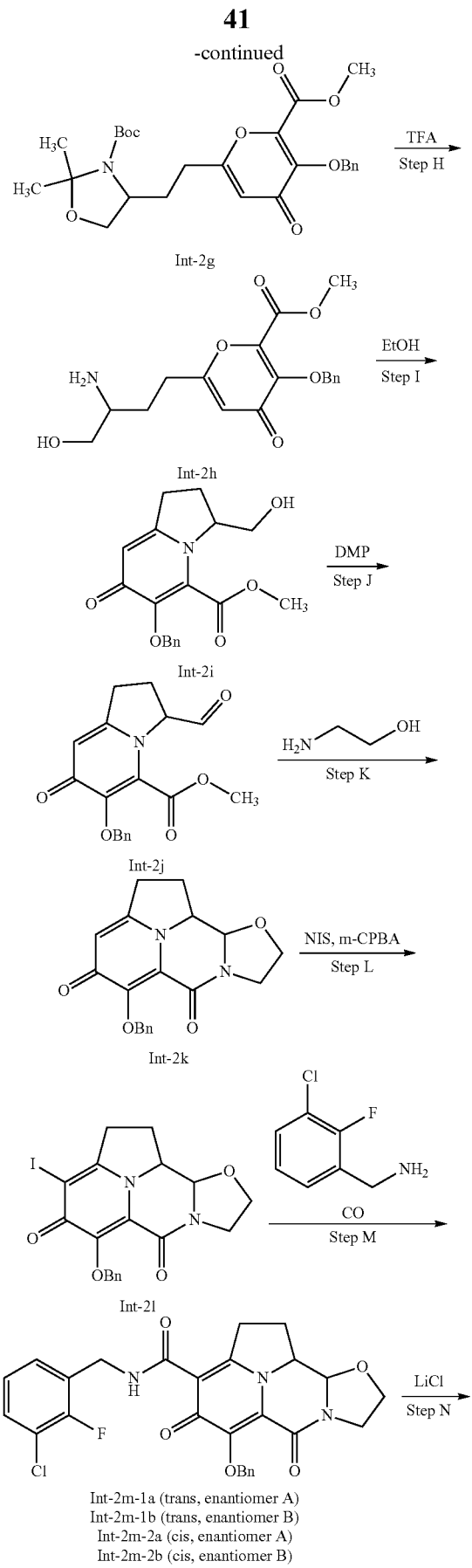
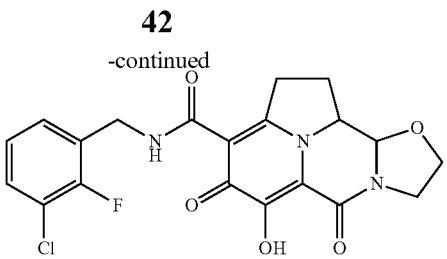

Step A—Synthesis of Intermediate Compound Int-2a

To a solution of compound 1 (15.03 g, 42.5 mmol) in methanol (150 mL) was added 4 N HCl in methanol (150 mL) at 0° C. The resulting mixture was stirred at room temperature for 6 hours. The reaction mixture was concentrated in vacuo, diluted with water (50 mL), extracted with ethyl acetate (3×200 mL), dried over anhydrous $Na_2SO_4$, and the organic phase concentrated in vacuo to provide Int-2a which was used without further purification. $^1$H NMR (400 MHz, $CDCl_3$) δ 7.45-7.43 (m, 1H), 7.38-7.34 (m, 4H), 6.61 (s, 1H), 5.28 (s, 2H), 4.53 (s, 2H), 3.86 (s, 3H). Mass Calc'd for $C_{15}H_{14}O_6$: 290.1, found 291.1 $(M+H)^+$.

Step B—Synthesis of Intermediate Compound Int-2b

To a stirred solution of methyl Int-2a (11.27 g, 38.7 mmol) in dichloromethane (200 mL) was added triethylamine (1.17 g, 116.1 mmol) and methanesulfonyl chloride (6.3 mL, 77.4 mmol) at 0° C. After stirring for 2 h at room temperature, the mixture was diluted with dichloromethane (200 mL) and washed with brine. The organic layer was dried over anhydrous $Na_2SO_4$, and concentrated in vacuo to provide Int-2b which was used without further purification. Mass Calc'd for $C_{16}H_{16}O_8S$: 368.1, found 369.1 $(M+H)^+$.

Step C—Synthesis of Intermediate Compound Int-2c

To a stirred solution of Int-2b (11.95 g, 32.47 mmol) in N,N-dimethylformamide (150 mL) was added NaBr (6.54 g, 64.11 mmol) at room temperature. After further stirring for 50 min, the reaction mixture was poured into water (100 mL) and extracted by ethyl acetate. The organic layer was dried over anhydrous $Na_2SO_4$ and concentrated in vacuo. The resulting residue was purified using column chromatography on silica gel (0 to 10% ethyl acetate in hexanes) to provide Int-2c. $^1$H NMR (400 MHz, $CDCl_3$) δ 7.45-7.46 (m, 2H), 7.34-7.36 (m, 3H), 6.53 (s, 1H), 5.30 (s, 2H), 4.19 (s, 2H), 3.80 (s, 3H). Mass Calc'd for $C_{15}H_{13}BrO_5$: 352.0, 354.0, found 353.0, 355.0 $(M+H)^+$.

Step D—Synthesis of Intermediate Compound Int-2d

To a solution of Int-2c (9.02 g, 25.6 mmol) in toluene (400 mL) was added trimethylphosphite (31.7 g, 256 mmol) and the mixture was heated to reflux for 86 hours. Excess trimethylphosphite was removed by distillation and the resulting oily residue was purified using column chromatography on silica gel (10% to 50% ethyl acetate in hexanes) to provide Int-2d. $^1$H NMR (400 MHz, $CDCl_3$) δ 7.45-7.46 (m, 2H), 7.32-7.35 (m, 3H), 6.43 (s, 1H), 5.29 (s, 2H), 3.80 (s, 3H), 3.78 (s, 6H), 3.10 (s, 2H). Mass Calc'd for $C_{17}H_{19}O_8P$: 382.1, found 383.1 $(M+H)^+$.

Step E—Synthesis of Intermediate Compound Int-2e

To solution of Int-2d (7.67 g, 19.9 mmol) in tetrahydrofuran (5 mL) was added a 2 M tetrahydrofuran solution of lithium diisopropylamine (12.93 mL, 25.87 mmol) under nitrogen and then the mixture was stirred at −78° C. for 30 min. Then tert-butyl 4-formyl-2,2-dimethyloxazolidine-3-carboxylate (5.9 g, 25.87 mmol) in tetrahydrofuran (5 mL) was added and the mixture was stirred at the same temperature for 2 hours. The mixture was quenched by the addition of aqueous 1 N HCl and concentrated in vacuo. The resulting residue was purified using column chromatography on silica gel (0% to 30% ethyl acetate in hexanes) to provide Int-2e. $^1$H NMR (400 MHz, CDCl$_3$) δ 7.45-7.47 (m, 2H), 7.30-7.37 (m, 3H), 6.59-6.66 (m, 1H), 6.31 (s, 1H), 6.15-6.27 (m, 2H), 5.31 (s, 2H), 4.44-4.57 (m, 3H), 4.08-4.15 (m, 1H), 3.87 (s, 1H), 1.42-1.66 (m, 15H). Mass Calc'd for $C_{26}H_{31}NO_8$: 485.2, found 486.2 (M+H)$^+$.

Step F—Synthesis of Intermediate Compound Int-2f

A mixture of Int-2e (5.49 g, 11.3 mmol) and 10% Pd(OH)$_2$ on carbon (1.2 g) in tetrahydrofuran (200 mL) was stirred at room temperature under H$_2$ (1 atm) for 10 min. The mixture was filtered and the filtrate was concentrated in vacuo to provide Int-2f, which was carried on to the subsequent step without further purification. Mass Calc'd for $C_{19}H_{27}NO_8$: 397.2, found 398.2 (M+H)$^+$.

Step G—Synthesis of Intermediate Compound Int-2g

To a solution of Int-2f (3.96 g, 9.97 mmol) in N,N-dimethylformamide (40 mL) was added potassium carbonate (4.13 g, 29.9 mmol) followed by benzyl bromide (3.40 g, 19.95 mmol) at 0° C. The mixture was stirred at room temperature for 16 hours. The mixture was quenched with water (20 mL) and extracted with ethyl acetate. The organic phase was washed with brine (20 mL), dried over anhydrous Na$_2$SO$_4$, filtered and the filtrate was concentrated in vacuo. The resulting residue was purified using column chromatography on silica gel (petroleum ether:ethyl acetate=3:1) to provide Int-2g. $^1$H NMR (400 MHz, CDCl$_3$) δ 7.46 (d, J=7.2 Hz, 2H), 7.31-7.38 (m, 3H), 6.31 (d, J=14.8 Hz, 1H), 5.29 (s, 2H), 3.97 (d, J=7.2 Hz, 2H), 3.85 (s, 3H), 3.68-3.77 (m, 1H), 2.58 (d, J=7.6 Hz, 2H), 1.97 (m, 2H), 1.42-1.52 (m, 15H). Mass Calc'd for $C_{26}H_{33}NO_8$: 487.2, found 488.2 (M+H)$^+$.

Step H—Synthesis of Intermediate Compound Int-2h

To a solution of Int-2g (4.36 g, 12.88 mmol) in dichloromethane (10 mL) was added dropwise trifluoroacetic acid (3 mL, 38.9 mmol) at 0° C. The mixture was stirred at room temperature for 3 hours. The mixture was concentrated in vacuo to provide crude Int-2h, which was used without further purification. Mass Calc'd for $C_{18}H_{21}NO_6$: 347.1, found 348.1 (M+H)$^+$.

Step I—Synthesis of Intermediate Compound Int-2i

A solution of Int-2h (3.14 g, 8.98 mmol) in ethanol (10 mL) was stirred at 90° C. for 3 hours. The mixture was concentrated in vacuo and purified using column chromatography on silica gel (dichloromethane:methanol=10:1) to provide Int-2i. $^1$H NMR (400 MHz, MeOD) δ 7.32-7.46 (m, 5H), 6.68 (s, 1H), 5.29 (d, J=10.4 Hz, 1H), 5.06 (d, J=10.4 Hz, 1H), 3.84 (s, 3H), 3.59-3.74 (m, 3H), 3.11-3.13 (m, 2H), 2.40-2.54 (m, 1H), 2.15-2.27 (m, 1H). Mass Calc'd for $C_{18}H_{19}NO_5$: 329.1, found 330.1 (M+H)$^+$.

Step J—Synthesis of Intermediate Compound Int-2j

To a solution of Int-2i (1.95 g, 5.9 mmol) in dichloromethane (20 mL) was added Dess-Martin reagent (7.53 g, 17.7 mmol) at 0° C. The mixture was stirred at 0° C. for 2 hours. The mixture was adjusted to pH 7 with saturated aqueous NaHCO$_3$ (50 mL) and extracted with dichloromethane (20 mL×3). The combined organic portions were washed with brine, dried over anhydrous Na$_2$SO$_4$, filtered and the filtrate was concentrated in vacuo. The resulting residue was purified using column chromatography on silica gel (dichloromethane:methanol=10:1) to provide Int-2j. $^1$H NMR (400 MHz, CDCl$_3$) δ 9.61 (brs, 1H), 7.32-7.38 (m, 5H), 6.51 (d, J=8.0 Hz, 1H), 5.19-5.36 (m, 2H), 3.75 (s, 3H), 3.35-3.36 (m, 1H), 2.97-3.03 (m, 2H), 2.32-2.51 (m, 2H). as Calc'd for $C_{18}H_{17}NO_5$: 327.1, found 328.2 (M+H)$^+$.

Step K—Synthesis of Intermediate Compound Int-2k

To a solution of Int-2j (1.56 g, 4.76 mmol) in tetrahydrofuran (4 mL) was added 2-aminoethanol (870.8 mg, 14.26 mmol) follow by acetic acid (855.3 mg, 14.26 mmol). The mixture was heated at 70° C. by microwave heating for 30 minutes. The mixture was concentrated in vacuo and the residue obtained was purified using column chromatography on silica gel (dichloromethane:methanol=10:1) to provide Int-2k. $^1$H NMR (400 MHz, CDCl$_3$) δ 7.56-7.65 (m, 2H), 7.26-7.34 (m, 3H), 6.41 (d, J=8 Hz, 1H), 5.16-5.38 (m, 2H), 4.84-5.03 (m, 1H), 4.61-4.62 (m, 1H), 4.12-4.34 (m, 1H), 3.75-3.79 (m, 3H), 2.95-3.04 (m, 2H), 2.02-2.28 (m, 2H). Mass Calc'd for $C_{19}H_{18}N_2O_4$: 338.1, found 339.2 (M+H)$^+$.

Step L—Synthesis of Intermediate Compound Int-2l

To a solution of Int-2k (933 mg, 2.75 mmol) in methanol (5 mL) was added m-CPBA (1.9 g, 11.0 mmol) followed by N-iodosuccinimide (2.5 g, 11.0 mmol). The mixture was stirred at 70° C. for 4 h, diluted with dichloromethane (20 mL) and washed with aq NaHSO$_3$ (5 mL), 5% aq NaOH (2 mL) and brine, dried over anhydrous Na$_2$SO$_4$, filtered and the filtrate was concentrated in vacuo. The resulting residue was purified using preparative TLC on silica gel (dichloromethane:methanol=10:1) to provide Int-2l. $^1$H NMR (400 MHz, CDCl$_3$) δ 7.67-7.68 (m, 2H), 7.26-7.37 (m, 3H), 5.12-5.26 (m, 2H), 4.96-5.01 (m, 1H), 4.44-4.54 (m, 1H), 4.15-4.20 (m, 1H), 3.75-3.79 (m, 3H), 3.14-3.34 (m, 3H), 2.30-2.55 (m, 1H). Mass Calc'd for $C_{19}H_{17}N_2O_4$: 464.0, found 465.0 (M+H)$^+$.

Step M—Synthesis of Intermediate Compounds Int-2m

A solution of Int-2l (700 mg, 1.50 mmol), 2,4-difluorobenzylamine (1.2 g, 7.5 mmol), N,N-diisopropylethylamine (0.97 g, 7.5 mmol), Pd(Ph$_3$P)$_4$ (86.6 mg, 0.075 mmol) in dimethylsulfoxide (3 mL) was stirred at 80° C. for 3 h under carbon monoxide (1 atm). The mixture was cooled to rt, diluted with ethyl acetate (30 mL) and filtered. The filtrate was washed with 0.5 N HCl (4 mL), saturated aqueous NaHCO$_3$ (5 mL) and brine (10 mL), dried over anhydrous Na$_2$SO$_4$, filtered and the filtrate was concentrated in vacuo. The resulting residue was purified using preparative TLC on silica gel (dichloromethane:methanol=20:1) to provide Int-2m-1 (trans) and Int-2m-2 (cis).

Int-2m-1: $^1$H NMR (400 MHz, CDCl$_3$) δ 10.81 (s, 1H), 7.55-7.57 (m, 2H), 7.23-7.31 (m, 5H) 6.96-6.98 (m, 1H), 5.30-5.32 (m, 1H), 5.10-5.12 (m, 1H), 4.72-4.73 (m, 1H), 4.59-4.63 (m, 2H), 4.44-4.48 (m, 2H), 3.80-3.81 (m, 1H), 3.72-3.74 (m, 2H), 3.33-3.35 (m, 2H), 2.33-2.35 (m, 2H). Mass Calc'd for $C_{27}H_{23}ClFN_3O_5$: 523.1, found 524.1 (M+H)$^+$.

Int-2m-2: $^1$H NMR (400 MHz, CDCl$_3$) δ 10.87 (s, 1H), 7.60-7.62 (m, 2H), 7.29-7.37 (m, 5H) 7.03-7.05 (m, 1H), 5.34-5.37 (m, 1H), 5.19-5.21 (m, 1H), 4.80-4.82 (m, 1H), 4.65-4.69 (m, 2H), 4.30-4.31 (m, 1H), 4.03-4.11 (m, 3H), 3.63-3.65 (m, 1H), 3.41-3.42 (m, 2H), 2.61-2.64 (m, 1H), 2.02-2.08 (m, 1H). Mass Calc'd for $C_{27}H_{23}ClFN_3O_5$: 523.1, found 524.1 (M+H)$^+$.

Resolution of Int-2m-1 (trans) to the enantiomers was accomplished with SFC (Chiralpak AS, 250×50 mm, 10 μm, 45% methanol in SC—CO$_2$, 200 ml/min, 220 nm) to provide Int-2m-1a (trans, enantiomer A) and Int-2m-1b (trans, enantiomer B).

Resolution of Int-2m-2 (cis) to the enantiomers was accomplished with SFC (OD, 250×50 mm, 10 μm, 45% methanol (0.1% NH$_3$.H$_2$O) in SC—CO$_2$, 200 mL/min) to provide Int-2m-2a (cis, enantiomer A) and Int-2m-2b (cis, enantiomer B).

Step N—Synthesis of Compound 2

To a solution of Int-2m-1a (trans, enantiomer A) (150 mg, 0.29 mmol) in N,N-dimethylformamide (4 mL) was added lithium chloride (121 mg, 2.9 mmol). The resulting solution was heated at 110° C. for 4 h, cooled to room temperature and purified directly by preparative RP-HPLC to provide compound 2. $^1$H NMR (400 MHz, CDCl$_3$) δ 10.72 (s, 1H), 7.28-7.29 (m, 2H), 7.00-7.03 (m, 1H) 4.89-4.92 (m, 1H), 4.66-4.67 (m, 2H), 4.40-4.41 (m, 1H), 4.13-4.15 (m, 3H), 3.76-3.77 (m, 1H), 3.65-3.67 (m, 1H), 3.42-3.45 (m, 1H), 2.65-2.70 (m, 1H), 2.08-2.11 (m, 1H). Mass Calc'd for C$_{20}$H$_{17}$ClFN$_3$O$_5$: 433.1, found 434.1 (M+H)$^+$ The following compounds of the present invention were made using the methodology described in Example 2, and substituting the appropriate reactants and/or reagents.

| Compound | Structure | Stereochemistry | Exact Mass [M + H]$^+$ |
|---|---|---|---|
| 3 | 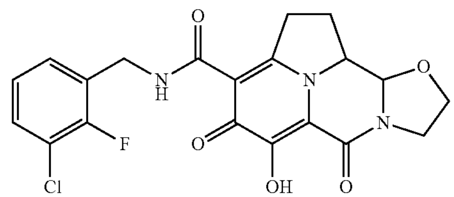 [SMILES: O=C(NCc1cccc(Cl)c1F)c1c2n3c(c(O)c1=O)C(=O)N1CCOC1C3CC2] | trans, enantiomer B | Calc'd 434.1, found 434.1 |
| 4 | 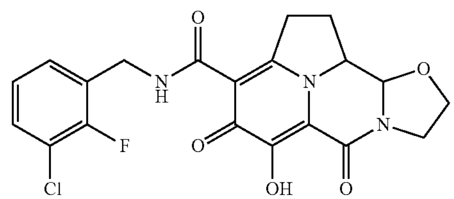 [SMILES: O=C(NCc1cccc(Cl)c1F)c1c2n3c(c(O)c1=O)C(=O)N1CCOC1C3CC2] | cis, enantiomer A | Calc'd 434.1, found 434.1 |
| 5 | 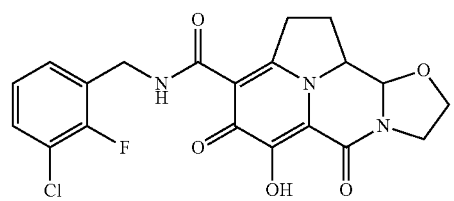 [SMILES: O=C(NCc1cccc(Cl)c1F)c1c2n3c(c(O)c1=O)C(=O)N1CCOC1C3CC2] | cis, enantiomer B | Calc'd 434.1, found 434.0 |

| Compound | $^1$H NMR |
|---|---|
| 3 | $^1$H NMR (400 MHz, CDCl$_3$) δ 10.72 (s, 1H), 7.28-7.29 (m, 2H), 7.00-7.03 (m, 1H) 4.89-4.92 (m, 1H), 4.66-4.67 (m, 2H), 4.40-4.41 (m, 1H), 4.13-4.15 (m, 3H), 3.76-3.77 (m, 1H), 3.65-3.67 (m, 1H), 3.42-3.45 (m, 1H), 2.65-2.70 (m, 1H), 2.08-2.11 (m, 1H) |
| 4 | $^1$H NMR (400 MHz, CDCl$_3$) δ 10.77 (s, 1H), 7.27-7.29 (m, 2H), 6.99-7.03 (m, 1H), 4.91-4.92 (m, 1H), 4.66-4.68 (m, 2H), 4.50-4.56 (m, 2H), 4.10-4.12 (m, 1H), 3.92-3.96 (m, 2H), 3.42-3.48 (m, 2H), 2.39-2.49 (m, 2H) |
| 5 | $^1$H NMR (400 MHz, CDCl$_3$) δ 10.77 (s, 1H), 7.27-7.29 (m, 2H), 6.99-7.03 (m, 1H), 4.91-4.92 (m, 1H), 4.66-4.68 (m, 2H), 4.50-4.56 (m, 2H), 4.10-4.12 (m, 1H), 3.92-3.96 (m, 2H), 3.42-3.48 (m, 2H), 2.39-2.49 (m, 2H) |

| Compound | Structure | Stereochemistry | Exact Mass [M + H]$^+$ |
|---|---|---|---|
| 6 | 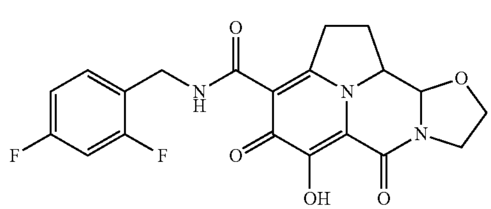 [SMILES: O=C(NCc1ccc(F)cc1F)c1c2n3c(c(O)c1=O)C(=O)N1CCOC1C3CC2] | trans, enantiomer A | Calc'd 418.1, found 418.2 |

-continued

| Compound | Structure | Stereochemistry | Exact Mass [M + H]+ |
|---|---|---|---|
| 7 | 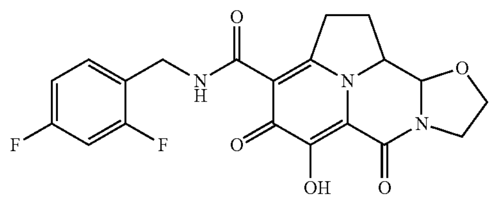 [SMILES: O=C(NCc1ccc(F)cc1F)c1c2n3c(c(O)c1=O)C(=O)N1CCOC1C3CC2] | trans, enantiomer B | Calc'd 418.1, found 418.2 |
| 8 | 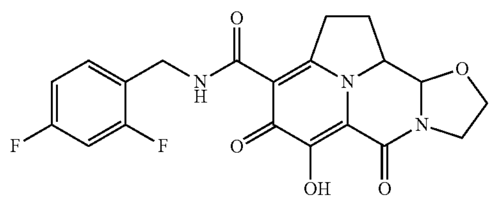 [SMILES: O=C(NCc1ccc(F)cc1F)c1c2n3c(c(O)c1=O)C(=O)N1CCOC1C3CC2] | cis, enantiomer A | Calc'd 418.1, found 418.2 |
| 9 | 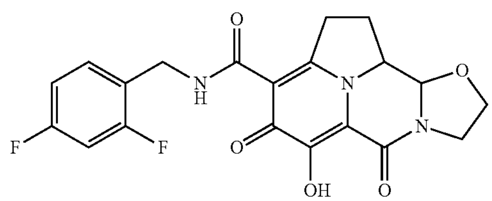 [SMILES: O=C(NCc1ccc(F)cc1F)c1c2n3c(c(O)c1=O)C(=O)N1CCOC1C3CC2] | cis, enantiomer B | Calc'd 418.1, found 418.2 |
| 10 | 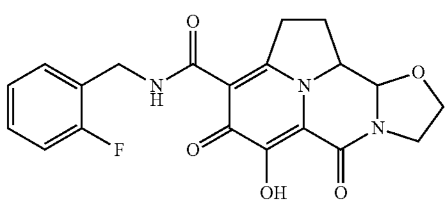 [SMILES: O=C(NCc1ccccc1F)c1c2n3c(c(O)c1=O)C(=O)N1CCOC1C3CC2] | cis, enantiomer A | Calc'd 400.1, found 400.1 |
| 11 | 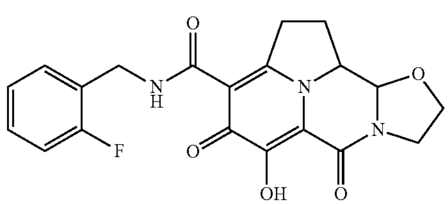 [SMILES: O=C(NCc1ccccc1F)c1c2n3c(c(O)c1=O)C(=O)N1CCOC1C3CC2] | cis, enantiomer B | Calc'd 400.1, found 400.1 |
| 12 | 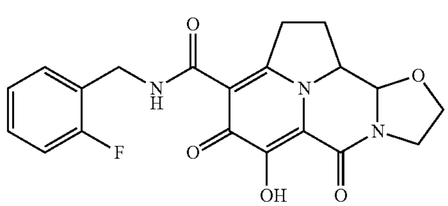 [SMILES: O=C(NCc1ccccc1F)c1c2n3c(c(O)c1=O)C(=O)N1CCOC1C3CC2] | trans, enantiomer A | Calc'd 400.1, found 400.1 |
| 13 | 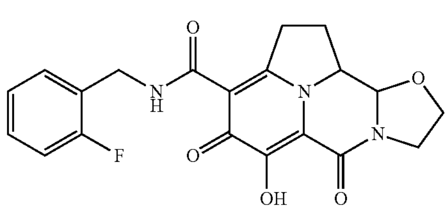 [SMILES: O=C(NCc1ccccc1F)c1c2n3c(c(O)c1=O)C(=O)N1CCOC1C3CC2] | trans, enantiomer B | Calc'd 400.1, found 400.1 |

-continued

| Compound | Structure | Stereochemistry | Exact Mass [M + H]+ |
|---|---|---|---|
| 14 | 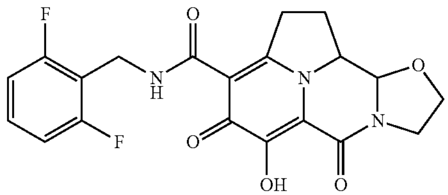 [SMILES: O=C(NCc1c(F)cccc1F)c1c2n3c(c(O)c1=O)C(=O)N1CCOC1C3CC2] | cis, enantiomer A | Calc'd 418.1, found 418.0 |
| 15 | 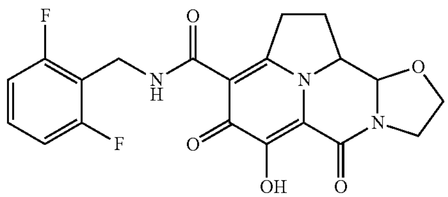 [SMILES: O=C(NCc1c(F)cccc1F)c1c2n3c(c(O)c1=O)C(=O)N1CCOC1C3CC2] | cis, enantiomer B | Calc'd 418.1, found 418.0 |
| 16 | 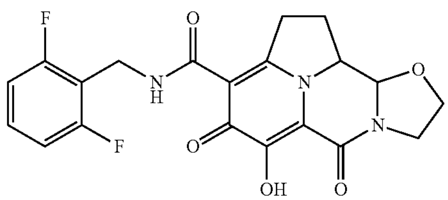 [SMILES: O=C(NCc1c(F)cccc1F)c1c2n3c(c(O)c1=O)C(=O)N1CCOC1C3CC2] | trans, enantiomer A | Calc'd 418.1, found 418.0 |
| 17 | 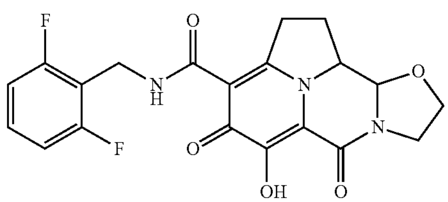 | trans, enantiomer B | Calc'd 418.1, found 418.0 |
| 18 | 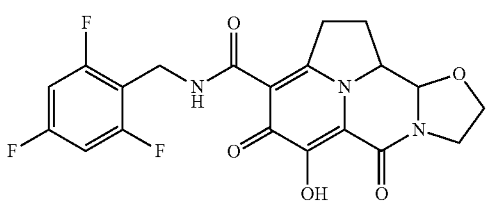 [SMILES: O=C(NCc1c(F)cc(F)cc1F)c1c2n3c(c(O)c1=O)C(=O)N1CCOC1C3CC2] | trans, enantiomer A | Calc'd 436.1, found 436.2 |
| 19 | 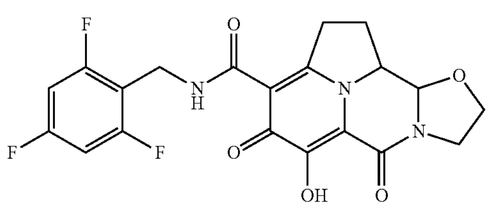 [SMILES: O=C(NCc1c(F)cc(F)cc1F)c1c2n3c(c(O)c1=O)C(=O)N1CCOC1C3CC2] | trans, enantiomer B | Calc'd 436.1, found 436.2 |
| 20 | 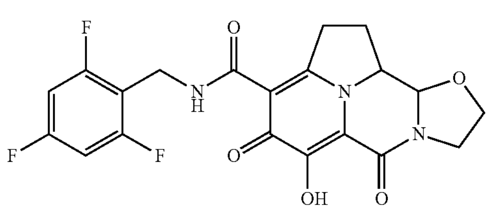 [SMILES: O=C(NCc1c(F)cc(F)cc1F)c1c2n3c(c(O)c1=O)C(=O)N1CCOC1C3CC2] | cis, enantiomer B | Calc'd 436.1, found 436.2 |

-continued

| Compound | Structure | Stereochemistry | Exact Mass [M + H]+ |
|---|---|---|---|
| 21 | 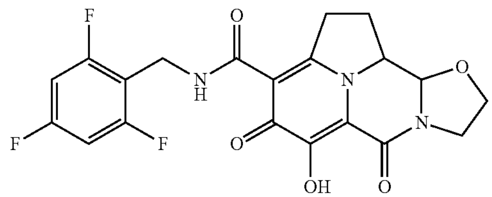 [SMILES: O=C(NCc1c(F)cc(F)cc1F)c1c2n3c(c(O)c1=O)C(=O)N1CCOC1C3CC2] | cis, enantiomer A | Calc'd 436.1, found 436.2 |
| 22 | 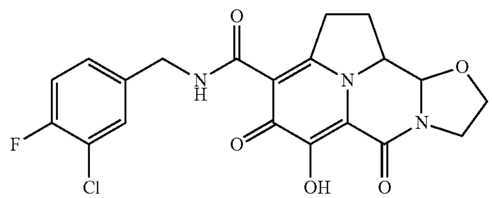 [SMILES: O=C(NCc1ccc(F)c(Cl)c1)c1c2n3c(c(O)c1=O)C(=O)N1CCOC1C3CC2] | cis, enantiomer A | Calc'd 434.1, found 434.1 |
| 23 | 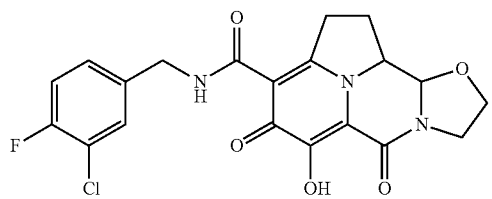 [SMILES: O=C(NCc1ccc(F)c(Cl)c1)c1c2n3c(c(O)c1=O)C(=O)N1CCOC1C3CC2] | cis, enantiomer B | Calc'd 434.1, found 434.1 |
| 24 | 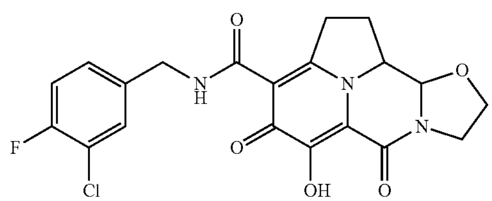 [SMILES: O=C(NCc1ccc(F)c(Cl)c1)c1c2n3c(c(O)c1=O)C(=O)N1CCOC1C3CC2] | trans, enantiomer A | Calc'd 434.1, found 434.1 |
| 25 | 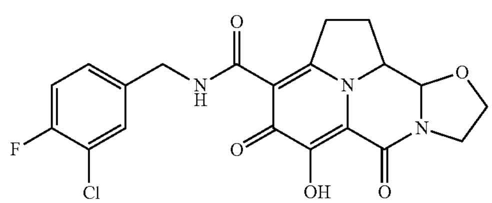 [SMILES: O=C(NCc1ccc(F)c(Cl)c1)c1c2n3c(c(O)c1=O)C(=O)N1CCOC1C3CC2] | trans, enantiomer B | Calc'd 434.1, found 434.1 |

| Compound | ¹H NMR |
|---|---|
| 6 | ¹H NMR (400 MHz, CDCl₃) δ 10.69 (s, 1 H), 7.25-7.36 (m, 1 H), 6.76-6.81 (m, 2 H), 4.90 (d, J = 8.8 Hz, 1 H), 4.59-4.61 (m, 2 H), 4.40-4.48 (m, 1 H), 4.13-4.17 (m, 3 H), 3.80-3.95 (m, 2 H), 3.39-3.42 (m, 1 H), 2.65-2.70 (m, 1 H), 2.05-2.11 (m, 1 H). |
| 7 | ¹H NMR (400 MHz, CDCl₃) δ 10.69 (s, 1 H), 7.32-7.38 (m, 1 H), 6.77-6.82 (m, 2 H), 4.90 (d, J = 8.8 Hz, 1 H), 4.59-4.61 (m, 2 H), 4.40-4.42 (m, 1 H), 4.13-4.20 (m, 3 H), 3.76-3.92 (m, 2 H), 3.41-3.43 (m, 1 H), 2.65-2.70 (m, 1 H), 2.05-2.11 (m, 1 H). |
| 8 | ¹H NMR (400 MHz, MeOD-d₄) δ 7.39-7.42 (m, 1 H), 6.90-6.97 (m, 2 H), 5.04 (d, J = 3.2 Hz, 1 H), 4.54-4.62 (m, 2 H), 4.40-4.42 (m, 1 H), 3.92-3.98 (m, 3 H), 3.52-3.57 (m, 1 H), 3.36-3.43 (m, 2 H), 2.49-2.50 (m, 1 H), 2.33-2.39 (m, 1 H). |
| 9 | ¹H NMR (400 MHz, MeOD-d₄) δ 7.41-7.42 (m, 1 H), 6.92-6.97 (m, 2 H), 5.04 (d, J = 3.2 Hz, 1 H), 4.40-4.77 (m, 4 H), 3.92-3.98 (m, 3 H), 3.34-3.57 (m, 2 H), 2.49-2.51 (m, 1 H), 2.33-2.38 (m, 1 H). |
| 10 | ¹H NMR (400 MHz, CDCl₃) δ 10.77 (s, 1H), 7.36-7.38 (m, 1H), 7.22-7.24 (m, 1H), 7.03-7.10 (m, 2H), 4.90-4.91 (d, J = 2.4 Hz, 1H), 4.60-4.66 (m, 3H), 4.46-4.49 (m, 1H), 4.08-4.15 (m, 1H), 3.90-3.96 (m, 2H), 3.47-3.50 (m, 2H), 2.41-2.46 (m, 2H). |
| 11 | ¹H NMR (400 MHz, CDCl₃) δ 10.77 (s, 1H), 7.36-7.38 (m, 1H), 7.22-7.24 (m, 1H), 7.03-7.10 (m, 2H), 4.90-4.91 (d, J = 2.4 Hz, 1H), 4.61-4.66 (m, 3H), 4.46-4.48 (m, 1H), 4.04-4.13 (m, 1H), 3.90-3.95 (m, 2H), 3.41-3.50 (m, 2H), 2.38-2.46 (m, 2H). |
| 12 | ¹H NMR (400 MHz, CDCl₃) δ 10.72 (s, 1H), 7.39 (s, 1H), 7.22-7.24 (m, 1H), 7.02-7.10 (m, 2H), 4.90-4.92 (d, J = 7.6 Hz, 1H), 4.67 (s, 2H), 4.41 (s, 1H), 4.16-4.17 (m, 3H), 3.89-3.91 (d, J = 8.4 Hz, 1H), 3.77 (s, 1H), 3.47-3.48 (m, 1H), 2.68 (s, 1H), 2.09-2.10 (m, 1H). |

53
-continued

| Compound | ¹H NMR |
|---|---|
| 13 | ¹H NMR (400 MHz, CDCl$_3$) δ 10.70 (s, 1H), 7.39 (s, 1H), 7.22-7.24 (m, 1H), 7.04-7.11 (m, 2H), 4.90-4.92 (d, J = 8 Hz, 1H), 4.67 (s, 2H), 4.41 (s, 1H), 4.14-4.18 (m, 3H), 3.90-3.92 (d, J = 9.2 Hz, 1H), 3.77 (s, 1H), 3.45-3.46 (m, 1H), 2.67 (s, 1H), 2.09-2.10 (m, 1H). |
| 14 | ¹H NMR (400 MHz, CDCl$_3$) δ 10.68 (s, 1 H), 7.18-7.23 (m, 1 H), 6.85-6.89 (m, 2 H), 4.91 (d, J = 3.2 Hz, 1 H), 4.68 (d, J = 4.4 Hz, 2 H), 4.48-4.57 (m, 2 H), 3.89-4.18 (m, 3 H), 3.39-3.49 (m, 2 H), 2.37-2.48 (m, 2 H). |
| 15 | ¹H NMR (400 MHz, CDCl$_3$) δ 10.67 (s, 1 H), 7.17-7.23 (m, 1 H), 6.85-6.89 (m, 2 H), 4.91 (d, J = 3.2 Hz, 1 H), 4.68 (d, J = 4.4 Hz, 2 H), 4.48-4.56 (m, 2 H), 3.89-4.18 (m, 3 H), 3.41-3.49 (m, 2 H), 2.37-2.47 (m, 2 H). |
| 16 | ¹H NMR (400 MHz, CDCl$_3$) δ 10.63 (s, 1 H), 7.27-7.32 (m, 1 H), 6.85-6.89 (m, 2 H), 4.87 (d, J = 8.8 Hz, 1 H), 4.69 (d, J = 4.4 Hz, 2 H), 4.14-4.26 (m, 3 H), 3.75-3.93 (m, 2 H), 3.42-3.49 (m, 2 H), 2.63-2.66 (m, 1 H), 2.03-2.09 (m, 1 H). |
| 17 | ¹H NMR (400 MHz, CDCl$_3$) δ 10.63 (s, 1 H), 7.27-7.32 (m, 1 H), 6.85-6.89 (m, 2 H), 4.87 (d, J = 8.8 Hz, 1 H), 4.69 (d, J = 4.4 Hz, 2 H), 4.14-4.26 (m, 3 H), 3.75-3.92 (m, 2 H), 3.40-3.49 (m, 2 H), 2.61-2.65 (m, 1 H), 2.03-2.06 (m, 1 H). |
| 18 | ¹H NMR (400 MHz, CDCl$_3$) δ 10.69 (s, 1H), 6.65-6.69 (m, 2H), 4.92 (m, 1H), 4.89 (m, 2H), 4.65-4.66(m, 1H), 4.14-4.20 (m, 3H), 3.93(m, 1H), 3.45-3.90 (m, 2H), 2.06-2.12 (m, 1H), 2.43-2.51 (m, 1H). |
| 19 | ¹H NMR (400 MHz, CDCl$_3$) δ 10.71 (s, 1H), 6.65-6.69 (t, 2H), 4.90-4.92 (m, 2H), 4.63-4.65 (m, 2H), 4.42-4.43 (m, 2H), 4.15-4.20 (m, 3H), 3.46-3.89 (m, 1H), 3.91(m, 1H), 3.78-3.80 (m, 1H), 2.07-2.12 (m, 1H). |
| 20 | ¹H NMR (400 MHz, CDCl$_3$) δ 10.74 (s, 1H), 6.65-6.69 (m, 2H), 4.93 (s, 1H), 4.64-4.65 (m, 2H), 4.64 (m, 2H), 4.50(m, 1H), 3.91-3.97 (m, 2H), 3.42-3.52 (m, 2H), 2.43-2.51 (m, 2H). |
| 21 | ¹H NMR (400 MHz, CDCl$_3$) δ 10.72 (s, 1H), 6.64-6.68 (m, 2H), 4.92 (s, 1H), 4.54-4.65 (m, 2H), 4.64 (m, 2H), 4.50 (m, 1H), 3.91-3.97 (m, 2H), 3.48-3.51 (m, 2H), 2.43-2.51 (m, 2H). |
| 22 | ¹H NMR (400 MHz, CDCl$_3$) δ 10.85 (s, 1H), 7.36-7.38 (m, 1 H),7.19-7.20 (m, 1H), 7.04-7.09 (m, 1H), 4.90-4.92 (m, 1 H), 4.49-4.54 (m, 4H), 4.11-4.14 (m, 1H), 3.91-3.97 (m, 2 H), 3.46-3.51 (m, 2 H), 2.43-2.52 (m, 2 H). |
| 23 | ¹H NMR (400 MHz, CDCl$_3$) δ 10.85 (s, 1H), 7.36-7.38 (m, 1 H), 7.19-7.20 (m, 1H), 7.04-7.09 (m, 1H), 4.90-4.92 (m, 1 H), 4.49-4.54 (m, 4H), 4.11-4.14 (m, 1H), 3.91-3.97 (m, 2 H), 3.46-3.51 (m, 2 H), 2.43-2.52 (m, 2 H). |
| 24 | ¹H NMR (400 MHz, CDCl$_3$) δ 10.77 (s, 1H), 7.36-7.38 (m, 1 H),7.19-7.20 (m, 1H), 7.04-7.09 (m, 1H), 4.90-4.92 (m, 1 H), 4.53-4.54 (m, 2H), 4.41-4.42 (m, 1 H), 4.14-4.19 (m, 3 H), 3.89-3.91 (m, 1H), 3.77-3.78 (m, 1 H), 3.40-3.43 (m, 1H), 2.66-2.69 (m, 1 H), 2.06-2.12 (m, 1 H). |
| 25 | ¹H NMR (400 MHz, CDCl$_3$) δ 10.77 (s, 1H), 7.36-7.38 (m, 1 H), 7.19-7.20 (m, 1H), 7.04-7.09 (m, 1H), 4.90-4.92 (m, 1 H), 4.53-4.54 (m, 2H), 4.41-4.42 (m, 1 H), 4.14-4.19 (m, 3 H), 3.89-3.91 (m, 1H), 3.77-3.78 (m, 1 H), 3.40-3.43 (m, 1H), 2.66-2.69 (m, 1 H), 2.06-2.12 (m, 1 H). |

Example 3

Preparation of Compound 26

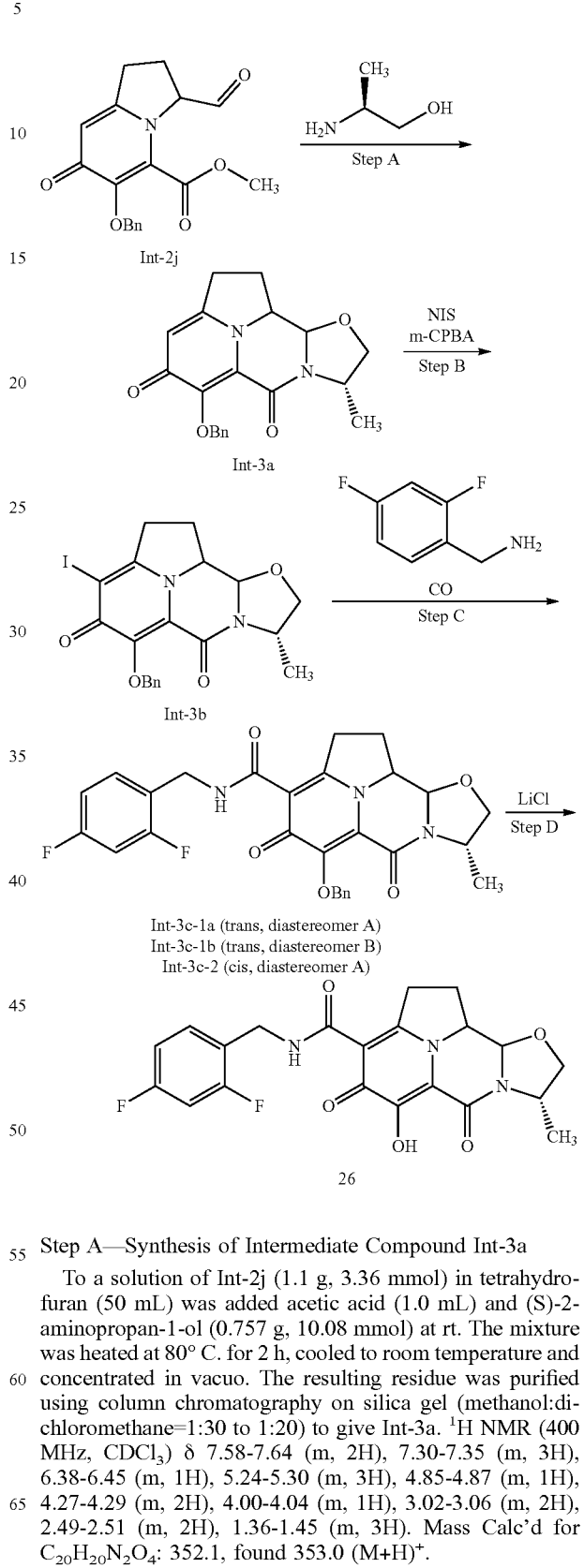

Step A—Synthesis of Intermediate Compound Int-3a

To a solution of Int-2j (1.1 g, 3.36 mmol) in tetrahydrofuran (50 mL) was added acetic acid (1.0 mL) and (S)-2-aminopropan-1-ol (0.757 g, 10.08 mmol) at rt. The mixture was heated at 80° C. for 2 h, cooled to room temperature and concentrated in vacuo. The resulting residue was purified using column chromatography on silica gel (methanol:dichloromethane=1:30 to 1:20) to give Int-3a. ¹H NMR (400 MHz, CDCl$_3$) δ 7.58-7.64 (m, 2H), 7.30-7.35 (m, 3H), 6.38-6.45 (m, 1H), 5.24-5.30 (m, 3H), 4.85-4.87 (m, 1H), 4.27-4.29 (m, 2H), 4.00-4.04 (m, 1H), 3.02-3.06 (m, 2H), 2.49-2.51 (m, 2H), 1.36-1.45 (m, 3H). Mass Calc'd for $C_{20}H_{20}N_2O_4$: 352.1, found 353.0 (M+H)$^+$.

Step B—Synthesis of Intermediate Compound Int-3b

To a solution of Int-3a (650 mg, 1.844 mmol) in methanol (10 mL) was added m-CPBA (796 mg, 3.69 mmol) and N-iodosuccinimide (1.66 mg, 7.38 mmol). The mixture was refluxed at 80° C. for 3 h, cooled to room temperature and quenched with 10 mL saturated aqueous of $Na_2SO_3$ and adjusted to pH 7.0 with 10% aqueous NaOH. The mixture was extracted with dichloromethane (30 mL×3) and the combined organic portions were dried over anhydrous $Na_2SO_4$, filtered, the filtrate was concentrated in vacuo. The resulting residue was purified using column chromatography on silica gel (methanol:dichloromethane=1:30 to 1:20) to provide Int-3b. $^1$H NMR (400 MHz, CDCl$_3$) δ 7.62-7.69 (m, 2H), 7.26-7.33 (m, 3H), 4.96-5.30 (m, 3H), 4.59 (s, 1H), 4.21-4.33 (m, 2H), 3.86 (s, 1H), 3.04-3.17 (m, 2H), 2.08-2.18 (m, 2H), 1.32-1.38 (m, 3H). Mass Calc'd for $C_{20}H_{19}IN_2O_4$: 478.0, found 479.1 (M+H)$^+$.

Step C—Synthesis of Intermediate Compound Int-3c

To a solution of Int-3b (700 mg, 1.308 mmol) in dimethylsulfoxide (20 mL) was added Pd(Ph$_3$P)$_4$ (483 mg, 0.418 mmol), N,N-diisopropylethylamine (2.92 mL, 16.73 mmol) and 2,4-difluorobenzylamine (1197 mg, 8.36 mmol). The mixture was heated at 80° C. for 2 h under carbon monoxide (1 atm), cooled to rt, diluted with ethyl acetate (60 mL) and filtered. The filtrate was washed with 0.2 M aqueous of HCl (2×10 mL), saturated aqueous of NaHCO$_3$ (10 mL) and brine (10 mL), dried over anhydrous Na$_2$SO$_4$, filtered and the filtrate was concentrated in vacuo. The resulting residue was purified using column chromatography on silica gel (petroleum ether:ethyl acetate=3:1 to 1:1) followed by preparative RP-HPLC to provide Int-3c-1 (trans) and Int-3c-2 (cis).

Int-3c-1: $^1$H NMR (400 MHz, CDCl$_3$) δ 10.80 (s, 1H), 7.56-7.61 (m, 2H), 7.24-7.35 (m, 4H), 6.78-6.80 (m, 2H), 5.14-5.27 (m, 2H), 4.83-4.85 (m, 1H), 4.57-4.58 (m, 2H), 4.38-4.41 (m, 1H), 4.25-4.32 (m, 1H), 4.04-4.11 (m, 2H), 3.89 (s, 1H), 3.35-3.44 (m, 1H), 2.50-2.53 (m, 1H), 1.96-2.01 (m, 1H), 1.34-1.41 (m, 3H). Mass Calc'd for $C_{28}H_{25}F_2N_3O_5$: 521.2, found 522.2 (M+H)$^+$.

Int-3c-2: $^1$H NMR (400 MHz, CDCl$_3$) δ 10.79 (s, 1H), 7.56-7.57 (m, 2H), 7.24-7.31 (m, 4H), 6.71-6.77 (m, 2H), 5.29-5.32 (d, J=10.0 Hz, 1H), 5.07-5.10 (d, J=10.0 Hz, 1H), 4.80-4.81 (d, J=3.6 Hz, 1H), 4.67 (m, 1H), 4.54-4.55 (m, 2H), 4.41 (m, 1H), 4.00-4.02 (m, 1H), 3.98 (m, 1H), 3.32-3.36 (m, 2H), 2.31-2.39 (m, 2H), 1.33-1.34 (m, 3H). Mass Calc'd for $C_{28}H_{25}F_2N_3O_5$: 521.2, found 522.2 (M+H)$^+$.

Resolution of Int-3c-1 (trans) to the diastereomers was accomplished with SFC (Chiral Pak AS, 250×30 mm, 5 μm, 40% IPA (0.1% NH$_3$H$_2$O) in SC—CO$_2$, 40 mL/min, 220 nm, 38° C.) to provide Int-3c-1a (trans, diastereomer A) and Int-3c-1b (trans, diastereomer B)

Int-3c-1a: $^1$H NMR (400 MHz, CDCl$_3$) δ 10.80 (s, 1H), 7.54-7.56 (m, 2H), 7.23-7.31 (m, 4H), 6.71-6.78 (m, 2H), 5.26-5.28 (d, J=10.4 Hz, 1H), 5.13-5.16 (d, J=10.0 Hz, 1H), 4.63-4.66 (d, J=8.8 Hz, 1H), 4.52-4.57 (m, 2H), 4.26-4.30 (m, 1H), 4.09-4.12 (m, 2H), 3.94-3.97 (m, 2H), 3.36-3.39 (m, 1H), 2.55-2.58 (m, 1H), 1.94-1.99 (m, 1H), 1.40-1.42 (m, 3H). Mass Calc'd for $C_{28}H_{25}F_2N_3O_5$: 521.2, found 522.2 (M+H)$^+$.

Int-3c-1b: $^1$H NMR (400 MHz, CDCl$_3$) δ 10.79 (s, 1H), 7.52-7.53 (m, 2H), 7.23-7.31 (m, 4H), 6.72-6.76 (m, 2H), 5.31-5.34 (d, J=10.0 Hz, 1H), 5.16-5.19 (d, J=10.8 Hz, 1H), 4.80-4.82 (d, J=8.8 Hz, 1H), 4.55 (m, 2H), 4.29-4.37 (m, 2H), 4.04-4.07 (m, 2H), 3.58-3.62 (m, 1H), 3.35 (m, 1H), 2.51-2.59 (m, 1H), 1.95-2.00 (m, 1H), 1.33-1.34 (m, 3H). Mass Calc'd for $C_{28}H_{25}F_2N_3O_5$: 521.2, found 522.2 (M+H)$^+$.

Step D—Synthesis of Compound 26

To a solution of Int-3c-1a (trans, diastereomer A) (68 mg, 0.130 mmol) in N,N-dimethylformamide (5 mL) was added lithium chloride (55.3 mg, 1.304 mmol). The mixture was heated to 80° C. for 5 h, cooled to room temperature and filtered. The filtrate was purified directly by preparative RP-HPLC to provide compound 26. $^1$H NMR (400 MHz, CDCl$_3$) δ 10.74 (s, 1H), 7.33-7.39 (m, 1H), 6.77-6.83 (m, 2H), 4.83-4.85 (d, J=8.4 Hz, 1H), 4.60-4.61 (m, 2H), 4.38 (s, 1H), 4.14-4.22 (m, 3H), 4.05-4.07 (m, 1H), 3.39-3.44 (m, 1H), 2.64-2.69 (m, 1H), 2.03-2.12 (m, 1H), 1.47-1.49 (m, 3H). Mass Calc'd for $C_{21}H_{19}F_2N_3O_5$: 431.1, found 432.1 (M+H)$^+$.

The following compounds of the present invention were made using the methodology described in Example 3, and substituting the appropriate reactants and/or reagents.

| Compound | Structure | Stereochemistry | Exact Mass [M + H]$^+$ |
|---|---|---|---|
| 27 | 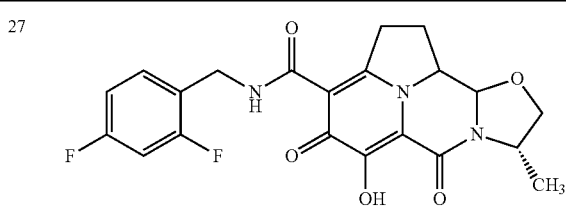 | trans, diastereomer B | Calc'd 432.1, found 432.1 |
| 28 | 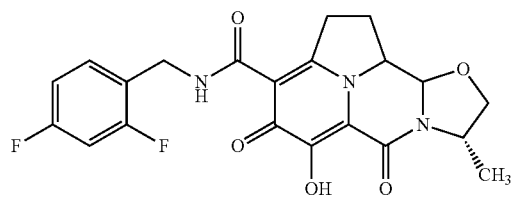 [SMILES: C[C@H]1COC2C3CCc4c(C(=O)NCc5ccc(F)cc5F)c(=O)c(O)c(n43)C(=O)N21] | cis, diastereomer A | Calc'd 432.1, found 432.1 |

| Compound | Structure | Stereochemistry | Exact Mass [M + H]+ |
|---|---|---|---|
| 29 | 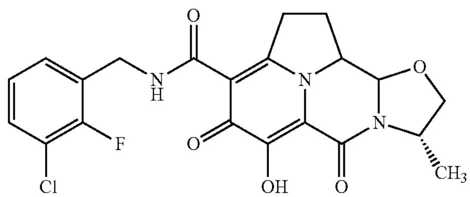 [SMILES: C[C@H]1COC2C3CCc4c(C(=O)NCc5cccc(Cl)c5F)c(=O)c(O)c(n43)C(=O)N21] | trans, diastereomer A | Calc'd 448.1, found 448.1 |
| 30 | 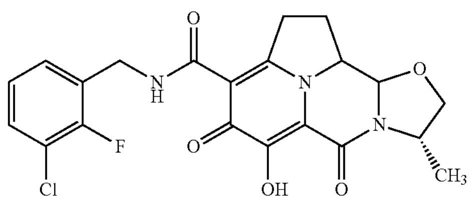 [SMILES: C[C@H]1COC2C3CCc4c(C(=O)NCc5cccc(Cl)c5F)c(=O)c(O)c(n43)C(=O)N21] | trans, diastermer B | Calc'd 448.1, found 448.1 |
| 31 | 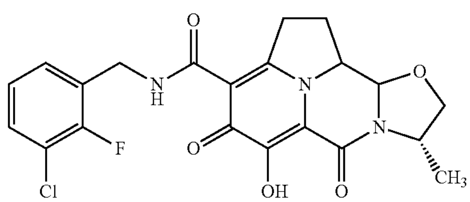 [SMILES: C[C@H]1COC2C3CCc4c(C(=O)NCc5cccc(Cl)c5F)c(=O)c(O)c(n43)C(=O)N21] | cis, diastereomer A | Calc'd 448.1, found 448.1 |

| Compound | 1H NMR |
|---|---|
| 27 | 1H NMR (400 MHz, CDCl3) δ 10.79 (s, 1H), 7.34-7.36 (m, 1H), 6.79-6.81 (m, 2H), 4.99-5.01 (d, J = 8.8 Hz, 1H), 4.60-4.61 (m, 2H), 4.42-4.45 (m, 2H), 4.12-4.21 (m, 2H), 3.72-3.73 (m, 1H), 3.42-3.44 (m, 1H), 2.65-2.70 (m, 1H), 2.08-2.11 (m, 1H), 1.47-1.49 (m, 3H). |
| 28 | 1H NMR (400 MHz, CDCl3) δ 10.77 (s, 1H), 7.30-7.34 (m, 1H), 6.75-6.81 (m, 2H), 4.92-4.93 (d, J = 4.0 Hz, 1H), 4.68-4.69 (m, 1H), 4.59-4.60 (m, 2H), 4.51-4.52 (m, 1H), 4.13-4.17 (m, 2H), 3.40-3.48 (m, 2H), 2.37-2.48 (m, 2H), 1.42-1.43 (m, 3H). |
| 29 | 1H NMR (400 MHz, CDCl3) δ 10.76 (s, 1H), 7.29-7.32 (m, 2H), 7.03-7.07 (m, 1H), 5.03-5.05 (d, J = 8.4 Hz, 1H), 4.68-4.70 (m, 2H), 4.45-4.48 (m, 2H), 4.14-4.22 (m, 2H), 3.75-3.76 (m, 1H), 3.44-3.46 (m, 1H), 2.65-2.70 (m, 1H), 2.08-2.14 (m, 1H), 1.50-1.51 (m, 3H). |
| 30 | 1H NMR (400 MHz, CDCl3) δ 10.80 (s, 1H), 7.29-7.32 (m, 2H), 7.02-7.06 (m, 1H), 4.86-4.89 (d, J = 8.8 Hz, 1H), 4.69-4.70 (d, 2H), 4.39-4.40 (m, 1H), 4.16-4.22 (m, 3H), 4.07-4.10 (m, 1H), 3.44-3.46 (m, 1H), 2.67-2.72 (m, 1H), 2.06-2.15 (m, 1H), 1.50-1.52 (m, 3H). |
| 31 | 1H NMR (400 MHz, CDCl3) δ 10.85 (s, 1H), 7.29-7.32 (m, 2H), 7.03-7.07 (m, 1H), 4.97-4.98 (d, J = 4.0 Hz, 1H), 4.69-4.74 (m, 3H), 4.55-4.56 (m, 1H), 4.17-4.21 (m, 2H), 3.49-3.52 (m, 2H), 2.41-2.54 (m, 2H), 1.46-1.48 (m, 3H). |

Example 4

Preparation of Compound 32

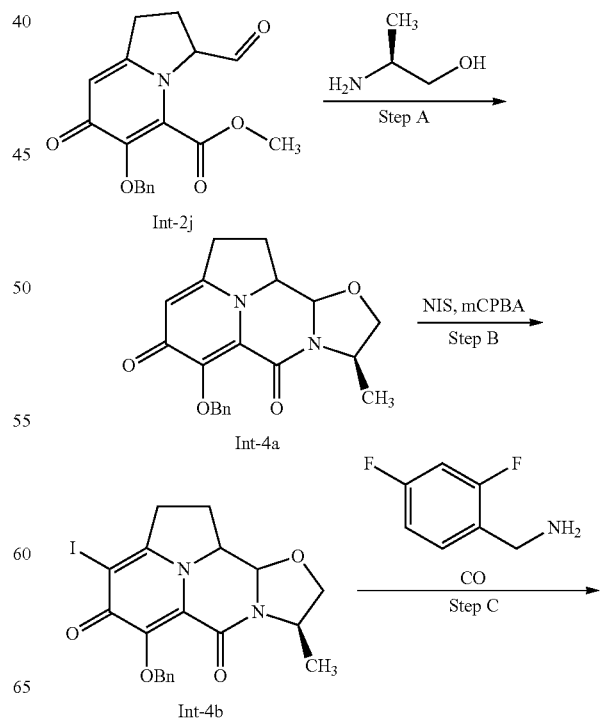

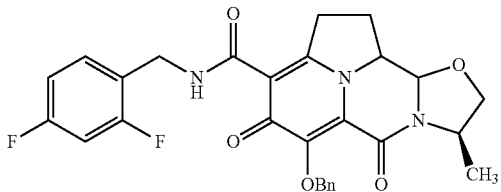

Int-4c-1a (trans, diastereomer A)
Int-4c-1b (trans, diastereomer B)
Int-4c-2 (cis, diastereomer A)

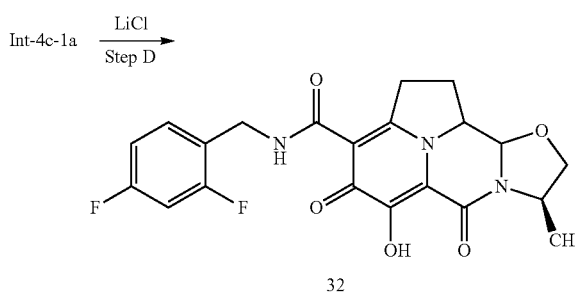

32

Step A—Synthesis of Intermediate Compound Int-4a

To a solution of Int-2j (1.1 g, 3.36 mmol) in tetrahydrofuran (50 mL) was added acetic acid (1.0 mL) and (S)-2-aminopropan-1-ol (0.757 g, 10.08 mmol) at rt. The mixture was heated at 80° C. for 2 h, cooled to room temperature and concentrated in vacuo. The resulting residue was purified using column chromatography on silica gel (methanol:dichloromethane, 1:30 to 1:20) to give compound Int-4a. $^1$H NMR (400 MHz, CDCl$_3$) δ 7.58-7.64 (m, 2H), 7.30-7.35 (m, 3H), 6.38-6.45 (m, 1H), 5.24-5.30 (m, 3H), 4.85-4.87 (m, 1H), 4.27-4.29 (m, 2H), 4.00-4.04 (m, 1H), 3.02-3.06 (m, 2H), 2.49-2.51 (m, 2H), 1.36-1.45 (m, 3H); Mass Calc'd for $C_{20}H_{20}N_2O_4$: 352.1, found 353.0 (M+H)$^+$.

Step B—Synthesis of Intermediate Compound Int-4b

To a solution of Int-4a (325 mg, 0.922 mmol) in methanol (10 mL) was added mCPBA (796 mg, 3.69 mmol) and N-iodosuccinimide (830 mg, 3.69 mmol). The mixture was refluxed at 80° C. for 3 h, cooled to room temperature and quenched with saturated aqueous Na$_2$SO$_3$ (10 mL). The pH was adjusted to pH 7 with 10% aqueous of NaOH. The mixture was extracted with dichloromethane (30 mL×3) and the combined organic portions were dried with anhydrous Na$_2$SO$_4$, filtered and the filtrate was concentrated in vacuo. The resulting residue was purified using column chromatography on silica gel (methanol:dichloromethane, 1:30 to 1:20) to give compound Int-4b. $^1$H NMR (400 MHz, CDCl$_3$) δ 7.62-7.69 (m, 2H), 7.26-7.33 (m, 3H), 4.96-5.30 (m, 3H), 4.59 (s, 1H), 4.21-4.33 (m, 2H), 3.86 (s, 1H), 3.04-3.17 (m, 2H), 2.08-2.18 (m, 2H), 1.32-1.38 (m, 3H); Mass Calc'd for $C_{20}H_{19}IN_2O_4$: 478.0, found 479.0 (M+H)$^+$.

Step C—Synthesis of Intermediate Compound Int-4c

To a solution of Int-4b (400 mg, 0.836 mmol) in dimethylsulfoxide (20 mL) was added Pd(Ph$_3$P)$_4$ (483 mg, 0.418 mmol), N,N-diisopropylethylamine (2.92 mL, 16.73 mmol) and 2,4-difluorobenzylamine (1197 mg, 8.36 mmol). The mixture was heated at 80° C. for 3.5 h under carbon monoxide (1 atm), cooled to rt, diluted with ethyl acetate and filtered. The filtrate was washed with 0.2 M aqueous of HCl (2×10 mL), saturated aqueous of NaHCO$_3$ and brine, dried by anhydrous Na$_2$SO$_4$, filtered and the filtrate was concentrated in vacuo. The resulting residue was purified using column chromatography on silica gel (petroleum ether:ethyl acetate=3:1 to 1:1) followed by preparative RP-HPLC to provide compound Int-4c-1 (trans) and Int-4c-2 (cis).

Int-4c-1: $^1$H NMR (400 MHz, CDCl$_3$) δ 10.80 (s, 1H), 7.56-7.61 (m, 2H), 7.24-7.35 (m, 4H), 6.78-6.80 (m, 2H), 5.14-5.27 (m, 2H), 4.83-4.85 (m, 1H), 4.57-4.58 (m, 2H), 4.38-4.41 (m, 1H), 4.25-4.32 (m, 1H), 4.04-4.11 (m, 2H), 3.89 (s, 1H), 3.35-3.44 (m, 1H), 2.50-2.53 (m, 1H), 1.96-2.01 (m, 1H), 1.34-1.41 (m, 3H); Mass Calc'd for $C_{28}H_{25}F_2N_3O_5$: 521.2, found 522.0 (M+H)$^+$.

Int-4c-2: $^1$H NMR (400 MHz, CDCl$_3$) δ 10.79 (s, 1H), 7.56-7.57 (m, 2H), 7.24-7.31 (m, 4H), 6.71-6.77 (m, 2H), 5.29 (d, J=10.0 Hz, 1H), 5.07 (d, J=10.0 Hz, 1H), 4.80 (d, J=3.6 Hz, 1H), 4.67-4.69 (m, 1H), 4.54-4.55 (m, 2H), 4.41-4.43 (m, 1H), 4.00-4.02 (m, 1H), 3.98-3.99 (m, 1H), 3.32-3.36 (m, 2H), 2.31-2.39 (m, 2H), 1.33-1.34 (m, 3H); Mass Calc'd for $C_{28}H_{25}F_2N_3O_5$: 521.2, found 522.0 (M+H)$^+$.

Separation of Int-4c-1 (trans) to the diastereomers was accomplished with SFC (ChiralPak AS, 5 μm, 250×30 mm, 40% IPA (contained 0.1% NH$_3$H$_2$O) in SC—CO$_2$, 220 nm, 38° C.) to provide Int-4c-1a (trans, diastereomer A) and Int-4c-1b (trans, diastereomer B)

Int-4c-1a: $^1$H NMR (400 MHz, CDCl$_3$) δ 10.80 (s, 1H), 7.54-7.56 (m, 2H), 7.23-7.31 (m, 4H), 6.71-6.78 (m, 2H), 5.26 (d, J=10.4 Hz, 1H), 5.13 (d, J=10.0 Hz, 1H), 4.63 (d, J=8.8 Hz, 1H), 4.52-4.57 (m, 2H), 4.26-4.30 (m, 1H), 4.09-4.12 (m, 2H), 3.94-3.97 (m, 2H), 3.36-3.39 (m, 1H), 2.55-2.58 (m, 1H), 1.94-1.99 (m, 1H), 1.40-1.42 (m, 3H); MS (M+H)$^+$: 522.

Int-4c-1b: $^1$H NMR (400 MHz, CDCl$_3$) δ 10.79 (s, 1H), 7.52-7.53 (m, 2H), 7.23-7.31 (m, 4H), 6.72-6.76 (m, 2H), 5.31 (d, J=10.0 Hz, 1H), 5.16 (d, J=10.8 Hz, 1H), 4.80 (d, J=8.8 Hz, 1H), 4.55 (m, 2H), 4.29-4.37 (m, 2H), 4.04-4.07 (m, 2H), 3.58-3.62 (m, 1H), 3.35 (m, 1H), 2.51-2.59 (m, 1H), 1.95-2.00 (m, 1H), 1.33-1.34 (m, 3H); MS (M+H)$^+$: 522.

Step D—Synthesis of Compound 32

To a solution of Int-4c-1a (trans, diastereomer A) (68 mg, 0.130 mmol) in N,N-dimethylformamide (5 mL) was added lithium chloride (55.3 mg, 1.304 mmol). The mixture was heated to 80° C. for 5 hours. The reaction mixture was filtered and the filtrate was purified using preparative RP-HPLC to provide compound 32. $^1$H NMR (400 MHz, CDCl$_3$) δ 10.74 (s, 1H), 7.33-7.39 (m, 1H), 6.77-6.83 (m, 2H), 4.83 (d, J=8.4 Hz, 1H), 4.60-4.61 (m, 2H), 4.38 (s, 1H), 4.14-4.22 (m, 3H), 4.05-4.07 (m, 1H), 3.39-3.44 (m, 1H), 2.64-2.69 (m, 1H), 2.03-2.12 (m, 1H), 1.47-1.49 (m, 3H); Mass Calc'd for $C_{21}H_{19}F_2N_3O_5$: 431.1, found 432.1 (M+H)$^+$.

The following compounds of the present invention were made using the methodology described in Example 4, and substituting the appropriate reactants and/or reagents.

| Compound | Structure | Stereochemistry | Exact Mass [M + H]+ |
|---|---|---|---|
| 33 | 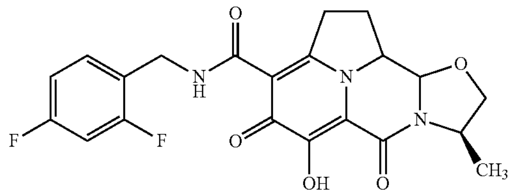 [SMILES: C[C@@H]1COC2C3CCc4c(C(=O)NCc5ccc(F)cc5F)c(=O)c(O)c(n43)C(=O)N21] | trans, diastereomer B | Calc'd 432.1, found 432.1 |
| 34 | 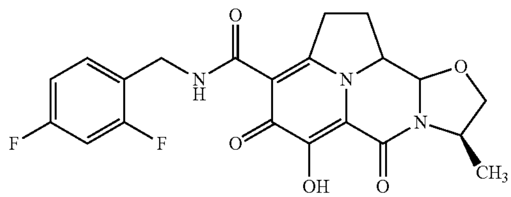 [SMILES: C[C@@H]1COC2C3CCc4c(C(=O)NCc5ccc(F)cc5F)c(=O)c(O)c(n43)C(=O)N21] | cis, diastereomer A | Calc'd 432.1, found 432.1 |

| Compound | 1H NMR |
|---|---|
| 33 | 1H NMR (400 MHz, CDCl3) δ 10.79 (s, 1H), 7.34-7.36 (m, 1H), 6.79-6.81 (m, 2H), 4.99 (d, J = 8.8 Hz, 1H), 4.60-4.61 (m, 2H), 4.42-4.45 (m, 2H), 4.12-4.21 (m, 2H), 3.72-3.73 (m, 1H), 3.42-3.44 (m, 1H), 2.65-2.70 (m, 1H), 2.08-2.11 (m, 1H), 1.47-1.49 (m, 3H). |
| 34 | 1H NMR (400 MHz, CDCl3) δ 10.77 (s, 1H), 7.30-7.34 (m, 1H), 6.75-6.81 (m, 2H), 4.92 (d, J = 4.0 Hz, 1H), 4.68-4.69 (m, 1H), 4.59-4.60 (m, 2H), 4.51-4.52 (m, 1H), 4.13-4.17 (m, 2H), 3.40-3.48 (m, 2H), 2.37-2.48 (m, 2H), 1.42-1.43 (m, 3H). |

Example 5

Preparation of Compound 35

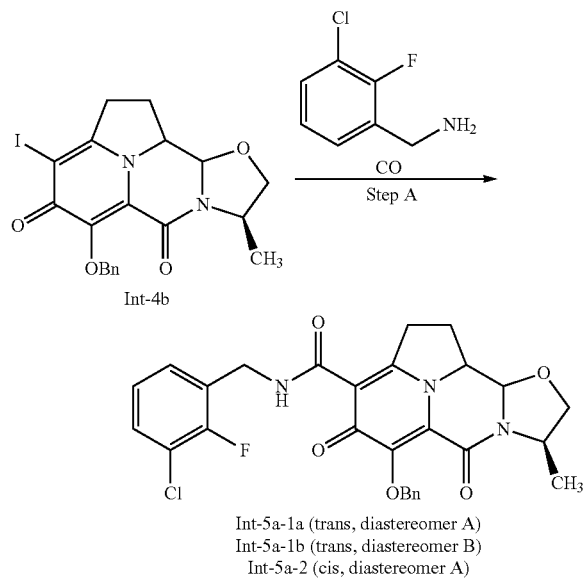

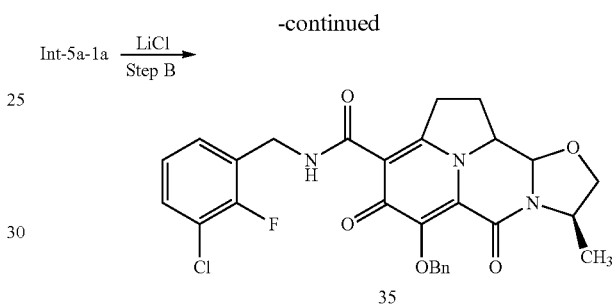

Step A—Synthesis of Intermediate Compound Int-5a

To a solution of Int-4b (380 mg, 0.795 mmol) in dimethylsulfoxide (12 mL) was added Pd(Ph3P)4 (459 mg, 0.397 mmol), N,N-diisopropylethylamine (2.78 mL, 15.89 mmol) and 3-chloro-2-fluorobenzylamine (1268 mg, 7.95 mmol). The mixture was heated at 80° C. for 3 h under carbon monoxide (1 atm), cooled to rt, diluted with ethyl acetate (100 mL) and filtered to remove the solids. The filtrate was washed with 0.2 M aqueous of HCl (2×15 mL), saturated aqueous of NaHCO3 and brine, dried with anhydrous Na2SO4, filtered and the filtrate was concentrated in vacuo. The crude residue was be purified using preparative RP-HPLC to provide compound Int-5a-1 (trans) and Int-5a-2 (cis).

Int-5a-1: 1H NMR (400 MHz, CDCl3) δ 10.95 (s, 1H), 7.56-7.61 (m, 2H), 7.24-7.34 (m, 5H), 7.02-7.04 (m, 1H), 5.21-5.36 (m, 2H), 4.85-4.87 (d, J=8.4 Hz, 1H), 4.65-4.71 (m, 2H), 4.34-4.36 (m, 2H), 4.00-4.16 (m, 2H), 3.65 (t, 1H), 3.41-3.43 (m, 1H), 2.58-2.64 (m, 1H), 2.02-2.05 (m, 1H), 1.38-1.47 (dd, 3H); Mass Calc'd for C28H25ClFN3O5: 537.1, found 538.2 (M+H)+.

Int-5a-2: 1H NMR (400 MHz, CDCl3) δ 10.87 (s, 1H), 7.56-7.57 (m, 2H), 7.21-7.32 (m, 5H), 6.96-6.98 (m, 1H), 5.30-5.32 (m, 1H), 5.07-5.10 (m, 1H), 4.80-4.81 (d, J=3.6 Hz, 1H), 4.60-4.68 (m, 3H), 4.42 (m, 1H), 3.99-4.03 (m, 2H), 3.27-3.36 (m, 2H), 2.32-2.39 (m, 2H), 1.33-1.35 (d, 3H); Mass Calc'd for C28H25ClFN3O5: 537.1, found 538.2 (M+H)+.

Separation of Int-5a-1 (trans) to the diastereomers was accomplished with SFC (OD, 250×30 mm, 10 μm, 55% ethanol (contained 0.1% NH3H2O) in SC—CO2, 80 mL/min, 220 nm, 38° C.) to provide compound Int-5a-1a (trans, diastereomer A) and Int-5a-1b (trans, diastereomer B).

Int-5a-1a: $^1$H NMR (400 MHz, CDCl$_3$) δ 10.90 (s, 1H), 7.59-7.61 (m, 2H), 7.27-7.36 (m, 5H), 7.03-7.05 (m, 1H), 5.38-5.40 (m, 1H), 5.23-5.25 (m, 1H), 4.87-4.89 (d, J=8.4 Hz, 1H), 4.67-4.68 (m, 2H), 4.41-4.43 (m, 1H), 4.34-4.37 (m, 1H), 4.10-4.13 (m, 2H), 3.63-3.66 (t, 1H), 3.41-3.42 (m, 1H), 2.57-2.64 (m, 1H), 2.01-2.07 (m, 1H), 1.39-1.41 (d, 3H); Mass Calc'd for C$_{28}$H$_{25}$ClFN$_3$O$_5$: 537.1, found 538.2 (M+H)$^+$.

Int-5a-1b: $^1$H NMR (400 MHz, CDCl$_3$) δ 10.85 (s, 1H), 7.55-7.57 (m, 2H), 7.22-7.31 (m, 5H), 6.97-6.99 (m, 1H), 5.26-5.28 (m, 1H), 5.13-5.16 (m, 1H), 4.65-4.67 (d, J=8.4 Hz, 1H), 4.60-4.63 (m, 2H), 4.24-4.26 (m, 1H), 4.08-4.12 (m, 2H), 3.91-3.95 (m, 2H), 3.35-3.38 (m, 1H), 2.54-2.57 (m, 1H), 1.97-2.00 (m, 1H), 1.40-1.41 (d, 3H); Mass Calc'd for C$_{28}$H$_{25}$ClFN$_3$O$_5$: 537.1, found 538.2 (M+H)$^+$.

Separation of Int-5a-2 (cis) was accomplished with SFC (Chralpak AD, 250×30 mm, 10 μm, 55% ethanol (contained 0.1% NH$_3$H$_2$O) in SC—CO$_2$, 80 mL/min, 220 nm, 38° C.) to provide Int-5a-2 (cis, diastereomer A). $^1$H NMR (400 MHz, CDCl$_3$) δ 10.83 (s, 1H), 7.56-7.58 (m, 2H), 7.22-7.32 (m, 5H), 6.96-6.98 (m, 1H), 5.29-5.32 (m, 1H), 5.07-5.09 (m, 1H), 4.78-4.79 (d, J 3.6 Hz, 1H), 4.60-4.68 (m, 3H), 4.41 (m, 1H), 3.98-4.02 (m, 2H), 3.32-3.35 (m, 2H), 2.30-2.38 (m, 2H), 1.32-1.34 (d, 3H); Mass Calc'd for C$_{28}$H$_{25}$ClFN$_3$O$_5$: 537.1, found 538.2 (M+H)$^+$.

Step B—Synthesis of Compound 35

To a solution of Int-5a-1a (82 mg, 0.152 mmol) in N,N-dimethylformamide (6 mL) was added lithium chloride (64.6 mg, 1.524 mmol). The mixture was heated to 80° C. for 2 h, cooled to room temperature and filtered. The filtrate was purified directly by preparative RP-HPLC to provide compound 35. $^1$H NMR (400 MHz, CDCl$_3$) δ 10.76 (s, 1H), 7.29-7.32 (m, 2H), 7.03-7.07 (m, 1H), 5.03-5.05 (d, J=8.4 Hz, 1H), 4.68-4.70 (m, 2H), 4.45-4.48 (m, 2H), 4.14-4.22 (m, 2H), 3.75-3.76 (m, 1H), 3.44-3.46 (m, 1H), 2.65-2.70 (m, 1H), 2.08-2.14 (m, 1H), 1.50-1.51 (m, 3H); Mass Calc'd for C$_{21}$H$_{19}$ClFN$_3$O$_5$: 447.1, found 448.1 (M+H)$^+$.

The following compounds of the present invention were made using the methodology described in Example 5, and substituting the appropriate reactants and/or reagents.

| Compound | $^1$H NMR |
|---|---|
| 36 | $^1$H NMR (400 MHz, CDCl$_3$) δ 10.80 (s, 1H), 7.29-7.32 (m, 2H), 7.02-7.06 (m, 1H), 4.86-4.89 (d, J = 8.8 Hz, 1H), 4.69-4.70 (d, 2H), 4.39-4.40 (m, 1H), 4.16-4.22 (m, 3H), 4.07-4.10 (m, 1H), 3.44-3.46 (m, 1H), 2.67-2.72 (m, 1H), 2.06-2.15 (m, 1H), 1.50-1.52 (m, 3H). |
| 37 | $^1$H NMR (400 MHz, CDCl$_3$) δ 10.85 (s, 1H), 7.29-7.32 (m, 2H), 7.03-7.07 (m, 1H), 4.97-4.98 (d, J = 4.0 Hz, 1H), 4.69-4.74 (m, 3H), 4.55-4.56 (m, 1H), 4.17-4.21 (m, 2H), 3.49-3.52 (m, 2H), 2.41-2.54 (m, 2H), 1.46-1.48 (m, 3H). |

Example 6

Preparation of Compound 38

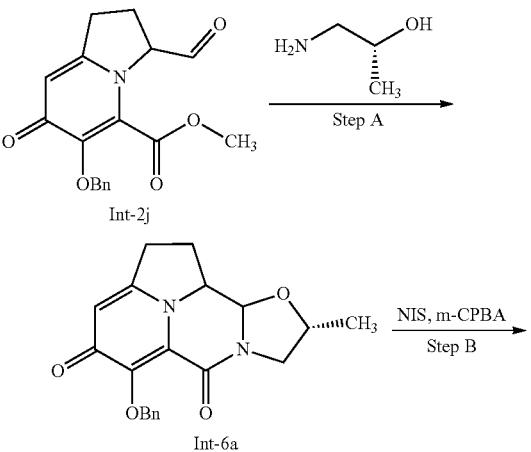

| Compound | Structure | Stereochemistry | Exact Mass [M + H]$^+$ |
|---|---|---|---|
| 36 | 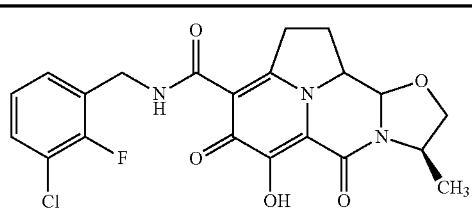 | trans, diastereomer B | Calc'd 448.1, found 448.1 |
| 37 | 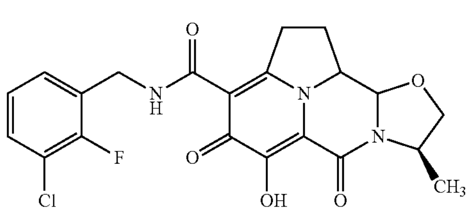 [SMILES: C[C@@H]1COC2C3CCc4c(C(=O)NCc5cccc(Cl)c5F)c(=O)c(O)c(n43)C(=O)N21] | cis, diastereomer A | Calc'd 448.1, found 448.1 |

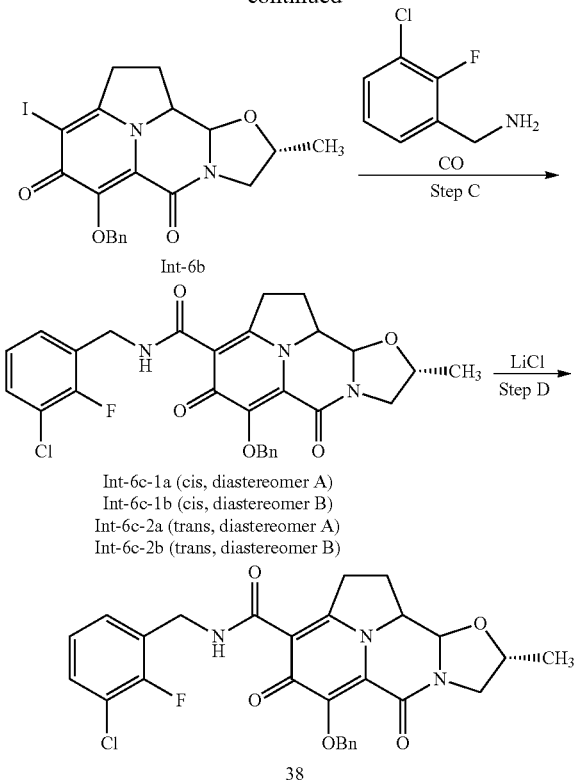

Step A—Synthesis of Intermediate Compound Int-6a

To a solution of Int-2j (300 mg, 0.917 mmol) and (R)-1-aminopropan-2-ol (1377 mg, 18.33 mmol) in tetrahydrofuran (50 mL) and acetic acid (1.58 mL). The mixture was stirred at 80° C. for 0.5 hour. The mixture was concentrated in vacuo and purified using column chromatography on silica gel (dichloromethane:methanol=20:1) to provide Int-6a. $^1$H NMR (400 MHz, CDCl$_3$) δ 7.60-7.65 (m, 2H), 7.28-7.36 (m, 3H), 6.43-6.47 (m, 1H), 5.34-5.39 (m, 1H), 5.20-5.25 (m, 1H), 4.86-4.95 (m, 1H), 4.38-4.48 (m, 1H), 4.20-4.23 (m, 1H), 3.95-4.11 (m, 1H), 3.02-3.12 (m, 3H), 2.49-2.55 (m, 1H), 2.28-2.33 (m, 1H), 1.30-1.45 (m, 3H). Mass Calc'd for C$_{20}$H$_{20}$N$_2$O$_4$: 352.1, found 353.0 (M+H)$^+$.

Step B—Synthesis of Intermediate Compound Int-6b

To a solution of Int-6a (170 mg, 0.482 mmol) in methanol (8 mL) was added m-CPBA (416 mg, 1.930 mmol) and N-iodosuccinimide (434 mg, 1.930 mmol) at 80° C. The mixture was stirred at 80° C. for 2 h, cooled to room temperature and extracted with CHCl$_3$/2-Propanol (V:V=3:1) (3×10 mL). The combined organics were washed with aqueous Na$_2$SO$_3$ (6 mL×2), 5% NaOH solution (4 mL×2) and brine, dried over anhydrous Na$_2$SO$_4$, filtered and the filtrate was concentrated in vacuo. The resulting residue was purified using column chromatography on silica gel (methanol:dichloromethane=1:20) to provide compound Int-6b. $^1$H NMR (400 MHz, CDCl$_3$) δ 7.65-7.70 (m, 2H), 7.30-7.38 (m, 3H), 5.29-5.38 (m, 1H), 4.96-5.12 (m, 1H), 4.65-4.70 (m, 1H), 4.17-4.24 (m, 2H), 3.22-3.26 (m, 1H), 3.06-3.13 (m, 2H), 2.50-2.53 (m, 1H), 2.06-2.35 (m, 2H), 1.35-1.41 (m, 3H). Mass Calc'd for C$_{20}$H$_{19}$IN$_2$O$_4$: 478.0, found 479.0 (M+H)$^+$.

Step C—Synthesis of Intermediate Compound Int-6c

To a solution of Int-6b (150 mg, 0.315 mmol) in dimethylsulfoxide (5 mL) was added 3-chloro-2-fluorobenzylamine (502.7 mg, 3.15 mmol), N,N-diisopropylethylamine (407.0 mg, 3.15 mmol) and Pd(PPh$_3$)$_4$ (182.0 mg, 0.158 mmol). The mixture was stirred under carbon monoxide (1 atm) at 80° C. for 2 h, cooled to room temperature and quenched with 1 N HCl (2 mL). The mixture was extracted with ethyl acetate, washed with brine, dried over anhydrous Na$_2$SO$_4$, filtered and the filtrate was concentrated in vacuo. The resulting residue was purified using column chromatography on silica gel (petroleum ether:ethyl acetate=5:1 to 1:2) to provide the mixture of diastereomers. Separation of the diastereomers was accomplished with SFC (OD, 250×30 mm, 10 nm, 40% ethanol+NH$_3$.H$_2$O in SC—CO$_2$, 80 mL/min, 220 nm) to provide compound Int-6c-1a (cis, diastereomer A), Int-6c-1b (cis, diastereomer B), Int-6c-2a (trans, diastereomer A), Int-6c-2b (trans, diastereomer B).

Int-6c-1a: $^1$H NMR (400 MHz, CDCl$_3$) δ 10.90 (br. s., 1H), 7.61-7.63 (d, J=7.2 Hz, 2H), 7.28-7.40 (m, 5H), 6.99-7.08 (m, 1H), 5.37-5.39 (d, J=10 Hz, 1H), 5.18-5.21 (d, J=10.4 Hz, 1H), 4.97-4.98 (d, J=3.6 Hz, 1H), 4.65-4.78 (m, 3H), 4.44-4.55 (m, 1H), 4.10-4.21 (m, 1H), 4.00-4.08 (m, 1H), 3.38 (m, 1H), 2.94 (m, 1H), 2.42 (m, 2H), 1.33-1.34 (d, J=5.6 Hz, 3H). Mass Calc'd for C$_{28}$H$_{25}$ClFN$_3$O$_5$: 537.1, found 538.1 (M+H)$^+$.

Int-6c-1b: $^1$H NMR (400 MHz, CDCl$_3$) δ 10.83 (br. s., 1H), 7.52-7.56 (m, 2H), 7.22-7.30 (m, 5H), 6.96-6.98 (m, 1H), 5.30-5.32 (d, J=10 Hz, 1H), 5.14-5.17 (d, J=10 Hz, 1H), 4.80-4.81 (d, J=4 Hz, 1H), 4.58-4.63 (m, 2H), 4.36-4.39 (m, 1H), 4.01-4.18 (m, 3H), 3.46-3.47 (m, 1H), 3.22-3.38 (m, 1H), 1.96-2.51 (m, 2H), 1.31-1.32 (m, 1H), 1.08-1.10 (d, J=6 Hz, 2H). Mass Calc'd for C$_{28}$H$_{25}$ClFN$_3$O$_5$: 537.1, found 538.1 (M+H)$^+$.

Int-6c-2a: $^1$H NMR (400 MHz, CDCl$_3$) δ 10.87-10.90 (m, 1H), 7.59-7.61 (d, J=6.8 Hz, 2H), 7.27-7.38 (m, 5H), 6.98-7.05 (m, 1H), 5.32-5.34 (d, J=9.6 Hz, 1H), 5.19-5.21 (d, J=9.6 Hz, 1H), 4.95-4.97 (d, J=8.8 Hz, 1H), 4.65-4.70 (m, 2H), 4.45-4.46 (m, 1H), 4.24-4.28 (m, 1H), 4.08-4.12 (m, 2H), 3.32-3.40 (m, 1H), 3.07-3.12 (m, 1H), 2.53-2.56 (m, 1H), 1.97-2.03 (m, 1H), 1.37-1.38 (d, J=5.6 Hz, 3H). Mass Calc'd for C$_{28}$H$_{25}$ClFN$_3$O$_5$: 537.1, found 538.1 (M+H)$^+$.

Int-6c-2b: $^1$H NMR (400 MHz, CDCl$_3$) δ 10.90 (br. s., 1H), 7.61-7.63 (d, J=7.2 Hz, 2H), 7.29-7.38 (m, 5H), 7.02-7.06 (m, 1H), 5.35-5.38 (d, J=10 Hz, 1H), 5.20-5.22 (d, J=10 Hz, 1H), 4.83-4.86 (d, J=8.8 Hz, 1H), 4.66-4.70 (m, 2H), 4.23-4.32 (m, 1H), 4.14-4.19 (m, 2H), 3.76-3.79 (m, 1H), 3.33-3.42 (m, 2H), 2.62-2.67 (m, 1H), 2.02-2.09 (m, 1H), 1.46-1.47 (d, J=5.6 Hz, 3H). Mass Calc'd for C$_{28}$H$_{25}$ClFN$_3$O$_5$: 537.1, found 538.1 (M+H)$^+$.

Step D—Synthesis of Compound 38

To a solution of compound Int-6c-1a (cis, diastereomer A) (20 mg, 0.037 mmol) in N,N-dimethylformamide (2 mL) was added lithium chloride (15.76 mg, 0.372 mmol). The resulting mixture was heated to 80° C. for 1.5 h and cooled to rt. The crude mixture was purified directly by preparative RP-HPLC to provide compound 38. $^1$H NMR (400 MHz, CDCl$_3$) δ 10.82 (s, 1H), 7.28-7.29 (m, 2H), 7.01-7.05 (m, 1H), 5.08-5.09 (d, J=3.6 Hz, 1H), 4.65-4.68 (m, 3H), 4.57 (s, 1H), 4.09-4.17 (m, 2H), 3.41-3.46 (m, 1H), 2.99-3.04 (m, 1H), 2.41-2.48 (m, 2H), 1.37-1.38 (d, J=6 Hz, 3H). Mass Calc'd for C$_{21}$H$_{19}$ClFN$_3$O$_5$: 447.1, found 448.1 (M+H)$^+$.

The following compounds of the present invention were made using the methodology described in Example 6, and substituting the appropriate reactants and/or reagents.

| Compound | Structure | derived from | Exact Mass [M + H]+ |
|---|---|---|---|
| 39 | 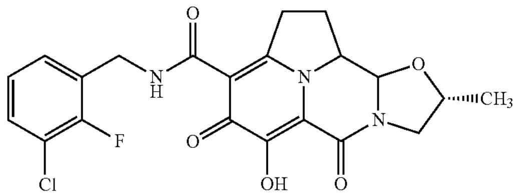 [SMILES: C[C@@H]1CN2C(=O)c3c(O)c(=O)c(C(=O)NCc4cccc(Cl)c4F)c4n3C(CC4)C2O1] | Int-6c-1b (cis, diastereomer B) | Calc'd 448.1, found 448.1 |
| 40 | 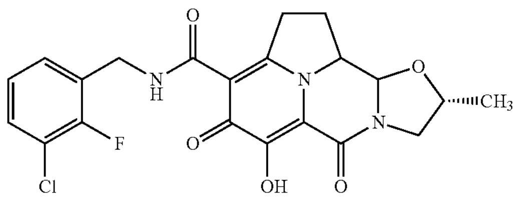 [SMILES: C[C@@H]1CN2C(=O)c3c(O)c(=O)c(C(=O)NCc4cccc(Cl)c4F)c4n3C(CC4)C2O1] | Int-6c-2a (trans, diastereomer A) | Calc'd 448.1, found 448.1 |
| 41 | 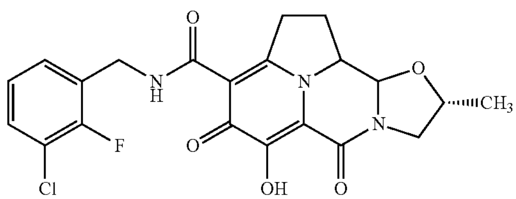 [SMILES: C[C@@H]1CN2C(=O)c3c(O)c(=O)c(C(=O)NCc4cccc(Cl)c4F)c4n3C(CC4)C2O1] | Int-6c-2b (trans, diastereomer B) | Calc'd 448.1, found 448.1 |

| Compound | 1H NMR |
|---|---|
| 39 | 1H NMR (400 MHz, CDCl3) δ 10.81 (s, 1H), 7.27-7.28 (m, 2H), 7.00-7.04 (m, 1H), 4.98 (s, 1H), 4.69 (s, 2H), 4.52 (s, 1H), 4.32-4.33 (d, J = 5.2 Hz, 1H), 4.12 (s, 1H), 4.01-4.05 (m, 1H), 3.58-3.63 (m, 1H), 3.41 (s, 1H), 2.46 (m, 2H), 1.21-1.22 (d, J = 6.4 Hz, 3H) |
| 40 | 1H NMR (400 MHz, CDCl3) δ 10.74 (s, 1H), 7.29-7.31 (m, 2H), 7.02-7.04 (m, 1H), 5.07-5.09 (d, J = 8.4 Hz, 1H), 4.68 (s, 2H), 4.56-4.57 (d, J = 5.2 Hz, 1H), 4.14-4.22 (m, 3H), 3.42-3.49 (m, 1H), 3.23-3.27 (m, 1H), 2.65 (s, 1H), 2.02-2.10 (m, 1H), 1.43-1.44 (d, J = 5.6 Hz, 3H) |
| 41 | 1H NMR (400 MHz, CDCl3) δ 10.74 (s, 1H), 7.28-7.29 (m, 2H), 7.00-7.04 (m, 1H), 4.96-4.98 (d, J = 8.4 Hz, 1H), 4.66-4.67 (d, J = 4.4 Hz, 2H), 4.43-4.45 (m, 1H), 4.16-4.19 (m, 2H), 3.87-3.91 (m, 1H), 3.30-3.50 (m, 2H), 2.64-2.69 (m, 1H), 2.05-2.10 (m, 1H), 1.49-1.50 (d, J = 6 Hz, 3H) |

Example 7

Preparation of Compound 42

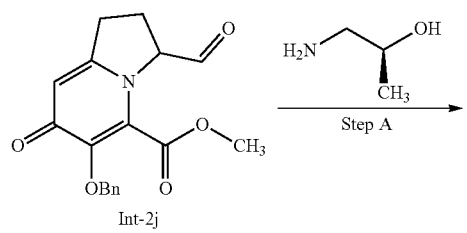

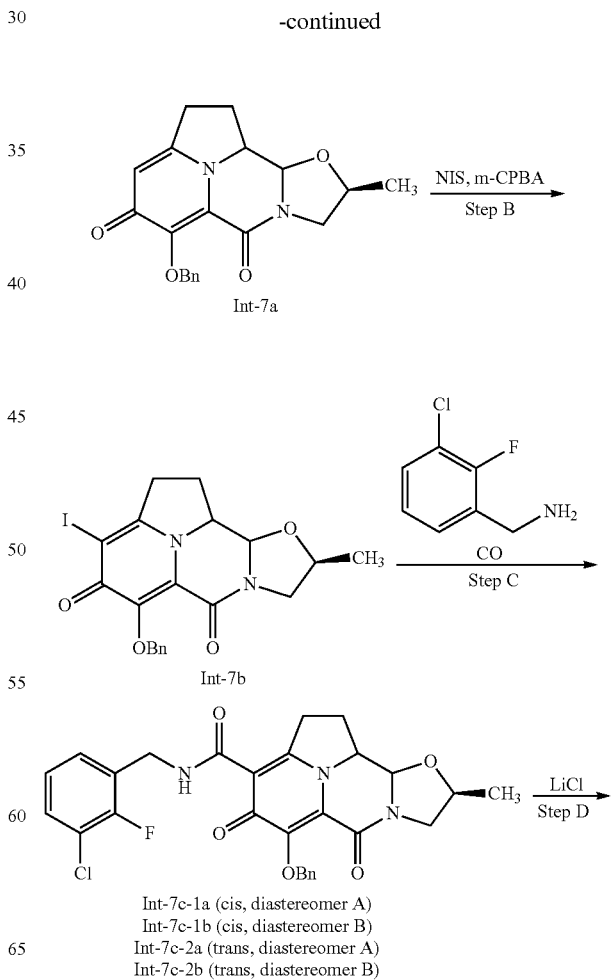

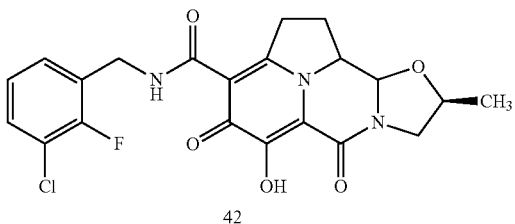

42

Step A—Synthesis of Intermediate Compound Int-7a

A solution of Int-2j (1.25 g, 3.82 mmol) and (S)-1-aminopropan-2-ol (1.434 g, 19.09 mmol) in tetrahydrofuran (100 ml) and acetic acid (2 ml) was heated at 80° C. for 0.5 hour. The mixture was concentrated in vacuo and purified using column chromatography on silica gel (dichloromethane:methanol=20:1) to provide Int-7a. $^1$H NMR (400 MHz, CDCl$_3$) δ 7.60-7.65 (m, 2H), 7.28-7.36 (m, 3H), 6.43-6.47 (m, 1H), 5.34-5.39 (m, 1H), 5.20-5.25 (m, 1H), 4.86-4.95 (m, 1H), 4.38-4.48 (m, 1H), 4.20-4.23 (m, 1H), 3.95-4.11 (m, 1H), 3.02-3.12 (m, 3H), 2.49-2.55 (m, 1H), 2.28-2.33 (m, 1H), 1.30-1.45 (m, 3H). Mass Calc'd for $C_{20}H_{20}N_2O_4$: 352.1, found 353.0 (M+H)$^+$.

Step B—Synthesis of Intermediate Compound Int-7b

To a solution of compound Int-7a (1 g, 2.84 mmol) in methanol (10 mL) was added mCPBA (2.449 g, 11.35 mmol) and N-iodosuccinimide (2.55 g, 11.35 mmol). The mixture was stirred at 75° C. for 2 hours. The mixture was concentrated in vacuo and quenched with aqueous Na$_2$SO$_3$ (30 mL) and 10% aq. NaOH (20 mL) and extracted with dichloromethane (50 mL×3). The organic phase was dried over anhydrous Na$_2$SO$_4$, filtered and the filtrate was concentrated in vacuo. The resulting residue was purified using column chromatography on silica gel (dichloromethane:methanol=20:1) to provide compound Int-7b. $^1$H NMR (400 MHz, CDCl$_3$) δ 7.54-7.74 (m, 2H), 7.27-7.41 (m, 3H), 5.36-5.47 (m, 1H), 5.18-5.25 (m, 1H), 4.91 (d, J=8.6 Hz, 1H), 4.19-4.41 (m, 2H), 3.93-4.08 (m, 1H), 3.60-3.68 (m, 1H), 3.20-3.33 (m, 1H), 3.05-3.19 (m, 1H), 2.98 (s, 1H), 2.76 (s, 1H), 1.35-1.47 (m, 3H). Mass Calc'd for $C_{20}H_{19}IN_2O_4$: 478.0, found 479.2 (M+H)$^+$.

Step C—Synthesis of Intermediate Compound Int-7e

To a solution of Int-7b (1.00 g, 2.09 mmol) in dimethylsulfoxide (20 mL) was added 3-chloro-2-fluorobenzylamine (1.668 g, 10.45 mmol), N,N-diisopropylethylamine (1.351 g, 10.45 mmol) and Pd(PPh$_3$)$_4$ (0.483 g, 0.418 mmol). The mixture was stirred under carbon monoxide (1 atm) at 80° C. for 2 h, cooled to rt, diluted with water (20 mL) and extracted with ethyl acetate. The organic portions were washed with aqueous HCl (0.2 M, 5 mL) and brine (10 mL), dried over anhydrous Na$_2$SO$_4$, filtered and the filtrate was concentrated in vacuo. The resulting residue was purified using column chromatography on silica gel (dichloromethane:methanol=20:1) to provide compound Int-7c. Mass Calc'd for $C_{28}H_{25}ClFN_3O_5$: 537.1, found 538.2 (M+H)$^+$.

Separation of the diastereomers was accomplished with SFC (Chralpak OJ, 250 mm×50 mm, 10 μm, 40% methanol (0.1% NH$_3$H$_2$O) in SC—CO$_2$, 200 mL/min, 220 nm) to provide early eluting compound Int-7c-2a (trans, diastereomer A) and later eluting Int-7c-1b (cis, diastereomer B) and a mixture that was further purified using RP-HPLC and SFC (Chralpak AD, 250 mm×30 mm, 10 μm, 55% IPA (0.1% NH$_3$H$_2$O) in SC—CO$_2$, 80 mL/min, 220 nm) to provide early eluting compound Int-7c-1a (cis, diastereomer A) and later eluting Int-7c-2b (trans, diastereomer B).

Int-7c-1a: $^1$H NMR (400 MHz, CDCl$_3$) δ 10.87-10.95 (m, 1H), 7.60 (d, J=6.8 Hz, 2H), 7.29-7.38 (m, 5H), 7.04 (t, J=8.3 Hz, 1H), 5.41 (d, J=10.3 Hz, 1H), 5.26 (d, J=10.3 Hz, 1H), 4.89 (d, J=8.5 Hz, 1H), 4.66-4.71 (m, 2H), 4.34-4.47 (m, 2H), 4.06-4.20 (m, 2H), 3.68 (dd, J=8.6, 6.6 Hz, 1H), 3.38-3.47 (m, 1H), 2.58-2.67 (m, 1H), 2.00-2.11 (m, 1H), 1.42 (d, J=6.0 Hz, 3H). Mass Calc'd for $C_{28}H_{25}ClFN_3O_5$: 537.1, found 538.2 (M+H)$^+$.

Int-7c-1b: $^1$H NMR (400 MHz, CDCl$_3$) δ 10.87-10.95 (m, 1H), 7.60 (d, J=6.8 Hz, 2H), 7.29-7.38 (m, 5H), 7.04 (t, J=8.3 Hz, 1H), 5.41 (d, J=10.3 Hz, 1H), 5.26 (d, J=10.3 Hz, 1H), 4.89 (d, J=8.5 Hz, 1H), 4.66-4.71 (m, 2H), 4.34-4.47 (m, 2H), 4.06-4.20 (m, 2H), 3.68 (dd, J=8.6, 6.6 Hz, 1H), 3.38-3.47 (m, 1H), 2.58-2.67 (m, 1H), 2.00-2.11 (m, 1H), 1.42 (d, J=6.0 Hz, 3H). Mass Calc'd for $C_{28}H_{25}ClFN_3O_5$: 537.1, found 538.2 (M+H)$^+$.

Int-7c-2a: $^1$H NMR (400 MHz, CDCl$_3$) δ 10.91 (s, 1H), 7.64 (d, J=7.0 Hz, 2H), 7.29-7.41 (m, 5H), 7.03 (s, 1H), 5.40 (d, J=10.0 Hz, 1H), 5.18 (d, J=10.0 Hz, 1H), 4.87-4.90 (m, 1H), 4.72-4.79 (m, 1H), 4.67-4.71 (m, 2H), 4.45-4.52 (m, 1H), 4.07-4.19 (m, 2H), 3.39-3.45 (m, 2H), 2.41-2.49 (m, 2H), 1.42 (d, J=6.8 Hz, 3H). Mass Calc'd for $C_{28}H_{25}ClFN_3O_5$: 537.1, found 538.2 (M+H)$^+$.

Int-7c-2b: $^1$H NMR (400 MHz, CDCl$_3$) δ 10.92 (brs, 1H), 7.63 (d, J=7.4 Hz, 2H), 7.28-7.40 (m, 5H), 7.04 (s, 1H), 5.31-5.38 (m, 1H), 5.23 (d, J=10.2 Hz, 1H), 4.65-4.76 (m, 2H), 4.35 (t, J=6.0 Hz, 1H), 4.14-4.22 (m, 2H), 4.00-4.07 (m, 2H), 3.38-3.48 (m, 1H), 2.58-2.70 (m, 1H), 1.96-2.12 (m, 2H), 1.49 (d, J=6.2 Hz, 3H). Mass Calc'd for $C_{28}H_{25}ClFN_3O_5$: 537.1, found 538.2 (M+H)$^+$.

Step D—Synthesis of Compound 42

To a solution of Int-7c-1a (cis, diastereomer A) (160 mg, 0.297 mmol) in N,N-dimethylformamide (5 mL) was added lithium chloride (126 mg, 2.97 mmol). The mixture was heated at 80° C. for 4 h, cooled to room temperature and purified directly by preparative RP-HPLC to provide compound 42. $^1$H NMR (400 MHz, CDCl$_3$) δ 10.59-11.08 (m, 1H), 7.27-7.38 (m, 2H), 6.97-7.10 (m, 1H), 5.09 (d, J=3.75 Hz, 1H), 4.64-4.76 (m, 3H), 4.53-4.63 (m, 1H), 4.07-4.23 (m, 2H), 3.37-3.53 (m, 1H), 3.03 (dd, J=7.72, 11.91 Hz, 1H), 2.36-2.55 (m, 2H), 1.39 (d, J=6.17 Hz, 3H). Mass Calc'd for $C_{21}H_{19}ClFN_3O_5$: 447.1, found 448.0. (M+H)$^+$.

The following compounds of the present invention were made using the methodology described in Example 7, and substituting the appropriate reactants and/or reagents.

| Compound | Structure | derived from | Exact Mass [M + H]+ |
|---|---|---|---|
| 43 | 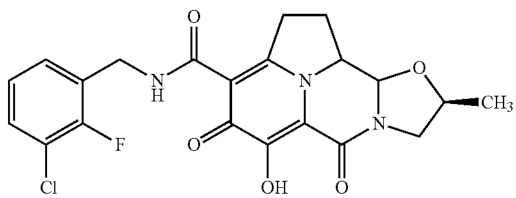 [SMILES: C[C@H]1CN2C(=O)c3c(O)c(=O)c(C(=O)NCc4cccc(Cl)c4F)c4n3C(CC4)C2O1] | Int-7c-1b (cis, diastereomer B) | Calc'd 448.1, found 448.1 |
| 44 | 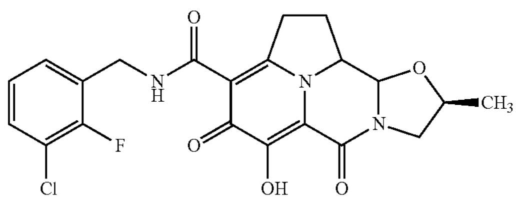 | Int-7c-2a (trans, diastereomer A) | Calc'd 448.1, found 448.1 |
| 45 | 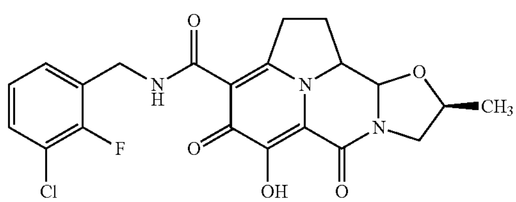 [SMILES: C[C@H]1CN2C(=O)c3c(O)c(=O)c(C(=O)NCc4cccc(Cl)c4F)c4n3C(CC4)C2O1] | Int-7c-2b (trans, diastereomer B) | Calc'd 448.1, found 448.1 |

| Compound | 1H NMR |
|---|---|
| 43 | 1H NMR (400 MHz, CDCl3) δ 10.63-10.91 (m, 1H), 7.26 (br s., 2H), 7.00 (t, J = 7.83 Hz, 1H), 4.96 (d, J = 3.53 Hz, 1H), 4.59-4.75 (m, 2H), 4.45-4.57 (m, 1H), 4.30 (d, J = 5.73 Hz, 1H), 4.12 (dd, J = 8.27, 19.07 Hz, 1H), 4.00 (dd, J = 4.41, 11.69 Hz, 1H), 3.59 (dd, J = 8.16, 11.47 Hz, 1H), 3.38 (td, J = 9.56, 19.02 Hz, 1H), 2.33-2.50 (m, 2H), 1.19 (d, J = 6.17 Hz, 3H). |
| 44 | 1H NMR (400 MHz, CDCl3) δ 10.53-11.02 (m, 1H), 7.29 (br s., 2H), 6.95-7.12 (m, 1H), 4.96 (d, J = 8.60 Hz, 1H), 4.68 (d, J = 5.29 Hz, 2H), 4.39-4.50 (m, 1H), 4.12-4.26 (m, 2H), 3.85-3.96 (m, 1H), 3.30-3.51 (m, 2H), 2.61-2.74 (m, 1H), 2.02-2.14 (m, 1H), 1.51 (d, J = 5.95 Hz, 3H). |
| 45 | 1H NMR (400 MHz, CDCl3) δ 10.47-10.90 (m, 1H), 7.25-7.31 (m, 2H), 6.95-7.06 (m, 1H), 5.06 (d, J = 8.82 Hz, 1H), 4.66 (d, J = 5.29 Hz, 2H), 4.47-4.59 (m, 1H), 4.20 (d, J = 5.95 Hz, 3H), 3.33-3.49 (m, 1H), 3.23 (dd, J = 6.51, 11.36 Hz, 1H), 2.57-2.69 (m, 1H), 2.00-2.11 (m, 1H), 1.42 (d, J = 6.17 Hz, 3H). |

Example 8

Preparation of Compound 46

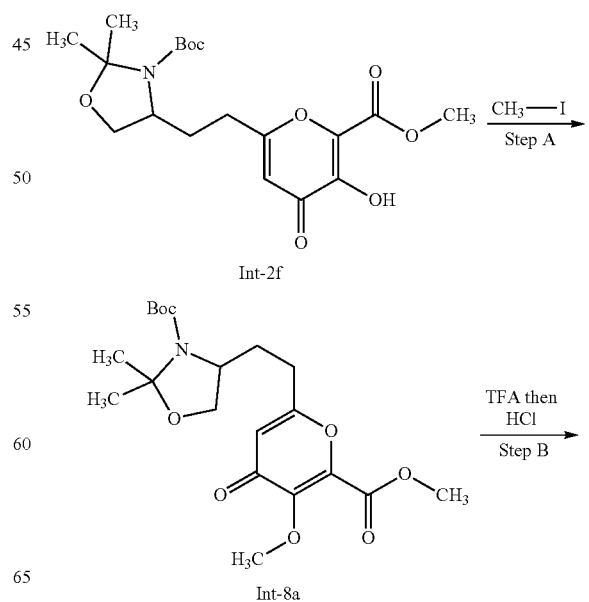

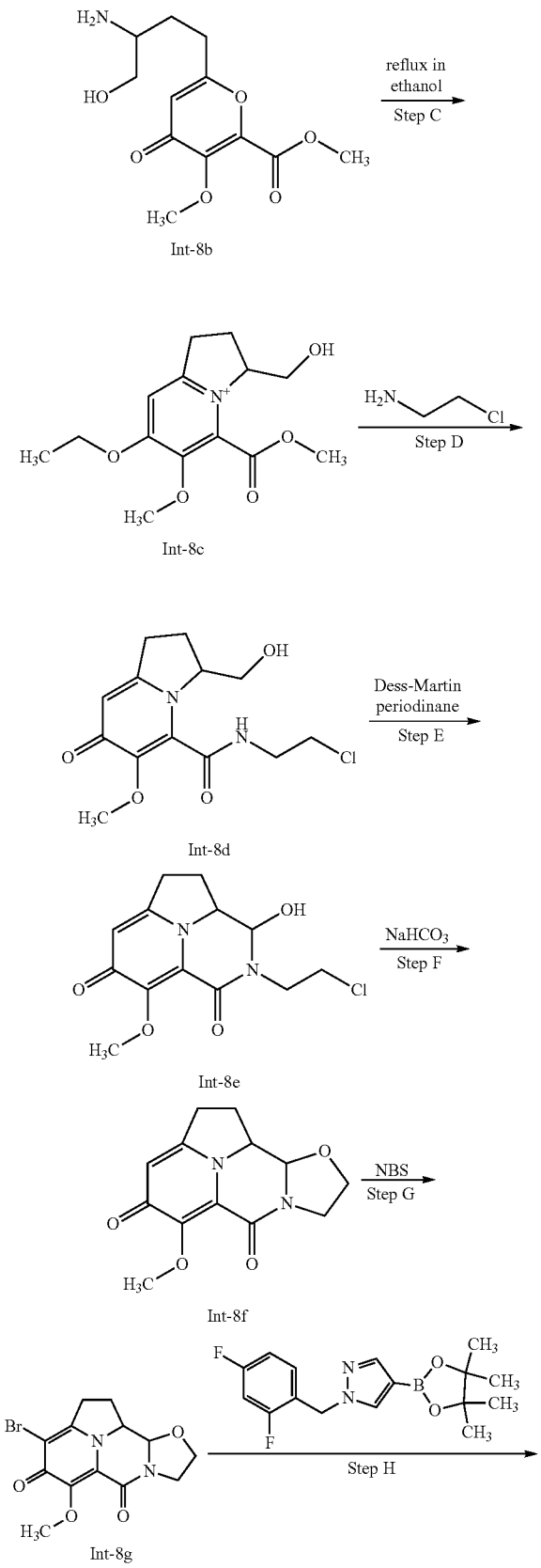

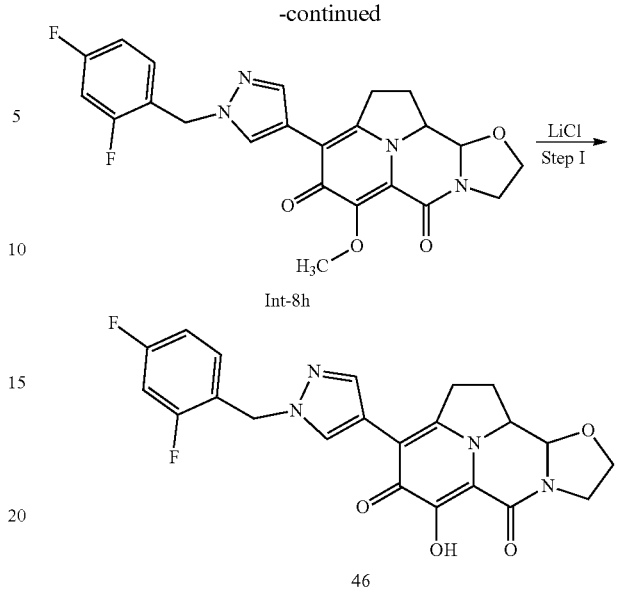

Step A—Synthesis of Intermediate Compound Int-8a

A 10-L 4-necked round-bottom flask purged and maintained with an inert atmosphere of nitrogen, was charged with a solution of Int-2f (250 g, 629 mmol, 1.00 equiv) in N,N-dimethylformamide (2.5 L), potassium carbonate (261 g, 1.89 mol, 3.00 equiv), and MeI (179 g, 1.26 mol, 2 equiv). The resulting mixture was stirred overnight at room temperature. The reaction was quenched by the addition of water (10 L). The resulting solution was extracted with ethyl acetate (3×2 L) and the combined organic portions were concentrated in vacuo. The resulting residue was purified using column chromatography on silica gel (ethyl acetate/petroleum ether, 1:5) to provide Int-8a. $^1$H NMR (400 MHz, CDCl$_3$): δ 1.38 (m, 12H), 1.60 (m, 3H), 2.08 (m, 2H), 2.59 (m, 2H), 3.76 (s, 1H), 4.01 (m, 8H), 6.32 (m, 1H). Mass Calc'd for $C_{20}H_{29}NO_8$: 411.2, found 434.2 (M+Na)$^+$.

Step B—Synthesis of Intermediate Compound Int-8b

A mixture of Int-8a (6.0 g, 14.58 mmol) in dichloromethane (120 mL) was treated with trifluoroacetic acid (30 mL) at 0° C. The mixture was stirred at room temperature for 4 h, concentrated in vacuo and the residue obtained was dissolved in methanol (120 mL) and treated with concentrated in vacuo HCl (0.25 mL). The resulting mixture was heated at reflux for 2 h, cooled to room temperature and concentrated in vacuo to provide Int-8b.

Step C—Synthesis of Intermediate Compound Int-8c

A solution of Int-8b (3.8 g, 14.01 mmol) in ethanol (100 mL) was refluxed for 2 hours. The mixture was concentrated in vacuo to provide Int-8c, which was used without further purification. Mass Calc'd for $C_{14}H_{20}NO_5^+$: 282.1, found 282.1 (M+H)$^+$.

Step D—Synthesis of Intermediate Compound Int-8d

To a solution of Int-8c (200 mg, 0.708 mmol) in ethanol (20 mL) was added 2-chloroethanamine (169 mg, 2.125 mmol) and the mixture was stirred at 80° C. for 8 hours. The mixture was concentrated in vacuo and the residue obtained was purified using preparative RP-HPLC to give Int-8d. $^1$H NMR (400 MHz, CDCl$_3$) δ 8.63 (s, 1H), 5.26-5.28 (m, 1H), 4.08-4.12 (m, 2H), 3.95-3.98 (m, 3H), 3.89 (s, 3H), 3.74-3.82 (m, 2H), 3.47-3.56 (m, 1H), 3.10-3.14 (m, 1H), 2.38-2.51 (m, 2H). Mass Calc'd for $C_{13}H_{17}ClN_2O_4$: 300.1, found 301.0 (M+H)$^+$.

Step E—Synthesis of Intermediate Compound Int-8e

A solution of Int-8d (80 mg, 0.266 mmol) in dichloromethane (8 mL) was treated with Dess-Martin reagent (226 mg, 0.532 mmol) at 0° C. and the mixture was stirred at 20° C. for 2 hours. The mixture was treated with saturated NaHCO$_3$ and the aqueous was extracted with dichloromethane. The combined organic portions were washed with brine and concentrated in vacuo. The resulting residue was purified using preparative TLC on silica gel (10% methanol in dichloromethane) to provide Int-8e. Mass Calc'd for $C_{13}H_{15}ClN_2O_4$: 298.1, found 299.0 (M+H)$^+$.

Step F—Synthesis of Intermediate Compound Int-8f

A solution of Int-8e (90 mg, 0.301 mmol) in dichloromethane (10 mL) was treated with NaHCO$_3$ (50.6 mg, 0.603 mmol) and the mixture was heated at 40° C. for 30 min, cooled to room temperature and concentrated in vacuo. The resulting residue was purified using preparative TLC on silica gel (10% methanol in dichloromethane) to provide Int-8f. $^1$H NMR (400 MHz, CDCl$_3$) δ 6.36 (s, 1H), 4.91-4.93 (m, 1H), 4.30-4.31 (m, 1H), 4.06-4.14 (m, 2H), 3.95 (s, 3H), 3.86-3.88 (m, 1H), 3.64-3.65 (m, 1H), 3.06-3.09 (m, 2H), 2.56-2.58 (m, 1H), 2.09-2.18 (m, 1H). Mass Calc'd for $C_{13}H_{14}N_2O_4$: 262.1, found 263.0 (M+H)$^+$.

Step G—Synthesis of Intermediate Compound Int-8g

To a solution of Int-8f (60 mg, 0.229 mmol) in dichloromethane (8 mL) was added NBS (81 mg, 0.458 mmol) at 0° C. The mixture was stirred at room temperature for 2 hours. The crude was purified directly by preparative TLC on silica gel (5% methanol in dichloromethane) to provide Int-8g. $^1$H NMR (400 MHz, CDCl$_3$) δ 4.94-4.96 (m, 1H), 4.30-4.33 (m, 1H), 4.23-4.25 (m, 1H), 4.09-4.11 (m, 1H), 4.05 (s, 3H), 3.90-3.93 (m, 1H), 3.68-3.69 (m, 1H), 3.14-3.33 (m, 2H), 2.63-2.66 (m, 1H), 2.16-2.23 (m, 1H). Mass Calc'd for $C_{13}H_{13}BrN_2O_4$: 340.0, found 341.2 (M+H)$^+$.

Step H—Synthesis of Intermediate Compound Int-8h

To a solution of Int-8g (10 mg, 0.029 mmol) in dioxane (3 mL) and water (0.3 mL) was added Cs$_2$CO$_3$ (32.5 mg, 0.100 mmol), Pd(Ph$_3$P)$_4$ (6.77 mg, 5.86 μmol) and 1-(2,4-difluorobenzyl)-4-(4,4,5,5-tetramethyl-1,3,2-dioxaborolan-2-yl)-1H-pyrazole (31.9 mg, 0.100 mmol). The mixture was heated with microwave irradiation at 130° C. for 1 hour. The reaction mixture was concentrated in vacuo and purified using preparative TLC on silica gel (methanol/dichloromethane=1/10) to provide Int-8h. $^1$H NMR (400 MHz, CDCl$_3$) δ 8.45 (s, 1H), 7.65 (s, 1H), 7.13-7.16 (m, 1H), 6.74-4.78 (m, 2H), 5.25 (s, 2H), 4.81-4.83 (m, 1H), 4.26-4.27 (m, 1H), 4.12-4.14 (m, 1H), 4.01-4.03 (m, 1H), 3.96 (s, 3H), 3.84-3.86 (m, 1H), 3.60-3.62 (m, 1H), 3.23-3.28 (m, 2H), 2.59-2.64 (m, 1H), 2.02-2.11 (m, 1H). Mass Calc'd for $C_{23}H_{20}F_2N_4O_4$: 454.1, found 455.1 (M+H)$^+$.

Step I—Synthesis of Compound 46

To a solution of Int-8h (12 mg, 0.027 mmol) in N,N-dimethylformamide (4 mL) was added anhydrous lithium chloride (10.92 mg, 0.26 mmol). The mixture was heated to 110° C. for 3 h, cooled to room temperature and purified directly by preparative RP-HPLC to provide compound 46. $^1$H NMR (400 MHz, dimethylsulfoxide-d$_6$) δ 8.47 (s, 1H), 7.89 (s, 1H), 7.23-7.31 (m, 2H), 7.05-7.08 (m, 1H), 5.38 (s, 2H), 4.99-5.02 (m, 1H), 4.36-4.42 (m, 1H), 3.98-4.04 (m, 2H), 3.58-3.72 (m, 2H), 3.42 (s, 1H), 3.24-3.26 (m, 2H), 2.09-2.11 (m, 2H). Mass Calc'd for $C_{22}H_{18}F_2N_4O_4$: 440.1, found 441.2 (M+H)$^+$.

Example 9

Preparation of Compound 47

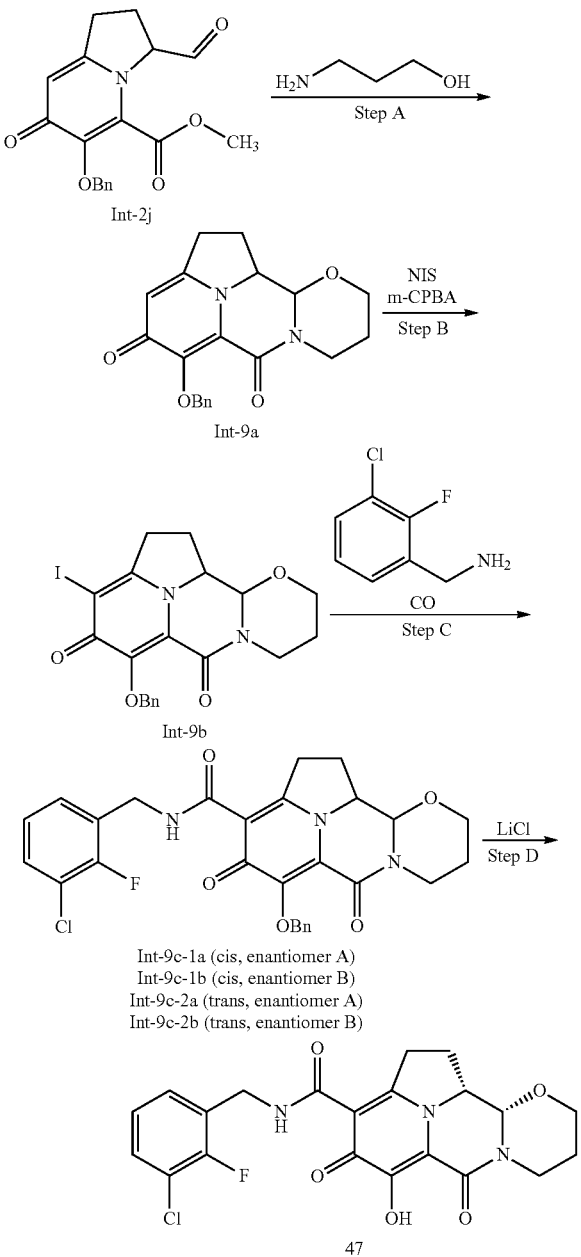

Step A—Synthesis of Intermediate Compound Int-9a

To a mixture of Int-2j (110 mg, 0.336 mmol) and 3-aminopropan-1-ol (75.67 mg, 1.01 mmol) in tetrahydrofuran (5 mL) was added acetic acid (0.05 mL) and the mixture was heated with microwave irradiation at 70° C. for 30 min and then concentrated in vacuo. The resulting residue was purified using preparative TLC on silica gel (methanol/dichloromethane=1/10) to provide Int-9a. $^1$H NMR (400 MHz, CDCl$_3$) δ 7.57-7.59 (m, 2H), 7.23-7.27 (m, 3H), 6.37-6.39 (m, 1H), 5.19-5.23 (m, 2H), 4.79-4.80 (m, 1H), 4.51-4.54 (m, 1H), 4.02-4.08 (m, 2H), 3.50-3.51 (m, 1H), 2.92-2.98 (m, 4H), 2.49-2.50 (m, 1H), 1.89-1.95 (m, 2H). Mass Calc'd for $C_{20}H_{20}N_2O_4$: 352.1, found 353.1 (M+H)$^+$.

Step B—Synthesis of Intermediate Compound Int-9b

To a solution of Int-9a (72.0 mg, 0.20 mmol) in methanol (5 mL) was added N-iodosuccinimide (153.6 mg, 0.68 mmol) and then 3-chlorobenzoperoxoic acid (117.5 mg, 0.68 mmol). The mixture was heated to 70° C. for 3 h and concentrated in vacuo. The resulting residue was dissolved in CHCl$_3$/isopropanol=3/1, washed with sodium sulfite (10 mL) and aqueous NaOH (0.5 N, 10 mL), dried over anhydrous Na$_2$SO$_4$, filtered and the filtrate was concentrated in vacuo. The resulting residue was purified using preparative TLC on silica gel (methanol:dichloromethane=1:10) to provide Int-9b. $^1$H NMR (400 MHz, CDCl$_3$) δ 7.68-7.69 (m, 2H), 7.35-7.36 (m, 3H), 5.28-5.31 (m, 2H), 5.19-5.21 (m, 1H), 4.80-4.83 (m, 1H), 4.58-4.60 (m, 1H), 4.29-4.31 (m, 1H), 4.07-4.10 (m, 1H), 3.53-3.58 (m, 1H), 3.19-3.25 (m, 1H), 3.00-3.04 (m, 2H), 2.10-2.12 (m, 1H), 1.73-1.76 (m, 1H), 1.56-1.58 (m, 1H). Mass Calc'd for C$_{20}$H$_{19}$IN$_2$O$_4$: 478.0, found 479.3 (M+H)$^+$.

Step C—Synthesis of Intermediate Compound Int-9c

To a solution of Int-9b (600 mg, 0.17 mmol) in dimethylsulfoxide (10 mL) was added N,N-diisopropylethylamine (1.096 mL, 6.27 mmol), (3-chloro-2-fluorophenyl)methanamine (601 mg, 3.76 mmol) and Pd(Ph$_3$P)$_4$ (290 mg, 0.251 mmol). The mixture was stirred at 80° C. under carbon monoxide (1 atm) for 1.5 hours. Water (10 mL) was added and the mixture was extracted with ethyl acetate. The combined organic portions were washed with brine, dried over by anhydrous Na$_2$SO$_4$, filtered and the filtrate was concentrated in vacuo. The crude product was purified using preparative TLC on silica gel eluting with EtOAc to provide Int-9c-1 (cis) and Int-9c-2 (trans).

Int-9c-1: $^1$H NMR (400 MHz, CDCl$_3$) δ 10.96 (brs, 1H), 7.64 (d, J=7.2 Hz, 2H), 7.27-7.38 (m, 5H), 7.00-7.02 (m, 1H), 5.28 (s, 2H), 4.93 (d, J=2.8 Hz, 1H), 4.83 (d, J=11.2 Hz, 1H), 4.65-4.68 (m, 2H), 4.42-4.44 (m, 1H), 4.06-4.24 (m, 2H), 3.90-3.92 (m, 1H), 3.30-3.43 (m, 1H), 3.04-3.16 (m, 1H), 2.22-2.46 (m, 2H), 1.81-1.99 (m, 1H), 1.50-1.52 (m, 1H). MS(M+H)$^+$: 538.1.

Int-9c-2: $^1$H NMR (400 MHz, CDCl$_3$) δ 10.94 (brs, 1H), 7.63 (d, J=7.2 Hz, 2H), 7.26-7.39 (m, 5H), 6.99-7.03 (m, 1H), 5.20-5.27 (m, 2H), 4.74 (d, J=8.4 Hz, 1H), 4.56-4.70 (m, 3H), 4.03-4.26 (m, 3H), 3.60-3.62 (m, 1H), 3.29-3.42 (m, 1H), 2.96-2.98 (m, 1H), 2.56-2.67 (m, 1H), 1.93-2.04 (m, 2H), 1.80-1.82 (m, 1H). MS(M+H)$^+$: 538.1.

Resolution of Int-9c-1 (cis) to the enantiomers was accomplished with SFC (Column: AS 250×30 mm I.D., 10 μm, condition: Base-MeOH, Begin B 40%, Flow Rate: 70 mL/min, Injections: 80, Wavelength: 220 nm) to provide Int-9c-1a (cis, enantiomer A) and Int-9c-1b (cis, enantiomer B)

Int-9c-1a: $^1$H NMR (400 MHz, CDCl$_3$) δ 10.96 (brs, 1H), 7.64 (d, J=7.2 Hz, 2H), 7.27-7.38 (m, 5H), 7.00-7.02 (m, 1H), 5.28 (s, 2H), 4.93 (d, J=2.8 Hz, 1H), 4.83 (d, J=11.2 Hz, 1H), 4.65-4.68 (m, 2H), 4.42-4.44 (m, 1H), 4.06-4.24 (m, 2H), 3.90-3.92 (m, 1H), 3.30-3.43 (m, 1H), 3.04-3.16 (m, 1H), 2.22-2.46 (m, 2H), 1.81-1.99 (m, 1H), 1.50-1.52 (m, 1H). MS(M+H)$^+$: 538.1.

Int-9c-1b: $^1$H NMR (400 MHz, CDCl$_3$) δ 10.89 (brs, 1H), 7.57 (d, J=7.2 Hz, 2H), 7.20-7.32 (m, 5H), 6.95-6.96 (m, 1H), 5.20 (d, J=1.6 Hz, 2H), 4.85 (d, J=3.2 Hz, 1H), 4.74 (d, J=8.8 Hz, 1H), 4.53-4.67 (m, 2H), 4.33-4.43 (m, 1H), 3.98-4.17 (m, 2H), 3.83-3.85 (m, 1H), 3.2-13.35 (m, 1H), 2.97-3.08 (m, 1H), 2.13-2.37 (m, 2H), 1.81-1.99 (m, 1H), 1.42-1.46 (m, 1H). MS(M+H)$^+$: 538.1.

Resolution of Int-9c-2 (trans) to the enantiomers was accomplished with SFC (Column: AS 250×30 mm I.D., 10 μm, condition: Base-MeOH, Begin B 35%, Flow Rate: 70 mL/min, Injections: 120, Wavelength: 220 nm) to provide Int-9c-2a (trans, enantiomer A) and Int-9c-2b (trans, enantiomer B).

Int-9c-2a: $^1$H NMR (400 MHz, CDCl$_3$) δ 10.91 (brs, 1H), 7.64 (d, J=7.2 Hz, 2H), 7.27-7.39 (m, 5H), 6.99-7.08 (m, 1H), 5.18-5.28 (m, 2H), 4.75 (d, J=8.8 Hz, 1H), 4.67 (d, J=5.2 Hz, 2H), 4.61 (d, J=13.2 Hz, 1H), 4.04-4.25 (m, 3H), 3.55-3.58 (m, 1H), 3.33-3.36 (m, 1H), 2.88-3.04 (m, 1H), 2.55-2.71 (m, 1H), 1.98-2.01 (m, 2H), 1.75-1.78 (m, 1H). MS(M+H)$^+$: 538.1.

Int-9c-2b: $^1$H NMR (400 MHz, CDCl$_3$) δ 10.91 (brs, 1H), 7.64 (d, J=7.2 Hz, 2H), 7.27-7.39 (m, 5H), 6.99-7.08 (m, 1H), 5.18-5.28 (m, 2H), 4.75 (d, J=8.8 Hz, 1H), 4.67 (d, J=5.2 Hz, 2H), 4.61 (d, J=13.2 Hz, 1H), 4.04-4.25 (m, 3H), 3.55-3.58 (m, 1H), 3.33-3.36 (m, 1H), 2.88-3.04 (m, 1H), 2.55-2.71 (m, 1H), 1.98-2.01 (m, 2H), 1.75-1.78 (m, 1H). MS(M+H)$^+$: 538.1.

Step D—Synthesis of Compound 47

To a solution of Int-9c-1b (cis, enantiomer B) (70 mg, 0.130 mmol) in N,N-dimethylformamide (3 mL) was added lithium chloride (55.2 mg, 1.301 mmol). The resulting solution was heated at 75° C. for 3 h. It was cooled to room temperature and filtered. The filtrate was purified using preparative RP-HPLC to provide compound 47. $^1$H NMR (400 MHz, CDCl$_3$) δ 10.87 (s, 1H), 7.26-7.32 (m, 2H), 7.00-7.02 (m, 1H), 5.03 (d, J=2.8 Hz, 1H), 4.78 (d, J=9.2 Hz, 1H), 4.66 (d, J=4.8 Hz, 2H), 4.45-4.50 (m, 1H), 4.21-4.24 (m, 1H), 4.04-4.07 (m, 1H), 3.94-3.97 (m, 1H), 3.33-3.36 (m, 1H), 3.09-3.24 (m, 1H), 2.24-2.46 (m, 2H), 1.94-2.11 (m, 1H), 1.59-1.62 (m, 1H). MS(M+H)$^+$: 448.0.

The following compounds of the present invention were made using the methodology described in Example 9, and substituting the appropriate reactants and/or reagents.

| Compound | Structure | Stereochemistry | Exact Mass [M + H]$^+$ |
|---|---|---|---|
| 48 | 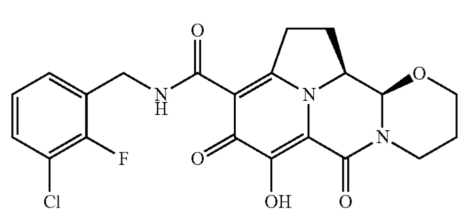 [SMILES: O=C(NCc1cccc(Cl)c1F)c1c2n3c(c(O)c1=O)C(=O)N1CCCO[C@@H]1[C@@H]3CC2] | cis, enantiomer A | Calc'd 448.1, found 448.0 |

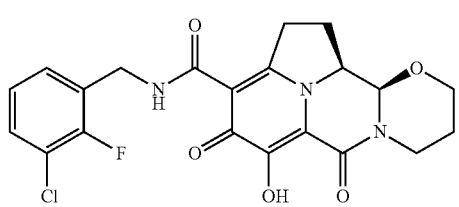

-continued

| Compound | Structure | Stereochemistry | Exact Mass [M + H]+ |
|---|---|---|---|
| 49 | 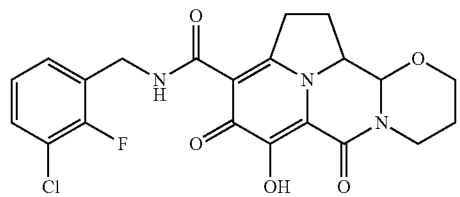 [SMILES: O=C(NCc1cccc(Cl)c1F)c1c2n3c(c(O)c1=O)C(=O)N1CCCOC1C3CC2] | trans, enantiomer A | Calc'd 448.1, found 448.0 |
| 50 | 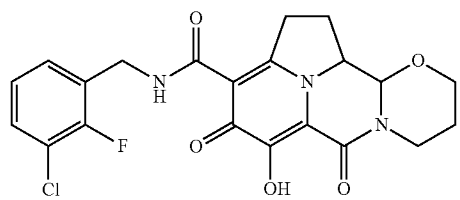 [SMILES: O=C(NCc1cccc(Cl)c1F)c1c2n3c(c(O)c1=O)C(=O)N1CCCOC1C3CC2] | trans, enantiomer B | Calc'd 448.1, found 448.0 |
| 51 | 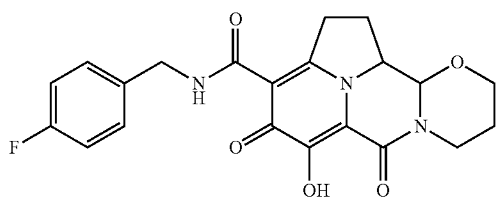 [SMILES: O=C(NCc1ccc(F)cc1)c1c2n3c(c(O)c1=O)C(=O)N1CCCOC1C3CC2] | cis, enantiomer A | Calc'd 414.1, found 414.1 |
| 52 | 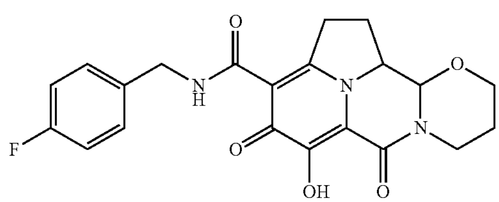 [SMILES: O=C(NCc1ccc(F)cc1)c1c2n3c(c(O)c1=O)C(=O)N1CCCOC1C3CC2] | cis, enantiomer B | Calc'd 414.1, found 414.1 |
| 53 | 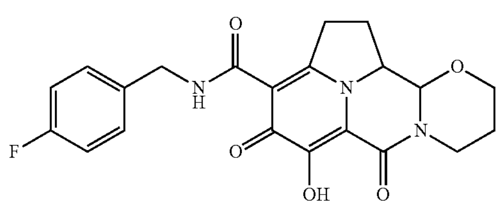 [SMILES: O=C(NCc1ccc(F)cc1)c1c2n3c(c(O)c1=O)C(=O)N1CCCOC1C3CC2] | trans, enantiomer A | Calc'd 414.1, found 414.1 |
| 54 | 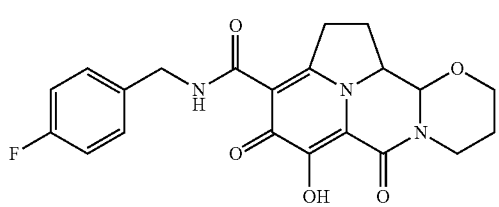 [SMILES: O=C(NCc1ccc(F)cc1)c1c2n3c(c(O)c1=O)C(=O)N1CCCOC1C3CC2] | trans, enantiomer B | Calc'd 414.1, found 414.1 |
| 55 | 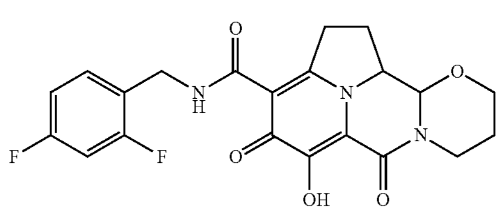 [SMILES: O=C(NCc1ccc(F)cc1F)c1c2n3c(c(O)c1=O)C(=O)N1CCCOC1C3CC2] | cis, enantiomer A | Calc'd 432.1, found 432.2 |

| Compound | Structure | Stereochemistry | Exact Mass [M + H]+ |
|---|---|---|---|
| 56 | 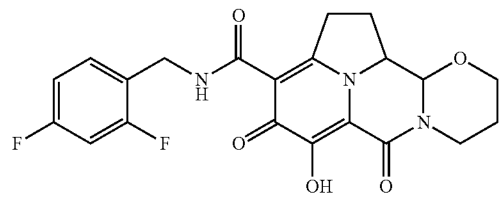 [SMILES: O=C(NCc1ccc(F)cc1F)c1c2n3c(c(O)c1=O)C(=O)N1CCCOC1C3CC2] | cis, enantiomer B | Calc'd 432.1, found 432.2 |
| 57 | 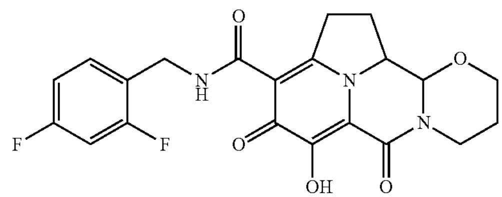 [SMILES: O=C(NCc1ccc(F)cc1F)c1c2n3c(c(O)c1=O)C(=O)N1CCCOC1C3CC2] | trans, enantiomer A | Calc'd 432.1, found 432.2 |
| 58 | 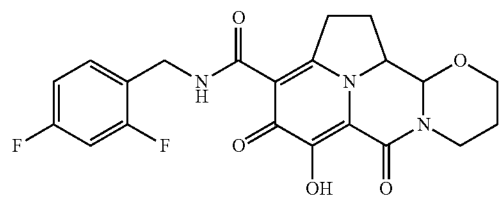 [SMILES: O=C(NCc1ccc(F)cc1F)c1c2n3c(c(O)c1=O)C(=O)N1CCCOC1C3CC2] | trans, enantiomer B | Calc'd 432.1, found 432.2 |
| 59 | 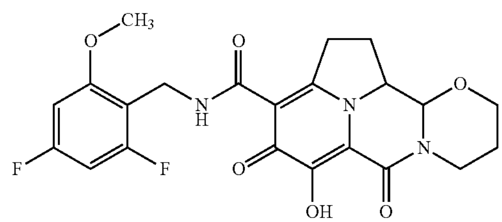 [SMILES: COc1cc(F)cc(F)c1CNC(=O)c1c2n3c(c(O)c1=O)C(=O)N1CCCOC1C3CC2] | cis, racemate | Calc'd 462.1, found 462.1 |

| Compound | 1H NMR |
|---|---|
| 48 | 1H NMR (400 MHz, CDCl3) δ 10.87 (s, 1H), 7.26-7.28 (m, 2H), 6.96-7.06 (m, 1H), 5.02 (d, J = 2.8 Hz, 1H), 4.79 (d, J = 10.8 Hz, 1H), 4.67 (d, J = 5.2 Hz, 2H), 4.44-4.46 (m, 1H), 4.19-4.28 (m, 1H), 4.06-4.09 (m, 1H), 3.94-3.96 (m, 1H), 3.32-3.35 (m, 1H), 3.15-3.18 (m, 1H), 2.24-2.45 (m, 2H), 1.95-2.12 (m, 1H), 1.59-1.62 (m, 1H). |
| 49 | 1H NMR (400 MHz, CDCl3) δ 10.81 (s, 1H), 7.27-7.32 (m, 2H), 6.99-7.07 (m, 1H), 4.93 (d, J = 8.4 Hz, 1H), 4.55-4.75 (m, 3H), 4.13-4.28 (m, 2H), 4.01-4.03 (m, 1H), 3.71-3.74 (m, 1H), 3.26-3.40 (m, 1H), 3.05-3.08 (m, 1H), 2.53-2.68 (m, 1H), 1.93-2.13 (m, 2H), 1.79-1.85 (m, 1H). |
| 50 | 1H NMR (400 MHz, CDCl3) δ 10.86 (s, 1H), 7.27-7.32 (m, 2H), 6.99-7.08 (m, 1H), 4.89 (d, J = 8.8 Hz, 1H), 4.53-4.73 (m, 3H), 4.17-4.28 (m, 2H), 4.06-4.10 (m, 1H), 3.70-3.72 (m, 1H), 3.28-3.44 (m, 1H), 3.01-3.05 (m, 1H), 2.57-2.73 (m, 1H), 1.94-2.19 (m, 2H), 1.78-1.84 (m, 1H). |
| 51 | 1H NMR (400 MHz, CDCl3) δ 10.84 (s, 1H), 7.28-7.31 (m, 2H), 6.95-6.99 (m, 2H), 5.00-5.05 (d, J = 2.0 Hz, 1H), 4.75-4.77 (m, 1H), 4.55-4.57 (m, 2H), 4.46 (m, 1H), 4.20-4.24 (m, 1H), 4.06 (m, 1H), 3.94-3.97 (t, 1H), 3.19-3.20 (m, 1H), 3.13-3.16 (m, 1H), 2.27-2.35 (m, 2H), 2.00-2.03 (m, 1H), 1.58-1.62 (m, 1H). |
| 52 | 1H NMR (400 MHz, CDCl3) δ 10.87 (s, 1H), 7.28-7.31 (m, 2H), 6.95-7.00 (m, 2H), 5.02 (d, J = 3.2 Hz, 1H), 4.76-4.79 (m, 1H), 4.55-4.56 (m, 2H), 4.45 (m, 1H), 4.21-4.25 (m, 1H), 3.98 (m, 1H), 3.95-3.98 (m, 1H), 3.17-3.20 (m, 1H), 3.14-3.18 (m, 1H), 2.30-2.37 (m, 2H), 2.01-2.04 (m, 1H), 1.59-1.63 (m, 1H). |
| 53 | 1H NMR (400 MHz, CDCl3) δ 10.79 (s, 1H), 7.29-7.32 (m, 2H), 6.96-7.00 (m, 2H), 4.86-4.88 (d, J = 8.4 Hz, 1H), 4.54-4.60 (m, 3H), 4.11-4.20 (m, 2H), 4.04-4.06 (m, 1H), 3.69-3.72 (m, 1H), 3.35-3.38 (m, 1H), 3.02-3.03 (m, 1H), 2.59-2.62 (m, 1H), 1.94-2.05 (m, 2H), 1.80-1.83 (m, 1H). |
| 54 | 1H NMR (400 MHz, CDCl3) δ 10.79 (s, 1H), 7.29-7.32 (m, 2H), 6.96-7.00 (m, 2H), 4.87-4.89 (d, J = 8.4 Hz, 1H), 4.56-4.60 (m, 3H), 4.16-4.20 (m, 2H), 4.03-4.08 (m, 1H), 3.69-3.73 (m, 1H), 3.34 (m, 1H), 3.03-3.04 (m, 1H), 2.59-2.62 (m, 1H), 1.97-2.08 (m, 2H), 1.80-1.83 (m, 1H). |
| 55 | 1H NMR (400 MHz, CDCl3) δ 10.92 (s, 1H), 7.41-7.42 (m, 1H), 6.85-6.87 (m, 2H), 5.09-5.10 (m, 1H), 4.84-4.87 (m, 1H), 4.67-4.68 (m, 1H), 4.52-4.56 (m, 2H), 4.51-4.53 (m, 1H), 4.29-4.30 (m, 1H), 4.14-4.16 (m, 1H), 4.00-4.06 (m, 1H), 3.43-3.45 (m, 1H), 3.21-3.28 (m, 1H), 2.37-2.46 (m, 1H), 2.08-2.14 (m, 1H), 1.67-1.71 (m, 1H). |
| 56 | 1H NMR (400 MHz, CDCl3) δ 10.92 (s, 1H), 7.41-7.42 (m, 1H), 6.85-6.87 (m, 2H), 5.09-5.10 (m, 1H), 4.84-4.87 (m, 1H), 4.67-4.68 (m, 1H), 4.52-4.56 (m, 2H), 4.51-4.53 (m, 1H), 4.29-4.30 (m, 1H), 4.14-4.16 (m, 1H), 4.00-4.06 (m, 1H), 3.43-3.45 (m, 1H), 3.21-3.28 (m, 1H), 2.37-2.46 (m, 1H), 2.08-2.14 (m, 1H), 1.67-1.71 (m, 1H). |

-continued

| Compound | ¹H NMR |
|---|---|
| 57 | ¹H NMR (400 MHz, CDCl₃) δ 10.84 (s, 1H), 7.34-7.35 (m, 1H), 6.77-6.81 (m, 2H), 4.86-4.89 (m, 1H), 4.60-4.61 (m, 3H), 4.20-4.22 (m, 2H), 4.06-4.11 (m, 1H), 3.70-3.73 (m, 1H), 3.43-3.48 (m, 1H), 3.02-3.06 (m, 1H), 2.63-2.66 (m, 1H), 2.02-2.06 (m, 2H), 1.84-1.86 (m, 1H). |
| 58 | ¹H NMR (400 MHz, CDCl₃ δ 10.84 (s, 1H), 7.34-7.35 (m, 1H), 6.77-6.81 (m, 2H), 4.86-4.89 (m, 1H), 4.60-4.61 (m, 3H), 4.20-4.22 (m, 2H), 4.06-4.11 (m, 1H), 3.70-3.73 (m, 1H), 3.43-3.48 (m, 1H), 3.02-3.06 (m, 1H), 2.63-2.66 (m, 1H), 2.02-2.06 (m, 2H), 1.84-1.86 (m, 1H). |
| 59 | ¹H NMR (400 MHz, CDCl₃) δ 6.41-6.43 (m, 2H), 4.83-4.86 (m, 1H), 4.58-4.60 (m, 3H), 4.15-4.18 (m, 3H), 3.88 (s, 3H), 3.66-3.72 (m, 1H), 3.40-3.42 (m, 2H), 2.65-2.66 (m, 2H), 2.62-2.63 (m, 1H), 1.81-1.93 (m, 3H). |

Example 10

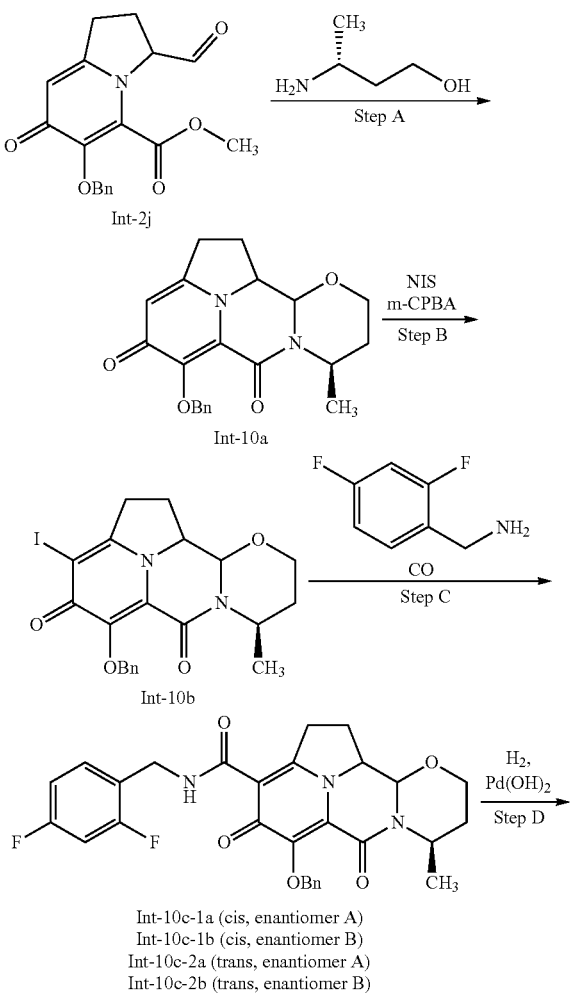

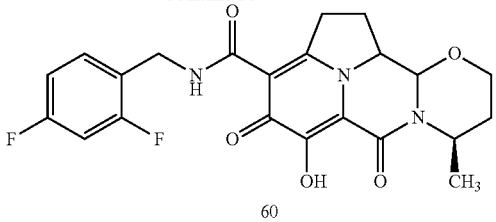

Step A—Synthesis of Intermediate Compound Int-10a

To a solution of Int-2j (1.00 g, 3.06 mmol) in tetrahydrofuran (40 mL) was added acetic acid (0.4 mL) and (S)-3-aminobutan-1-ol (2.72 g, 30.6 mmol). The mixture was stirred at 80° C. for 3 h, cooled to room temperature and purified directly by preparative RP-HPLC to provide Int-10a. ¹H NMR (400 MHz, CDCl₃) δ 7.57-7.68 (m, 2H), 7.27-7.36 (m, 3H), 6.38-6.47 (m, 1H), 5.30 (d, J=2.8 Hz, 1H), 5.07 (d, J=2.8 Hz, 1H), 4.81-4.98 (m, 1H), 4.27-4.41 (m, 1H), 3.77-4.18 (m, 3H), 2.90-3.11 (m, 2H), 2.35-2.62 (m, 1H), 2.13-2.30 (m, 1H), 1.93-2.10 (m, 2H), 1.19-1.25 (m, 3H); Mass Calc'd for $C_{21}H_{22}N_2O_4$: 366.2, found 367.2 $(M+H)^+$.

Step B—Synthesis of Intermediate Compound Int-10b

To a solution of Int-10a (50 mg, 0.136 mmol) in methanol (3 mL) was added 3-chlorobenzoperoxoic acid (118 mg, 0.546 mmol) and N-iodosuccinimide (123 mg, 0.546 mmol). The mixture was stirred at 80° C. for 2 h, cooled to rt, quenched with saturated aqueous $Na_2SO_3$ (5 mL) and extracted with ethyl acetate (20 mL×3). The organic phase was dried over anhydrous $Na_2SO_4$, filtered and the filtrate was concentrated in vacuo. The resulting residue was purified using column chromatography on silica gel (DCM:methanol=20:1) to provide Int-10b. ¹H NMR (400 MHz, CDCl₃) δ 7.62-7.71 (m, 2H), 7.26-7.38 (m, 3H), 5.14-5.34 (m, 2H), 4.82-4.98 (m, 2H), 4.25-4.33 (m, 1H), 3.97-4.07 (m, 1H), 3.86-3.96 (m, 1H), 3.13-3.25 (m, 1H), 2.96-3.12 (m, 1H), 2.34-2.59 (m, 1H), 1.99-2.26 (m, 2H), 1.32-1.37 (m, 1H), 1.23 (d, J=6.4 Hz, 3H). Mass Calc'd for $C_{21}H_{21}IN_2O_4$: 492.1, found 493.2 $(M+H)^+$.

Step C—Synthesis of Intermediate Compound Int-10e

To a solution of Int-10b (150 mg, 0.305 mmol) in dimethylsulfoxide (3 mL) was added 2,4-difluorobenzylamine (436 mg, 3.05 mmol), N,N-diisopropylethylamine (0.266 mL, 1.523 mmol) and $Pd(PPh_3)_4$ (70.4 mg, 0.061 mmol). The mixture was stirred at 80° C. for 2 h under carbon monoxide (1 atm), cooled to room temperature and diluted with ethyl acetate (80 mL×2). The organic phase was washed with 0.5 N aqueous HCl (10 mL) and brine, dried over anhydrous $Na_2SO_4$, filtered and the filtrate was concentrated in vacuo. The resulting residue was purified using preparative TLC on silica gel (100% ethyl acetate) to provide compound Int-10c-1 (cis) and compound Int-10c-2 (trans).

Int-10c-1: ¹H NMR (400 MHz, CDCl₃) δ 10.92 (s, 1H), 7.64 (d, J=7.2 Hz, 2H), 7.28-7.40 (m, 4H), 6.74-6.86 (m, 2H), 5.13 (d, J=6.4 Hz, 1H), 5.10 (d, J=3.2 Hz, 1H), 4.89 (d, J=8.4 Hz, 1H), 4.54-4.68 (m, 2H), 4.34-4.37 (m, 2H), 4.01-4.15 (m, 2H), 3.86-3.99 (m, 1H), 3.31-3.43 (m, 1H), 2.23-2.46 (m, 2H), 2.01-2.17 (m, 2H), 1.43 (d, J=7.2 Hz, 3H); Mass Calc'd for $C_{29}H_{27}F_2N_3O_5$: 535.2, found 536.2 $(M+H)^+$.

Int-10c-2: ¹H NMR (400 MHz, CDCl₃) δ 10.88 (s, 1H), 7.60 (d, J=7.2 Hz, 2H), 7.27-7.39 (m, 4H), 6.74-6.86 (m, 2H), 5.22-5.32 (m, 2H), 4.89-4.95 (m, 1H), 4.60 (d, J=6 Hz, 2H), 4.04-4.22 (m, 3H), 3.89-3.99 (m, 1H), 3.79-3.89 (m, 1H), 3.24-3.41 (m, 1H), 2.55-2.70 (m, 1H), 2.14-2.28 (m, 1H), 1.96-2.02 (m, 1H), 1.56-1.59 (m, 1H), 1.24-1.25 (m, 3H); Mass Calc'd for $C_{29}H_{27}F_2N_3O_5$: 535.2, found 536.2 $(M+H)^+$.

Separation of Int-10c-1(cis) to the diastereomers was accomplished with SFC (Chralpak AS, 250×30 mm, 5 μm, 30% methanol (0.1% $NH_3·H_2O$) in $SC-CO_2$, 60 mL/min, 38° C., 220 nm) to provide Int-10c-1a (cis, diastereomer A) and Int-10c-1b (cis, diastereomer B).

Int-10c-1a: $^1$H NMR (400 MHz, CDCl$_3$) δ 10.92 (s, 1H), 7.64 (d, J=6.8 Hz, 2H), 7.28-7.40 (m, 4H), 6.76-6.83 (m, 2H), 5.22-5.32 (m, 2H), 5.07-5.17 (m, 2H), 4.52-4.68 (m, 2H), 4.22-4.37 (m, 1H), 4.01-4.15 (m, 2H), 3.92-3.96 (m, 1H), 3.32-3.39 (m, 1H), 2.24-2.47 (m, 2H), 2.10-2.16 (m, 2H), 1.43 (d, J=7.2 Hz, 3H).

Int-10c-1b: $^1$H NMR (400 MHz, CDCl$_3$) δ 11.04 (s, 1H), 7.59 (d, J=6.8 Hz, 2H), 7.31-7.41 (m, 4H), 6.74-6.87 (m, 2H), 5.22 (s, 2H), 4.73 (s, 1H), 4.61 (d, J=4 Hz, 2H), 4.43-4.49 (m 1H), 4.03-4.20 (m, 2H), 3.89-3.94 (m, 1H), 3.50-3.55 (m, 1H), 3.30-3.43 (m, 1H), 2.17-2.27 (m, 2H), 1.98-2.14 (m, 2H), 1.82 (d, J=6.8 Hz, 3H).

Separation of Int-10c-2 (trans) to the diastereomers was accomplished with SFC (Chralpak AS, 250×30 mm, 5 μm, 30% methanol 0.1% $NH_3H_2O$) in $SC-CO_2$, 60 mL/min, 38° C., 220 nm) to provide Int-10c-2a (trans, diastereomer A) and Int-10c-2b (trans, diastereomer B).

Int-10c-2a: $^1$H NMR (400 MHz, CDCl$_3$) δ 10.84 (s, 1H), 7.60 (d, J=7.2 Hz, 2H), 7.26-7.39 (m, 4H), 6.74-6.85 (m, 2H), 5.12 (d, J=8.8 Hz, 2H), 5.0 (s, 1H), 4.33-4.66 (m, 4H), 3.76-3.87 (m, 3H), 3.17-3.20 (m, 1H), 2.38-2.40 (m, 1H), 1.94-2.03 (m, 2H), 1.55-1.58 (m, 1H), 1.23 (d, J 7.2 Hz, 3H).

Int-10c-2b: $^1$H NMR (400 MHz, CDCl$_3$) δ 10.90 (s, 1H), 7.62 (d, J=7.2 Hz, 2H), 7.28-7.40 (m, 4H), 6.75-6.86 (m, 2H), 5.30 (d, J=9.6 Hz, 1H), 5.19 (d, J=9.6 Hz, 1H), 4.86 (d, J=8.8 Hz, 1H), 4.58-4.64 (m, 2H), 4.06-4.16 (m, 4H), 3.70-3.72 (m, 1H), 3.33-3.42 (m, 1H), 2.52-2.60 (m, 2H), 1.88-1.98 (m, 2H), 1.24 (d, J=3.6 Hz, 3H).

Step D—Synthesis of Compound 60

To a solution of Int-10c-1a (cis, diastereomer A) (50 mg, 0.093 mmol) in tetrahydrofuran (10 mL) was added Pd—C (19.87 mg, 0.019 mmol). The mixture was stirred at 30° C. for 30 min under hydrogen (1 atm). The mixture was filtered and the filtrate was concentrated in vacuo. The resulting residue was purified using preparative RP-HPLC to provide compound 60. $^1$H NMR (400 MHz, CDCl$_3$) δ 10.87 (s, 1H), 7.29-7.42 (m, 1H), 6.71-6.89 (m, 2H), 5.22 (d, J=3.2 Hz, 1H), 5.08-5.20 (d, J=3.2 Hz 1H), 4.61 (d, J=4.8 Hz, 2H), 4.40-4.44 (m, 1H), 4.02-4.16 (m, 3H), 3.35-3.40 (m, 1H), 2.31-2.43 (m, 2H), 2.17-2.19 (m, 1H), 1.47-1.50 (m, 4H). Mass Calc'd for $C_{22}H_{21}F_2N_3O_5$: 445.1, found 446.2 $(M+H)^+$.

The following compounds of the present invention were made using the methodology described in Example 10, and substituting the appropriate reactants and/or reagents.

| Compound | Structure | Stereochemistry | Exact Mass [M + H]+ |
|---|---|---|---|
| 61 | 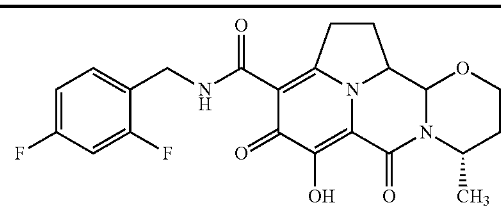 | cis, diastereomer B | Calc'd 446.2, found 446.2 |
| 62 | 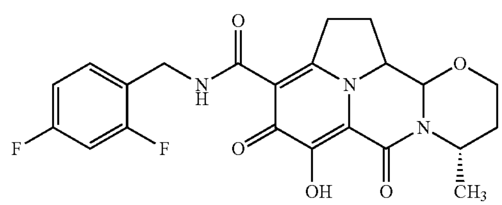 [SMILES: C[C@H]1CCOC2C3CCc4c(C(=O)NCc5ccc(F)cc5F)c(=O)c(O)c(n43)C(=O)N21] | trans, diastereomer A | Calc'd 446.2, found 446.2 |
| 63 | 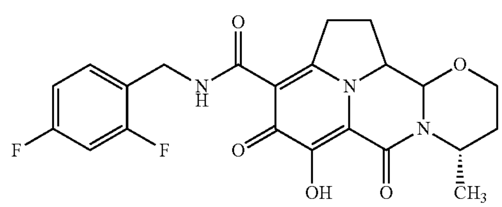 [SMILES: C[C@H]1CCOC2C3CCc4c(C(=O)NCc5ccc(F)cc5F)c(=O)c(O)c(n43)C(=O)N21] | trans, diastereomer B | Calc'd 446.2, found 446.2 |

| Compound | $^1$H NMR |
|---|---|
| 61 | $^1$H NMR (400 MHz, CDCl$_3$) δ 10.84 (s, 1H), 7.32-7.38 (m, 1H), 6.74-6.83 (m, 2H), 4.83-4.87 (m, 1H), 4.58-4.63 (m, 2H), 4.20-4.43 (m, 3H), 3.89-3.99 (m, 1H), 3.56-3.64 (m, 1H), 2.32-2.39 (m, 2H), 2.11-2.16 (m, 3H), 1.85 (d, J = 7.2 Hz, 3H). |
| 62 | $^1$H NMR (400 MHz, CDCl$_3$) δ 10.80 (s, 1H), 7.31-7.41 (m, 1H), 6.74-6.85 (m, 2H), 4.99 (d, J = 8.4 Hz, 1H), 4.79-4.89 (m, 1H), 4.60-4.84 (m, 2H), 3.96-4.10 (m, 4H), 3.29-3.43 (m, 1H), 2.60-2.68 (m, 1H), 2.21-2.30 (m, 1H), 1.99-2.06 (m, 1H), 1.60-1.63 (m, 1H), 1.34 (d, J = 6.8 Hz, 3H). |
| 63 | $^1$H NMR (400 MHz, CDCl$_3$) δ 10.81 (s, 1H), 7.31-7.35 (m, 1H), 6.74-6.84 (m, 2H), 5.06 (d, J = 8.8 Hz, 1H), 4.55-4.64 (m, 3H), 4.05-4.20 (m, 4H), 3.34-3.37 (m, 1H), 2.57-2.64 (m, 1H), 2.32-2.36 (m, 1H), 1.97-1.99 (m, 2H), 1.48 (d, J = 6.4 Hz, 3H). |

Example 11

Preparation of Compound 64

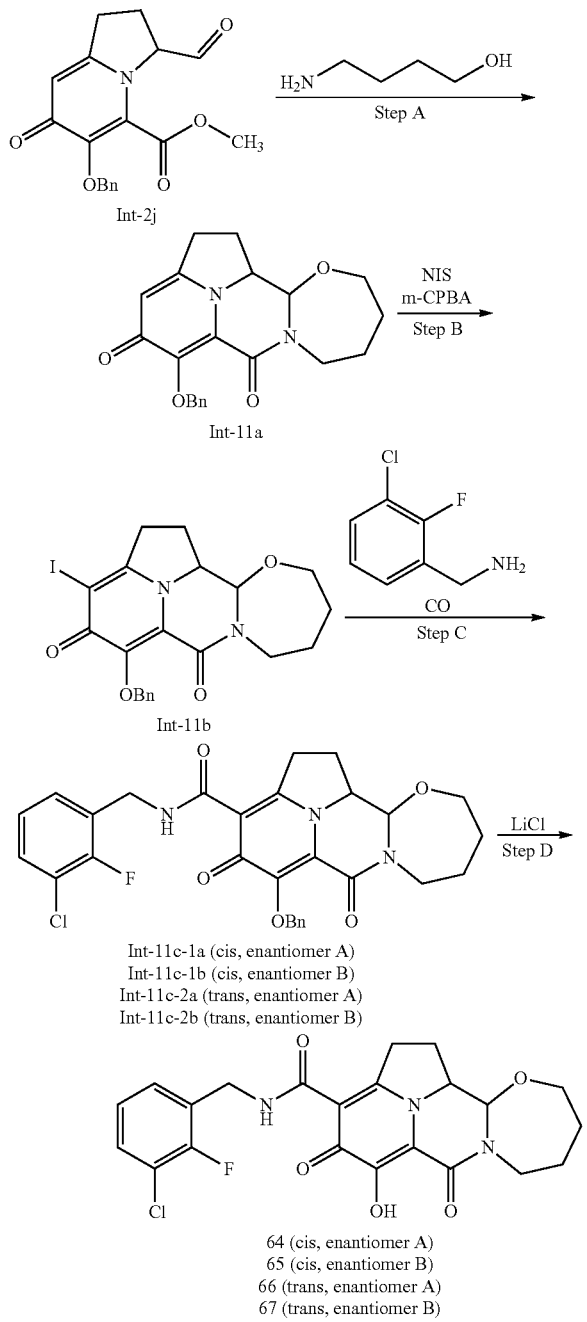

Int-11c-1a (cis, enantiomer A)
Int-11c-1b (cis, enantiomer B)
Int-11c-2a (trans, enantiomer A)
Int-11c-2b (trans, enantiomer B)

64 (cis, enantiomer A)
65 (cis, enantiomer B)
66 (trans, enantiomer A)
67 (trans, enantiomer B)

Step A—Synthesis of Intermediate Compound Int-11a

To a mixture of Int-2j (400 mg, 1.22 mmol) in tetrahydrofuran (20 mL) was added acetic acid (0.3 mL) and 4-aminobutan-1-ol (1089 mg, 12.22 mmol). The mixture was stirred at 80° C. for 2.5 h, cooled to room temperature and concentrated in vacuo. The resulting residue was purified using column chromatography on silica gel (dichloromethane:methanol=15:1) to provide Int-11a. $^1$H NMR (400 MHz, CDCl$_3$) δ 7.54-7.58 (m, 2H), 7.22-7.26 (m, 3H), 6.35 (s, 1H), 5.30-5.43 (m, 1H), 5.15-5.21 (m, 1H), 4.69-4.74 (m, 1H), 4.34-4.50 (m, 1H), 4.13-4.15 (m, 2H), 3.97-4.03 (m, 1H), 3.51-3.56 (m, 2H), 2.94-2.97 (m, 2H), 2.28-2.34 (m, 2H), 1.82-2.03 (m, 3H). Mass Calc'd for C$_{21}$H$_{22}$N$_2$O$_4$: 366.2, found 367.1 (M+H)$^+$.

Step B—Synthesis of Intermediate Compound Int-11b

To a mixture of Int-11a (200 mg, 0.547 mmol) in methanol (20 mL) was added meta-chloroperoxybenzoic acid (m-CPBA) (472 mg, 3.28 mmol) and N-iodosuccinimide (493 mg, 3.28 mmol). The mixture was stirred at 80° C. for 2 h, cooled to rt, quenched with saturated aqueous NaHSO$_3$ (5 mL) and extracted with ethyl acetate. The organic phase was dried over anhydrous Na$_2$SO$_4$, filtered and the filtrate was concentrated in vacuo. The resulting residue was purified using column chromatography on silica gel (dichloromethane:methanol=20:1) to provide Int-11b. $^1$H NMR (400 MHz, CDCl$_3$) δ 7.65-7.67 (m, 2H), 7.28-7.32 (m, 3H), 5.32-5.35 (m, 1H), 5.15-5.17 (m, 1H), 4.82-4.85 (m, 1H), 4.36-4.40 (m, 1H), 4.17-4.20 (m, 1H), 4.09-4.13 (m, 1H), 3.58-3.63 (m, 2H), 3.16-3.23 (m, 1H), 2.51-2.52 (m, 2H), 1.84-1.88 (m, 2H), 1.72-1.77 (m, 2H), 1.66-1.68 (m, 1H). Mass Calc'd for C$_{21}$H$_{21}$IN$_2$O$_4$: 492.1, found 493.1 (M+H)$^+$.

Step C—Synthesis of Intermediate Compound Int-11e

To a solution of Int-11b in dimethylsulfoxide (4 mL) was added 3-chloro-2-fluorobenzylamine (324 mg, 2.031 mmol), N,N-diisopropylethylamine (263 mg, 2.031 mmol) and Pd(Ph$_3$P)$_4$ (94 mg, 0.081 mmol). The mixture was stirred at 80° C. for 2 h under carbon monoxide (1 atm). The mixture was cooled to room temperature and diluted with ethyl acetate (80 mL) and filtered. The organic phase was washed with aqueous HCl (0.2 M, 10 mL) and brine, dried over anhydrous Na$_2$SO$_4$, filtered and the filtrate was concentrated in vacuo. The resulting residue was purified using preparative TLC on silica gel (100% ethyl acetate) to provide Int-11c-1 (cis) and Int-11c-2 (trans).

Int-11c-1: $^1$H NMR (400 MHz, CDCl$_3$) δ 10.94 (s, 1H), 7.55 (d, J=7.2 Hz, 2H), 7.22-7.30 (m, 4H), 6.91-7.02 (m, 2H), 5.15-5.36 (m, 2H), 4.75-4.83 (m, 2H), 4.55-4.65 (m, 2H), 4.36-4.46 (m, 2H), 3.98-4.07 (m, 2H), 3.52-3.69 (m, 1H), 3.28-3.31 (m, 1H), 2.18-2.29 (m, 2H), 1.84-2.09 (m, 4H). Mass Calc'd for C$_{29}$H$_{27}$ClFN$_3$O$_5$: 551.2, found 552.1 (M+H)$^+$.

Int-11c-2: $^1$H NMR (400 MHz, CDCl$_3$) δ 10.88 (s, 1H), 7.55 (d, J=7.2 Hz, 2H), 7.21-7.33 (m, 4H), 6.89-7.01 (m, 2H), 5.14-5.27 (m, 2H), 4.72 (d, J=8.8 Hz, 1H), 4.61 (s, 2H), 4.11-4.24 (m, 3H), 3.98-4.10 (m, 2H), 3.61-3.66 (m, 1H), 3.28 (s, 1H), 2.45-2.53 (m, 2H), 2.13-2.27 (m, 4H). Mass Calc'd for C$_{29}$H$_{27}$ClFN$_3$O$_5$: 551.2, found 552.1 (M+H)$^+$.

Resolution of Int-11c-1 to the enantiomers was accomplished with SFC (Chiralpak AS, 250×30 mm, 20 μm, 40% methanol (0.1% NH$_3$.H$_2$O) in SC—CO$_2$, 80 mL/min, 220 nm) to provide Int-11c-1a (cis, enantiomer A) and Int-11c-1b (cis, enantiomer B).

Resolution of Int-11c-2 to the enantiomers was accomplished with SFC (Chiralpak AS, 250×30 mm, 20 μm, 40% methanol (0.1% NH$_3$.H$_2$O) in SC—CO$_2$, 80 mL/min, 220 nm) to provide Int-11c-2a (trans, enantiomer A) and Int-11c-2b (trans, enantiomer B).

Step D—Synthesis of Compound 64

To a solution of compound Int-11e-1a (cis, enantiomer A) (10 mg, 0.02 mmol) in N,N-dimethylformamide (3 mL) was added lithium chloride (7.9 mg, 0.18 mmol). The mixture was stirred at 80° C. for 4 h, cooled to room temperature and purified directly by preparative RP-HPLC to provide compound 64 (cis, enantiomer A). $^1$H NMR (400 MHz, CDCl$_3$) δ 10.89 (s, 1H), 7.28-7.47 (m, 2H), 7.01-7.03 (m, 1H), 4.95 (s, 1H), 4.67 (d, J=4.4 Hz, 2H), 4.51-4.58 (m, 2H), 4.05-4.09 (m, 1H), 3.89-3.93 (m, 1H), 3.65-3.75 (m, 1H), 3.39-3.43 (m, 1H), 3.09-3.13 (m, 1H), 2.09-2.35 (m, 3H), 1.71-1.97 (m, 3H). Mass Calc'd for C$_{22}$H$_{21}$ClFN$_3$O$_5$: 461.1, found 462.2 (M+H)$^+$.

The following compounds of the present invention were made using the methodology described in Example 11, and substituting the appropriate reactants and/or reagents.

| Compound | Structure | Stereochemistry | Exact Mass [M + H]+ |
|---|---|---|---|
| 65 | 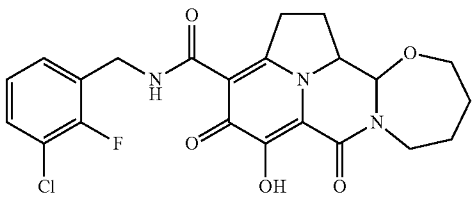 [SMILES: O=C(NCc1cccc(Cl)c1F)c1c2n3c(c(O)c1=O)C(=O)N1CCCCOC1C3CC2] | cis, enantiomer B | Calc'd 462.1, found 462.2 |
| 66 | 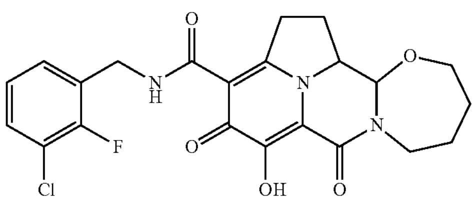 [SMILES: O=C(NCc1cccc(Cl)c1F)c1c2n3c(c(O)c1=O)C(=O)N1CCCCOC1C3CC2] | trans, enantiomer A | Calc'd 462.1, found 462.2 |
| 67 | 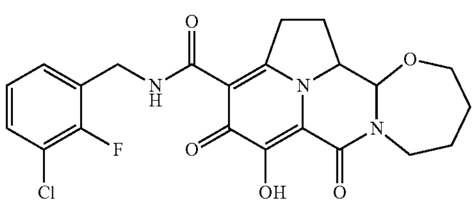 [SMILES: O=C(NCc1cccc(Cl)c1F)c1c2n3c(c(O)c1=O)C(=O)N1CCCCOC1C3CC2] | trans, enantiomer B | Calc'd 462.1, found 462.2 |

| Compound | $^1$H NMR |
|---|---|
| 65 | $^1$H NMR (400 MHz, CDCl$_3$) δ 10.91 (s, 1 H), 7.27-7.32 (m, 2 H), 6.99-7.03 (m, 1 H), 4.96 (s, 1 H), 4.68 (d, J = 4.4 Hz, 2 H), 4.50-4.58 (m, 2 H), 4.09-4.14 (m, 1 H), 3.90-3.93 (m, 1 H), 3.67-3.75 (m, 1 H), 3.36-3.42 (m, 1 H), 3.09-3.14 (m, 1 H), 2.10-2.38 (m, 3 H), 1.75-1.92 (m, 3 H) |
| 66 | $^1$H NMR (400 MHz, CDCl$_3$) δ 10.82 (s, 1 H), 7.26-7.32 (m, 2 H), 6.98-7.05 (m, 1 H), 4.98 (d, J = 8.8 Hz, 1 H), 4.67 (d, J = 5.2 Hz, 2 H), 4.11-4.28 (m, 3 H), 3.94-3.96 (m, 1 H), 3.80-3.82 (m, 2 H), 3.35-3.38 (m, 1 H), 2.61-2.67 (m, 2 H), 1.95-2.10 (m, 4 H) |
| 67 | $^1$H NMR (400 MHz, CDCl$_3$) δ 10.85 (s, 1 H), 7.26-7.31 (m, 2 H), 7.00-7.02 (m, 1 H), 4.99 (d, J = 8.8 Hz, 1 H), 4.67 (d, J = 5.2 Hz, 2 H), 4.05-4.26 (m, 3 H), 3.94-3.97 (m, 1 H), 3.72-3.87 (m, 2 H), 3.30-3.35 (m, 1 H), 2.56-2.72 (m, 2 H), 1.97-2.09 (m, 3 H), 1.83-1.84 (m, 1 H) |

Example 12

Preparation of Compound 68

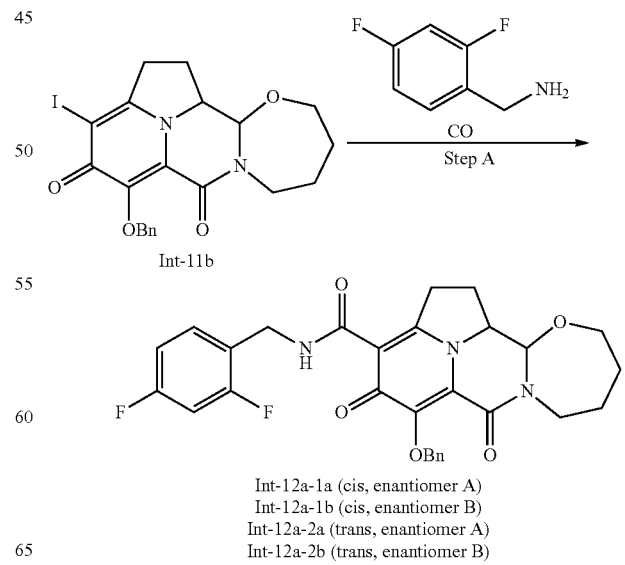

Int-12a-1a (cis, enantiomer A)
Int-12a-1b (cis, enantiomer B)
Int-12a-2a (trans, enantiomer A)
Int-12a-2b (trans, enantiomer B)

Int-12a-1a (cis, enantiomer A) $\xrightarrow[\text{Step B}]{\text{LiCl}}$

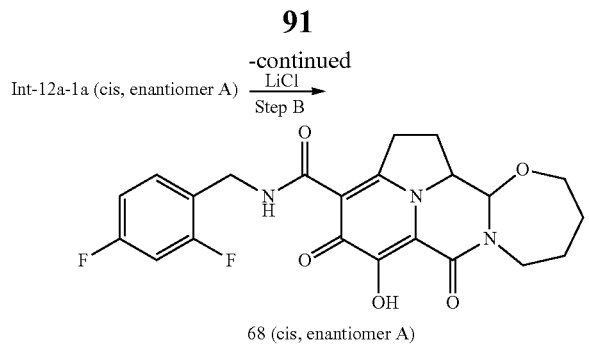

68 (cis, enantiomer A)

Step A—Synthesis of Intermediate Compounds Int-12a

To a solution of Int-11b (80 mg, 0.16 mmol) in dimethylsulfoxide (4 mL) was added N,N-diisopropylethylamine (156 mg, 0.81 mmol), 2,4-difluorobenzylamine (116 mg, 0.81 mmol) and Pd(Ph$_3$P)$_4$ (37.0 mg, 0.03 mmol). The mixture was stirred at 85° C. under carbon monoxide (1 atm) for 2 h, cooled to rt, diluted with water (10 mL) and extracted with ethyl acetate. The combined organics were washed with brine, dried over anhydrous Na$_2$SO$_4$ and concentrated in vacuo. The crude product was purified using preparative TLC on silica gel (methanol:dichloromethane=1:20) to provide compound Int-12a-1 (trans) and compound Int-12a-2 (cis).

Int-12a-1: $^1$H NMR (400 MHz, CDCl$_3$) δ 10.95 (s, 1H), 7.60-7.62 (m, 2H), 7.28-7.38 (m, 4H), 6.77-6.83 (m, 2H), 5.35-5.38 (m, 1H), 5.20-5.22 (m, 1H), 4.84 (s, 1H), 4.58-4.64 (m, 2H), 4.49-4.53 (m, 2H), 4.06-4.14 (m, 1H), 3.70-3.71 (m, 1H), 3.62-3.64 (m, 1H), 3.32-3.40 (m, 1H), 3.03-3.06 (m, 1H), 2.28-2.32 (m, 2H), 2.08-2.14 (m, 1H). 1.80-1.85 (m, 2H), 1.68-1.72 (m, 1H). Mass Calc'd for C$_{29}$H$_{27}$F$_2$N$_3$O$_5$: 535.2, found 536.2 (M+H)$^+$.

Int-12a-2: $^1$H NMR (400 MHz, CDCl$_3$) δ 10.89 (s, 1H), 7.61-7.63 (m, 2H), 7.29-7.27 (m, 4H), 6.77-6.84 (m, 2H), 5.30-5.32 (m, 1H), 5.17-5.22 (m, 1H), 4.77-4.79 (m, 1H), 4.59-4.63 (m, 2H), 4.22-4.24 (m, 2H), 4.07-4.11 (m, 2H), 3.62-3.65 (m, 2H), 3.30-3.40 (m, 1H), 2.54-2.60 (m, 1H), 1.91-2.01 (m, 3H), 1.79-1.82 (m, 2H). Mass Calc'd for C$_{29}$H$_{27}$F$_2$N$_3$O$_5$: 535.2, found 536.2 (M+H)$^+$.

Resolution of Int-12a-1 (trans) to the enantiomers was accomplished with SFC (Chiralpak AD-3, 50×4.6 mm, 3 μm, 40% methanol (0.05% DEA) in SC—CO$_2$, 4 mL/min, 220 nm) to provide Int-12a-1a (trans, enantiomer A) and Int-12a-1b (trans, enantiomer B).

Resolution of Int-12a-2 (cis) to the enantiomers was accomplished with SFC (Chiralpak AS-H, 150×4.6 mm, 5 μm, 5% to 40% ethanol (0.05% DEA) in SC—CO$_2$, 3 mL/min, 220 nm) to provide Int-12a-2a (cis, enantiomer A) and Int-12a-2b (cis, enantiomer B).

Step B—Synthesis of Compound 68

To a solution of Int-12a-1a (trans, enantiomer A) (10 mg, 0.019 mmol) in N,N-dimethylformamide (5 mL) was added lithium chloride (8.1 mg, 0.19 mmol). The resulting solution was heated at 90° C. for 1.5 h, cooled to room temperature and purified directly by preparative RP-HPLC to provide compound 68. $^1$H NMR (400 MHz, CDCl$_3$) δ 10.82 (s, 1H), 7.35-7.37 (m, 1H), 6.77-6.82 (m, 2H), 4.98-5.01 (m, 1H), 4.62 (s, 2H), 4.10-4.27 (m, 3H), 3.92-3.96 (m, 1H), 3.81-3.86 (m, 2H), 3.36-3.38 (m, 1H), 2.63-2.65 (m, 1H), 2.01-2.03 (m, 2H), 1.86 (s, 3H). Mass Calc'd for C$_{22}$H$_{21}$F$_2$N$_3$O$_5$: 445.1, found 446.1 (M+H)$^+$.

The following compounds of the present invention were made using the methodology described in Example 12, and substituting the appropriate reactants and/or reagents.

| Compound | Structure | Stereochemistry | Exact Mass [M + H]$^+$ |
|---|---|---|---|
| 69 | 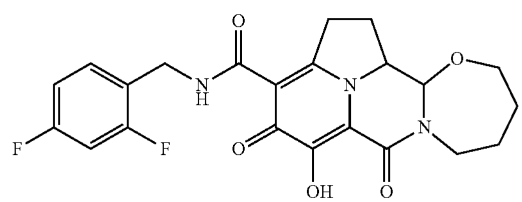 [SMILES: O=C(NCc1ccc(F)cc1F)c1c2n3c(c(O)c1=O)C(=O)N1CCCCOC1C3CC2] | trans, enantiomer B | Calc'd 446.2, found 446.2 |
| 70 | 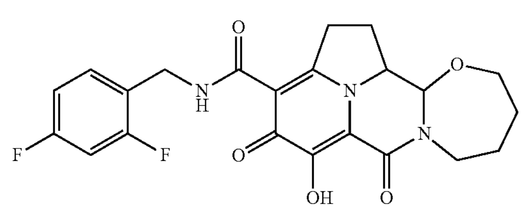 [SMILES: O=C(NCc1ccc(F)cc1F)c1c2n3c(c(O)c1=O)C(=O)N1CCCCOC1C3CC2] | cis, enantiomer A | Calc'd 446.2, found 446.1 |
| 71 | 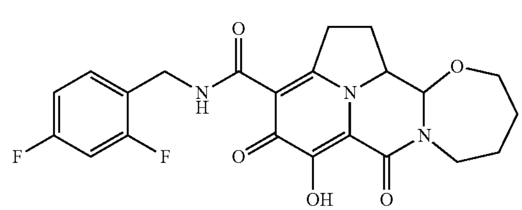 [SMILES: O=C(NCc1ccc(F)cc1F)c1c2n3c(c(O)c1=O)C(=O)N1CCCCOC1C3CC2] | cis, enantiomer B | Calc'd 446.2, found 446.1 |

| Compound | ¹H NMR |
|---|---|
| 69 | ¹H NMR (400 MHz, CDCl₃) δ 10.81 (s, 1H), 7.34-7.37 (m, 1H), 6.77-6.84 (m, 2H), 4.99-5.01 (m, 1H), 4.61-4.62 (m, 2H), 4.09-4.27 (m, 3H), 3.94-3.96 (m, 1H), 3.80-3.86 (m, 2H), 3.36-3.38 (m, 1H), 2.62-2.65 (m, 1H), 1.97-2.05 (m, 2H), 1.86 (s, 3H). |
| 70 | ¹H NMR (400 MHz, CDCl₃) δ 10.85 (s, 1H), 7.34-7.37 (m, 1H), 6.77-6.83 (m, 2H), 4.96 (s, 1H), 4.53-4.61 (m, 4H), 4.10 (s, 1H), 3.91-3.95 (m, 1H), 3.69-3.74 (m, 1H), 3.35 (s, 1H), 3.11-3.14 (m, 1H), 2.35 (s, 2H), 2.17-2.18 (m, 1H), 1.91-1.93 (m, 2H), 1.78-1.80 (m, 1H). |
| 71 | ¹H NMR (400 MHz, CDCl₃) δ 10.86 (s, 1H), 7.34-7.40 (m, 1H), 6.77-6.83 (m, 2H), 4.95-4.96 (m, 1H), 4.50-4.63 (m, 4H), 4.08-4.10 (m, 1H), 3.92-3.93 (m, 1H), 3.72-3.74 (m, 1H), 3.32-3.42 (m, 1H), 3.10-3.14 (m, 1H), 2.34-2.38 (m, 2H), 2.15-2.18 (m, 1H), 1.91-1.95 (m, 2H), 1.77-1.81 (m, 1H). |

Example 13

Preparation of Compound 72

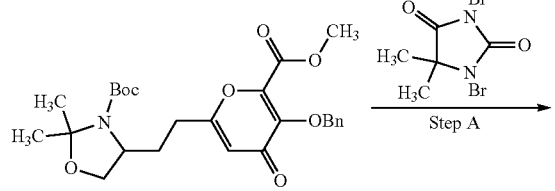

Int-2g

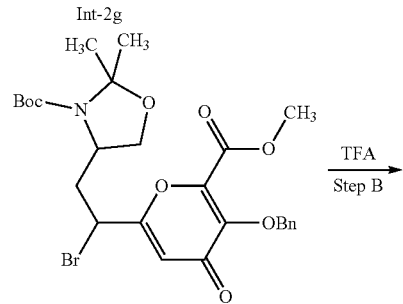

Int-13a

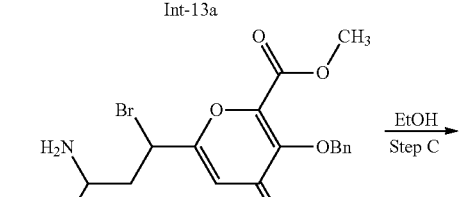

Int-13b

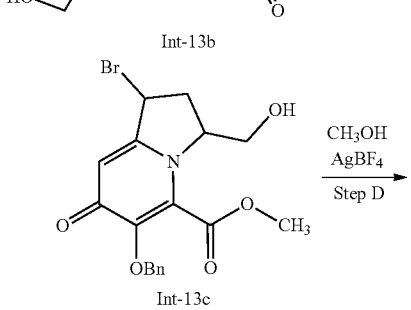

Int-13c

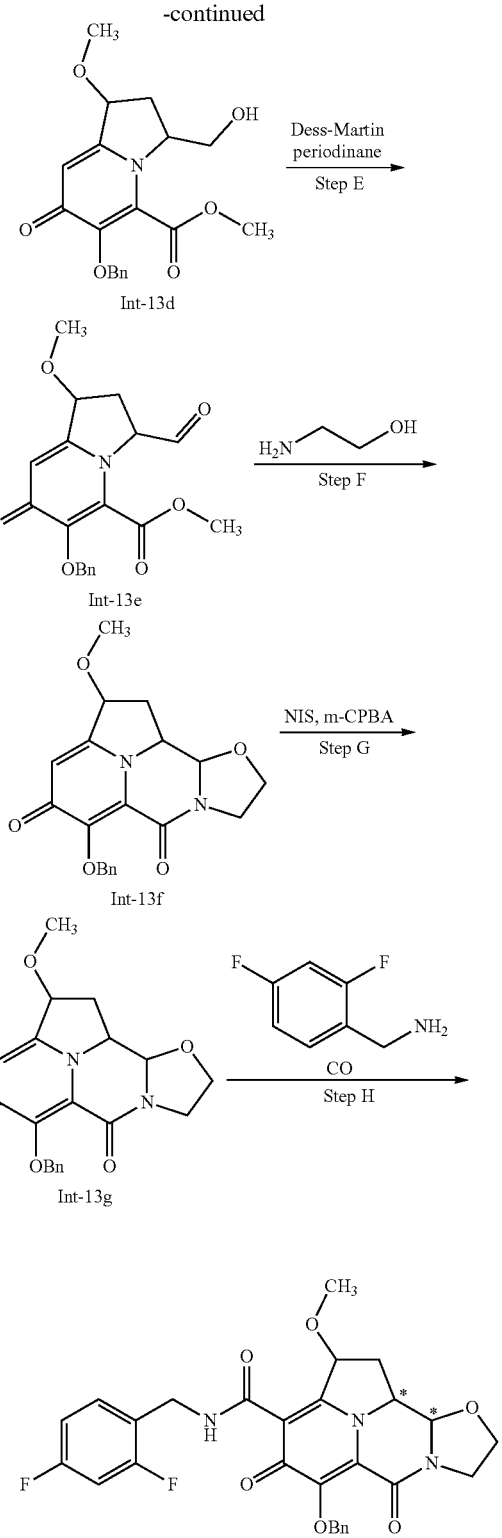

Int-13h-1a (trans-1, enantiomer A)
Int-13h-1b (trans-1, enantiomer B)
Int-13h-2a (trans-2, enantiomer A)
Int-13h-2b (trans-2, enantiomer B)
Int-13h-3a (cis-1, enantiomer A)
Int-13h-3b (cis-1, enantiomer B)
Int-13h-4a (cis-2, enantiomer A)
Int-13h-4b (cis-2, enantiomer B)

Int-13h-1a (trans-1, enantiomer A) $\xrightarrow{\text{LiCl}}$ Step 1

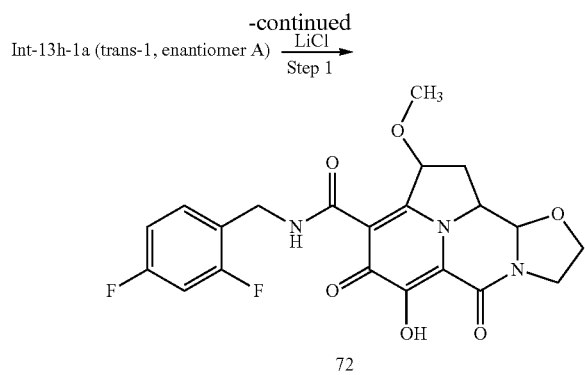

72

Step A—Synthesis of Intermediate Compound Int-13a

To a solution of Int-2g (2g, 4.10 mmol) in tetrahydrofuran (15 mL) was added dropwise LiHMDS (4.51 mL, 4.51 mmol) at −78° C. After 0.5 h, the mixture was treated with 1,3-dibromo-5,5-dimethylimidazolidine-2,4-dione (0.469 g, 1.641 mmol) in tetrahydrofuran (5 mL) at −78° C. The mixture was stirred at 15° C. for 2 hours. The reaction was quenched at 15° C. with methanol (5 mL) followed by the addition of saturated aqueous NH$_4$Cl (10 mL) and extracted with ethyl acetate. The combined organic portions were washed with brine (20 mL), dried over anhydrous Na$_2$SO$_4$, filtered and the filtrate was concentrated in vacuo. The resulting residue was purified using column chromatography on silica gel (petroleum ether:ethyl acetate=3:1) to provide Int-13a. $^1$H NMR (400 MHz, CDCl$_3$) δ 7.29-7.58 (m, 5H), 6.56 (d, J=7.50 Hz, 1H), 5.30 (s, 2H) 3.79-4.05 (m, 6H), 2.29-2.64 (m, 3H), 1.38-1.62 (m, 15H). Mass Calc'd for C$_{26}$H$_{32}$BrNO$_8$: 565.1, found 566.1 (M+H)$^+$.

Step B—Synthesis of Intermediate Compound Int-13b

To a solution of Int-13a (0.8 g, 1.412 mmol) in dichloromethane (20 mL) was added trifluoroacetic acid (4 mL, 51.9 mmol) at 0° C. The mixture was stirred at 0° C. for 3 hours. The mixture was concentrated in vacuo at low temperature (i.e., less then rt) to provide crude Int-13b, which was used immediately in the next step without further purification.

Step C—Synthesis of Intermediate Compound Int-13c

A solution of Int-13b (0.6 g, 1.41 mmol) in ethanol (100 mL) was heated at 80° C. for 4 h, cooled to room temperature and concentrated in vacuo. The mixture was purified using column chromatography on silica gel (dichloromethane:methanol=10:1) to provide Int-13c. $^1$H NMR (400 MHz, CD$_3$OD) δ 7.31-7.39 (m, 5H), 6.72 (s, 1H), 5.57-5.63 (m, 1H), 5.02-5.33 (m, 2H), 3.55-3.96 (m, 6H), 2.44-2.88 (m, 2H). Mass Calc'd for C$_{18}$H$_{18}$BrNO$_5$: 407.0, found 408.0 (M+H)$^+$.

Step D—Synthesis of Intermediate Compound Int-13d

A solution of Int-13c (100 mg, 0.245 mmol) in methanol (2 mL) was treated with silver(I) tetrafluoroborate (95 mg, 0.490 mmol) and stirred at 30° C. for 4 hours. The mixture was filtered and the filtrate was concentrated in vacuo. The resulting residue was purified using preparative TLC on silica gel (dichloromethane:methanol=15:1) to provide Int-13d. $^1$H NMR (400 MHz, CDCl$_3$) δ 7.29-7.61 (m, 5H), 6.36-6.60 (m, 1H), 5.39-5.52 (m, 1H), 5.23-5.35 (m, 1H), 4.86-5.18 (m, 2H), 4.49-4.66 (m, 1H) 4.01-4.41 (m, 1H), 3.66-3.83 (m, 3H) 3.35-3.44 (m, 3H), 2.36-2.84 (m, 1H), 1.62-2.19 (m, 1H). Mass Calc'd for C$_{19}$H$_{21}$NO$_6$: 359.1, found 360.0 (M+H)$^+$.

Step E—Synthesis of Intermediate Compound Int-13e

To a solution of Int-13d (800 mg, 2.226 mmol) in dichloromethane (15 mL) was added Dess-Martin reagent (1888 mg, 4.45 mmol). The mixture was stirred at 0° C. for 4 h, quenched with saturated aqueous NaHCO$_3$ (10 mL) and extracted with dichloromethane. The combined organic portions were dried over anhydrous Na$_2$SO$_4$, filtered and the filtrate was concentrated in vacuo. The resulting residue was purified using column chromatography on silica gel (dichloromethane:methanol=20:1) to provide Int-13e. Mass Calc'd for C$_{19}$H$_{19}$NO$_6$: 357.1, found 358.1 (M+H)$^+$.

Step F—Synthesis of Intermediate Compound Int-13f

To a solution of Int-13e (600 mg, 1.679 mmol) in tetrahydrofuran (40 mL) was added acetic acid (0.4 mL) and 2-aminoethanol (513 mg, 8.39 mmol). The mixture was stirred at 80° C. for 0.5 h, cooled to room temperature and concentrated in vacuo. The resulting residue was purified using column chromatography on silica gel (dichloromethane:methanol=20:1) to provide Int-13f. Mass Calc'd for C$_{20}$H$_{20}$N$_2$O$_5$: 368.1, found 369.1 (M+H)$^+$.

Step G—Synthesis of Intermediate Compound Int-13g

To a solution of Int-13f (400 mg, 1.086 mmol) in methanol (10 mL) was added N-iodosuccinimide (733 mg, 3.26 mmol) and m-CPBA (703 mg, 3.26 mmol). The mixture was stirred at 70° C. for 2 h, cooled to rt, quenched with saturated aqueous Na$_2$SO$_3$ (10 mL) and extracted with dichloromethane. The organic phase was washed with saturated aqueous NaHCO$_3$ (20 mL) and brine, dried over anhydrous Na$_2$SO$_4$, filtered and the filtrate was concentrated in vacuo. The resulting residue was purified using column chromatography on silica gel (dichloromethane:methanol=20:1) to provide Int-13g. Mass Calc'd for C$_{20}$H$_{19}$IN$_2$O$_5$: 494.0, found 495.1 (M+H)$^+$.

Step H—Synthesis of Intermediate Compound Int-13h

To a solution of Int-13g (300 mg, 0.607 mmol) in dimethylsulfoxide (10 mL) was added N,N-diisopropylethylamine (392 mg, 3.03 mmol), 2,4-difluorobenzylamine (347 mg, 2.428 mmol) and Pd(Ph$_3$P)$_4$ (140 mg, 0.121 mmol). The mixture was stirred at 80° C. for 1.5 h under carbon monoxide (1 atm). The mixture was cooled to rt, diluted with ethyl acetate and washed with 1N aqueous HCl (30 mL), saturated aqueous NaHCO$_3$ and brine, dried over anhydrous Na$_2$SO$_4$, filtered and the filtrate was concentrated in vacuo. The resulting residue was purified using preparative TLC on silica gel (100% ethyl acetate) to provide Int-13h-1 (trans-1), Int-13h-2 (trans-2), Int-13h-3 (cis-1) and Int-13h-4 (cis-2), where trans or cis refer to the relative stereochemistry of the carbons at the ring fusions (denoted with asterisks).

Int-13h-1: $^1$H NMR (400 MHz, CDCl$_3$) δ 10.75-10.90 (m, 1H), 7.56-7.65 (m, 2H), 7.28-7.44 (m, 4H), 6.74-6.87 (m, 2H), 6.05 (d, J=4.8 Hz, 1H), 5.36 (d, J=9.8 Hz, 1H), 5.20 (d, J=9.8 Hz, 1H), 4.65-4.77 (m, 2H), 4.53-4.63 (m, 1H), 4.25-4.32 (m, 2H), 3.85-4.10 (m, 2H), 3.63-3.64 (m, 1H), 3.49 (s, 3H), 2.57-2.70 (m, 1H), 2.01-2.03 (m, 1H). Mass Calc'd for C$_{28}$H$_{25}$F$_2$N$_3$O$_6$: 537.2, found 538.1 (M+H)$^+$.

Int-13h-2: $^1$H NMR (400 MHz, CDCl$_3$) δ 10.07 (br. s, 1H), 7.60 (d, J=7.2 Hz, 2H), 7.29-7.44 (m, 4H), 6.75-6.86 (m, 2H), 5.70-5.75 (m, 1H), 5.38 (d, J=10.2 Hz, 1H), 5.26 (d, J=10.2 Hz, 1H), 4.89-4.90 (m, 1H), 4.65-4.67 (m, 2H), 4.29-4.37 (m, 1H), 3.88-4.12 (m, 3H), 3.65-3.67 (m, 1H), 3.48 (s, 3H), 2.92-3.04 (m, 1H), 2.11-2.21 (m, 1H). Mass Calc'd for C$_{28}$H$_{25}$F$_2$N$_3$O$_6$: 537.2, found 538.1 (M+H)$^+$.

Int-13h-3: $^1$H NMR (400 MHz, CDCl$_3$) δ 10.78 (br. s, 1H), 7.53 (d, J=6.8 Hz, 2H), 7.22-7.35 (m, 4H), 6.73-6.82 (m, 2H), 5.90-6.01 (m, 1H), 5.32 (d, J=10.2 Hz, 1H), 5.16 (d, J=10.2 Hz, 1H), 4.33-4.79 (m, 5H), 3.60-3.85 (m, 2H), 3.30-3.49 (m, 4H), 2.33-2.48 (m, 2H). Mass Calc'd for $C_{28}H_{25}F_2N_3O_6$: 537.2, found 538.1 (M+H)$^+$.

Int-13h-4: $^1$H NMR (400 MHz, CDCl$_3$) δ 9.86 (br. s, 1H), 7.53 (d, J=7.2 Hz, 2H), 7.23-7.32 (m, 4H), 6.68-6.79 (m, 2H), 5.57-5.59 (m, 1H), 5.34 (d, J=10.2 Hz, 1H), 5.15 (d, J=10.2 Hz, 1H), 4.58-4.76 (m, 3H), 4.33-4.51 (m, 2H), 3.72-3.90 (m, 2H), 3.27-3.45 (m, 4H), 2.77-2.89 (m, 1H), 2.33-2.44 (m, 1H). Mass Calc'd for $C_{28}H_{25}F_2N_3O_6$: 537.2, found 538.1 (M+H)$^+$.

Separation of Int-13h-1 (trans-1) was accomplished with SFC (Chralpak AD 250×30 mm, 10 μm, 50% IPA in SC—CO$_2$, 80 mL/min, 220 nm) to provide Int-13h-1a (trans-1, enantiomer A (SFC $R_t$=3.59 min) and Int-13h-1b (trans-1, enantiomer B) (SFC: $R_t$=4.53 min).

Int-13h-1a: $^1$H NMR (400 MHz, CDCl$_3$) δ 10.75-10.86 (m, 1H), 7.56-7.65 (m, 2H), 7.28-7.43 (m, 4H), 6.74-6.87 (m, 2H), 6.05 (d, J=5.2 Hz, 1H), 5.36 (d, J=9.8 Hz, 1H), 5.18 (d, J=9.8 Hz, 1H), 4.65-4.77 (m, 2H), 4.53-4.63 (m, 1H), 4.25-4.36 (m, 2H), 3.85-4.10 (m, 2H), 3.63-3.64 (m, 1H), 3.49 (s, 3H), 2.57-2.70 (m, 1H), 1.99-2.11 (m, 1H). Mass Calc'd for $C_{28}H_{25}F_2N_3O_6$: 537.2, found 538.1 (M+H)$^+$.

Int-13h-1b: $^1$H NMR (400 MHz, CDCl$_3$) δ 10.75-10.86 (m, 1H), 7.56-7.65 (m, 2H), 7.28-7.43 (m, 4H), 6.80-6.82 (m, 2H), 6.01 (d, J=5.2 Hz, 1H), 5.36 (d, J=9.8 Hz, 1H), 5.18 (d, J=9.8 Hz, 1H), 4.65-4.77 (m, 2H), 4.60-4.63 (m, 1H), 4.25-4.30 (m, 2H), 3.85-3.96 (m, 2H), 3.56-3.57 (m, 1H), 3.49 (s, 3H), 2.61-2.70 (m, 1H), 2.05-2.07 (m, 1H). Mass Calc'd for $C_{28}H_{25}F_2N_3O_6$: 537.2, found 538.1 (M+H)$^+$.

Separation of Int-13h-2 (trans-2) was accomplished with SFC (Chralpak AS 250×30 mm, 5 μm, 20% ethanol in SC—CO$_2$, 60 mL/min, 220 nm) to Int-13h-2a (trans-2, enantiomer A) (SFC: $R_t$=3.115 min) and Int-13h-2b (trans-2, enantiomer B) (SFC: $R_t$=3.21 min).

Int-13h-2a: $^1$H NMR (400 MHz, CDCl$_3$) δ 9.86-9.93 (m, 1H), 7.60 (d, J=7.2 Hz, 2H), 7.29-7.44 (m, 4H), 6.75-6.86 (m, 2H), 5.51-5.52 (m, 1H), 5.23 (d, J=10.8 Hz, 1H), 5.18 (d, J=10.8 Hz, 1H), 4.86-4.88 (m, 1H), 4.60-4.64 (m, 2H), 4.29-4.37 (m, 1H), 3.88-4.12 (m, 3H), 3.65-3.67 (m, 1H), 3.48 (s, 3H), 2.78-2.82 (m, 1H), 2.04-2.08 (m, 1H). Mass Calc'd for $C_{28}H_{25}F_2N_3O_6$: 537.2, found 538.1 (M+H)$^+$.

Int-13h-2b: $^1$H NMR (400 MHz, CDCl$_3$) δ 9.88-9.90 (m, 1H), 7.58-7.60 (m, 2H), 7.26-7.39 (m, 4H), 6.79-6.81 (m, 2H), 5.53-5.54 (m, 1H), 5.25 (d, J=10 Hz, 1H), 5.18 (d, J=10 Hz, 1H), 4.86-4.88 (m, 1H), 4.60-4.65 (m, 2H), 4.29-4.37 (m, 1H), 3.88-4.12 (m, 3H), 3.57-3.63 (m, 1H), 3.41 (s, 3H), 2.81-2.84 (m, 1H), 2.05-2.10 (m, 1H). Mass Calc'd for $C_{28}H_{25}F_2N_3O_6$: 537.2, found 538.1 (M+H)$^+$.

Separation of Int-13h-3 (cis-1) was accomplished with SFC (Chralpak AS, 250×30 mm, 5 μm, 35% ethanol in SC—CO$_2$, 50 mL/min, 220 nm) to provide Int-13h-3a (cis-1, enantiomer A) (SFC: $R_t$=4.23 min) and Int-13h-3b (cis-1, enantiomer B) (SFC: $R_t$=3.54 min).

Int-13h-3a: $^1$H NMR (400 MHz, CDCl$_3$) δ 10.76 (br. s, 1H), 7.60 (d, J=6.8 Hz, 2H), 7.29-7.35 (m, 4H), 6.79-6.83 (m, 2H), 6.01 (d, J=4.4 Hz, 1H), 5.38 (d, J=10.4 Hz, 1H), 5.20 (d, J=10.4 Hz, 1H), 4.52-4.85 (m, 5H), 3.74-3.86 (m, 2H), 3.44-3.49 (m, 4H), 2.44-2.50 (m, 2H). Mass Calc'd for $C_{28}H_{25}F_2N_3O_6$: 537.2, found 538.1 (M+H)$^+$.

Int-13h-3b: $^1$H NMR (400 MHz, CDCl$_3$) δ 10.76 (brs, 1H), 7.60 (d, J=6.8 Hz, 2H), 7.29-7.35 (m, 4H), 6.79-6.83 (m, 2H), 6.01 (d, J=4.4 Hz, 1H), 5.38 (d, J=10.4 Hz, 1H), 5.20 (d, J=10.4 Hz, 1H), 4.52-4.85 (m, 5H), 3.74-3.86 (m, 2H), 3.44-3.49 (m, 4H), 2.44-2.50 (m, 2H). Mass Calc'd for $C_{28}H_{25}F_2N_3O_6$: 537.2, found 538.1 (M+H)$^+$.

Separation of Int-13h-4 (cis-2) was accomplished with SFC (Chralpak AS, 250×30 mm, 5 μm, 35% ethanol in SC—CO$_2$, 50 mL/min, 220 nm) to provide Int-13h-4a (cis-2, enantiomer A) (SFC: $R_t$=3.072 min) and Int-13h-4b (cis-2, enantiomer B) (SFC: $R_t$=4.385 min).

Int-13h-4a: $^1$H NMR (400 MHz, CDCl$_3$) δ 9.90 (brs, 1H), 7.60 (d, J=7.2 Hz, 2H), 7.29-7.39 (m, 4H), 6.76-6.81 (m, 2H), 5.57-5.61 (m, 1H), 5.34 (d, J=10.4 Hz, 1H), 5.15 (d, J=10.4 Hz, 1H), 4.39-4.73 (m, 5H), 3.84-3.87 (m, 2H), 3.41-3.47 (m, 4H), 2.83-2.87 (m, 1H), 2.40-2.42 (m, 1H). Mass Calc'd for $C_{28}H_{25}F_2N_3O_6$: 537.2, found 538.1 (M+H)$^+$.

Int-13h-4b: $^1$H NMR (400 MHz, CDCl$_3$) δ 9.92 (brs, 1H), 7.60 (d, J=7.2 Hz, 2H), 7.29-7.39 (m, 4H), 6.76-6.81 (m, 2H), 5.57-5.61 (m, 1H), 5.34 (d, J=10.4 Hz, 1H), 5.15 (d, J=10.4 Hz, 1H), 4.40-4.75 (m, 5H), 3.81-3.88 (m, 2H), 3.42-3.48 (m, 4H), 2.85-2.88 (m, 1H), 2.40-2.43 (m, 1H). Mass Calc'd for $C_{28}H_{25}F_2N_3O_6$: 537.2, found 538.1 (M+H)$^+$.

Step I—Synthesis of Compound 72

To a solution of Int-13h-1a (trans-1, enantiomer A) (12 mg, 0.022 mmol) in N,N-dimethylformamide (2 mL) was added lithium chloride (9.5 mg, 0.22 mmol). The resulting solution was heated to 80° C. for 3 h, cooled to room temperature and purified directly by preparative RP-HPLC to give compound 72. $^1$H NMR (400 MHz, CDCl$_3$) δ 10.74 (s, 1H), 7.33-7.39 (m, 1H), 6.79-6.85 (m, 2H), 6.07 (d, J=4.8 Hz, 1H), 4.86 (d, J=8.8 Hz, 1H), 4.61-4.69 (m, 2H), 4.40-4.44 (m, 2H), 4.15-4.18 (m, 1H), 3.75-3.91 (m, 2H), 3.48 (s, 3H), 2.70-2.75 (m, 1H), 2.11-2.13 (m, 1H). Mass Calc'd for $C_{21}H_{19}F_2N_3O_6$: 447.1, found 448.1 (M+H)$^+$.

The following compounds of the present invention were made using the methodology described in Example 13, and substituting the appropriate reactants and/or reagents.

| Compound | Structure | Stereochemistry | Exact Mass [M + H]$^+$ |
|---|---|---|---|
| 73 | 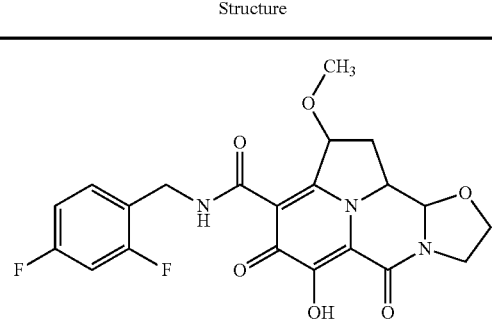 | trans-1, enantiomer B | Calc'd 448.1, found 448.1 |

-continued

| Compound | Structure | Stereochemistry | Exact Mass [M + H]+ |
|---|---|---|---|
| 74 | 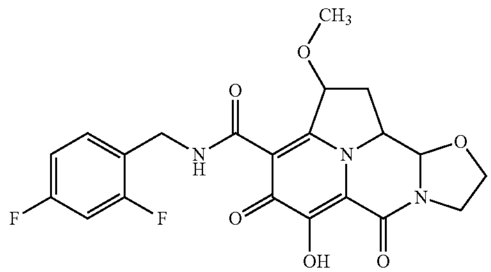 [SMILES: COC1CC2C3OCCN3C(=O)c3c(O)c(=O)c(C(=O)NCc4ccc(F)cc4F)c1n32] | trans-2, enantiomer A | Calc'd 448.1, found 448.1 |
| 75 | 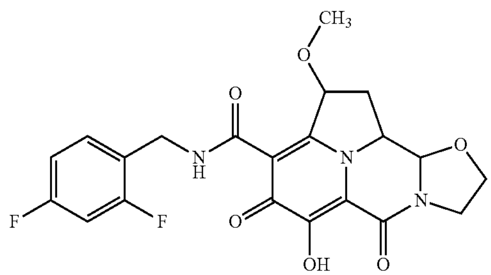 [SMILES: COC1CC2C3OCCN3C(=O)c3c(O)c(=O)c(C(=O)NCc4ccc(F)cc4F)c1n32] | trans-2, enantiomer B | Calc'd 448.1, found 448.1 |
| 76 | 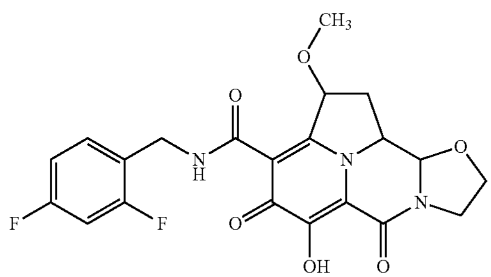 [SMILES: COC1CC2C3OCCN3C(=O)c3c(O)c(=O)c(C(=O)NCc4ccc(F)cc4F)c1n32] | cis-1, enantiomer A | Calc'd 448.1, found 448.1 |
| 77 | 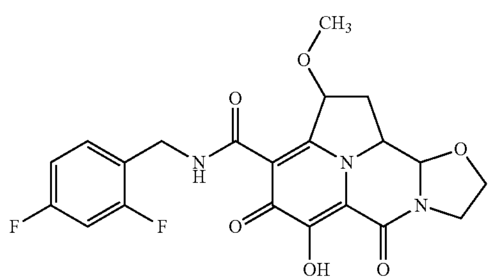 [SMILES: COC1CC2C3OCCN3C(=O)c3c(O)c(=O)c(C(=O)NCc4ccc(F)cc4F)c1n32] | cis-1, enantiomer B | Calc'd 448.1, found 448.1 |
| 78 | 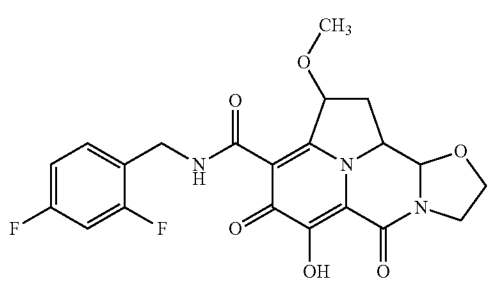 [SMILES: COC1CC2C3OCCN3C(=O)c3c(O)c(=O)c(C(=O)NCc4ccc(F)cc4F)c1n32] | cis-2, enantiomer A | Calc'd 448.1, found 448.1 |

| Compound | Structure | Stereochemistry | Exact Mass [M + H]+ |
|---|---|---|---|
| 79 | 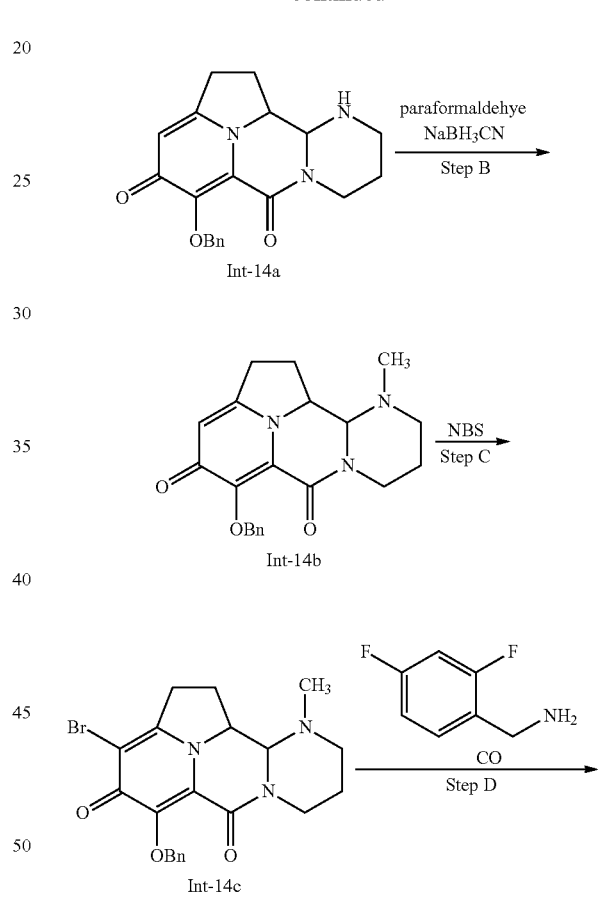 | cis-2, enantiomer B | Calc'd 448.1, found 448.1 |

| Compound | 1H NMR |
|---|---|
| 73 | 1H NMR (400 MHz, CDCl3) δ 10.72 (s, 1H), 7.34-7.40 (m, 1H), 6.79-6.85 (m, 2H), 6.05 (d, J = 4.8 Hz, 1H), 4.87 (d, J = 8.8 Hz, 1H), 4.61-4.69 (m, 2H), 4.41-4.43 (m, 2H), 4.15-4.17 (m, 1H), 3.75-3.90 (m, 2H), 3.48 (s, 3H), 2.69-2.74 (m, 1H), 2.11-2.13 (m, 1H). |
| 74 | 1H NMR (400 MHz, CDCl3) δ 10.02 (s, 1H), 7.34-7.38 (m, 1H), 6.77-6.83 (m, 2H), 5.69-5.72 (m, 1H), 4.97 (d, J = 8.8 Hz, 1H), 4.04-4.69 (m, 5H), 3.75-3.90 (m, 2H), 3.49 (s, 3H), 3.06-3.09 (m, 1H), 2.13-2.20 (m, 1H). |
| 75 | 1H NMR (400 MHz, CDCl3) δ 10.05 (s, 1H), 7.34-7.38 (m, 1H), 6.77-6.83 (m, 2H), 5.71-5.72 (m, 1H), 4.98 (d, J = 8.8 Hz, 1H), 4.04-4.69 (m, 5H), 3.75-3.90 (m, 2H), 3.49 (s, 3H), 3.06-3.13 (m, 1H), 2.15-2.20 (m, 1H). |
| 76 | 1H NMR (400 MHz, CDCl3) δ 10.81 (s, 1H), 7.32-7.38 (m, 1H), 6.77-6.83 (m, 2H), 6.01 (d, J = 4.8 Hz, 1H), 4.92 (d, J = 3.6 Hz, 1H), 4.59-4.84 (m, 4H), 3.88-3.95 (m, 2H), 3.51-3.53 (m, 4H), 2.45-2.55 (m, 2H). |
| 77 | 1H NMR (400 MHz, CDCl3) δ 10.73 (s, 1H), 7.32-7.38 (m, 1H), 6.77-6.83 (m, 2H), 6.01 (d, J = 4.8 Hz, 1H), 4.92 (d, J = 3.6 Hz, 1H), 4.59-4.84 (m, 4H), 3.88-3.95 (m, 2H), 3.51-3.53 (m, 4H), 2.48-2.56 (m, 2H). |
| 78 | 1H NMR (400 MHz, CDCl3) δ 9.94 (s, 1H), 7.36-7.38 (m, 1H), 6.77-6.81 (m, 2H), 5.69-5.60 (m, 1H), 4.89 (s, 1H), 4.50-4.67 (m, 4H), 3.96-3.98 (m, 2H), 3.49-3.53 (m, 4H), 2.91-2.99 (m, 1H), 2.44-2.46 (m, 1H). |
| 79 | 1H NMR (400 MHz, CDCl3) δ 9.94 (s, 1H), 7.36-7.38 (m, 1H), 6.77-6.81 (m, 2H), 5.69-5.60 (m, 1H), 4.89 (s, 1H), 4.50-4.67 (m, 4H), 3.96-3.98 (m, 2H), 3.49-3.54 (m, 4H), 2.92-2.99 (m, 1H), 2.44-2.46 (m, 1H). |

Example 14

Preparation of Compound 80

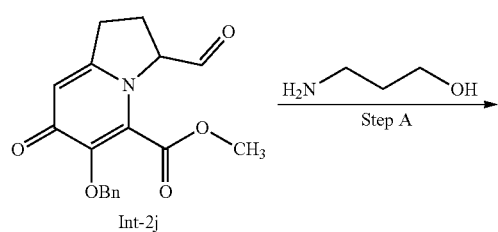

-continued

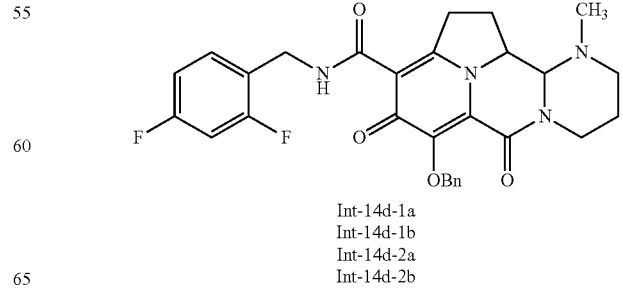

-continued

Int-14d-1a $\xrightarrow{\text{LiCl}}$ Step E

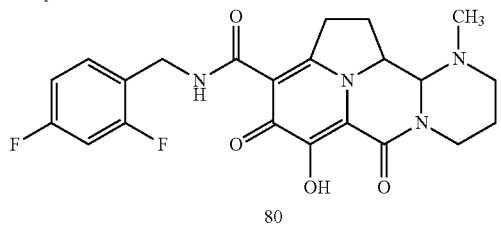

80

Step A—Synthesis of Intermediate Compound Int-14a

To a solution of Int-2j (1.00 g, 3.06 mmol) in tetrahydrofuran (30 mL) was added propane-1,3-diamine (6.79 g, 92 mmol) followed by acetic acid (1 mL). The mixture was stirred at 70° C. for 15 min, cooled to room temperature and concentrated in vacuo. The resulting residue was purified using column chormatography on silica gel (dichloromethane:methanol=20:1-10:1) to provide Int-14a. $^1$H NMR (400 MHz, CDCl$_3$) δ 7.56-7.60 (m, 2H), 7.22-7.29 (m, 3H), 6.33-6.36 (m, 1H), 5.14-5.23 (m, 2H), 4.40-4.46 (m, 1H), 4.15-4.17 (m, 1H), 4.02-4.03 (m, 1H), 2.83-3.01 (m, 4H), 2.33-2.56 (m, 3H), 1.68-1.81 (m, 2H). Mass Calc'd for $C_{20}H_{21}N_3O_3$: 351.2, found 352.0 (M+H)$^+$.

Step B—Synthesis of Intermediate Compound Int-14b

To a solution of Int-14a (400 mg, 1.024 mmol) in methanol (10 mL) and dichloromethane (10 mL) was added paraformaldehyde (300 mg, 0.427 mmol) and NaCNBH$_3$ (134 mg, 2.134 mmol). The mixture was stirred at 28° C. for 12 hours. The mixture was concentrated in vacuo and the residue obtained was purified using column chromatography on silica gel (dichloromethane:methanol=10:1-7:1) to give Int-14b. $^1$H NMR (400 MHz, CDCl$_3$) δ 7.52-7.58 (m, 2H), 7.20-7.28 (m, 3H), 6.38-6.40 (m, 1H), 5.18-5.47 (m, 2H), 4.43-4.61 (m, 1H), 4.21-4.26 (m, 1H), 4.13-4.19 (m, 1H), 3.42 (s, 3H), 2.85-2.89 (m, 4H), 2.45-2.85 (m, 3H), 1.95-1.99 (m, 2H). Mass Calc'd for $C_{21}H_{23}N_3O_3$: 365.2, found 366.3 (M+H)$^+$.

Step C—Synthesis of Intermediate Compound Int-14c

To a solution of Int-14b (260 mg, 0.712 mmol) in dichloromethane (10 mL), was added N-bromosuccinimide (146 mg, 0.821 mmol). The mixture was stirred at −15° C. for 1.5 mins, quenched with saturated aqueous of Na$_2$SO$_3$ (2 mL) and extracted with dichloromethane. The combined organic portions were dried with anhydrous Na$_2$SO$_4$, filtered and the filtrate was concentrated in vacuo. The crude product was purified using column chromatography on silica gel (methanol:dichloromethane=1:20-1:10) to give Int-14c. $^1$H NMR (400 MHz, CDCl$_3$) δ 7.60-7.67 (m, 2H), 7.24-7.31 (m, 3H), 5.18-5.27 (m, 2H), 4.39-4.60 (m, 2H), 2.83-3.01 (m, 6H), 2.97 (s, 3H), 2.40-2.45 (m, 2H), 2.01-2.06 (m, 1H), 1.70-1.71 (m, 1H). Mass Calc'd for $C_{21}H_{22}BrN_3O_3$: 443.1, found 444.1 (M+H)$^+$.

Step D—Synthesis of Intermediate Compound Int-14d

To a solution of Int-14c (260 mg, 0.565 mmol) in dimethylsulfoxide (1.5 mL) and methanol (5 mL) was added 2,4-difluorobenzylamine (405 mg, 2.815 mmol), Pd(Ph$_3$P)$_4$ (52.0 mg, 0.056 mmol) and N,N-diisopropylethylamine (0.985 ml, 5.625 mmol). The mixture was stirred under carbon monoxide at 80° C. for 14 h, cooled to rt, diluted with water and extracted with ethyl acetate. The combined organic portions were washed with brine, dried over anhydrous Na$_2$SO$_4$, filtered and the filtrate was concentrated in vacuo. The resulting residue was purified using preparative TLC on silica gel (dichloromethane/methanol=10/1) to provide Int-14d-1 (diastereomer 1) and Int-14d-2 (diastereomer 2).

Int-14d-1: $^1$H NMR (400 MHz, CDCl$_3$) δ 10.91 (s, 1H), 7.45-7.52 (m, 2H), 7.27-7.39 (m, 4H), 6.73-6.89 (m, 2H), 5.16-5.29 (m, 3H), 4.53-4.61 (m, 3H), 4.29 (s, 2H), 4.05-4.10 (m, 1H), 2.99-3.01 (m, 1H), 2.87-2.97 (m, 3H), 2.52 (s, 3H), 1.99-2.04 (m, 2H), 1.68-1.79 (m, 1H). Mass Calc'd for $C_{29}H_{28}F_2N_4O_4$: 534.2, found 535.1 (M+H)$^+$.

Int-14d-2: $^1$H NMR (400 MHz, CDCl$_3$) δ 11.00 (s, 1H), 7.41-7.62 (m, 2H), 7.31-7.41 (m, 4H), 6.80-6.91 (m, 2H), 5.24-5.47 (m, 3H), 4.54-4.88 (m, 3H), 4.15-4.19 (m, 2H), 2.97-3.11 (m, 4H), 2.90-2.95 (m, 1H), 2.36-2.47 (m, 3H), 2.27 (s, 3H). Mass Calc'd for $C_{29}H_{28}F_2N_4O_4$: 534.2, found 535.1 (M+H)$^+$.

Resolution of Int-14d-1 to the enantiomers was accomplished with SFC (Chralpak AD, 250 mm×30 mm, 5 μm, 40% methanol in SC—CO$_2$, 60 mL/min, 220 nm) to provide Int-14d-1a (diastereomer 1, enantiomer A) and Int-14d-1b (diastereomer 1, enantiomer B).

Resolution of Int-14d-2 to the enantiomers was accomplished with SFC (Chralpak AS, 250 mm×30 mm, 5 μm, 40% methanol in SC—CO$_2$, 40 mL/min, 220 nm) to provide Int-14d-2a (diastereomer 2, enantiomer A) and Int-14d-2b (diastereomer 2, enantiomer B).

Step E—Synthesis of Compound 80

To a solution of Int-14d-1a (12 mg, 0.022 mmol) in N,N-dimethylformamide (2 mL) was added LiCl (19.03 mg, 0.449 mmol). The resulting solution was heated at 80° C. for 2 h, cooled to room temperature and purified using preparative RP-HPLC to provide compound 80. $^1$H NMR (400 MHz, CDCl$_3$) δ 10.76 (s, 1H), 7.26-7.32 (m, 2H), 6.70-6.76 (m, 2H), 4.44-4.54 (m, 4H), 4.25-4.26 (m, 1H), 4.02-4.10 (m, 1H), 2.96-3.32 (m, 4H), 2.48 (s, 4H), 2.00-2.05 (m, 2H), 1.56-1.60 (m, 1H). Mass Calc'd for $C_{22}H_{22}F_2N_4O_4$: 444.2, found 445.2 (M+H)$^+$.

The following compounds of the present invention were made using the methodology described in Example 14, and substituting the appropriate reactants and/or reagents.

| Compound | Structure | Stereochemistry | Exact Mass [M + H]$^+$ |
|---|---|---|---|
| 81 | 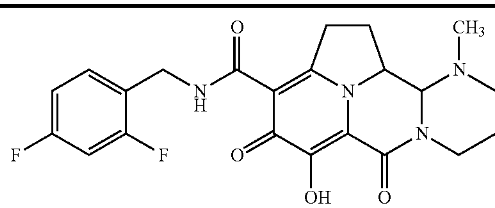 | diastereomer 1, enantiomer B | Calc'd 445.2, found 445.2 |

-continued

| Compound | Structure | Stereochemistry | Exact Mass [M + H]+ |
|---|---|---|---|
| 82 | 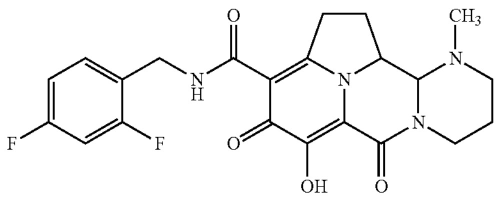 [SMILES: CN1CCCN2C(=O)c3c(O)c(=O)c(C(=O)NCc4ccc(F)cc4F)c4n3C(CC4)C12] | diastereomer 2, enantiomer A | Calc'd 445.2, found 445.2 |
| 83 | 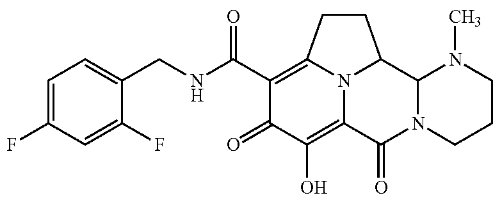 [SMILES: CN1CCCN2C(=O)c3c(O)c(=O)c(C(=O)NCc4ccc(F)cc4F)c4n3C(CC4)C12] | diastereomer 2, enantiomer B | Calc'd 445.2, found 445.2 |
| 84 | 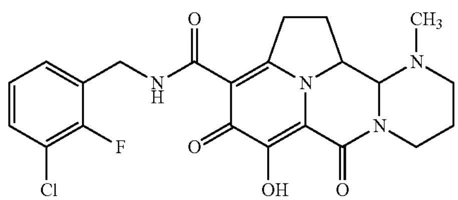 [SMILES: CN1CCCN2C(=O)c3c(O)c(=O)c(C(=O)NCc4cccc(Cl)c4F)c4n3C(CC4)C12] | diastereomer 1, enantiomer A | Calc'd 461.1, found 461.1 |
| 85 | 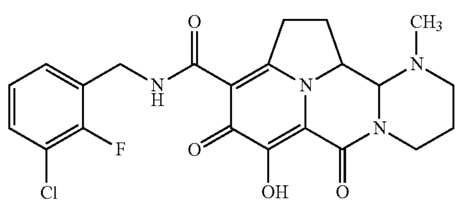 [SMILES: CN1CCCN2C(=O)c3c(O)c(=O)c(C(=O)NCc4cccc(Cl)c4F)c4n3C(CC4)C12] | diastereomer 1, enantiomer B | Calc'd 461.1, found 461.1 |
| 86 | 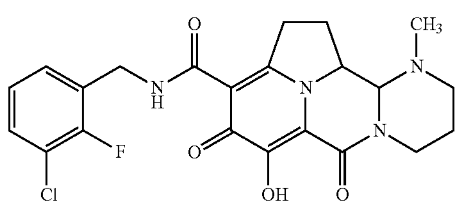 [SMILES: CN1CCCN2C(=O)c3c(O)c(=O)c(C(=O)NCc4cccc(Cl)c4F)c4n3C(CC4)C12] | diastereomer 2, enantiomer A | Calc'd 461.1, found 461.1 |
| 87 | 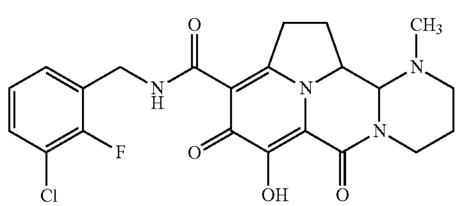 [SMILES: CN1CCCN2C(=O)c3c(O)c(=O)c(C(=O)NCc4cccc(Cl)c4F)c4n3C(CC4)C12] | diastereomer 2, enantiomer B | Calc'd 461.1, found 461.1 |

| Compound | $^1$H NMR |
|---|---|
| 81 | $^1$H NMR (400 MHz, CDCl$_3$) δ 10.78 (s, 1H), 7.26-7.32 (m, 2H), 6.70-6.76 (m, 2H), 4.45-4.54 (m, 4H), 4.26-4.27 (m, 1H), 4.02-4.06 (m, 1H), 2.96-3.31 (m, 4H), 2.49 (s, 4H), 2.03-2.10 (m, 2H), 1.58-1.60 (m, 1H). |
| 82 | $^1$H NMR (400 MHz, CDCl$_3$) δ 10.83 (s, 1H), 7.26-7.32 (m, 2H), 6.64-6.72 (m, 2H), 4.77-4.83 (m, 2H), 4.48-4.56 (m, 3H), 4.07-4.09 (m, 1H), 3.65-3.67 (m, 1H), 3.27-3.31 (m, 2H), 3.00-3.25 (m, 2H), 2.32-2.37 (m, 3H), 2.27 (s, 3H). |
| 83 | $^1$H NMR (400 MHz, CDCl$_3$) δ 10.83 (s, 1H), 7.26-7.32 (m, 2H), 6.64-6.72 (m, 2H), 4.77-4.82 (m, 2H), 4.48-4.57 (m, 3H), 4.10-4.12 (m, 1H), 3.64-3.67 (m, 1H), 3.26-3.31 (m, 2H), 2.93-3.04 (m, 2H), 2.29-2.37 (m, 3H), 2.27 (s, 3H). |
| 84 | $^1$H NMR (400 MHz, CDCl$_3$) δ 10.75 (brs, 1H), 7.28 (s, 2H), 7.03 (t, J = 7.5 Hz, 1H), 4.51-4.78 (m, 4H), 4.41 (d, J = 6.6 Hz, 1H), 3.99 (dd, J = 18.9, 8.7 Hz, 1H), 3.00-3.43 (m, 4H), 2.44-2.72 (m, 4H), 1.97-2.19 (m, 2H), 1.72 (d, J = 12.8 Hz, 1H). |
| 85 | $^1$H NMR (400 MHz, CDCl$_3$) δ 10.79 (brs, 1H), 7.28 (brs, 2H), 7.02 (t, J = 7.4 Hz, 1H), 4.51-4.72 (m, 4H), 4.40 (d, J = 7.1 |

| Com-pound | ¹H NMR |
|---|---|
| | Hz, 1H), 4.03 (dd, J = 19.0, 8.8 Hz, 1H), 3.28-3.46 (m, 1H), 2.99-3.23 (m, 3H), 2.62 (brs, 4H), 1.97-2.22 (m, 2H), 1.71 (d, J = 13.7 Hz, 1H). |
| 86 | ¹H NMR (400 MHz, CDCl₃) δ 10.83 (br. s., 1H), 7.27 (br. s., 2H), 6.95-7.08 (m, 1H), 5.11 (br. s., 1H), 4.86 (d, J = 12.8 Hz, 1H), 4.65 (br. s., 3H), 4.16 (dd, J = 17.8, 8.5 Hz, 1H), 3.34-3.53 (m, 2H), 3.02-3.22 (m, 2H), 2.09-2.56 (m, 6H), 1.42-1.61 (m, 1H). |
| 87 | ¹H NMR (400 MHz, CDCl₃) δ 10.83 (brs, 1H), 7.25-7.29 (m, 2H), 7.01 (t, J = 7.6 Hz, 1H), 5.09 (brs, 1H), 4.86 (d, J = 13.9 Hz, 1H), 4.55-4.74 (m, 3H), 4.16 (dd, J = 18.6, 8.7 Hz, 1H), 3.45 (d, J = 11.2 Hz, 2H), 3.04-3.19 (m, 2H), 2.10-2.50 (m, 6H), 1.54 (d, J = 14.3 Hz, 1H). |

Example 15

Preparation of Compound 88

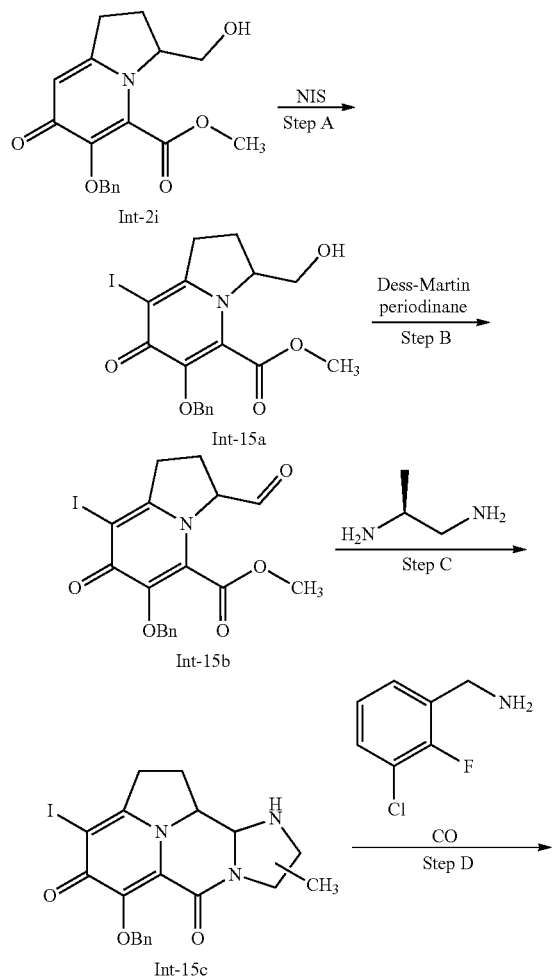

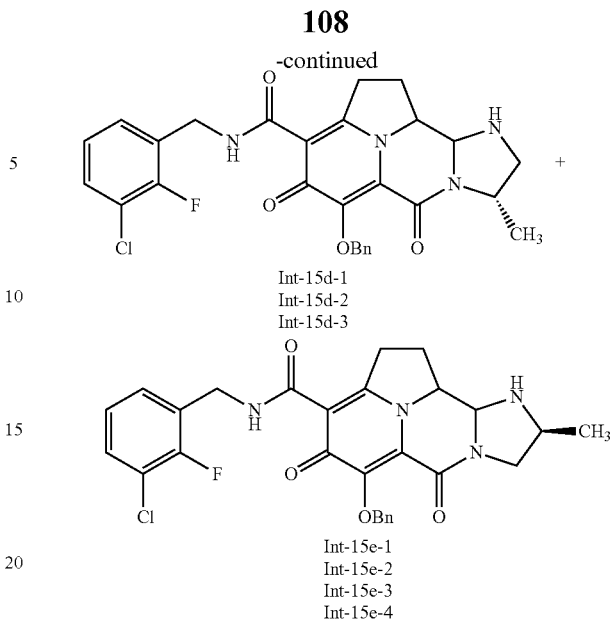

Step A—Synthesis of Intermediate Compound Int-15a

To a solution of Int-2i (1.50 g, 4.55 mmol) in methanol (30 ml) was added 3-chlorobenzoperoxoic acid (2.95 g, 13.66 mmol) and N-iodosuccinimide (3.07 g, 13.66 mmol). The mixture was stirred at 70° C. for 2 h, cooled to rt. The mixture was quenched with saturated aqueous $Na_2SO_3$ (20 mL) and extracted with dichloromethane. The organic phase was dried over anhydrous $Na_2SO_4$, filtered and the filtrate was concentrated in vacuo. The resulting residue was purified using column chromatography on silica gel (DCM:MeOH=20:1) to provide Int-15a. Mass Calc'd for $C_{18}H_{18}INO_5$: 455.0, found 456.0 (M+H)⁺.

Step B—Synthesis of Intermediate Compound Int-15b

To a solution of Int-15a (900 mg, 1.977 mmol) in dichloromethane (20 ml) was added Dess-Martin reagent (1677 mg, 3.95 mmol). The mixture was stirred at 0° C. for 4 h, quenched with saturated aqueous $NaHCO_3$ (10 mL) and extracted with dichloromethane. The organic phase was dried over anhydrous $Na_2SO_4$, filtered and the filtrate was concentrated in vacuo. The resulting residue was purified using column chromatography on silica gel (DCM:

MeOH=20:1) to provide Int-15b. Mass Calc'd for $C_{18}H_{16}INO_5$: 453.0, found 454.0 (M+H)$^+$.

Step C—Synthesis of Intermediate Compound Int-15c

To a solution of Int-15b (700 mg, 1.544 mmol) in tetrahydrofuran (20 mL) was added acetic acid (0.2 mL) and (S)-propane-1,2-diamine (229 mg, 3.09 mmol). The mixture was stirred at 80° C. for 0.5 h cooled to room temperature and concentrated in vacuo. The resulting residue was purified using column chromatography on silica gel (dichloromethane:methanol=10:1) to provide compound Int-15c as a mixture of isomers. $^1$H NMR (400 MHz, CDCl$_3$) δ 7.65-7.82 (m, 2H), 7.28-7.45 (m, 3H), 4.99-5.20 (m, 2H), 4.70-4.82 (m, 1H), 4.43-4.52 (m, 1H), 4.08-4.34 (m, 2H), 3.95-3.97 (m, 1H), 2.84-3.31 (m, 2H), 2.24-2.38 (m, 1H), 1.90-2.07 (m, 1H), 1.10-1.16 (m, 3H).

Step D—Synthesis of Intermediate Compound Int-15d

To a solution of Int-15c (500 mg, 1.048 mmol) in dimethylsulfoxide (20 mL) was added N,N-diisopropylethylamine (0.915 mL, 5.24 mmol), 3-chloro-2-fluorobenzylamine (669 mg, 4.19 mmol) and Pd(Ph$_3$P)$_4$ (242 mg, 0.210 mmol). The mixture was stirred at 80° C. for 2 h under carbon monoxide (1 atm), cooled to room temperature and filtered. The filtrate was concentrated in vacuo and the residue obtained was purified using SFC (Chralpak AD, 250×30 mm, 10 μm, 50% isopropanol in SC—CO$_2$, 80 mL/min, 220 nm) followed by SFC (Chralpak OJ, 250×30 mm, 10 μm, 30% methanol in SC—CO$_2$, 80 mL/min, 220 nm) to provide the following compounds.

Int-15d-1: $^1$H NMR (400 MHz, CDCl$_3$) δ 10.87 (s, 1H), 7.60-7.62 (m, 2H), 7.26-7.36 (m, 5H), 7.03-7.05 (m, 1H), 5.07-5.28 (m, 2H), 4.63-4.69 (m, 2H), 4.49-4.51 (m, 2H), 4.36-4.37 (m, 1H), 4.07-4.10 (m, 1H), 3.70-3.72 (m, 1H), 3.34-3.37 (m, 2H), 2.22-2.55 (m, 2H), 1.32 (d, J=6.8 Hz, 3H). Mass Calc'd for $C_{28}H_{26}ClFN_4O_4$: 536.2, found 537.2 (M+H)$^+$. SFC: OJ, R$_t$=1.46 min.

Int-15d-2: $^1$H NMR (400 MHz, CDCl$_3$) δ 10.93 (s, 1H), 7.62-7.64 (m, 2H), 7.26-7.36 (m, 5H), 7.03-7.05 (m, 1H), 5.18-5.33 (m, 2H), 4.65-4.69 (m, 2H), 4.41-4.43 (m, 1H), 4.08-4.10 (m, 2H), 3.70-3.74 (m, 1H), 3.19-3.49 (m, 3H), 2.49-2.54 (m, 1H), 1.95-2.01 (m, 1H), 1.32 (d, J=6 Hz, 3H). Mass Calc'd for $C_{28}H_{26}ClFN_4O_4$: 536.2, found 537.2 (M+H)$^+$. SFC: OJ, R$_t$=3.43 min.

Int-15d-3: $^1$H NMR (400 MHz, CDCl$_3$) δ 10.95 (s, 1H), 7.60-7.62 (m, 2H), 7.26-7.36 (m, 5H), 7.01-7.05 (m, 1H), 5.20-5.33 (m, 2H), 4.65-4.70 (m, 2H), 4.28-4.30 (m, 2H), 4.09-4.13 (m, 2H), 3.02-3.22 (m, 3H), 2.53-2.57 (m, 1H), 1.94-1.99 (m, 1H), 1.42 (d, J=6.4 Hz, 3H). Mass Calc'd for $C_{28}H_{26}ClFN_4O_4$: 536.2, found 537.2 (M+H)$^+$. SFC: OJ, R$_t$=1.42 min.

Int-15e-1: $^1$H NMR (400 MHz, CDCl$_3$) δ 10.88 (s, 1H), 7.60-7.62 (m, 2H), 7.26-7.36 (m, 5H), 7.03-7.05 (m, 1H), 5.11-5.28 (m, 2H), 4.65-4.66 (m, 2H), 4.49-4.58 (m, 3H), 4.08-4.11 (m, 1H), 3.29-3.38 (m, 2H), 2.74-2.76 (m, 1H), 2.16-2.40 (m, 2H), 1.20 (d, J=4 Hz, 3H). Mass Calc'd for $C_{28}H_{26}ClFN_4O_4$: 536.2, found 537.2 (M+H)$^+$. SFC: OJ, R$_t$=1.64 min.

Int-15e-2: $^1$H NMR (400 MHz, CDCl$_3$) δ 10.87 (s, 1H), 7.60-7.62 (m, 2H), 7.26-7.36 (m, 5H), 7.03-7.05 (m, 1H), 5.12-5.31 (m, 2H), 4.40-4.69 (m, 4H), 4.07-4.10 (m, 1H), 3.86-3.87 (m, 1H), 3.32-3.45 (m, 3H), 2.11-2.41 (m, 2H), 1.17 (d, J=5.6 Hz, 3H). Mass Calc'd for $C_{28}H_{26}ClFN_4O_4$: 536.2, found 537.2 (M+H)$^+$. SFC: OJ, R$_t$=1.86 min.

Int-15e-3: $^1$H NMR (400 MHz, CDCl$_3$) δ 10.92 (s, 1H), 7.60-7.62 (m, 2H), 7.26-7.36 (m, 5H), 7.03-7.05 (m, 1H), 5.19-5.36 (m, 2H), 4.66-4.68 (m, 2H), 4.36-4.47 (m, 2H), 4.00-4.07 (m, 2H), 3.32-3.33 (m, 2H), 2.79-2.83 (m, 1H), 2.50-2.51 (m, 1H), 1.95-1.99 (m, 1H), 1.30 (d, J=6.4 Hz, 3H). Mass Calc'd for $C_{28}H_{26}ClFN_4O_4$: 536.2, found 537.2 (M+H)$^+$. SFC: OJ, R$_t$=3.79 min.

Int-15e-4: $^1$H NMR (400 MHz, CDCl$_3$) δ 10.93 (s, 1H), 7.62-7.64 (m, 2H), 7.26-7.36 (m, 5H), 7.03-7.05 (m, 1H), 5.18-5.33 (m, 2H), 4.55-4.67 (m, 3H), 3.99-4.11 (m, 3H), 3.28-3.33 (m, 2H), 2.68-2.73 (m, 1H), 2.43-2.45 (m, 1H), 1.94-1.97 (m, 1H), 1.21 (d, J=6.4 Hz, 3H). Mass Calc'd for $C_{28}H_{26}ClFN_4O_4$: 536.2, found 537.2 (M+H)$^+$. SFC: OJ, R$_t$=1.61 min.

Step E—Synthesis of Compound 88

To a solution of Int-15d-1 (10 mg, 0.019 mmol) in dichloromethane (3 mL) was added trifluoroacetic acid (1 mL, 12.98 mmol) at 0° C. The mixture was stirred at 18° C. for 2 hours. The mixture was concentrated in vacuo and the residue obtained was purified using preparative RP-HPLC to provide compound 88. $^1$H NMR (400 MHz, CDCl$_3$) δ 9.73 (s, 1H), 7.30-7.38 (m, 2H), 7.13-7.17 (m, 1H), 5.51 (s, 1H), 4.88-4.90 (d, J=5.2 Hz, 1H), 4.61-4.72 (m, 3H), 3.87-3.92 (m, 1H), 3.67-3.72 (m, 1H), 3.18-3.22 (m, 2H), 2.61-2.63 (m, 1H), 2.27-2.32 (m, 1H), 1.55-1.57 (d, J=6.4 Hz, 3H). Mass Calc'd for $C_{21}H_{20}ClFN_4O_4$: 446.1, found 447.1 (M+H)$^+$.

The following compounds of the present invention were made using the methodology described in Example 15, and substituting the appropriate reactants and/or reagents.

| Compound | Structure | derived from | Exact Mass [M + H]$^+$ |
|---|---|---|---|
| 89 | 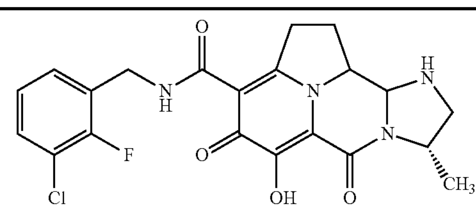 | Int-15d-2 | Calc'd 447.1, found 447.1 |
| 90 | 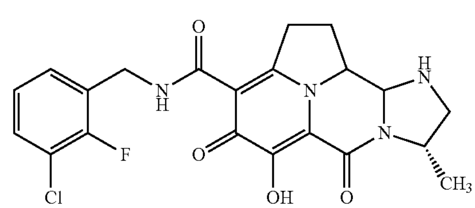 [SMILES: C[C@H]1CNC2C3CCc4c(C(=O)NCc5cccc(Cl)c5F)c(=O)c(O)c(n43)C(=O)N21] | Int-15d-3 | Calc'd 447.1, found 447.1 |

| Compound | ¹H NMR |
|---|---|
| 89 | ¹H NMR (400 MHz, MeOD) δ 7.31-7.40 (m, 2H), 7.10-7.14 (m, 1H), 4.85-4.90 (m, 1H), 4.83-4.85 (m, 2H), 4.34-4.37 (m, 2H), 3.93-3.98 (m, 1H), 3.60-3.65 (m, 1H), 3.34-3.37 (m, 1H), 2.94-2.99 (m, 1H), 2.57-2.60 (m, 1H), 2.06-2.11 (m, 1H), 1.42-1.44 (d, J = 6.4 Hz, 3H). |
| 90 | ¹H NMR (400 MHz, CDCl₃) δ 10.84 (s, 1H), 7.25-7.29 (m, 2H), 7.00-7.04 (m, 1H), 4.67-4.68 (m, 1H), 4.32-4.45 (m, 2H), 4.18 (s, 2H), 3.34-3.38 (m, 2H), 3.13-3.16 (m, 1H), 2.62-2.63 (m, 1H), 2.05 (m, 1H), 1.43-1.44 (d, J = δ Hz, 3H). |

Step F—Synthesis of Compound 91

To a solution of Int-15e-1 (10 mg, 0.019 mmol) in dichloromethane (1.5 mL) was added trifluoroacetic acid (0.5 mL, 6.49 mmol). The mixture was stirred at 15° C. for 1.5 hours. The mixture was concentrated in vacuo and purified using preparative RP-HPLC to provide 91. ¹H NMR (400 MHz, CDCl₃) δ 9.74 (s, 1H), 7.30-7.37 (m, 2H), 7.12-7.16 (m, 1H), 5.57 (s, 1H), 4.75-4.82 (m, 2H), 4.57-4.61 (m, 2H), 4.22-4.23 (m, 1H), 3.56-3.58 (m, 1H), 3.10-3.16 (m, 2H), 2.63-2.65 (m, 1H), 2.23-2.32 (m, 1H), 1.57 (d, J=5.6 Hz, 3H). Mass Calc'd for C₂₁₁-120ClFN₄O₄: 446.1, found 447.1 (M+H)⁺.

The following compounds of the present invention were made using the methodology described in Example 15, and substituting the appropriate reactants and/or reagents.

| Compound | ¹H NMR |
|---|---|
| 92 | ¹H NMR (400 MHz, CDCl₃) δ 9.82 (s, 1H), 7.26-7.35 (m, 2H), 7.15-7.17 (m, 1H), 5.35 (s, 1H), 4.52-4.64 (m, 3H), 3.96-4.07 (m, 2H), 3.83-3.85 (m, 1H), 3.50-3.53 (m, 1H), 3.12-3.14 (m, 1H), 2.57-2.61 (m, 1H), 2.23-2.32 (m, 1H), 1.67 (d, J = 5.2 Hz, 3H). |
| 93 | ¹H NMR (400 MHz, CDCl₃) δ 10.57 (s, 1H), 7.26-7.28 (m, 2H), 6.99-7.03 (m, 1H), 4.73 (d, J = 7.8 Hz, 1H), 4.61 (d, J = 5.2 Hz, 1H), 4.34-4.46 (m, 1H), 4.04-4.07 (m, 1H), 3.88-3.90 (m, 1H), 3.72-3.74 (m, 1H), 3.26-3.28 (m, 2H), 2.58-2.63 (m, 1H), 2.01-2.05 (m, 1H), 1.43 (d, J = 6.2 Hz, 3H). |
| 94 | ¹H NMR (400 MHz, CDCl₃) δ 10.55 (s, 1H), 7.26-7.28 (m, 2H), 6.98-7.02 (m, 1H), 4.90 (d, J = 9.6 Hz, 1H), 4.60 (d, J = 4.8 Hz, 2H), 4.26-4.30 (m, 1H), 4.01-4.12 (m, 2H), 3.74-3.75 (m, 1H), 3.09-3.14 (m, 2H), 2.56-2.59 (m, 1H), 1.97-2.02 (m, 1H), 1.37 (d, J = 6.4 Hz, 3H). |

| Compound | Structure | derived from | Exact Mass [M + H]⁺ |
|---|---|---|---|
| 92 | 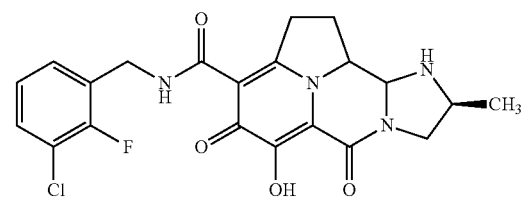 [SMILES: C[C@H]1CN2C(=O)c3c(O)c(=O)c(C(=O)NCc4cccc(Cl)c4F)c4n3C(CC4)C2N1] | Int-15e-2 | Calc'd 447.1, found 447.1 |
| 93 | 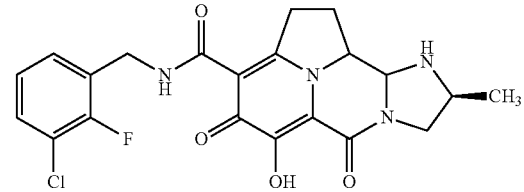 [SMILES: C[C@H]1CN2C(=O)c3c(O)c(=O)c(C(=O)NCc4cccc(Cl)c4F)c4n3C(CC4)C2N1] | Int-15e-3 | Calc'd 447.1, found 447.1 |
| 94 | 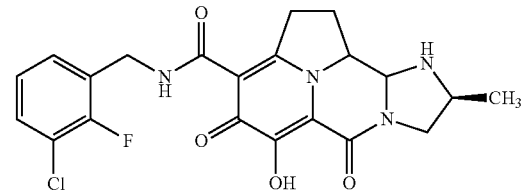 [SMILES: C[C@H]1CN2C(=O)c3c(O)c(=O)c(C(=O)NCc4cccc(Cl)c4F)c4n3C(CC4)C2N1] | Int-15e-4 | Calc'd 447.1, found 447.1 |

Example 16

Preparation of Compound 95

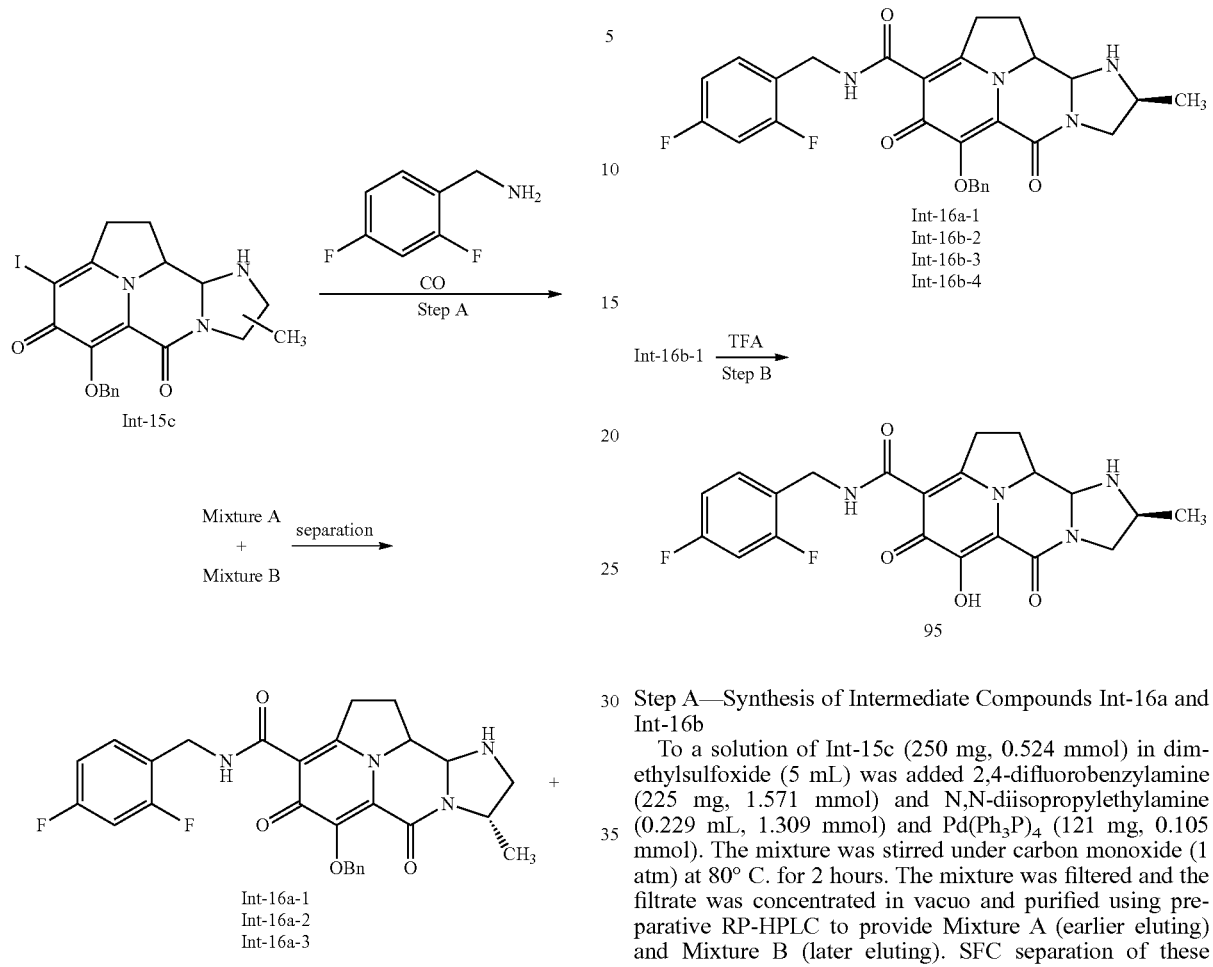

Step A—Synthesis of Intermediate Compounds Int-16a and Int-16b

To a solution of Int-15c (250 mg, 0.524 mmol) in dimethylsulfoxide (5 mL) was added 2,4-difluorobenzylamine (225 mg, 1.571 mmol) and N,N-diisopropylethylamine (0.229 mL, 1.309 mmol) and Pd(Ph$_3$P)$_4$ (121 mg, 0.105 mmol). The mixture was stirred under carbon monoxide (1 atm) at 80° C. for 2 hours. The mixture was filtered and the filtrate was concentrated in vacuo and purified using preparative RP-HPLC to provide Mixture A (earlier eluting) and Mixture B (later eluting). SFC separation of these mixtures was conducted according to the following scheme.

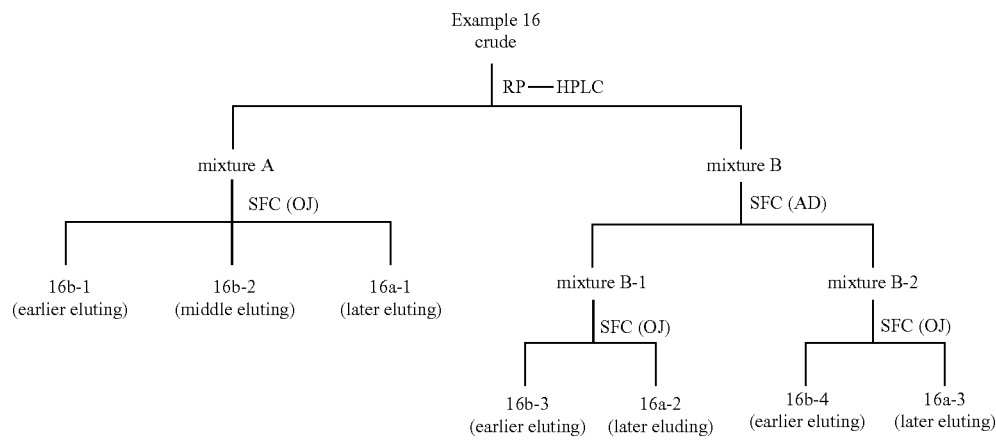

The mixture A (75 mg, 0.072 mmol) were separated by SFC (Chralpak OJ, 250×30 mm, 10 μm, 30% methanol in SC—CO$_2$, 80 mL/min, 220 nm) to provide 16b-1 and 16b-2 and 16a-1.

16b-1: $^1$H NMR (400 MHz, CDCl$_3$): δ 10.87 (s, 1H), 7.60-7.62 (m, 2H), 7.26-7.36 (m, 4H), 6.77-6.81 (m, 2H), 5.07-5.26 (m, 2H), 4.49-4.60 (m, 5H), 4.36-4.38 (m, 1H), 3.29-3.38 (m, 2H), 3.45-3.54 (m, 2H), 3.22-3.25 (m, 1H), 1.31-1.32 (m, 3H). Mass Calc'd for C$_{28}$H$_{26}$F$_2$N$_4$O$_4$: 520.2, found 521.2 (M+H)$^+$.

16b-2: $^1$H NMR (400 MHz, CDCl$_3$): δ 10.88 (s, 1H), 7.60-7.62 (m, 2H), 7.26-7.36 (m, 4H), 6.77-6.83 (m, 2H), 5.11-5.28 (m, 2H), 4.51-4.60 (m, 5H), 4.08-4.11 (m, 1H), 3.29-3.33 (m, 2H), 3.72-3.76 (m, 1H), 3.40-3.42 (m, 1H), 3.17-3.20 (m, 1H), 1.21-1.24 (m, 3H). Mass Calc'd for C$_{28}$H$_{26}$F$_2$N$_4$O$_4$: 520.2, found 521.2 (M+H)$^+$.

16a-1: $^1$H NMR (400 MHz, CDCl$_3$): δ 10.68 (s, 1H), 7.60-7.62 (m, 2H), 7.26-7.36 (m, 4H), 6.77-6.84 (m, 2H), 5.12-5.22 (m, 2H), 4.51-4.59 (m, 4H), 4.07-4.10 (m, 1H), 3.89-3.90 (m, 1H), 3.57-3.58 (m, 1H), 3.27-3.30 (m, 2H), 3.15-3.43 (m, 2H), 1.20-1.22 (m, 3H). Mass Calc'd for C$_{28}$H$_{26}$F$_2$N$_4$O$_4$: 520.2, found 521.2 (M+H)$^+$.

The Mixture B (250 mg, 0.240 mmol) was separated by SFC (Chralpak AD, 250×30 mm, 10 μm, 55% IPA in SC—CO$_2$, 80 mL/min, 220 nm) to provide mixture B-1 (earlier eluting) and mixture B-2 (later eluting).

The mixture B-1 was separated by SFC (Chralpak OJ, 250×30 mm, 10 μm, 30% methanol in SC—CO$_2$, 80 mL/min, 220 nm) to provide 16b-3 and 16a-2.

16b-3: $^1$H NMR (400 MHz, CDCl$_3$): δ 10.92 (s, 1H), 7.62-7.63 (m, 2H), 7.28-7.36 (m, 4H), 6.79-6.84 (m, 2H), 5.11-5.24 (m, 2H), 4.58-4.59 (m, 2H), 4.43-4.45 (m, 1H), 4.26-4.27 (m, 1H), 3.97-4.03 (m, 2H), 3.21-3.23 (m, 2H), 3.68-3.72 (m, 1H), 3.47-3.52 (m, 1H), 1.90-1.95 (m, 1H), 1.24-1.25 (m, 3H). Mass Calc'd for C$_{28}$H$_{26}$F$_2$N$_4$O$_4$: 520.2, found 521.2 (M+H)$^+$.

16a-2: $^1$H NMR (400 MHz, CDCl$_3$): δ 10.90 (s, 1H), 7.62-7.63 (m, 2H), 7.28-7.36 (m, 4H), 6.77-6.81 (m, 2H), 5.05-5.12 (m, 2H), 4.57-4.59 (m, 2H), 4.38-4.40 (m, 1H), 4.01-4.04 (m, 2H), 3.51-3.52 (m, 1H), 3.23-3.26 (m, 2H), 3.99-3.02 (m, 1H), 3.28-3.33 (m, 1H), 1.86-1.89 (m, 1H), 1.21-1.23 (m, 3H). Mass Calc'd for C$_{28}$H$_{26}$F$_2$N$_4$O$_4$: 520.2, found 521.2 (M+H)$^+$.

The mixture B-2 (130 mg, 0.125 mmol) were separated by SFC (Chralpak OJ, 250×30 mm, 10 μm, 30% methanol in SC—CO$_2$, 80 mL/min, 220 nm) to provide 16b-4 and 16a-3.

16b-4: $^1$H NMR (400 MHz, CDCl): δ 10.89 (s, 1H), 7.61-7.63 (m, 2H), 7.28-7.38 (m, 4H), 6.79-6.84 (m, 2H), 5.16-5.29 (m, 2H), 4.58-4.62 (m, 2H), 4.25-4.29 (m, 2H), 4.06-4.10 (m, 2H), 3.98-3.19 (m, 3H), 3.50-3.53 (m, 1H), 1.90-1.95 (m, 1H), 1.39-1.40 (m, 3H). Mass Calc'd for C$_{28}$H$_{26}$F$_2$N$_4$O$_4$: 520.2, found 521.2 (M+H)$^+$.

16a-3: $^1$H NMR (400 MHz, CDCl$_3$): δ10.85 (s, 1H), 7.63-7.64 (m, 2H), 7.28-7.36 (m, 4H), 6.78-6.85 (m, 2H), 5.10-5.26 (m, 2H), 4.54-4.61 (m, 3H), 4.00-4.12 (m, 3H), 3.29-3.33 (m, 2H), 3.70-3.75 (m, 1H), 3.45-3.46 (m, 1H), 1.91-1.96 (m, 1H), 1.21-1.23 (m, 3H). Mass Calc'd for C$_{28}$H$_{26}$F$_2$N$_4$O$_4$: 520.2, found 521.2 (M+H)$^+$.

Step B—Synthesis of Compound 95

To a solution of 16b-1 (15 mg, 0.029 mmol) in dichloromethane (2 mL) was added trifluoroacetic acid (0.5 mL, 6.49 mmol). The mixture was stirred at room temperature for 1.5 hours. The mixture was concentrated in vacuo and the residue obtained was purified using RP-HPLC to provide compound 95. $^1$H NMR (400 MHz, CD$_3$OD): δ 7.42-7.48 (m, 1H), 6.94-7.00 (m, 2H), 5.23 (d, J=4.4 Hz, 1H), 4.96-5.06 (m, 1H), 4.75-4.82 (m, 2H), 4.47-4.61 (m, 2H), 4.09-4.11 (m, 1H), 3.80-3.82 (m, 1H), 3.10-3.16 (m, 1H), 3.53-3.63 (m, 1H), 3.05-3.17 (m, 1H), 1.47 (d, J=6.4 Hz, 3H). Mass Calc'd for C$_{21}$H$_{20}$F$_2$N$_4$O$_4$: 430.1, found 431.0 (M+H)$^+$.

The following compounds of the present invention were made using the methodology described in Example 16, and substituting the appropriate reactants and/or reagents.

| Compound | Structure | derived from | Exact Mass [M + H]$^+$ |
|---|---|---|---|
| 96 | 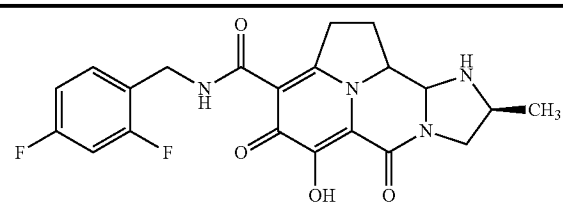 | Int-16b-2 | Calc'd 431.2, found 431.0 |
| 97 | 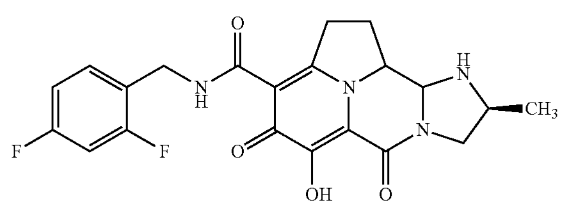 [SMILES: C[C@H]1CN2C(=O)c3c(O)c(=O)c(C(=O)NCc4ccc(F)cc4F)c4n3C(CC4)C2N1] | Int-16b-3 | Calc'd 431.2, found 431.0 |
| 98 | 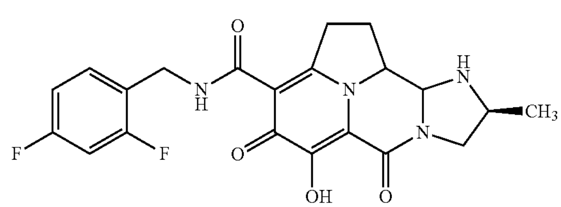 [SMILES: C[C@H]1CN2C(=O)c3c(O)c(=O)c(C(=O)NCc4ccc(F)cc4F)c4n3C(CC4)C2N1] | Int-16b-4 | Calc'd 431.2, found 431.0 |

| Compound | Structure | derived from | Exact Mass [M + H]+ |
|---|---|---|---|
| 99 | 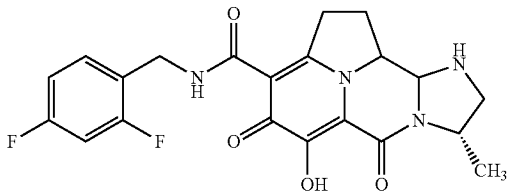 [SMILES: C[C@H]1CNC2C3CCc4c(C(=O)NCc5ccc(F)cc5F)c(=O)c(O)c(n43)C(=O)N21] | Int-16a-1 | Calc'd 431.2, found 431.0 |
| 100 | 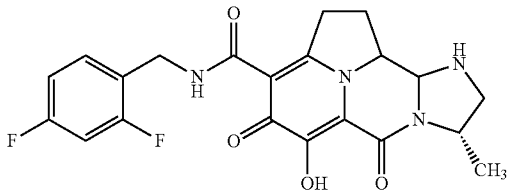 [SMILES: C[C@H]1CNC2C3CCc4c(C(=O)NCc5ccc(F)cc5F)c(=O)c(O)c(n43)C(=O)N21] | Int-16a-2 | Calc'd 431.2, found 431.0 |
| 101 | 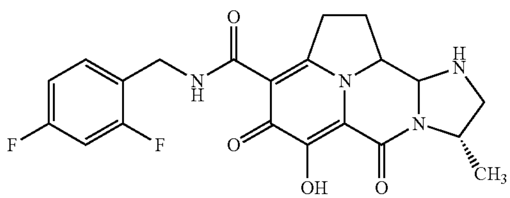 [SMILES: C[C@H]1CNC2C3CCc4c(C(=O)NCc5ccc(F)cc5F)c(=O)c(O)c(n43)C(=O)N21] | Int-16a-3 | Calc'd 431.2, found 431.0 |

| Compound | ¹H NMR |
|---|---|
| 96 | ¹H NMR (400 MHz, CD₃OD): δ 7.42-7.48 (m, 1H), 6.92-6.99 (m, 2H), 5.21-5.23 (m, 1H), 4.96-5.06 (m, 1H), 4.52-4.61 (m, 2H), 3.80-3.94 (m, 4 H), 3.30-3.32 (m, 1H), 3.53-3.59 (m, 1H), 3.05-3.17 (m, 1H), 1.50 (d, J = 6.4 Hz, 3H). |
| 97 | ¹H NMR (400 MHz, CD₃OD): δ 7.42-7.48 (m, 1H), 6.88-6.96 (m, 2H), 4.80-4.83 (m, 1H), 4.47-4.56 (m, 3H), 3.77-4.01 (m, 3H), 3.37-3.42 (m, 2H), 3.56-3.61 (m, 1H), 3.05-3.11 (m, 1H), 1.45 (d, J = 6.4 Hz, 3H). |
| 98 | ¹H NMR (400 MHz, CD₃OD): δ 7.42-7.48 (m, 1H), 6.88-6.96 (m, 2H), 5.01-5.03 (m, 2H), 4.47-4.56 (m, 3H), 3.96-4.15 (m, 3H), 3.33-3.42 (m, 1H), 3.56-3.61 (m, 1H), 3.05-3.11 (m, 1H), 1.42 (d, J = 6.4 Hz, 3H). |
| 99 | ¹H NMR (400 MHz, CD₃OD): δ 7.44-7.48 (m, 1H), 6.95-7.01 (m, 2H), 5.29 (br., 1H), 4.99 (br., 1H), 4.87 (br., 2H), 4.50-4.62 (m, 2H), 3.96 (br., 1H), 3.73-3.78 (m, 1H), 3.07 (br., 1H), 2.55-2.62 (m, 1H), 2.10-2.18 (m, 1H), 1.48 (d, J = 4.8 Hz, 3H). |
| 100 | ¹H NMR (400 MHz, CD₃OD): δ 7.38-7.43 (m, 1H), 6.89-6.96 (m, 2H), 4.87 (br., 1H), 4.54 (s, 2H), 4.35-4.37 (m, 2H), 3.89-3.96 (m, 1H), 3.63-3.68 (m, 1H), 3.33-3.35 (m, 1H), 2.98-3.03 (m, 1H), 2.54-2.57 (m, 1H), 2.04-2.09 (m, 1H), 1.42 (d, J = 6.4 Hz, 3H). |
| 101 | ¹H NMR (400 MHz, CD₃OD): δ 7.37-7.43 (m, 1H), 6.88-6.96 (m, 2H), 4.57-4.60 (m, 3H), 4.42-4.44 (m, 1H), 4.29-4.31 (m, 1H), 3.93-3.98 (m, 1H), 3.34-3.39 (m, 2H), 3.18-3.21 (m, 1H), 2.54-2.59 (m, 1H), 2.04-2.09 (m, 1H), 1.40 (d, J = 6.4 Hz, 3H). |

Example 17

Preparation of Compound 102

To a solution of compound 91 (6.8 mg, 0.015 mmol) in dichloromethane (1 mL) and methanol (1 mL) was added acetic acid (0.1 mL), paraformaldehyde (5.48 mg, 0.061 mmol) and NaBH₃CN (2.87 mg, 0.046 mmol). The mixture was stirred at 40° C. for 4 hours. The mixture was concentrated in vacuo and the residue obtained was purified using preparative RP-HPLC to provide compound 102. ¹H NMR (400 MHz, CDCl₃): δ 10.78 (br. s., 1H), 7.26-7.31 (m, 2H), 6.99-7.06 (m, 1H), 4.55-4.82 (m, 4H), 4.44-4.45 (m, 1H), 4.15-4.23 (m, 1H), 3.48-3.52 (m, 1H), 3.22-3.25 (m, 1H), 2.85-2.87 (m, 1H), 2.59-2.65 (m, 1H), 2.41-2.45 (m, 1H), 2.09 (s, 3H), 1.34 (d, J=6.8 Hz, 3H). Mass Calc'd for C₂₂H₂₂ClFN₄O₄: 460.1, found 461.1 (M+H)⁺.

The following compounds of the present invention were made using the methodology described in Example 17 and substituting the appropriate reactants and/or reagents.

| Compound | Structure | Starting Material Compound No. | Exact Mass [M + H]+ |
|---|---|---|---|
| 103 | 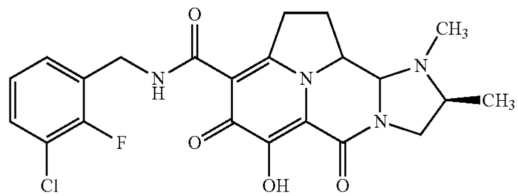 [SMILES: C[C@H]1CN2C(=O)c3c(O)c(=O)c(C(=O)NCc4cccc(Cl)c4F)c4n3C(CC4)C2N1C] | 92 | Calc'd 461.1, found 460.1 |
| 104 | 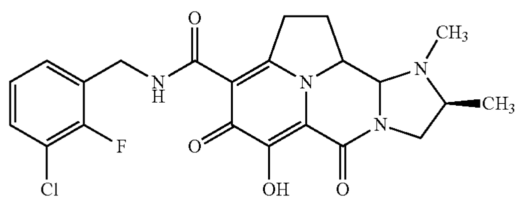 [SMILES: C[C@H]1CN2C(=O)c3c(O)c(=O)c(C(=O)NCc4cccc(Cl)c4F)c4n3C(CC4)C2N1C] | 93 | Calc'd 461.1, found 460.1 |
| 105 | 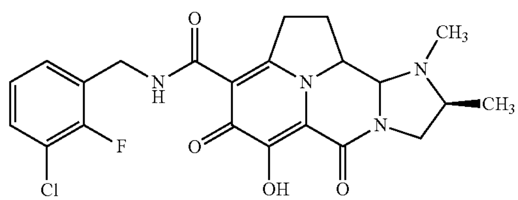 [SMILES: C[C@H]1CN2C(=O)c3c(O)c(=O)c(C(=O)NCc4cccc(Cl)c4F)c4n3C(CC4)C2N1C] | 94 | Calc'd 461.1, found 460.1 |
| 106 | 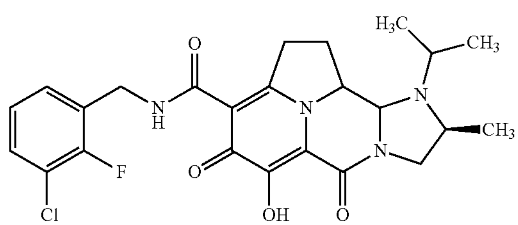 [SMILES: CC(C)N1C2C3CCc4c(C(=O)NCc5cccc(Cl)c5F)c(=O)c(O)c(n43)C(=O)N2C[C@@H]1C] | 93 | Calc'd 488.2, found 489.1 |
| 107 | 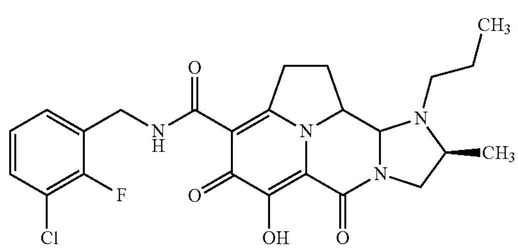 [SMILES: CCCN1C2C3CCc4c(C(=O)NCc5cccc(Cl)c5F)c(=O)c(O)c(n43)C(=O)N2C[C@@H]1C] | 93 | Calc'd 488.2, found 489.1 |
| 108 | 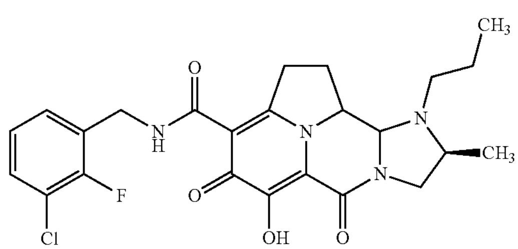 [SMILES: CCCN1C2C3CCc4c(C(=O)NCc5cccc(Cl)c5F)c(=O)c(O)c(n43)C(=O)N2C[C@@H]1C] | 94 | Calc'd 488.2, found 489.1 |

-continued

| Compound | Structure | Starting Material Compound No. | Exact Mass [M + H]+ |
|---|---|---|---|
| 109 | 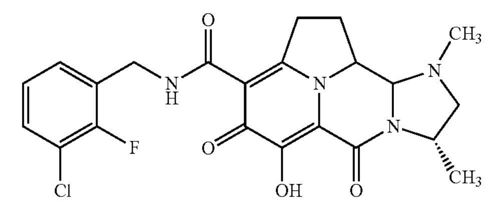 [SMILES: C[C@H]1CN(C)C2C3CCc4c(C(=O)NCc5cccc(Cl)c5F)c(=O)c(O)c(n43)C(=O)N21] | 89 | Calc'd 461.1, found 461.1 |
| 110 | 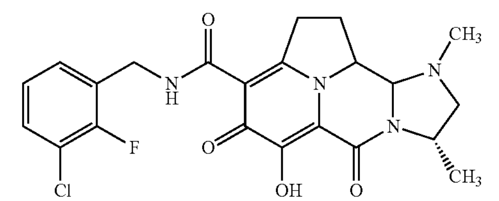 [SMILES: C[C@H]1CN(C)C2C3CCc4c(C(=O)NCc5cccc(Cl)c5F)c(=O)c(O)c(n43)C(=O)N21] | 90 | Calc'd 461.1, found 461.1 |
| 111 | 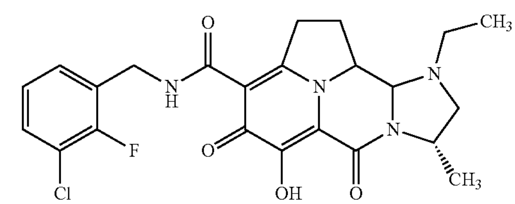 [SMILES: CCN1C[C@H](C)N2C(=O)c3c(O)c(=O)c(C(=O)NCc4cccc(Cl)c4F)c4n3C(CC4)C12] | 89 | Calc'd 475.2, found 475.2 |
| 112 | 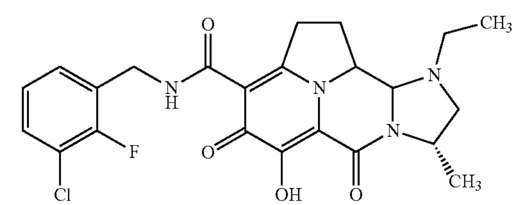 [SMILES: CCN1C[C@H](C)N2C(=O)c3c(O)c(=O)c(C(=O)NCc4cccc(Cl)c4F)c4n3C(CC4)C12] | 90 | Calc'd 475.2, found 475.2 |
| 113 | 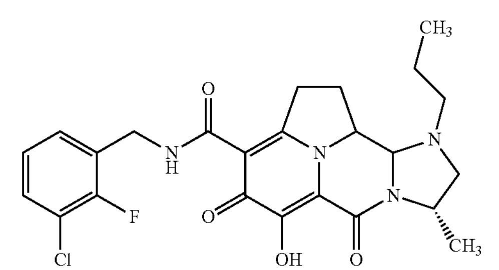 [SMILES: CCCN1C[C@H](C)N2C(=O)c3c(O)c(=O)c(C(=O)NCc4cccc(Cl)c4F)c4n3C(CC4)C12] | 89 | Calc'd 489.2, found 489.1 |
| 114 | 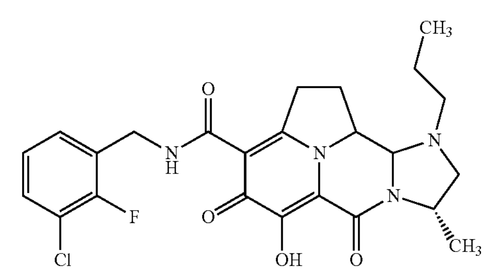 [SMILES: CCCN1C[C@H](C)N2C(=O)c3c(O)c(=O)c(C(=O)NCc4cccc(Cl)c4F)c4n3C(CC4)C12] | 90 | Calc'd 489.2, found 489.1 |

| Compound | Structure | Starting Material Compound No. | Exact Mass [M + H]+ |
|---|---|---|---|
| 115 | 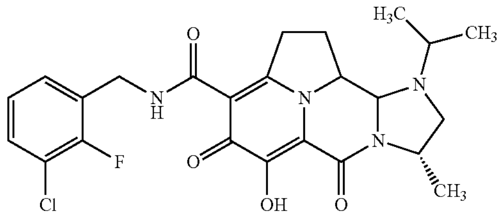 [SMILES: CC(C)N1C[C@H](C)N2C(=O)c3c(O)c(=O)c(C(=O)NCc4cccc(Cl)c4F)c4n3C(CC4)C12] | 89 | Calc'd 489.2, found 489.0 |

Example 18

Preparation of Compound 116

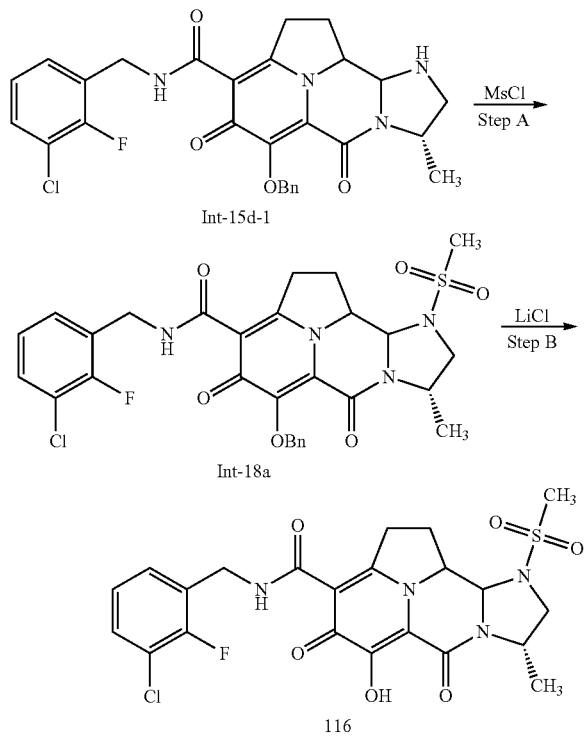

Step A—Synthesis of Intermediate Compound Int-18a

To a solution of Int-15d-1 (35 mg, 0.065 mmol) in dichloromethane (2 mL) was added triethylamine (0.027 mL, 0.196 mmol) and methanesulfonyl chloride (7.62 μL, 0.098 mmol) at 0 C. The mixture was stirred at room temperature for 60 hours. The mixture was purified directly by preparative TLC on silica gel (5% methanol in dichloromethane) to provide Int-18a. $^1$H NMR (400 MHz, CDCl$_3$): δ 10.82 (t, J=5.5 Hz, 1H), 7.56 (d, J=6.7 Hz, 2H), 7.20-7.41 (m, 5H), 6.98-7.10 (m, 1H), 5.24 (d, J=1.2 Hz, 2H), 4.57-4.77 (m, 3H), 4.02-4.21 (m, 2H), 3.54-3.78 (m, 3H), 3.31 (ddd, J=8.6, 11.1, 19.1 Hz, 1H), 3.03 (s, 3H), 2.32-2.45 (m, 1H), 2.12-2.27 (m, 1H), 1.30 (d, J=6.7 Hz, 3H). Mass Calc'd for $C_{29}H_{28}ClFN_4O_6S$: 614.1, found 615.2 (M+H)+.

Step B—Synthesis of Compound 116

To a solution of Int-18a (15 mg, 0.024 mmol) in N,N-dimethylformamide (2 mL) was added lithium chloride (10.34 mg, 0.244 mmol). The resulting solution was heated to 80° C. for 2 h, cooled to room temperature and purified directly by preparative RP-HPLC to provide compound 116. $^1$H NMR (400 MHz, CDCl$_3$): δ 10.61 (br. s., 1H), 7.27-7.36 (m, 2H), 6.98-7.09 (m, 1H), 5.46 (br. s., 1H), 4.66 (br. s., 3H), 4.05-4.28 (m, 2H), 3.58-3.80 (m, 2H), 3.26-3.48 (m, 1H), 3.12 (s, 3H), 2.58 (br. s., 1H), 2.33 (br. s., 1H), 1.36-1.48 (m, 3H). Mass Calc'd for $C_{22}H_{22}ClFN_4O_6S$: 524.1, found 525.1 (M+H)+.

The following compounds of the present invention were made using the methodology described in Example 18, and substituting the appropriate reactants and/or reagents.

| Compound | Structure | derived from | Exact Mass [M + H]+ |
|---|---|---|---|
| 117 | 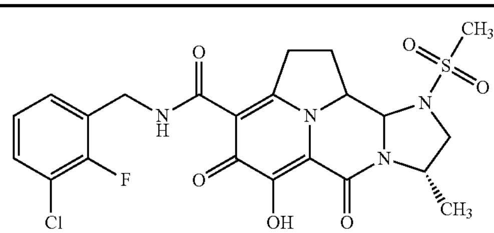 | Int-15d-2 | Calc'd 525.1, found 525.0 |

-continued

| Compound | Structure | derived from | Exact Mass [M + H]+ |
|---|---|---|---|
| 118 | 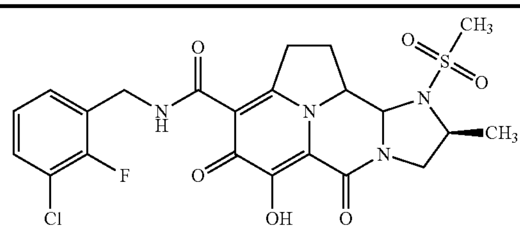 | Int-15e-3 | Calc'd 525.1, found 525.1 |
| 119 | 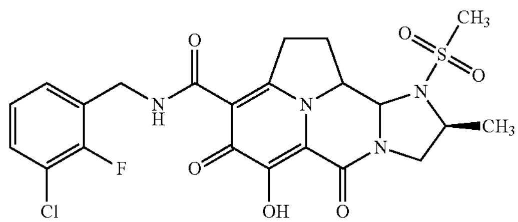 [SMILES: C[C@H]1CN2C(=O)c3c(O)c(=O)c(C(=O)NCc4cccc(Cl)c4F)c4n3C(CC4)C2N1S(C)(=O)=O] | Int-15e-4 | Calc'd 525.1, found 525.1 |

| Compound | 1H NMR |
|---|---|
| 117 | 1H NMR (400 MHz, CDCl3): δ 10.68 (br. s., 1H), 7.27-7.33 (m, 2H), 7.04 (t, J = 7.6 Hz, 1H), 5.24 (d, J = 9.0 Hz, 1H), 4.67 (br. s., 2H), 4.28 (d, J = 5.5 Hz, 1H), 4.06-4.18 (m, 2H), 4.01 (dd, J = 6.0, 11.7 Hz, 1H), 3.23-3.41 (m, 2H), 3.06 (s, 3H), 2.63 (br. s., 1H), 2.28 (br. s., 1H), 1.64 (d, J = 5.3 Hz, 3H). |
| 118 | 1H NMR (400 MHz, dimethylsulfoxide-d6): δ 10.64-10.77 (m, 1H), 10.34 (s, 1H), 7.43-7.53 (m, 1H), 7.25-7.37 (m, 1H), 7.17 (t, J = 7.8 Hz, 1H), 5.27 (d, J = 9.4 Hz, 1H), 4.37-4.69 (m, 3H), 4.21-4.31 (m, 1H), 3.73-3.92 (m, 2H), 3.49 (dd, J = 11.7, 6.3 Hz, 1H), 3.18 (br. s., 1H), 3.10 (s, 2H), 2.24-2.36 (m, 1H), 1.98-2.11 (m, 1H), 1.05-1.41 (m, 3H). |
| 119 | 1H NMR (400 MHz, dimethylsulfoxide-d6): δ 10.72 (br. s., 1H), 10.45 (s, 1H), 7.41-7.52 (m, 1H), 7.29 (d, J = 7.4 Hz, 1H), 7.12-7.21 (m, 1H), 5.37 (d, J = 9.8 Hz, 1H), 4.70 (d, J = 6.6 Hz, 1H), 4.55 (d, J = 5.0 Hz, 2H), 3.98-4.16 (m, 2H), 3.81 (dd, J = 18.9, 8.8 Hz, 1H), 3.10-3.23 (m, 3H), 2.64 (br. s., 2H), 2.02-2.12 (m, 1H), 1.29-1.52 (m, 3H). |

Example 19

Preparation of Compound 120

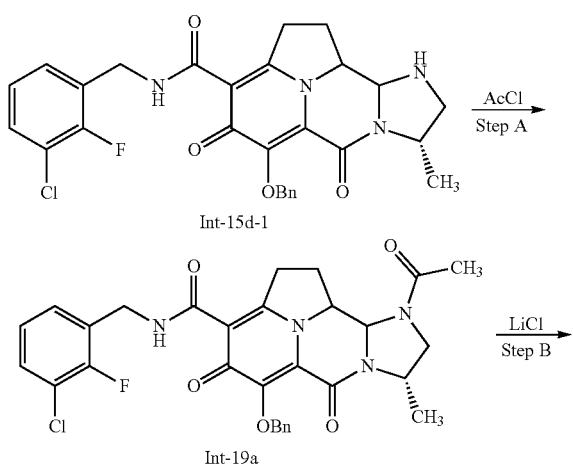

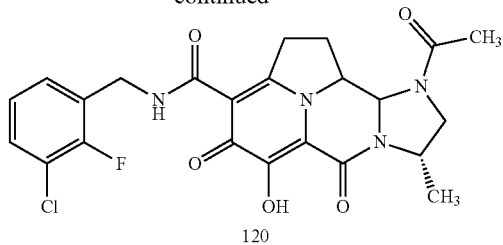

120

Step A—Synthesis of Intermediate Compound Int-19a

To a solution of Int-15d-1 (35 mg, 0.065 mmol) in dichloromethane (3 mL) was added triethylamine (19.79 mg, 0.196 mmol) and acetyl chloride (10.23 mg, 0.130 mmol) at 0° C. The mixture was stirred at 0° C. for 0.5 hours. The mixture was purified using preparative TLC on silica gel (5% methanol in dichloromethane) to provide Int-19a. 1H NMR (400 MHz, CDCl3): δ 10.85 (t, J=5.6 Hz, 1H), 7.54 (d, J=6.8 Hz, 2H), 7.22-7.37 (m, 5H), 6.98-7.07 (m, 1H), 5.38 (d, J=9.5 Hz, 1H), 5.17-5.28 (m, 2H), 4.51-4.77 (m, 3H), 3.99-4.12 (m, 2H), 3.71 (dd, J=6.3, 10.5 Hz, 1H), 3.47 (d, J=10.4 Hz, 1H), 3.16-3.31 (m, 1H), 2.22-2.50 (m, 2H), 2.13 (s, 3H), 1.24 (d, J=6.6 Hz, 3H). Mass Calc'd for $C_{30}H_{28}ClFN_4O_5$: 578.2, found 579.2 (M+H)+.

Step B—Synthesis of Compound 120

To a solution of Int-19a (35 mg, 0.060 mmol) in N,N-dimethylformamide (2 mL) was added lithium chloride (25.6 mg, 0.604 mmol). The resulting solution was heated to 80° C. for 2 h, cooled to room temperature and purified directly by preparative RP-HPLC to provide compound 120. 1H NMR (400 MHz, CDCl3): δ 10.68 (br. s., 1H), 7.26-7.34 (m, 2H), 7.03 (t, J=7.8 Hz, 1H), 5.53 (d, J=9.3 Hz, 1H), 4.70-4.79 (m, 1H), 4.59-4.69 (m, 2H), 4.04-4.18 (m, 2H), 3.81 (dd, J=6.2, 10.4 Hz, 1H), 3.59 (d, J=10.6 Hz, 1H), 3.26 (td, J=9.5, 18.7 Hz, 1H), 2.45-2.58 (m, 2H), 2.21 (s, 3H), 1.35 (d, J=6.6 Hz, 3H). Mass Calc'd for $C_{23}H_{22}ClFN_4O_5$: 488.1, found 489.1 (M+H)+.

The following compounds of the present invention were made using the methodology described in Example 19, and substituting the appropriate reactants and/or reagents.

| Compound | Structure | derived from | Exact Mass [M + H]+ |
|---|---|---|---|
| 121 | ![structure] | Int-15d-2 | Calc'd 489.1, found 489.1 |
| 122 | ![structure] | Int-15e-3 | Calc'd 489.1, found 489.1 |
| 123 | ![structure] | Int-15e-4 | Calc'd 489.1, found 489.1 |

| Compound | ¹H NMR |
|---|---|
| 121 | ¹H NMR (400 MHz, CDCl₃): δ 10.79 (br. s., 1H), 7.29 (d, J = 7.0 Hz, 2H), 6.99-7.08 (m, 1H), 5.43 (d, J = 9.4 Hz, 1H), 4.68 (d, J = 5.1 Hz, 2H), 4.00-4.26 (m, 4H), 3.21-3.43 (m, 2H), 2.52-2.62 (m, 1H), 2.42-2.50 (m, 1H), 2.21 (s, 3H), 1.69 (d, J = 5.9 Hz, 3H). |
| 122 | ¹H NMR (400 MHz, CDCl₃): δ 10.73 (br. s., 1H), 7.28-7.33 (m, 2H), 7.00-7.06 (m, 1H), 5.43 (d, J = 9.2 Hz, 1H), 4.68 (d, J = 5.5 Hz, 2H), 4.34 (t, J = 6.5 Hz, 1H), 4.04-4.19 (m, 3H), 3.62 (dd, J = 11.6, 6.5 Hz, 1H), 3.29 (dt, J = 19.1, 9.7 Hz, 1H), 2.50-2.58 (m, 2H), 2.23 (s, 3H), 1.42 (d, J = 6.6 Hz, 3H). |
| 123 | ¹H NMR (400 MHz, CDCl₃): δ 10.75 (br. s., 1H), 7.30 (d, J = 6.4 Hz, 2H), 7.03 (t, J = 7.8 Hz, 1H), 5.30 (d, J = 8.8 Hz, 1H), 4.68 (d, J = 5.3 Hz, 2H), 4.37 (d, J = 3.3 Hz, 1H), 4.11-4.26 (m, 3H), 3.54 (d, J = 11.7 Hz, 1H), 3.24-3.32 (m, 1H), 2.80-2.86 (m, 1H), 2.53 (d, J = 11.0 Hz, 1H), 2.24 (s, 3H), 1.47 (d, J = 6.2 Hz, 3H). |

Example 20

Preparation of Compound 124

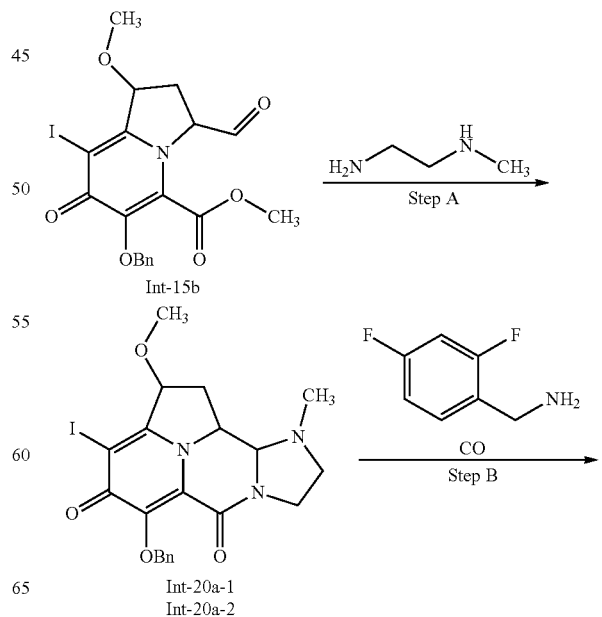

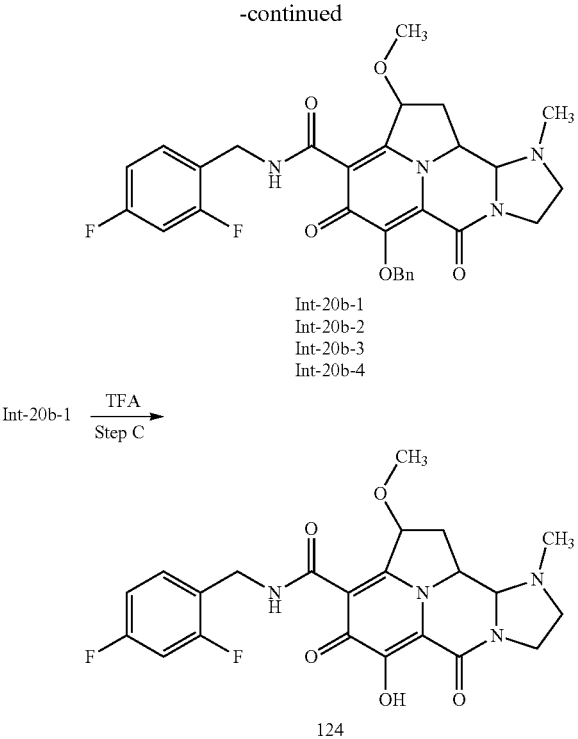

Int-20b-1
Int-20b-2
Int-20b-3
Int-20b-4

Int-20b-1 →(TFA, Step C)→ 124

Step A—Synthesis of Intermediate Compounds Int-20a

To a solution of Int-15b (400 mg, 0.828 mmol) in tetrahydrofuran (10 mL) was added acetic acid (0.1 mL) and N-methylethane-1,2-diamine (123 mg, 1.655 mmol). The mixture was stirred at 80° C. for 0.5 h, cooled to room temperature and concentrated in vacuo. The resulting residue was purified using column chromatography on silica gel (5% methanol in dichloromethane) to provide Int-20a-1 and Int-20a-2. Mass Calc'd for $C_{21}H_{22}IN_3O_4$: 507.1, found 508.1 $(M+H)^+$.

Step B—Synthesis of Intermediate Compounds Int-20b

To a solution of Int-20a-1 (270 mg, 0.532 mmol) in dimethylsulfoxide (5 mL) was added N,N-diisopropylethylamine (0.465 mL, 3.66 mmol), 2,4-difluorobenzylamine (305 mg, 3.129 mmol) and $Pd(Ph_3P)_4$ (123 mg, 0.106 mmol). The mixture was stirred at 80° C. for 2 h under carbon monoxide (1 atm), cooled to rt, diluted with water and extracted with ethyl acetate. The combined organic portions were dried over sodium sulfate, filtered and the filtrate was concentrated in vacuo. The resulting residue was purified using preparative TLC on silica gel (5% methanol in dichloromethane) followed by preparative RP-HPLC purification and then followed by SFC (Chralpak AD, 250 mm×30 mm, 10 μm, ethanol in SC—$CO_2$, 80 mL/min, 220 nm) to provide Int-20b-1 and Int-20b-2

Int-20b-1: $^1$H NMR (400 MHz, $CD_3OD$): δ 7.52-7.65 (m, 3H), 7.32 (d, J=3.9 Hz, 3H), 6.85-7.01 (m, 2H), 4.89-5.04 (m, 3H), 4.54 (s, 2H), 4.02-4.14 (m, 1H), 3.74 (d, J=9.4 Hz, 1H), 3.48-3.59 (m, 2H), 3.24 (d, J=6.7 Hz, 1H), 3.17 (s, 3H), 3.61-3.73 (m, 1H), 3.49 (q, J=8.7 Hz, 1H), 3.35 (s, 3H), 1.57-1.72 (m, 1H). Mass Calc'd for $C_{29}H_{28}F_2N_4O_5$: 550.2, found 551.3 $(M+H)^+$.

Int-20b-2: $^1$H NMR (400 MHz, $CD_3OD$): δ 7.47-7.62 (m, 3H), 7.32 (d, J=5.9 Hz, 3H), 6.89-7.00 (m, 2H), 5.03-5.15 (m, 3H), 4.57 (s, 2H), 4.06-4.17 (m, 1H), 3.78 (d, J=9.4 Hz, 1H), 3.52-3.64 (m, 2H), 3.27 (br. s., 4H), 3.84-3.00 (m, 1H), 3.58 (q, J=9.1 Hz, 1H), 3.43 (s, 3H), 1.75-1.86 (m, 1H). Mass Calc'd for $C_{29}H_{28}F_2N_4O_5$: 550.2, found 551.3 $(M+H)^+$.

Intermediate compounds Int-20b-3 and Int-20b-4 were prepared in a similar manner from Int-20a-2.

Int-20b-3: $^1$H NMR (400 MHz, $CD_3OD$): δ 7.42-7.58 (m, 3H), 7.31 (d, J=7.0 Hz, 3H), 6.89-7.01 (m, 2H), 5.81 (d, J=5.1 Hz, 1H), 5.05-5.23 (m, 2H), 4.60 (br. s., 2H), 4.29-4.43 (m, 1H), 3.73 (d, J=9.0 Hz, 1H), 3.54-3.63 (m, 2H), 3.42 (s, 3H), 3.65 (dd, J=13.3, 5.5 Hz, 1H), 3.49-3.59 (m, 1H), 3.44 (s, 3H), 1.93-3.13 (m, 2H). Mass Calc'd for $C_{29}H_{28}F_2N_4O_5$: 550.2, found 551.2 $(M+H)^+$.

Int-20b-4: $^1$H NMR (400 MHz, $CD_3OD$): δ 7.42-7.62 (m, 3H), 7.31 (d, J=6.7 Hz, 3H), 6.84-7.05 (m, 2H), 5.80 (d, J=4.7 Hz, 1H), 5.07-5.19 (m, 2H), 4.54-4.66 (m, 2H), 4.35 (dd, J=14.5, 9.0 Hz, 1H), 3.73 (d, J=9.4 Hz, 1H), 3.59 (d, J=5.1 Hz, 2H), 3.42 (s, 3H), 3.65 (dd, J=13.1, 4.9 Hz, 1H), 3.49-3.58 (m, 1H), 3.44 (s, 3H), 3.04 (br. s., 2H). Mass Calc'd for $C_{29}H_{28}F_2N_4O_5$: 550.2, found 551.2 $(M+H)^+$.

Step C—Synthesis of Compound 124

To a mixture of Int-20b-1 (85.0 mg, 0.154 mmol) in dichloromethane (2 mL) was added trifluoroacetic acid (0.4 mL, 5.2 mmol), and the mixture was stirred at 25° C. for 2 hours. The mixture was concentrated in vacuo and the residue obtained was purified using preparative RP-HPLC to provide compound 124. $^1$H NMR (400 MHz, $CD_3OD$): δ 7.45-7.59 (m, 1H), 6.87-7.01 (m, 2H), 5.36 (t, J=7.3 Hz, 1H), 4.50-4.68 (m, 2H), 4.10-4.22 (m, 1H), 4.02 (d, J=9.5 Hz, 1H), 3.74-3.85 (m, 1H), 3.57-3.70 (m, 1H), 3.44 (d, J=8.6 Hz, 1H), 3.39 (s, 3H), 3.18-3.27 (m, 1H), 3.68-3.80 (m, 1H), 3.56 (s, 3H), 1.97-3.09 (m, 1H). Mass Calc'd for $C_{22}H_{22}F_2N_4O_5$: 460.2, found 461.1 $(M+H)^+$.

The following compounds of the present invention were made using the methodology described in Example 20, and substituting the appropriate reactants and/or reagents.

| Compound | Structure | derived from | Exact Mass $[M + H]^+$ |
|---|---|---|---|
| 125 | 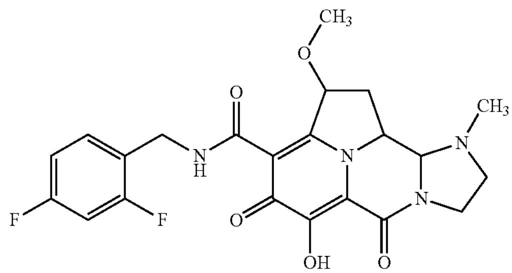 [SMILES: COC1CC2C3N(C)CCN3C(=O)c3c(O)c(=O)c(C(=O)NCc4ccc(F)cc4F)c1n32] | Int-20b-2 | Calc'd 461.2, found 461.1 |

| Compound | Structure | derived from | Exact Mass [M + H]+ |
|---|---|---|---|
| 126 | | Int-20b-3 | Calc'd 461.2, found 461.1 |
| 127 | | Int-20b-4 | Calc'd 461.2, found 461.1 |
| Compound | ¹H NMR |
|---|---|
| 125 | ¹H NMR (400 MHz, CD₃OD): δ 7.46-7.60 (m, 1H), 6.85-7.02 (m, 2H), 5.40 (t, J = 7.3 Hz, 1H), 4.53-4.68 (m, 2H), 4.10-4.21 (m, 1H), 3.98 (d, J = 9.5 Hz, 1H), 3.73-3.84 (m, 1H), 3.57-3.69 (m, 1H), 3.41 (s, 4H), 3.20-3.28 (m, 1H), 3.65-3.78 (m, 1H), 3.54 (s, 3H), 1.97-3.10 (m, 1H). |
| 126 | ¹H NMR (400 MHz, CD₃OD): δ 7.38-7.50 (m, 1H), 6.88-7.02 (m, 2H), 5.89 (d, J = 5.3 Hz, 1H), 4.54-4.71 (m, 2H), 4.40-4.51 (m, 1H), 3.75-3.90 (m, 2H), 3.59-3.71 (m, 1H), 3.47 (s, 3H), 3.38-3.44 (m, 1H), 3.79 (dd, J = 13.1, 5.4 Hz, 1H), 3.63-3.74 (m, 1H), 3.53 (s, 3H), 3.16-3.26 (m, 1H). |
| 127 | ¹H NMR (400 MHz, CD₃OD): δ 7.44 (d, J = 7.1 Hz, 1H), 6.85-7.01 (m, 2H), 5.89 (d, J = 5.3 Hz, 1H), 4.56-4.69 (m, 2H), 4.46 (d, J = 5.7 Hz, 1H), 3.75-3.89 (m, 2H), 3.65 (dd, J = 17.9, 10.4 Hz, 1H), 3.47 (s, 3H), 3.39-3.44 (m, 1H), 3.79 (dd, J = 13.0, 5.1 Hz, 1H), 3.68 (d, J = 8.8 Hz, 1H), 3.53 (s, 3H), 3.22 (br. s., 1H). |
Example 21
Preparation of Compound 128
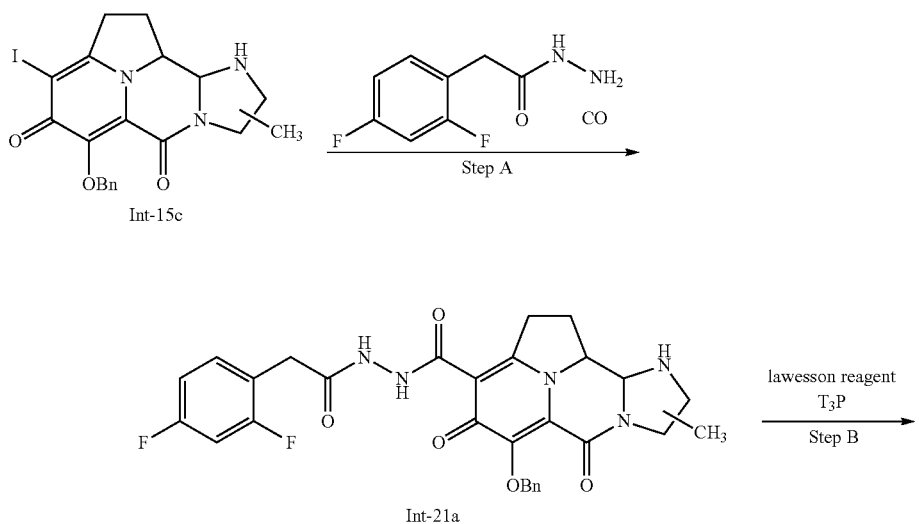

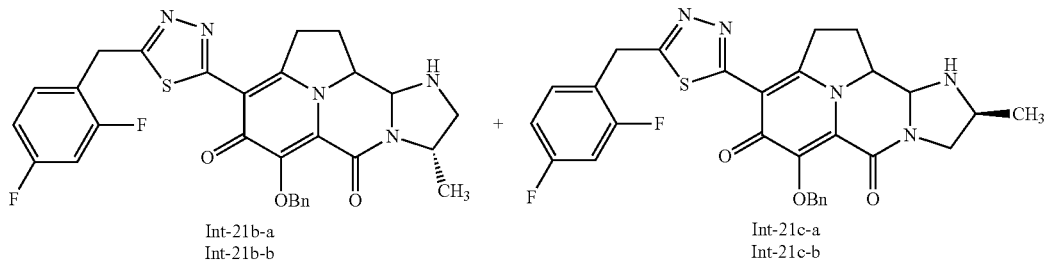

Int-21b-a
Int-21b-b

Int-21c-a
Int-21c-b

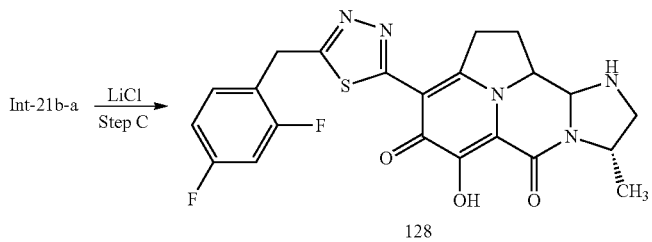

128

Step A—Synthesis of Intermediate Compound Int-21a

To a mixture of Int-15c (1.2 g, 1.257 mmol) in dimethylsulfoxide (8 mL) was added N,N-diisopropylethylamine (1.098 mL, 6.29 mmol), Pd(Ph$_3$P)$_4$ (145 mg, 0.126 mmol) and 2-(2,4-difluorophenyl)acetohydrazide (468 mg, 2.51 mmol). The mixture was stirred at 80° C. under carbon monoxide (1 atm) for 1 h, cooled to room temperature and filtered. The filtrate was diluted with water (40 mL) and extracted with ethyl acetate. The combined organic portions were concentrated in vacuo and the residue obtained was purified using column chromatography on silica gel (5% methanol/dichloromethane) to provide Int-21a. $^1$H NMR (dimethylsulfoxide-d$_6$): δ 12.44 (br s, 1H), 10.79 (br s, 1H), 7.58 (d, J=7.3 Hz, 2H), 7.30-7.46 (m, 3H), 7.17-7.25 (m, 1H), 7.02-7.10 (m, 1H), 5.75 (s, 1H), 5.02-5.17 (m, 2H), 4.47-4.68 (m, 2H), 4.33-4.42 (m, 1H), 3.95 (dd, J=10.9, 5.6 Hz, 1H), 3.80 (dd, J=17.8, 8.8 Hz, 1H), 3.56-3.64 (m, 2H), 2.94-3.04 (m, 1H), 2.74-2.83 (m, 1H), 2.38 (d, J=11.9 Hz, 1H), 1.86-2.03 (m, 2H), 1.10-1.27 (m, 3H). Mass Calc'd for C$_{29}$H$_{27}$F$_2$N$_5$O$_5$: 563.2, found 564.3 (M+H)$^+$.

Step B—Synthesis of Intermediate Compounds Int-21b and Int-21e

To a solution of Int-21a (200 mg, 0.177 mmol) in tetrahydrofuran (15 mL) was added Lawesson reagent (718 mg, 1.774 mmol), followed by 2,4,6-tripropyl-1,3,5,2,4,6-trioxatriphosphinane 2,4,6-trioxide (T3P) (226 mg, 0.710 mmol). The mixture was stirred at 80° C. for 8 hours. The mixture was washed with water (10 mL×2) and the aqueous layer was extracted with dichloromethane. The combined organic portions were dried over anhydrous Na$_2$SO$_4$, filtered and the filtrate was concentrated in vacuo. The resulting residue was purified using column chromatography on silica gel (5% methanol/dichloromethane) to provide the thiadiazole product. Resolution by SFC (Chralpak AD, 250 mm×30 mm, 10 μm, 60% IPA in SC—CO$_2$, 60 mL/min, 220 nm) afforded compounds Int-21b-a, Int-21b-b, Int-21c-a, Int-21c-b.

Int-21b-a: $^1$H NMR (chloroform-d): δ 7.69 (d, J=7.0 Hz, 2H), 7.31-7.41 (m, 4H), 6.81-6.90 (m, 2H), 5.39 (d, J=9.7 Hz, 1H), 5.17 (d, J=9.4 Hz, 1H), 4.59 (d, J=9.2 Hz, 1H), 4.32-4.47 (m, 3H), 4.06-4.22 (m, 2H), 3.46 (dd, J=19.8, 10.1 Hz, 1H), 3.23 (dd, J=11.7, 6.2 Hz, 1H), 2.55-2.73 (m, 2H), 2.09-2.20 (m, 1H), 1.28 (br. s., 3H).

Int-21b-b: $^1$H NMR (chloroform-d): δ 7.67 (d, J=7.0 Hz, 2H), 7.29-7.41 (m, 4H), 6.80-6.90 (m, 2H), 5.42 (d, J=9.9 Hz, 1H), 5.20-5.33 (m, 1H), 4.35-4.53 (m, 3H), 4.10-4.31 (m, 3H), 3.56 (d, J=9.9 Hz, 1H), 3.11-3.26 (m, 1H), 3.02 (d, J=11.0 Hz, 1H), 2.64 (br. s., 1H), 2.01-2.21 (m, 2H), 1.43 (d, J=6.2 Hz, 3H).

Int-21c-a: $^1$H NMR (chloroform-d): δ 7.69 (d, J=7.0 Hz, 2H), 7.29-7.44 (m, 4H), 6.77-6.91 (m, 2H), 5.21 (d, J=9.5 Hz, 1H), 5.11 (d, J=9.5 Hz, 1H), 4.53 (d, J=9.3 Hz, 1H), 4.39 (s, 2H), 4.04-4.20 (m, 2H), 3.31-3.59 (m, 3H), 3.05-3.24 (m, 2H), 2.46 (br. s., 1H), 2.07-2.17 (m, 1H), 1.20 (d, J=5.9 Hz, 3H).

Int-21c-b: $^1$H NMR (chloroform-d): δ 7.72 (d, J=7.3 Hz, 2H), 7.32-7.48 (m, 4H), 6.80-6.91 (m, 2H), 5.15 (d, J=9.3 Hz, 1H), 4.95 (d, J=9.3 Hz, 1H), 4.75 (d, J=9.7 Hz, 1H), 4.33-4.41 (m, 2H), 3.91-4.05 (m, 3H), 3.21-3.32 (m, 1H), 3.09 (br. s., 1H), 2.33-2.46 (m, 2H), 2.15-2.25 (m, 2H), 1.05 (d, J=6.2 Hz, 3H).

Step C—Synthesis of Compound 128

To a solution of Int-21b-a (8 mg, 0.014 mmol) in N,N-dimethylformamide (2 mL) was added lithium chloride (6.04 mg, 0.142 mmol). The mixture was stirred at 80° C. for 5 h, cooled to room temperature and purified directly by RP-HPLC to provide compound 128. $^1$H NMR (chloroform-d): δ 7.28-7.36 (m, 1H), 6.86 (d, J=7.9 Hz, 2H), 4.71 (d, J=9.4 Hz, 1H), 4.45 (s, 2H), 4.37 (d, J=5.7 Hz, 1H), 4.14-4.28 (m, 2H), 3.46-3.59 (m, 2H), 2.94 (dd, J=12.1, 5.3 Hz, 1H), 2.72 (br. s., 1H), 2.18 (d, J=10.4 Hz, 1H), 1.45 (d, J=6.4 Hz, 3H). Mass Calc'd for C$_{22}$H$_{19}$F$_2$N$_5$O$_3$S: 471.1, found 472.2 (M+H)$^+$.

The following compounds of the present invention were made using the methodology described in Example 21, and substituting the appropriate reactants and/or reagents.

| Compound | Structure | Exact Mass [M + H]+ |
|---|---|---|
| 129 | 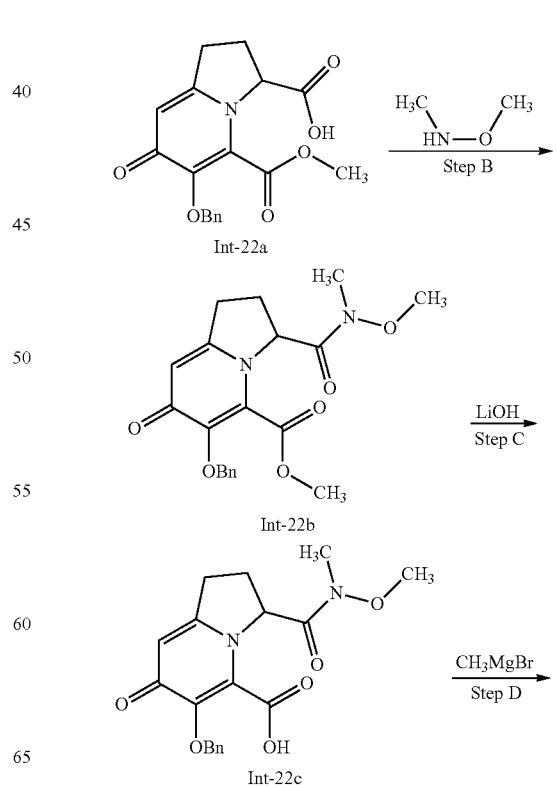 | Calc'd 472.1, found 472.1 |
| 130 | | Calc'd 472.1, found 472.1. |
| 131 | | Calc'd 472.1, found 472.1 |
| Compound | 1H NMR |
|---|---|
| 129 | 1H NMR (chloroform-d)): δ 7.30-7.36 (m, 1H), 6.81-6.90 (m, 2H), 4.44-4.53 (m, 3H), 4.24-4.37 (m, 3H), 3.49-3.56 (m, 1H), 3.37 (dd, J = 11.5, 6.8 Hz, 1H), 3.15 (d, J = 11.4 Hz, 1H), 2.18 (s, 2H), 1.44 (d, J = 6.2 Hz, 3H). |
| 130 | 1H NMR (dimethylsulfoxide-d6): δ 7.46-7.58 (m, 1H), 7.23-7.35 (m, 1H), 7.07-7.15 (m, 1H), 4.75 (d, J = 9.4 Hz, 1H), 4.53-4.62 (m, 1H), 4.47 (s, 2H), 3.90-3.96 (m, 2H), 3.74-3.79 (m, 2H), 3.40-3.47 (m, 1H), 3.09 (t, J = 10.0 Hz, 1H), 2.02-2.16 (m, 1H), 1.31 (d, J = 6.2 Hz, 3H). |
| 131 | 1H NMR (chloroform-d): δ 7.33 (d, J = 7.0 Hz, 1H), 6.86 (br. s., 2H), 4.84 (br. s., 1H), 4.45 (s, 2H), 4.23 (br. s., 2H), 3.63 (br. s., 1H), 3.50 (s, 2H), 3.03-3.10 (m, 1H), 2.18 (s, 2H), 1.38 (d, J = 6.2 Hz, 3H). |
Example 22
Preparation of Compound 132
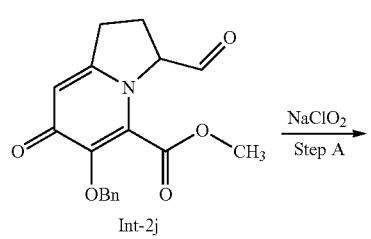

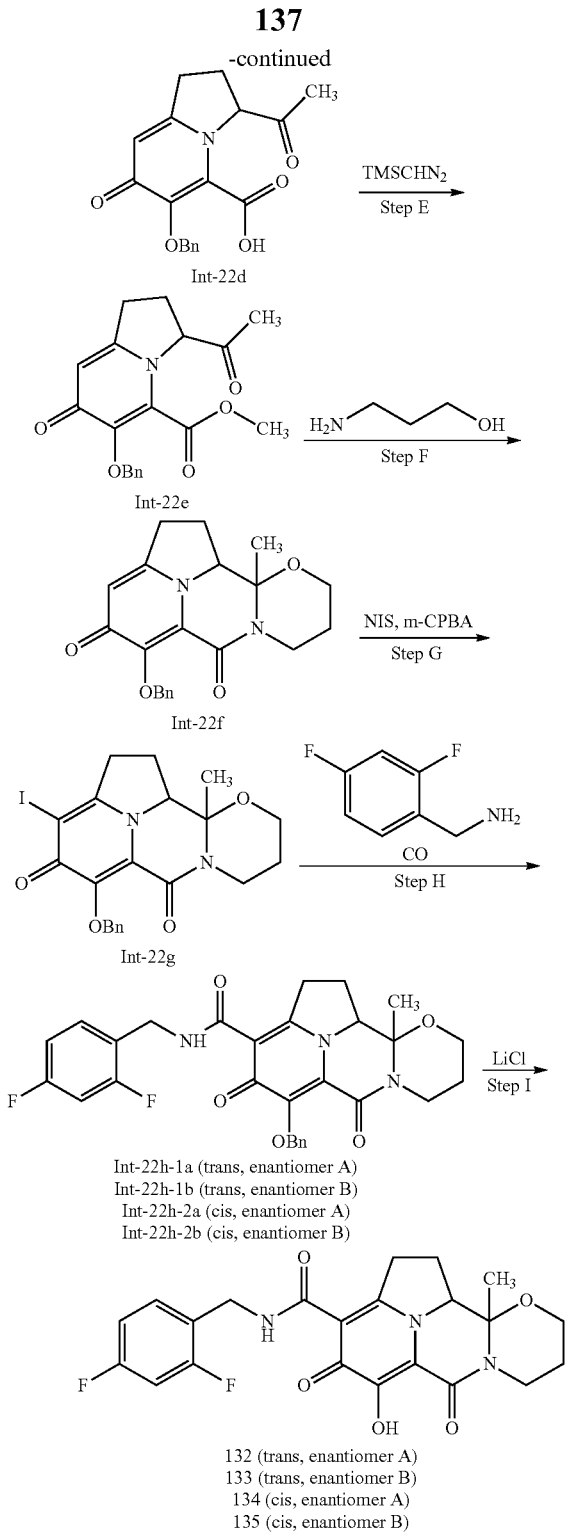

Int-22d
Int-22e
Int-22f
Int-22g
Int-22h-1a (trans, enantiomer A)
Int-22h-1b (trans, enantiomer B)
Int-22h-2a (cis, enantiomer A)
Int-22h-2b (cis, enantiomer B)

132 (trans, enantiomer A)
133 (trans, enantiomer B)
134 (cis, enantiomer A)
135 (cis, enantiomer B)

Step A—Synthesis of Intermediate Compound Int-22a

To a solution of Int-2j (500 mg, 1.528 mmol) in tBuOH (6 mL) and water (2 mL) was added sodium chlorite (414 mg, 4.58 mmol) and sodium dihydrogenphosphate (550 mg, 4.58 mmol). The mixture was stirred at 10° C. for 2 hours. The mixture was concentrated in vacuo and purified using preparative TLC on silica gel (dichloromethane:methanol=5:1) to provide compound Int-22a. $^1$H NMR (400 MHz, CDCl$_3$) δ 7.27-7.35 (m, 6H), 5.45-5.50 (m, 1H), 5.04-5.28 (m, 2H), 3.80 (s, 3H), 3.10-3.15 (m, 2H), 2.50-2.57 (m, 2H). Mass Calc'd for $C_{18}H_{17}NO_6$: 343.1, found 344.1 (M+H)$^+$.

Step B—Synthesis of Intermediate Compound Int-22b

To a solution of Int-22a (300 mg, 0.874 mmol) in dichloromethane (2 mL) was added N,O-dimethylhydroxylamine hydrochloride (94 mg, 0.961 mmol), 4-methylmorpholine (97 mg, 0.961 mmol) and 1-ethyl-3-(3-dimethylaminopropyl)carbodiimide (EDC) (184 mg, 0.961 mmol). The mixture was stirred at 10 C for 1 h, quenched with water (10 mL) and extracted with dichloromethane. The combined organic portions were dried over anhydrous Na$_2$SO$_4$, filtered and the filtrate was concentrated in vacuo. The resulting residue was purified using column chromatography (dichloromethane:methanol=20:1) to provide compound Int-22b. $^1$H NMR: (400 MHz, CDCl$_3$) δ 7.45 (d, J=7.2 Hz, 2H), 7.27-7.38 (m, 3H), 6.43 (s, 1H), 5.69-5.63 (m, 1H), 5.51 (d, J=10.8 Hz, 1H), 5.05 (d, J=10.8 Hz, 1H), 3.79 (s, 3H), 3.71 (s, 3H), 3.21 (s, 3H), 2.92-3.14 (m, 2H), 2.52-2.65 (m, 1H), 2.14-2.23 (m, 1H). Mass Calc'd for $C_{20}H_{22}N_2O_6$: 386.1, found 387.1 (M+H)$^+$.

Step C—Synthesis of Intermediate Compound Int-22c

To a solution of Int-22b (400 mg, 1.035 mmol) in tetrahydrofuran (2 mL) was added 2 M aqueous of LiOH (2.070 mL, 4.14 mmol). The mixture was stirred at 15 C for 1 hour. The mixture was adjusted to pH 6 with 1N aqueous of HCl and concentrated in vacuo to provide compound Int-22c, which was used in the next step without further purification. $^1$H NMR (400 MHz, CD$_3$OD) δ 7.51-7.53 (m, 2H), 7.23-7.30 (m, 3H), 6.46 (s, 1H), 5.65-5.68 (m, 1H), 5.51 (d, J=10.8 Hz, 1H), 5.05 (d, J=10.8 Hz, 1H), 3.83 (s, 3H), 3.14-3.19 (m, 5H), 2.54-2.63 (m, 1H), 2.20-2.26 (m, 1H). Mass Calc'd for $C_{19}H_{20}N_2O_6$: 372.1, found 373.1 (M+H)$^+$.

Step D—Synthesis of Intermediate Compound Int-22d

To a solution of Int-22c (200 mg, 0.537 mmol) in tetrahydrofuran (5 mL) was added methylmagnesium bromide (1.074 mL, 3.22 mmol) at −78° C. The mixture was warmed to 45° C. and stirred for 3 hours. The mixture was quenched with 1N aqueous of HCl (2 mL) and extracted with dichloromethane. The combined organic portions were concentrated in vacuo and the residue obtained was purified using preparative RP-HPLC to provide Int-22d. Mass Calc'd for $C_{18}H_{17}NO_5$: 327.1, found 328.1 (M+H)$^+$.

Step E—Synthesis of Intermediate Compound Int-22e

To a solution of Int-22d (50 mg, 0.153 mmol) in methanol (0.2 mL) and dichloromethane (2 mL) was added TMS-diazomethane (0.153 mL, 0.306 mmol) at 0° C. The mixture was stirred at 15° C. for 1 hour. The mixture was concentrated in vacuo and purified using preparative TLC on silica gel (dichloromethane:methanol=20:1) to provide Int-22e. $^1$H NMR (400 MHz, CDCl$_3$) δ 7.42 (d, J=6.8 Hz, 2H), 7.27-7.37 (m, 3H), 6.44 (s, 1H), 5.37 (d, J=10.8 Hz, 1H), 5.20-5.26 (m, 1H), 5.19 (d, J=10.8 Hz, 1H), 3.70 (s, 3H), 2.97-0.04 (m, 2H), 2.50-2.60 (m, 1H), 2.20 (s, 3H), 2.09-2.18 (m, 1H). Mass Calc'd for $C_{19}H_{19}NO_5$: 341.1, found 342.1 (M+H)$^+$.

Step F—Synthesis of Intermediate Compound Int-22f

To a solution of Int-22e (40 mg, 0.117 mmol) in tetrahydrofuran (4 mL) was added acetic acid (0.1 mL) and 3-aminopropan-1-ol (44.0 mg, 0.586 mmol). The mixture was stirred at 80° C. for 6 hours. The mixture was concentrated in vacuo and the residue obtained was purified using preparative TLC on silica gel (dichloromethane:methanol=10:1) to provide Int-22f. $^1$H NMR (400 MHz, CDCl$_3$) δ 7.53-7.67 (m, 2H), 7.25-7.38 (m, 3H), 6.54 (s, 1H), 5.50-5.52 (m, 1H), 5.45 (d, J=10.2 Hz, 1H), 5.20 (d, J=10.2 Hz, 1H), 5.04-5.09 (m, 1H), 4.51-4.70 (m, 1H), 4.08-4.38 (m, 2H), 3.74-3.93 (m, 1H), 3.35-3.47 (m, 1H), 2.89-3.11

(m, 2H) 2.16-2.49 (m, 2H) 2.08 (s, 3H). Mass Calc'd for $C_{21}H_{22}N_2O_4$: 366.2, found 367.2 $(M+H)^+$.

Step G—Synthesis of Intermediate Compound Int-22g

To a solution of Int-22f (30 mg, 0.082 mmol) in methanol (2 mL) was added m-CPBA (70.6 mg, 0.328 mmol) and N-iodosuccinimide (73.7 mg, 0.328 mmol). The mixture was stirred at 80° C. for 2 h, cooled to rt, quenched with saturated aqueous $Na_2SO_3$ (10 mL) and extracted with dichloromethane. The combined organic portions were washed with saturated aqueous $NaHCO_3$ and brine, dried over anhydrous $Na_2SO_4$, filtered and the filtrate was concentrated in vacuo. The resulting residue was purified using preparative TLC on silica gel (dichloromethane:methanol=10:1) to provide Int-22g. $^1$H NMR (400 MHz, $CDCl_3$) δ 7.58-7.71 (m, 2H), 7.27-7.38 (m, 3H), 5.30-5.44 (m, 1H), 5.15-5.22 (m, 1H), 4.42-4.68 (m, 2H), 3.76-4.14 (m, 2H), 2.93-3.45 (m, 3H), 1.70-2.51 (m, 3H), 1.62 (s, 3H), 1.33-1.52 (m, 1H). Mass Calc'd for $C_{21}H_{21}IN_2O_4$: 492.1, found 493.1 $(M+H)^+$.

Step H—Synthesis of Intermediate Compounds Int-22h

To a solution of Int-22g (30 mg, 0.061 mmol) in dimethylsulfoxide (10 mL) was added N,N-diisopropylethylamine (0.053 mL, 0.305 mmol), 2,4-difluorobenzylamine (26.2 mg, 0.183 mmol) and $Pd(Ph_3P)_4$ (14.08 mg, 0.012 mmol). The mixture was stirred at 80° C. for 1.5 h under carbon monoxide (1 atm). The mixture was diluted with ethyl acetate and washed with 1N aqueous HCl, saturated aqueous $NaHCO_3$ and brine, dried over anhydrous $Na_2SO_4$, filtered and the filtrate was concentrated in vacuo. The resulting residue was purified using preparative TLC on silica gel (100% ethyl acetate) to provide Int-22h-1 and Int-22h-2.

Int-22h-1: $^1$H NMR (400 MHz, $CDCl_3$) δ 10.92 (brs, 1H), 7.29-7.48 (m, 6H), 6.80-6.84 (m, 2H), 5.08-5.53 (m, 2H), 4.51-4.69 (m, 3H), 4.30-4.44 (m, 1H), 3.67-4.09 (m, 3H), 3.30-3.42 (m, 2H), 2.18-2.57 (m, 1H), 2.00 (s, 3H), 1.80-1.92 (m, 3H). Mass Calc'd for $C_{29}H_{27}F_2N_3O_5$: 535.2, found 536.1 $(M+H)^+$.

Int-22h-2: $^1$H NMR (400 MHz, $CDCl_3$) δ 10.92 (brs, 1H), 7.34-7.71 (m, 6H), 6.80-6.84 (m, 2H), 5.08-5.29 (m, 2H), 4.54-4.71 (m, 2H), 4.14-4.33 (m, 1H), 3.61-4.09 (m, 4H), 3.30-3.42 (m, 2H), 2.24-2.57 (m, 2H), 1.55-1.92 (m, 5H). Mass Calc'd for $C_{29}H_{27}F_2N_3O_5$: 535.2, found 536.1 $(M+H)^+$.

Compound Int-22h-1 was resolved by SFC (Chralpak AS, 250×30 mm, 10 μm, 35% ethanol in SC—$CO_2$, 80 mL/min, 220 nm) to provide Int-22h-1a and Int-22h-1b.

Compound Int-22h-2 was resolved by SFC (Chralpak AS, 250×30 mm, 10 μm, 35% ethanol in SC—$CO_2$, 80 mL/min, 220 nm) to provide Int-22h-2a and Int-22h-2b.

Step I—Synthesis of Compound 132

To a solution of Int-22h-1a (10 mg, 0.019 mmol) in N,N-dimethylformamide (3 mL) was added lithium chloride (3.17 mg, 0.075 mmol) and the mixture was stirred at 75° C. for 4 hours. The mixture was cooled to room temperature and purified directly by preparative RP-HPLC to provide compound 132. $^1$H NMR (400 MHz, $CDCl_3$) δ 10.86 (brs, 1H), 7.35 (s, 1H), 6.81 (d, J=6.8 Hz, 2H), 4.36-4.69 (m, 4H), 3.86-4.16 (m, 3H), 3.15-3.41 (m, 2H), 2.05-2.48 (m, 2H), 1.77-1.87 (m, 2H), 1.44 (s, 3H). Mass Calc'd for $C_{22}H_{21}F_2N_3O_5$: 445.1, found 446.2 $(M+H)^+$.

The following compounds of the present invention were made using the methodology described in Example 22, and substituting the appropriate reactants and/or reagents.

| Compound | Structure | derived from | Exact Mass [M + H]$^+$ |
|---|---|---|---|
| 133 | (structure) | Int-22h-1b | Calc'd 446.2, found 446.2 |
| 134 | (structure) | Int-22h-2a | Calc'd 446.2, found 446.2 |
| 135 | (structure) | Int-22h-2b | Calc'd 446.2, found 446.2 |

| Compound | $^1$H NMR |
|---|---|
| 133 | $^1$H NMR (400 MHz, $CDCl_3$) δ 10.86 (brs, 1H), 7.35 (s, 1H), 6.80 (d, J = 7.6 Hz, 2H), 4.36-4.67 (m, 4H), 3.87-4.13 (m, 3H), 3.15-3.41 (m, 2H), 2.46-2.48 (m, 1H), 1.80-2.11 (m, 3H), 1.43 (s, 3H). |
| 134 | $^1$H NMR (400 MHz, $CDCl_3$) δ 10.87 (brs, 1H), 7.36 (d, J = 6.8 Hz, 1H), 6.74-6.86 (m, 2H), 4.57-4.74 (m, 3H), 4.18-4.34 (m, 2H), 3.86-4.05 (m, 2H), 3.38-3.54 (m, 2H), |

| Compound | $^1$H NMR |
|---|---|
|  | 2.34-2.45 (m, 2H), 1.97-1.99 (m, 1H), 1.80 (s, 3H), 1.59 (d, J = 13.8 Hz, 1H). |
| 135 | $^1$H NMR (400 MHz, CDCl$_3$) δ 10.88 (brs, 1H), 7.36 (d, J = 6.2 Hz, 1H), 6.80 (d, J = 8.6 Hz, 2H), 4.56-4.72 (m, 3H), 4.19-4.33 (m, 2H), 3.93-4.06(m, 2H), 3.38-3.54 (m, 2H), 2.31-2.47 (m, 2H), 1.97-1.99 (m, 1H), 1.81 (s, 3H), 1.59 (d, J = 12.6 Hz, 1H). |

Example 23

Preparation of Compounds 136 and 137

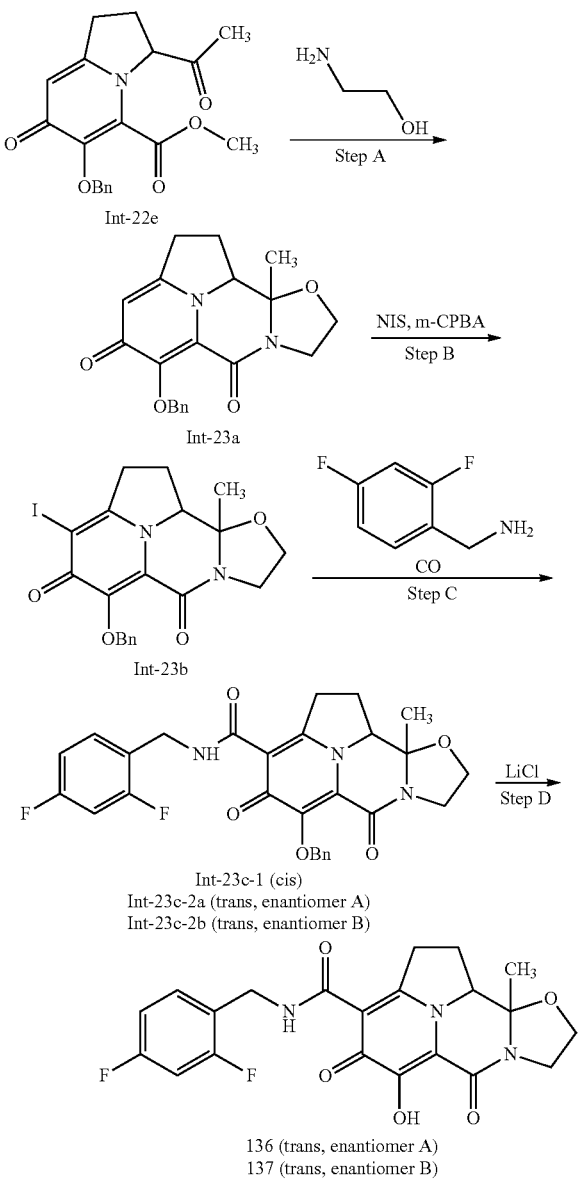

Step A—Synthesis of Intermediate Compound Int-23a

To a solution of Int-22e (250 mg, 0.732 mmol) in tetrahydrofuran (15 mL) and acetic acid (0.2 mL) was added 2-aminoethanol (179 mg, 2.93 mmol). The mixture was stirred at 80° C. for 12 hours. The mixture was concentrated in vacuo and the residue obtained was purified using preparative TLC on silica gel (5% methanol/dichloromethane) to provide Int-23a. $^1$H NMR (400 MHz, CDCl$_3$) δ 7.53-7.59 (m, 2H), 7.23-7.35 (m, 3H), 6.38-6.44 (m, 1H), 5.52 (d, J=10.4 Hz, 1H), 5.22 (d, J=10.6 Hz, 1H), 4.03-4.26 (m, 4H), 3.54-3.63 (m, 1H), 3.04-3.08 (m, 2H), 2.35-2.44 (m, 1H), 1.99-2.13 (m, 1H), 1.07 (s, 3H). Mass Calc'd for C$_{20}$H$_{20}$N$_2$O$_4$: 352.1, found 353.1 (M+H)$^+$.

Step B—Synthesis of Intermediate Compound Int-23b

To a solution of Int-23a (120 mg, 0.341 mmol) in methanol (5 mL) was added m-CPBA (147 mg, 0.681 mmol) and N-iodosuccinimide (153 mg, 0.681 mmol). The mixture was stirred at 70° C. for 1 h, cooled to room temperature and quenched with saturated aqueous NaHCO$_3$ (5 mL). The mixture was extracted with dichloromethane. The organic phase was dried over anhydrous Na$_2$SO$_4$, filtered and the filtrate was concentrated in vacuo. The resulting residue was purified using column chromatography on silica gel (5% methanol/dichloromethane) to provide Int-23b. $^1$H NMR (400 MHz, CDCl$_3$) δ 7.57-7.63 (m, 2H), 7.26-7.38 (m, 3H), 5.51 (d, J=10.2 Hz, 1H), 5.18 (d, J=10.2 Hz, 1H), 4.38-4.42 (m, 1H), 4.04-4.24 (m, 3H), 3.56-3.65 (m, 1H), 3.26-3.32 (m, 1H), 3.11-3.22 (m, 1H), 2.38-2.50 (m, 1H), 2.10-2.22 (m, 1H), 1.15 (s, 3H).

Step C—Synthesis of Intermediate Compound Int-23c

A solution of Int-23b (120 mg, 0.251 mmol) in dimethylsulfoxide (3 mL) was added Pd(Ph$_3$P)$_4$ (58.0 mg, 0.050 mmol), N,N-diisopropylethylamine (0.044 ml, 0.251 mmol) and 2,4-difluorobenzylamine (144 mg, 1.004 mmol). The mixture was stirred at 80° C. for 2 h under carbon monoxide (1 atm), cooled to room temperature and diluted with ethyl acetate. The organic phase was washed with 1N aqueous HCl and saturated aqueous NaHCO$_3$, dried over anhydrous Na$_2$SO$_4$, filtered and the filtrate was concentrated in vacuo. The resulting residue was purified using preparative TLC on silica gel (100% ethyl acetate) to provide Int-23c-1 (cis), Int-23c-2 (trans). Compound Int-23c-2 (trans) was separated further by SFC (OD, 250 mm×30 mm, 10 μm, 40% ethanol in SC—CO$_2$, 80 mL/min, 220 nm) to provide Int-23c-2a (trans, enantiomer A) and Int-23c-2b (trans, enantiomer B). Int-23c-2a: $^1$H NMR (400 MHz, CDCl$_3$) δ 10.79-10.96 (m, 1H), 7.53-7.55 (m, 2H), 7.27-7.35 (m, 4H), 6.73-6.87 (m, 2H), 5.44 (d, J=10.2 Hz, 1H), 5.19 (d, J=10.2 Hz, 1H), 4.51-4.69 (m, 2H), 4.01-4.32 (m, 5H), 3.57-3.63 (m, 1H), 3.34-3.45 (m, 1H), 2.37-2.49 (m, 1H), 1.97-2.09 (m, 1H), 1.08 (s, 3H). Mass Calc'd for C$_{28}$H$_{25}$F$_2$N$_3$O$_5$: 521.2, found 522.2 (M+H)$^+$.

Int-23c-2b: $^1$H NMR (400 MHz, CDCl$_3$) δ 10.87 (s, 1H), 7.55 (d, J=7.01 Hz, 2H), 7.27-7.42 (m, 4H), 6.75-6.84 (m, 2H), 5.44 (d, J=10.2 Hz, 1H), 5.19 (d, J=10.2 Hz, 1H), 4.51-4.70 (m, 2H), 3.98-4.29 (m, 5H), 3.55-3.64 (m, 1H), 3.32-3.46 (m, 1H), 2.37-2.50 (m, 1H), 1.93-2.10 (m, 1H), 1.09 (s, 3H). Mass Calc'd for C$_{28}$H$_{25}$F$_2$N$_3$O$_5$: 521.2, found 522.2 (M+H)$^+$.

Step D—Synthesis of Compounds 136 and 137

To a solution of Int-23c-2a (trans, enantiomer A) (25 mg, 0.048 mmol) in N,N-dimethylformamide (2 mL) was added lithium chloride (20.32 mg, 0.479 mmol). The mixture was stirred at 80° C. for 4 h, cooled to room temperature and purified directly by RP-HPLC to provide compound 136. $^1$H NMR (400 MHz, CDCl$_3$) δ 10.78 (s, 1H), 7.30-7.39 (m, 1H), 6.76-6.86 (m, 2H), 4.54-4.67 (m, 2H), 4.13-4.35 (m, 4H), 4.02-4.10 (m, 1H), 3.68-3.79 (m, 1H), 3.39-3.48 (m, 1H), 2.48-2.58 (m, 1H), 2.06-2.20 (m, 1H), 1.32 (s, 3H). Mass Calc'd for C$_{21}$H$_{19}$F$_2$N$_3$O$_5$: 431.1, found 432.1 (M+H)$^+$.

Compound 137 was prepared in a similar manner from Int-23c-2b (trans, enantiomer B). $^1$H NMR (400 MHz, CDCl$_3$) δ 10.76 (s, 1H), 7.30-7.40 (m, 1H), 6.75-6.86 (m, 2H), 4.53-4.67 (m, 2H), 4.00-4.35 (m, 5H), 3.68-3.79 (m, 1H), 3.39-3.45 (m, 1H), 2.46-2.57 (m, 1H), 2.05-2.18 (m, 1H), 1.32 (s, 3H). Mass Calc'd for C$_{21}$H$_{19}$F$_2$N$_3$O$_5$: 431.1, found 432.1 (M+H)$^+$.

Example 24

Preparation of Compounds 138 and 139

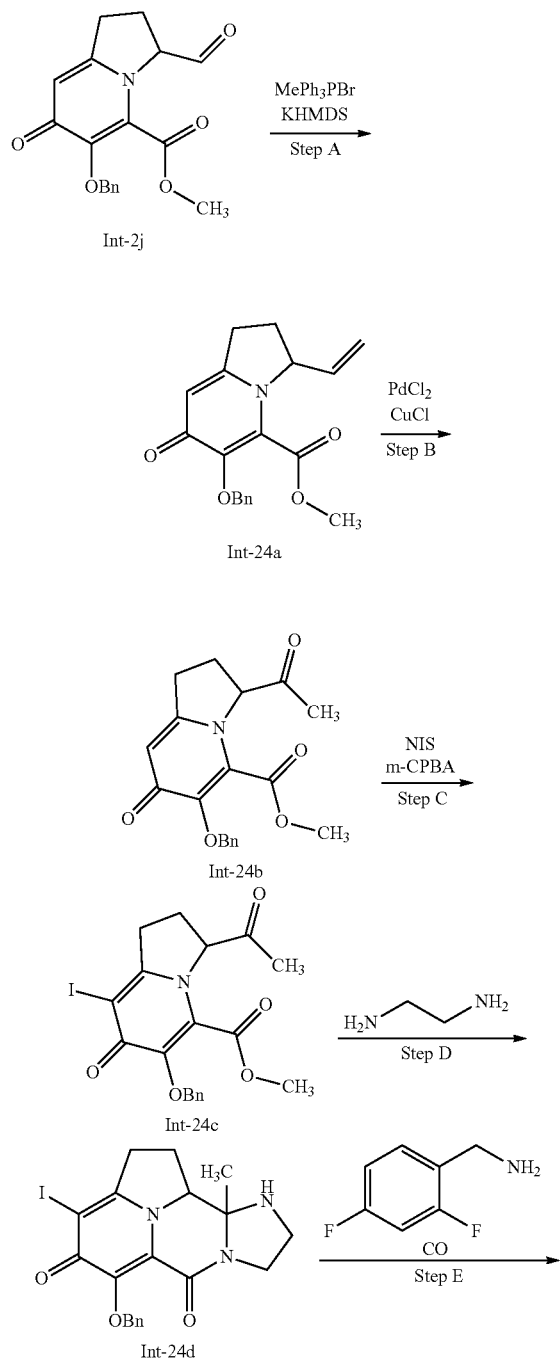

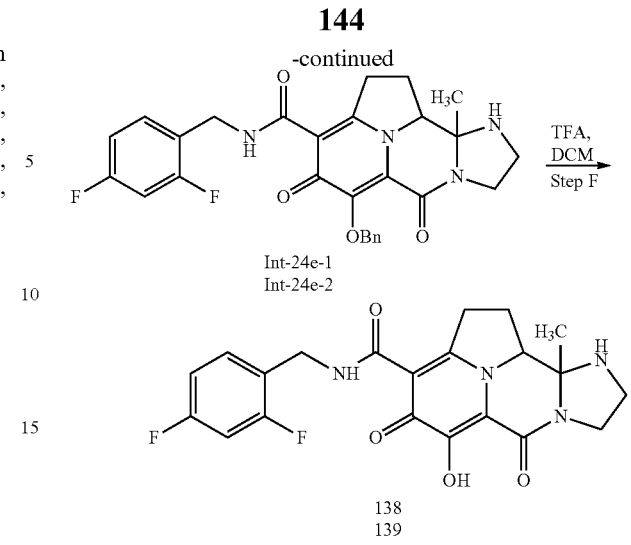

Step A—Synthesis of Intermediate Compound Int-24a

To a solution of bromo(methyl)triphenylphosphorane (0.917 g, 2.57 mmol) in tetrahydrofuran (15 mL) was added KHMDS (2.57 mL, 2.57 mmol) at −78° C. and the mixture was warmed to reflux. To the refluxing solution was added a solution of Int-2j (0.7 g, 2.1 mmol) in tetrahydrofuran (5 mL). The mixture was stirred at 80° C. for 1 h, cooled to rt, quenched with water (20 mL) and extracted with ethyl acetate. The combined organic portions were dried over anhydrous Na$_2$SO$_4$, filtered and the filtrate was concentrated in vacuo. The resulting residue was purified using column chromatography on silica gel (10% methanol in dichloromethane) to provide Int-24a. $^1$H NMR (chloroform-d): δ 7.73-7.75 (m, 2H), 7.29-7.60 (m, 3H), 6.41 (s, 1H), 5.67-5.79 (m, 1H), 5.44 (d, J=11 Hz, 1H), 5.08-5.25 (m, 2H), 5.00 (d, J=11.4 Hz), 3.69 (s, 3H), 2.90-3.07 (m, 3H), 2.36-2.53 (m, 2H). Mass Calc'd for C$_{19}$H$_{19}$NO$_4$: 325.1, found 325.9 (M+H)$^+$.

Step B—Synthesis of Intermediate Compound Int-24b

To a solution of Int-24a (300 mg, 0.922 mmol) in N,N-dimethylformamide (10 mL) and water (1 mL) was added copper(I) chloride (137 mg, 1.38 mmol) and palladium(II) chloride (32.7 mg, 0.184 mmol). The mixture was stirred at 30° C. under oxygen (1 atm) for 30 hours. The mixture was filtered and the filtrate was diluted with water (10 mL) and extracted with ethyl acetate. The combined organic portions were dried over anhydrous Na$_2$SO$_4$, filtered and the filtrate was concentrated in vacuo. The resulting residue was purified using column chromatography on silica gel (10% methanol in dichloromethane) to provide Int-24b. $^1$H NMR (chloroform-d): δ 7.54 (d, J=6.6 Hz, 2H), 7.33-7.42 (m, 3H), 7.10 (s, 1H), 5.36 (d, J=10.8 Hz, 1H), 5.18 (d, J=10.8 Hz, 1H), 3.74 (s, 3H), 3.06-3.17 (m, 3H), 2.55-2.72 (m, 1H), 2.16-2.24 (m, 4H). Mass Calc'd for C$_{19}$H$_{19}$NO$_5$: 341.1, found 342.1 (M+H)$^+$.

Step C—Synthesis of Intermediate Compound Int-24c

To a solution of Int-24b (250 mg, 0.732 mmol) in methanol (10 mL) was added mCPBA (316 mg, 1.465 mmol) and N-iodosuccinimide (330 mg, 1.465 mmol). The mixture was stirred at 30° C. for 1 hour. The mixture was quenched with saturated aqueous Na$_2$SO$_3$ (5 mL) and extracted with dichloromethane. The combined organic portions were dried over anhydrous Na$_2$SO$_4$, filtered and the filtrate was concentrated in vacuo. The resulting residue was purified using column chromatography on silica gel (10% methanol in dichloromethane) to provide Int-24c. $^1$H NMR (chloroform-d): δ

7.42-7.50 (m, 2H), 7.28-7.37 (m, 3H), 5.37 (d, J=10.5 Hz, 1H), 5.16 (d, J=10.5 Hz, 1H), 3.73 (s, 3H), 3.07-3.29 (m, 3H), 2.53-2.66 (m, 1H), 2.13-2.24 (m, 4H). Mass Calc'd for $C_{19}H_{18}INO_5$: 467.0, found 468.1 $(M+H)^+$.

Step D—Synthesis of Intermediate Compound Int-24d

To a solution of Int-24c (170 mg, 0.364 mmol) in tetrahydrofuran (2 mL) was added acetic acid (0.1 mL) and ethane-1,2-diamine (109 mg, 1.819 mmol). The mixture was stirred at 80° C. for 2 h, cooled to room temperature and concentrated in vacuo. The resulting residue was purified using column chromatography on silica gel (10% methanol in dichloromethane) to provide Int-24d. $^1$H NMR (chloroform-d): δ 7.69 (d, J=7 Hz, 2H), 7.28-7.39 (m, 3H), 5.45 (d, J=10.4 Hz, 1H), 5.27 (d, J=10 Hz, 1H), 4.55-4.56 (m, 1H), 4.39-4.41 (m, 1H), 3.90 (d, J=5.5 Hz, 1H), 3.45-3.48 (m, 1H), 3.30-3.37 (m, 1H), 3.08-3.23 (m, 1H), 2.92-3.05 (m, 1H), 2.27-2.45 (m, 1H), 1.96-2.06 (m, 1H). Mass Calc'd for $C_{20}H_{20}IN_3O_3$: 477.1, found 478.2 $(M+H)^+$.

Step E—Synthesis of Intermediate Compound Int-24e

To a solution of Int-24d (100 mg, 0.210 mmol) in dimethylsulfoxide (3 mL) was added Pd(Ph$_3$P)$_4$ (48.4 mg, 0.042 mmol), N,N-diisopropylethylamine (0.037 mL, 0.210 mmol) and 2,4-difluorobenzylamine (120 mg, 0.838 mmol). The mixture was stirred at 80° C. for 2 h under carbon monoxide (1 atm), cooled to room temperature and filtered. The filtrate was purified directly by preparative RP-HPLC to provide Int-24e. Mass Calc'd for $C_{28}H_{26}F_2N_4O_4$: 520.2, found 521.1 $(M+H)^+$.

Separation of Int-24e by SFC (Chralpak AS, 250 mm×30 mm, 5 μm, 35-40% ethanol in SC—CO$_2$, 120 mL/min, 220 nm) afforded Int-24e-1 (earlier eluting) and Int-24e-2 (later eluting).

Step F—Synthesis of Compound 138 and Compound 139

To a solution of Int-24e-1 (7 mg, 0.013 mmol) in dichloromethane (3 mL) was added trifluoroacetic acid (0.5 mL). The mixture was stirred at 30° C. for 2 h and then concentrated in vacuo. The resulting residue was purified using preparative RP-HPLC to provide compound 138. $^1$H NMR (chloroform-d): δ 10.77 (br. s., 1H), 7.36 (d, J=6.8 Hz, 1H), 6.74-6.87 (m, 2H), 4.57-4.62 (m, 2H), 4.26 (d, J=9.7 Hz, 1H), 4.15-4.18 (m, 1H), 3.92-3.99 (m, 1H), 3.57-3.63 (m, 1H), 3.33-3.48 (m, 3H), 2.49-2.52 (m, 1H), 2.09-2.12 (m, 1H), 1.30 (s, 3H). Mass Calc'd for $C_{21}H_{20}F_2N_4O_4$: 430.1, found 431.1 $(M+H)^+$.

Compound 139 was prepared from Int-24e-2 using a similar procedure. $^1$H NMR (chloroform-d): δ 10.79 (br. s., 1H), 7.36 (d, J=7.7 Hz, 1H), 6.76-6.80 (m, 2H), 4.57-4.62 (m, 2H), 4.26 (d, J=8 Hz, 1H), 4.13-4.19 (m, 1H), 3.94-3.95 (m, 1H), 3.59-3.62 (m, 1H), 3.43-3.45 (m, 3H), 2.49-2.52 (m, 1H), 2.09-2.12 (m, 1H), 1.30 (s, 3H). Mass Calc'd for $C_{21}H_{20}F_2N_4O_4$: 430.1, found 431.1 $(M+H)^+$.

Example 25

Preparation of Compounds 140 and 141

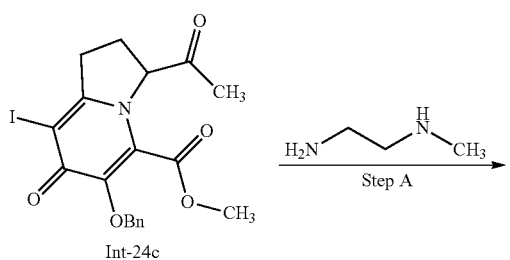

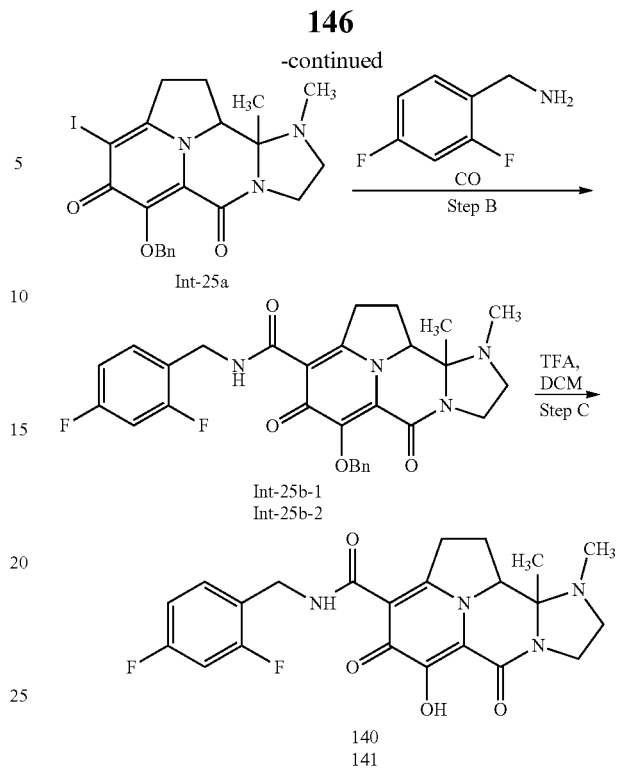

Step A—Synthesis of Intermediate Compound Int-25a

To a solution of Int-24c (300 mg, 0.642 mmol) in tetrahydrofuran (10 mL) and trifluoroacetic acid (0.3 mL) was added N-methylethane-1,2-diamine (238 mg, 3.21 mmol). The mixture was stirred at 80° C. for 1 h, cooled to room temperature and concentrated in vacuo. The resulting residue was purified using column chromatography on silica gel (10% methanol in dichloromethane) to provide Int-25a. Mass Calc'd for $C_{21}H_{22}IN_3O_3$: 491.1, found 492.1 $(M+H)^+$.

Step B—Synthesis of Intermediate Compound Int-25b

To a solution of Int-25a (150 mg, 0.305 mmol) in dimethylsulfoxide (3 mL) was added N,N-diisopropylethylamine (0.267 mL, 1.526 mmol), Pd(Ph$_3$P)$_4$ (70.6 mg, 0.061 mmol) and 2,4-difluorobenzylamine (131 mg, 0.916 mmol). The mixture was stirred at 80° C. for 1 h under carbon monoxide (1 atm), cooled to room temperature and filtered. The filtrate was purified directly by preparative RP-HPLC to provide Int-25b. Mass Calc'd for $C_{29}H_{28}F_2N_4O_4$: 534.2, found 535.3 $(M+H)^+$.

Separation of Int-25b was accomplished by SFC (Chralpak AD, 250 mm×30 mm, 10 μm, isopropanol in SC—CO$_2$, 80 mL/min, 220 nm) to provide Int-25b-1 and Int-25b-2.

Int-25b-1: $^1$H NMR (chloroform-d): δ 10.95 (br. s., 1H), 7.28-7.60 (m, 6H), 6.74-6.88 (m, 2H), 5.45 (d, J=9.9 Hz, 1H), 5.17 (d, J=9.9 Hz, 1H), 4.54-4.70 (m, 2H), 4.11-4.27 (m, 2H), 3.64-3.79 (m, 2H), 3.35-3.52 (m, 2H), 3.25 (t, J=7.6 Hz, 1H), 2.72-2.84 (m, 1H), 2.44-2.56 (m, 1H), 2.37 (s, 3H), 0.91 (s, 3H).

Int-25b-2: $^1$H NMR (chloroform-d): δ 10.95 (br. s., 1H), 7.28-7.71 (m, 6H), 6.74-6.86 (m, 2H), 5.45 (d, J=10 Hz, 1H), 5.17 (d, J=10.2 Hz, 1H), 4.53-4.69 (m, 2H), 4.12-4.27 (m, 2H), 3.65-3.79 (m, 2H), 3.35-3.44 (m, 2H), 3.25 (t, J=8.1 Hz, 1H), 2.72-2.83 (m, 1H), 2.44-2.56 (m, 1H), 2.06 (s, 3H), 0.87 (s, 3H).

Step C—Synthesis of Compounds 140 and 141

To a solution of Int-25b-1 (25 mg, 0.047 mmol) in N,N-dimethylformamide (5 mL) was added lithium chloride (19.83 mg, 0.468 mmol). The mixture was stirred at 75° C.

for 2 h, cooled to room temperature and purified directly by preparative RP-HPLC to provide compound 140. $^1$H NMR (chloroform-d): δ 10.84 (br. s., 1H), 7.30-7.39 (m, 1H), 6.74-6.86 (m, 2H), 4.54-4.66 (m, 2H), 4.16-4.30 (m, 1H), 3.71-3.88 (m, 2H), 3.34-3.49 (m, 2H), 2.87-2.92 (m, 1H), 2.51-2.59 (m, 1H), 2.42 (s, 3H), 2.03-2.14 (m, 1H), 1.14 (s, 3H). Mass Calc'd for $C_{22}H_{22}F_2N_4O_4$: 444.2, found 445.1 (M+H)$^+$ Compound 141 was prepared from Int-25b-2 using a similar procedure. $^1$H NMR (chloroform-d): δ 10.86 (br. s., 1H), 7.30-7.39 (m, 1H), 6.76-6.86 (m, 2H), 4.57-4.66 (m, 2H), 4.33 (dd, J=10.5, 7.4 Hz, 1H), 4.21 (dd, J=18.9, 9.5 Hz, 1H), 3.75-3.88 (m, 2H), 3.40-3.51 (m, 2H), 2.90-2.92 (m, 1H), 2.53-2.63 (m, 1H), 2.45 (s, 3H), 2.05-2.19 (m, 1H), 1.14 (s, 3H). Mass Calc'd for $C_{22}H_{22}F_2N_4O_4$: 444.2, found 445.1 (M+H)$^+$.

Example 26

Preparation of Compounds 142 and 143

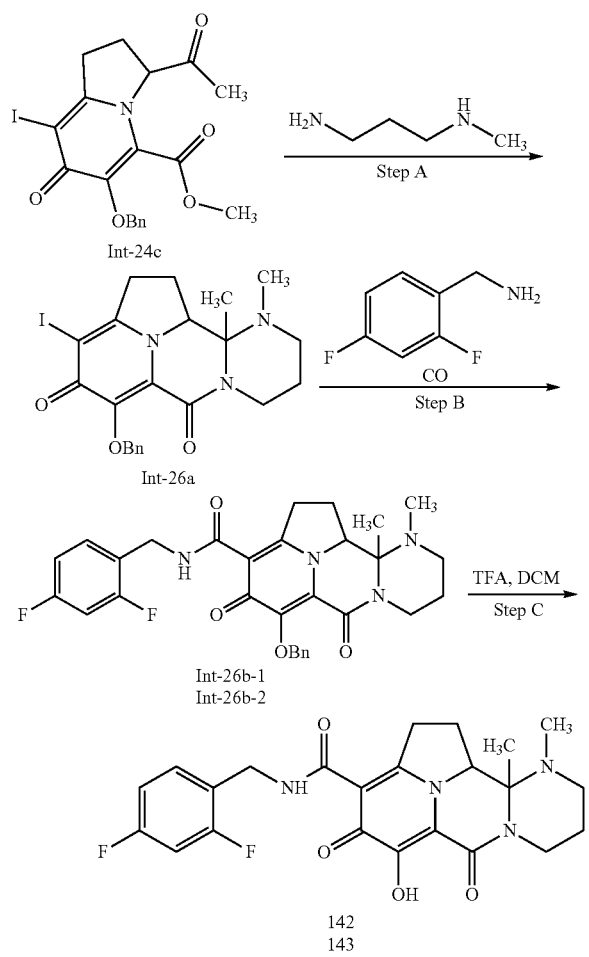

Step A—Synthesis of Intermediate Compound Int-26a

To a solution of Int-24c (300 mg, 0.642 mmol) in tetrahydrofuran (10 mL) and acetic acid (0.5 mL) was added N-methylpropane-1,3-diamine (283 mg, 3.21 mmol). The mixture was stirred at 80° C. for 5 h, cooled to room temperature and concentrated in vacuo. The resulting residue was purified using column chromatography on silica gel (10% methanol in dichloromethane) to provide Int-26a. Mass Calc'd for $C_{22}H_{24}IN_3O_3$: 505.1, found 506.1 (M+H)$^+$.

Step B—Synthesis of Intermediate Compound Int-26b

To a solution of Int-26a (250 mg, 0.495 mmol) in dimethylsulfoxide (3 mL) was added N,N-diisopropylethylamine (0.432 mL, 2.474 mmol), Pd(Ph$_3$P)$_4$ (114 mg, 0.099 mmol) and 2,4-difluorobenzylamine (212 mg, 1.484 mmol). The mixture was stirred at 80° C. for 1 h under carbon monoxide (1 atm), cooled to room temperature and filtered. The filtrate was purified using preparative RP-HPLC to provide Int-26b. $^1$H NMR (400 MHz, chloroform-d): δ 10.95 (br. s., 1H), 7.52-7.54 (m, 2H), 7.27-7.44 (m, 4H), 6.76-6.87 (m, 2H), 5.36 (d, J=10.2 Hz, 1H), 5.19 (d, J=10.2 Hz, 1H), 4.46-4.69 (m, 4H), 4.07 (dd, J=19.2, 9.8 Hz, 1H), 3.35-3.50 (m, 1H), 3.13-3.24 (m, 1H), 2.90-3.05 (m, 2H), 2.60 (s, 3H), 2.38-2.47 (m, 1H), 1.97-2.12 (m, 2H), 1.75 (d, J=9.8 Hz, 1H), 1.15 (s, 3H). Mass Calc'd for $C_{30}H_{30}F_2N_4O_4$: 548.2, found 549.2 (M+H)$^+$.

Separation of Int-26b was accomplished by SFC (Chralpak AD, 250 mm×30 mm, 10 μm, 55% isopropanol in SC—CO$_2$, 80 mL/min) to provide Int-26b-1 and Int-26b-2.

Step C—Synthesis of Compounds 142 and 143

To a solution of Int-26b-1 (40 mg, 0.073 mmol) in dichloromethane (3 mL) was added trifluoroacetic acid (0.3 mL) at 0° C. The mixture was stirred at room temperature for 1 h and then concentrated in vacuo. The resulting residue was purified using preparative RP-HPLC to provide compound 142. $^1$H NMR (chloroform-d): δ 10.80 (br. s., 1H), 7.31-7.41 (m, 1H), 6.75-6.86 (m, 2H), 4.43-4.75 (m, 4H), 4.09 (dd, J=19.3, 9.6 Hz, 1H), 3.8-3.48 (m, 2H), 2.95-3.19 (m, 2H), 2.68 (s, 3H), 2.42-2.55 (m, 1H), 2.02-2.20 (m, 2H), 1.75 (d, J=11.4 Hz, 1H), 1.44 (s, 3H). Mass Calc'd for $C_{23}H_{24}F_2N_4O_4$: 458.2, found 459.1 (M+H)$^+$.

Compound 143 was prepared from Int-26b-2 using a similar procedure. $^1$H NMR (chloroform-d): δ 10.81 (br. s., 1H), 7.31-7.39 (m, 1H), 6.75-6.86 (m, 2H), 4.54-4.70 (m, 3H), 4.46 (dd, J=13.8, 5.5 Hz, 1H), 4.08 (dd, J=19.1, 9.6 Hz, 1H), 3.26-3.48 (m, 2H), 3.13 (td, J=13.4, 4.6 Hz, 1H), 2.97 (d, J=13.8 Hz, 1H), 2.66 (s, 3H), 2.41-2.52 (m, 1H), 2.03-2.19 (m, 2H), 1.73 (d, J=11.4 Hz, 1H), 1.42 (s, 3H). Mass Calc'd for $C_{23}H_{24}F_2N_4O_4$: 458.2, found 459.1 (M+H)$^+$.

Example 27

Preparation of Intermediate Compound Int-27d

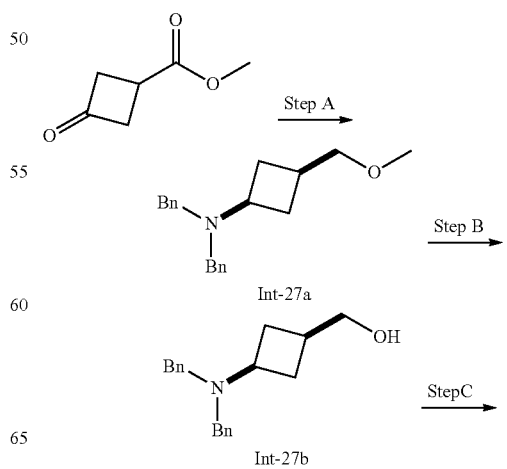

149
-continued

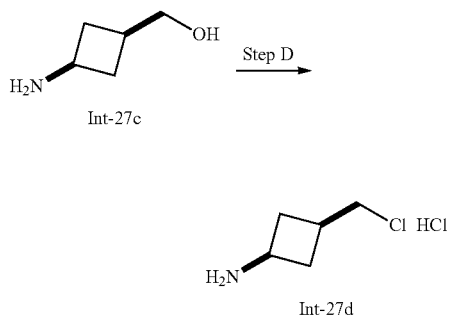

Step A—Synthesis of Compound Int-27a

To a solution of methyl 3-oxocyclobutanecarboxylate (50 g, 390 mmol) in AcOH (10 mL) and THF (400 mL), was added dibenzylamine (231 g, 1171 mmol), followed by NaBH(OAc)$_3$ (165 g, 780 mmol) at 28° C. The mixture was stirred at 28° C. for 10 h. The mixture was concentrated in vacuo and diluted with H$_2$O (300 mL). The mixture was adjusted to pH=8 with aqueous NaHCO$_3$, and then extracted with EtOAc (300 mL×3). The combined organic layers were concentrated in vacuo and the residue was purified using silica gel chromatography (petroleum ether:EtOAc=100:1 to 30:1) to provide compound Int-27a. MS (M+H)$^+$: 310.2

Step B—Synthesis of Compound Int-27b

To a solution of LiAlH$_4$ (14 g, 369 mmol) in THF (400 mL) stirred at 0° C., was added a solution of compound Int-27a (100 g, 323 mmol) in THF (100 mL) dropwise. The mixture was stirred at 0° C. for 1 h. It was quenched by sequentially adding H$_2$O (14.0 mL), 10% NaOH (28.0 mL) and H$_2$O (56.0 mL) under an ice bath. The resulting mixture was dried over anhydrous MgSO$_4$. The solution was filtered, and the filtrate was concentrated in vacuo to provide compound Int-27b. The crude product was used in the next step without further purification. MS (M+H)$^+$: 282.1

Step C—Synthesis of Compound Int-27c

To a solution of compound Int-27b (80 g, 284 mmol) in ethanol (300 mL) was added AcOH (10 mL), followed by Pd/C (10% wt., 30.3 g, 28.4 mmol). The mixture was stirred at 26° C. for 12 h under H$_2$ atmosphere. The mixture was then filtered. The filtrate was concentrated under vacuum to afford compound Int-27c. The crude product was used in the next step without further purification. MS (M+H)$^+$: 102.0

Step D—Synthesis of Compound Int-27d

To a solution of compound Int-27c (3.5 g, 34.6 mmol) in ethanol (30 mL) was added 2 N aqueous HCl (17.3 mL, 34.6 mmol). The mixture was stirred at 25° C. for 0.5 h. The mixture was concentrated in vacuo to afford crude hydrochloride. This material was stirred in chloroform (10 mL) at 0° C., and sulfurous dichloride (3.79 mL, 51.9 mmol) was then added. The mixture was stirred at 60° C. for 12 h. The resulting mixture was concentrated in vacuo to remove the solvent. The solid residue was washed with EtOAc (20 mL×3) to afford compound Int-27d. The product was used in the next step without further purification. $^1$H NMR (400 MHz, DMSO-d$_6$) δ 8.37 (br s, 2H), 3.63 (d, J=6.85 Hz, 2H), 3.48-3.55 (m, 1H), 2.34-2.41 (m, 1H), 2.24-2.33 (m, 2H), 1.88-1.99 (m, 2H).

150

Example 28

Preparation of Compounds 144-147

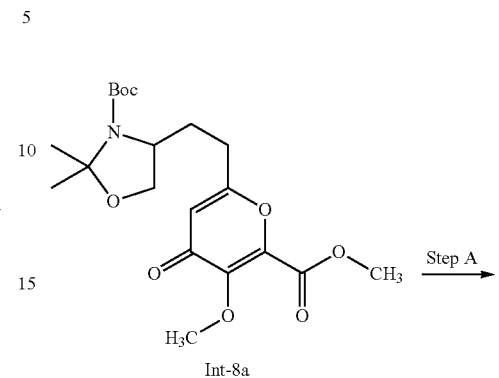
Int-8a

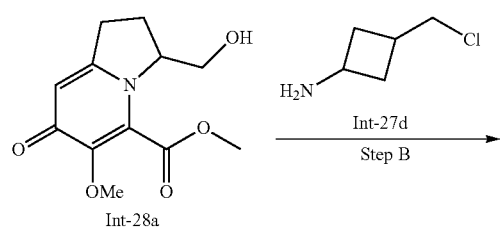
Int-28a

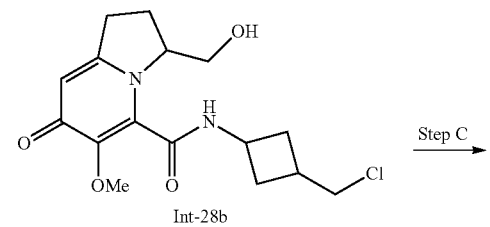
Int-28b

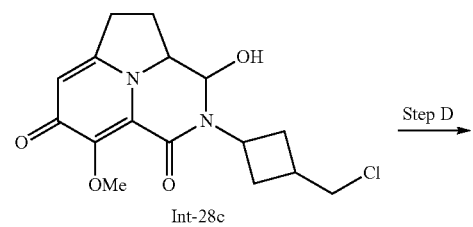
Int-28c

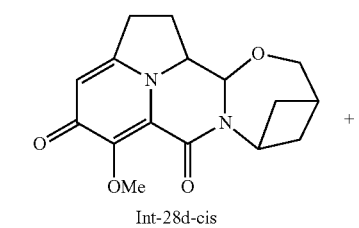
Int-28d-cis

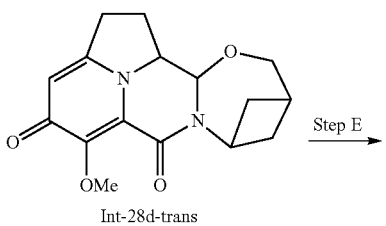
Int-28d-trans

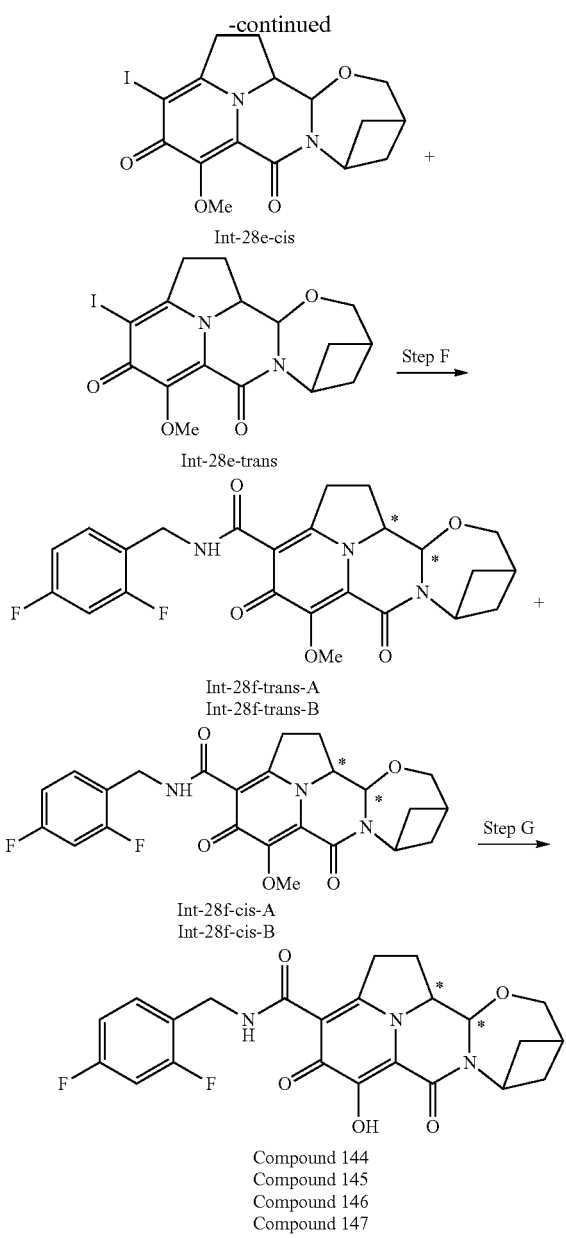

Int-28e-cis

Int-28e-trans

Int-28f-trans-A
Int-28f-trans-B

Int-28f-cis-A
Int-28f-cis-B

Compound 144
Compound 145
Compound 146
Compound 147

Step A—Synthesis of Compound Int-28a

To a solution of compound Int-8a (7 g, 17.01 mmol) in DCM (20 ml) was added TFA (2 ml, 26.0 mmol). The reaction was stirred at room temperature for 30 min. The solvent was removed under vacuum, the residue was dissolved MeOH (40 ml) and was heated at reflux for 4 h. The reaction mixture was concentrated under vacuum, the residue was purified by a silica gel column eluting with 10% MeOH/DCM to provide compound Int-28a. MS (M+H)$^+$: 254.1.

Step B—Synthesis of Compound Int-28b

To a solution of compound Int-28a (5 g, 19.74 mmol) in EtOH (120 mL) was added triethylamine (22.01 mL, 158 mmol), followed by compound Int-27d (4.72 g, 30.3 mmol). The mixture was stirred at 80° C. for 0.5 h. The solvent was removed under vacuum, the residue was purified by a silica gel column (EtOAc:MeOH=30:1 to 10:1) to give compound Int-28b. MS (M+H)$^+$: 341.1.

Step C—Synthesis of Compound Int-28c

To a solution of compound Int-28b (1.8 g, 5.28 mmol) in dichloromethane (50 mL) was added Dess Martin periodinane (5.60 g, 13.20 mmol) at 0° C. The mixture was stirred at 20° C. for 5 h. It was quenched with saturated aqueous Na$_2$SO$_3$ (8 mL) solution and saturated aqueous NaHCO$_3$ (8 mL) solution. The organic layer was dried over anhydrous Na$_2$SO$_4$, filtered and concentrated under vacuum. The residue was purified by a silica gel column (dichloromethane:MeOH=50:1 to 20:1) to give compound Int-28c. MS (M+H)$^+$: 338.9.

Step D—Synthesis of Compound Int-28d-cis and Compound int-28d-trans

To a solution of compound Int-28c (100 mg, 0.295 mmol) in DMF (4 mL) was added Cs$_2$CO$_3$ (193 mg, 0.590 mmol) at 20° C. The mixture was stirred at 60° C. for 12 h. The mixture was concentrated under vacuum. The residue was purified by a preparative silica gel TLC plate (dichloromethane:MeOH=15:1) to give compound Int-28d-trans, and compound Int-28d-cis. MS (M+H)$^+$: 303.1

Compound Int-28d-trans: $^1$H NMR (400 MHz, CDCl$_3$) δ 6.32 (s, 1H), 5.32 (dt, J=4.11, 7.14 Hz, 1H), 5.12 (d, J=8.61 Hz, 1H), 4.20 (ddd, J=6.55, 8.56, 10.12 Hz, 1H), 4.07-4.15 (m, 1H), 3.91 (s, 3H), 3.82 (d, J=11.93 Hz, 1H), 2.89-3.05 (m, 2H), 2.65-2.72 (m, 1H), 2.56-2.63 (m, 1H), 2.52 (br dd, J=3.62, 7.34 Hz, 1H), 2.04-2.16 (m, 2H), 1.77-1.84 (m, 2H).

Compound Int-28d-cis: $^1$H NMR (400 MHz, CDCl$_3$) δ 6.41 (s, 1H), 5.22 (d, J=3.52 Hz, 1H), 4.76-4.84 (m, 1H), 4.45 (ddd, J=3.42, 6.75, 10.56 Hz, 1H), 3.84-3.93 (m, 4H), 3.72-3.79 (m, 1H), 2.96-3.08 (m, 2H), 2.72 (td, J=7.07, 13.84 Hz, 1H), 2.53-2.65 (m, 2H), 2.38-2.49 (m, 1H), 2.24-2.33 (m, 1H), 1.95 (br dd, J=8.12, 13.60 Hz, 1H), 1.69 (dd, J=8.02, 11.15 Hz, 1H).

Step E—Synthesis of Compound Int-28e-cis and Compound Int-28e-trans

To a mixture of compound Int-28d-trans (100 mg, 0.331 mmol) in MeOH (5 mL) was added m-CPBA (57.1 mg, 0.331 mmol) and N-iodosuccinimide (149 mg, 0.662 mmol) under N$_2$ atmosphere and then the mixture was stirred at 80° C. for 2 h. The mixture was cooled to 25° C. and quenched with Na$_2$SO$_3$ solution (2 mL). The mixture was then adjust to pH=7 with 10% NaOH. It was diluted with dichloromethane (20 mL). The organic layer was dried over anhydrous Na$_2$SO$_4$, filtered and the filtrate was concentrated. The residue was treated with MeOH (20 mL) and filtered. The filter cake was dried to afford compound Int-28e-trans. NMR (400 MHz, CDCl$_3$) δ 7.27 (s, 1H), 5.06-5.26 (m, 2H), 4.27-4.46 (m, 1H), 4.02-4.11 (m, 1H), 3.98 (s, 3H), 3.75-3.78 (m, 1H), 3.15 (br dd, J=9.39, 17.21 Hz, 1H), 2.89-3.07 (m, 1H), 2.51-2.71 (m, 3H), 2.00-2.18 (m, 2H), 1.78 (br dd, J=7.14, 13.20 Hz, 1H). MS (M+H)$^+$: 429.1

To a mixture of compound Int-28d-cis (30 mg, 0.099 mmol) in MeOH (2 mL) was added m-CPBA (34.2 mg, 0.198 mmol) and N-iodosuccinimide (44.7 mg, 0.198 mmol) under N$_2$ atmosphere and then the mixture was stirred at 80° C. for 2 hours. The mixture was cooled to 25° C., quenched with Na$_2$SO$_3$ solution (0.5 mL). The mixture was then diluted with DCM (5 mL) and dried over anhydrous Na$_2$SO$_4$. The mixture was then filtered and the filtrate was concentrated. The residue was purified by a silica gel column (EtOAc:MeOH=10:1 to 4:1) to give compound Int-28e-cis. MS (M+H)$^+$: 429.0

Step F—Synthesis of Compound Int-28f-cis-A/B and Compound Int-28f-trans-A/B

To a solution of compound Int-28e-trans (80 mg, 0.187 mmol) in DMSO (2 mL) was added diisopropylethylamine (0.163 mL, 0.934 mmol), Pd(Ph$_3$P)$_4$ (43.2 mg, 0.037 mmol) and (2,4-difluorophenyl)methanamine (53.5 mg, 0.374 mmol). The mixture was stirred at 80° C. for 1.5 h under carbon monoxide (1 atm). The reaction was diluted with water (10 mL), and extracted with EtOAc (10 mL×4). The organic layer was washed with 1M HCl (2 mL) and brine (5 mL). It was dried over anhydrous $Na_2SO_4$, filtered, and concentrated. The residue was purified by a silica gel column (dichloromethane:MeOH=20:1) to give the desired product as a racemic mixture, which was further separated by SFC(Column AS (250 mm*30 mm, 10 μm); Condition 0.1% $NH_3H_2O$ MeOH Begin B 45%; End B 45%; FlowRate (mL/min) 80; Injections 80) to give compound Int-28f-trans-A and compound Int-28f-trans-B. MS (M+H)$^+$: 472.2.

Compound Int-28f-trans-A: $^1$H NMR (400 MHz, CDCl$_3$) δ 10.83 (br t, J=5.48 Hz, 1H), 7.30-7.40 (m, 1H), 6.73-6.83 (m, 2H), 5.30-5.39 (m, 1H), 5.14 (d, J=8.61 Hz, 1H), 4.52-4.64 (m, 2H), 4.25-4.34 (m, 1H), 4.19 (dd, J=3.52, 11.74 Hz, 1H), 4.09 (dd, J=9.39, 19.17 Hz, 1H), 3.98 (s, 3H), 3.87 (d, J=11.74 Hz, 1H), 3.37 (ddd, J=8.80, 10.96, 19.37 Hz, 1H), 2.63-2.79 (m, 3H), 2.60 (td, J=3.86, 7.53 Hz, 1H), 2.19 (dd, J=7.43, 11.74 Hz, 1H), 2.00-2.12 (m, 1H), 1.85 (dd, J=7.43, 12.91 Hz, 1H)

Compound Int-28f-trans-B: $^1$H NMR (400 MHz, CDCl$_3$) δ 10.84 (br t, J=5.67 Hz, 1H), 7.31-7.40 (m, 1H), 6.75-6.84 (m, 2H), 5.32-5.40 (m, 1H), 5.13 (d, J=8.61 Hz, 1H), 4.52-4.66 (m, 2H), 4.27-4.35 (m, 1H), 4.19 (dd, J=4.11, 12.33 Hz, 1H), 4.11 (dd, J=9.39, 19.17 Hz, 1H), 3.99 (s, 3H), 3.88 (d, J=12.13 Hz, 1H), 3.38 (ddd, J=8.80, 10.96, 19.37 Hz, 1H), 2.64-2.80 (m, 3H), 2.56-2.63 (m, 1H), 2.20 (dd, J=7.43, 11.74 Hz, 1H), 2.00-2.13 (m, 1H), 1.84 (dd, J=7.43, 13.30 Hz, 1H)

To a solution of compound Int-28e-cis (34 mg, 0.079 mmol) in DMSO (2 mL) was added diisopropylethylamine (0.069 mL, 0.397 mmol), Pd(Ph$_3$P)$_4$ (18.35 mg, 0.016 mmol) and (2,4-difluorophenyl)methanamine (22.73 mg, 0.159 mmol). The mixture was stirred at 80° C. for 1.5 h under carbon monoxide (1 atm). The mixture was diluted with water (5 mL), extracted with EtOAc (10 mL×5). The organic layer was washed with brine (8 mL). The organic layer was dried over anhydrous $Na_2SO_4$, filtered, and concentrated. The crude product was purified by a silica gel preparative TLC plate (dichloromethane:MeOH=20:1) to give the desired product as a racemic mixture, which was further separated by SFC (Instrument SFC-8 Method Column AD (250 mm*30 mm, 10 μm) Condition 0.1% $NH_3H_2O$ EtOH Begin B 45% End B 45% Gradient Time (min) 100% B Hold Time (min) FlowRate (mL/min) 80 Injections 60) to give compound Int-28f-cis-A and compound Int-28f-cis-B. MS (M+H)$^+$: 472.0.

Step G—Synthesis of Compound 144-147

To a solution of compound Int-28f-trans-A (25 mg, 0.053 mmol) in MeCN (5 mL) was added magnesium bromide (48.8 mg, 0.265 mmol). The mixture was stirred at 25° C. for 1 h. The resulting mixture was filtered and purified by preparative reverse phase HPLC to give compound 144. $^1$H NMR (400 MHz, CDCl$_3$) δ 10.83 (br t, J=5.48 Hz, 1H), 7.32-7.38 (m, 1H), 6.76-6.83 (m, 2H), 5.40-5.43 (m, 1H), 5.20 (d, J=8.4 Hz, 1H), 4.59-4.61 (m, 2H), 4.22-4.25 (m, 1H), 4.22 (dd, J=4.8, 12.8 Hz, 1H), 4.09 (dd, J=8.8, 19.6 Hz, 1H), 3.90 (d, J=12.0 Hz, 1H), 3.35 (ddd, J=8.80, 10.96, 19.37 Hz, 1H), 2.72 (td, J=3.86, 7.53 Hz, 1H), 2.66-2.69 (m, 3H), 2.23 (dd, J=7.6, 11.6 Hz, 1H), 2.00-2.12 (m, 1H), 1.90 (dd, J=7.6, 12.8 Hz, 1H). MS (M+H)$^+$: 458.1

The following compounds of the present invention were made using the methodology described in Step G of Example 28, and substituting the appropriate reactants.

Compound 145 (from compound Int-28f-trans-B): $^1$H NMR (400 MHz, CDCl$_3$) δ 10.83 (br t, J=5.48 Hz, 1H), 7.32-7.38 (m, 1H), 6.76-6.83 (m, 2H), 5.40-5.43 (m, 1H), 5.20 (d, J=8.4 Hz, 1H), 4.59-4.61 (m, 2H), 4.22-4.25 (m, 1H), 4.22 (dd, J=4.8, 12.8 Hz, 1H), 4.09 (dd, J=8.8, 19.6 Hz, 1H), 3.90 (d, J=12.0 Hz, 1H), 3.35 (ddd, J=8.80, 10.96, 19.37 Hz, 1H), 2.72 (td, J=3.86, 7.53 Hz, 1H), 2.66-2.69 (m, 3H), 2.23 (dd, J=7.6, 11.6 Hz, 1H), 2.00-2.12 (m, 1H), 1.90 (dd, J=7.6, 12.8 Hz, 1H). MS (M+H)$^+$: 458.1

Compound 146 (from compound Int-28f-cis-A): $^1$H NMR (400 MHz, CDCl$_3$) δ 10.83 (br t, J=5.2 Hz, 1H), 7.34 (dd, J=8.0, 15.2 Hz, 1H), 6.76-6.83 (m, 2H), 5.39 (d, J=3.2 Hz, 1H), 4.80 (dd, J=6.0, 9.6 Hz, 1H), 4.60 (d, J=4.2 Hz, 2H), 4.50-4.54 (m, 1H), 4.10 (dd, J=9.2, 19.2 Hz, 1H), 3.94 (dd, J=3.2, 12.8 Hz, 1H), 3.83 (d, J=12.0 Hz, 1H), 3.40 (dt, J=8.8, 20.0 Hz, 1H), 2.82 (dt, J=7.2, 13.6 Hz, 1H), 2.66-2.72 (m, 2H), 2.44-2.49 (m, 1H), 2.40-2.45 (m, 1H), 2.07 (dd, J=8.0, 13.2 Hz, 1H), 1.73-1.78 (m, 1H). MS (M+H)$^+$: 458.1

Compound 147 (from compound Int-28f-cis-B): $^1$H NMR (400 MHz, CDCl$_3$) δ 10.83 (br t, J=5.2 Hz, 1H), 7.34 (dd, J=8.0, 15.2 Hz, 1H), 6.76-6.83 (m, 2H), 5.39 (d, J=3.2 Hz, 1H), 4.80 (dd, J=6.0, 9.6 Hz, 1H), 4.60 (d, J=4.2 Hz, 2H), 4.50-4.54 (m, 1H), 4.10 (dd, J=9.2, 19.2 Hz, 1H), 3.94 (dd, J=3.2, 12.8 Hz, 1H), 3.83 (d, J=12.0 Hz, 1H), 3.40 (dt, J=8.8, 20.0 Hz, 1H), 2.82 (dt, J=7.2, 13.6 Hz, 1H), 2.66-2.72 (m, 2H), 2.44-2.49 (m, 1H), 2.40-2.45 (m, 1H), 2.07 (dd, J=8.0, 13.2 Hz, 1H), 1.73-1.78 (m, 1H). MS (M+H)$^+$: 458.1 (dd, J=7.6, 12.8 Hz, 1H). MS (M+H)$^+$: 458.1

Example 29

Preparation of Compounds 148-151

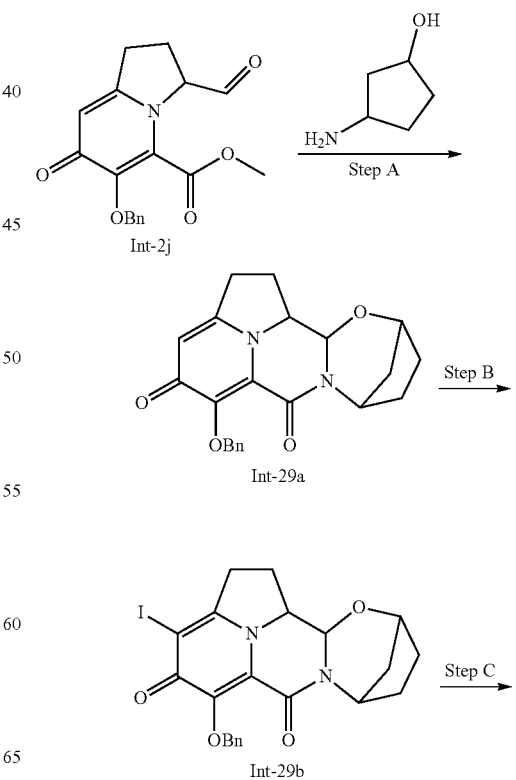

-continued

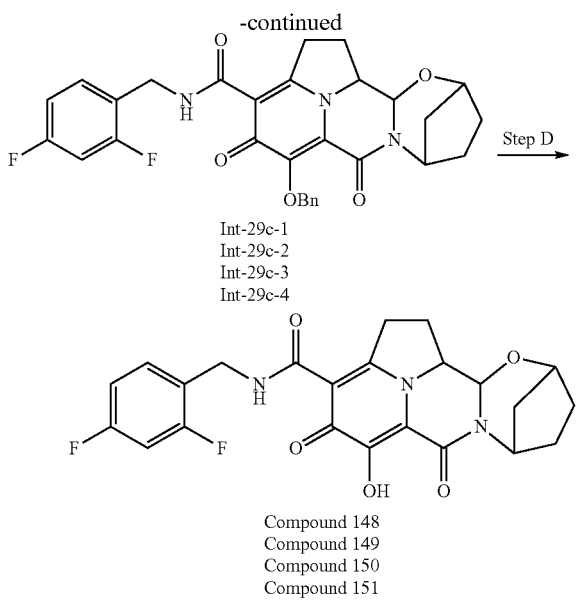

Int-29c-1
Int-29c-2
Int-29c-3
Int-29c-4

Step D

Compound 148
Compound 149
Compound 150
Compound 151

Step A—Synthesis of Compound Int-29a

To a solution of compound Int-2j (1.0 g, 3.06 mmol) in THF (15 mL) was added 3-aminocyclopentanol (0.927 g, 9.17 mmol) and AcOH (0.3 mL). The mixture was stirred at 80° C. for 4 h. The solvent was removed under vacuum, the residue was purified by a silica gel column eluting with 5% MeOH/dichloromethane to afford compound Int-29a. MS (M+H)$^+$: 379.1

Step B—Synthesis of Compound Int-29b

To a solution of compound Int-29a (700 mg, 1.850 mmol) in MeOH (15 mL) was added N-iodosuccinimide (832 mg, 3.70 mmol), m-CPBA (798 mg, 3.70 mmol) at 70° C. The mixture was stirred for 2 h at 70° C. It was quenched with aqueous Na$_2$SO$_3$ (3 mL), and then concentrated in vacuum. The residue was purified by a silica gel column eluting with 10% MeOH/dichloromethane to afford compound Int-29b. $^1$H NMR (400 MHz, CDCl$_3$): δ 7.69 (d, J=7.06 Hz, 2H), 7.29-7.38 (m, 3H), 5.31-5.43 (m, 2H), 5.08-5.24 (m, 2H), 4.92-5.02 (m, 1H), 4.54-4.64 (m, 1H), 4.28 (dd, J=15.99, 9.59 Hz, 1H), 2.97-3.26 (m, 2H), 2.97-2.99 (m, 1H), 2.46-2.60 (m, 1H), 2.28-2.42 (m, 1H), 2.00-2.09 (m, 2H), 1.75-1.88 (m, 1H), 1.47-1.60 (m, 1H). MS (M+H)$^+$: 505.1

Step C—Synthesis of Compound Int-29c-1 to Compound Int-29c-4

To a solution of compound Int-29b (200 mg, 0.397 mmol) in DMSO (5 mL) was added diisopropylethylamine (0.346 mL, 1.983 mmol), Pd(Ph$_3$P)$_4$ (92 mg, 0.079 mmol) and (2,4-difluorophenyl)methanamine (114 mg, 0.793 mmol). The mixture was stirred at 80° C. for 1 h under carbon monoxide (1 atm). The mixture was filtered and the filtrate was acidified with aqueous HCl (5 mL, 2 M), and then extracted with EtOAc (15 mL×2). The combined organic layer was washed with brine (10 mL), dried over Na$_2$SO$_4$, filtered and concentrated under vacuum. The residue was purified by a silica gel column eluting with 6% MeOH/dichloromethane to give the desired product was a mixture of stereoisomers. MS (M+H)$^+$: 548.2. This material was further separated by SFC ("Column: AD (250 mm*30 mm, 10 μm) Mobile phase: 45% Base-IPA (contained 0.1% NH$_3$.H$_2$O) in CO$_2$; Flow rate: 80 mL/min; Wavelength: 220 nm") to afford compound Int-29c-1 (the first eluting isomer), compound Int-29c-2 (the second eluting isomer), compound Int-29c-3 (the third eluting isomer), and compound Int-29c-4 (the fourth eluting isomer).

Compound Int-29c-1: $^1$H NMR (400 MHZ, CDCl$_3$): δ 10.90 (br t, J=5.51 Hz, 1H), 7.63 (d, J=6.84 Hz, 2H), 7.28-7.39 (m, 4H), 6.74-6.86 (m, 2H), 5.15-5.33 (m, 4H), 4.56-4.64 (m, 3H), 4.36 (ddd, J=11.14, 7.17, 3.53 Hz, 1H), 3.99-4.13 (m, 1H), 3.27-3.39 (m, 1H), 2.07-2.39 (m, 4H), 1.95-2.01 (m, 2H), 1.83 (br s, 1H), 1.39 (br d, J=12.57 Hz, 1H).

Compound Int-29c-2: $^1$H NMR (400 MHz, CDCl$_3$): δ 10.91 (br t, J=5.73 Hz, 1H), 10.77-11.04 (m, 1H), 7.63 (d, J=7.06 Hz, 2H), 7.28-7.40 (m, 4H), 6.74-6.87 (m, 2H), 5.16-5.33 (m, 4H), 4.56-4.67 (m, 3H), 4.36 (ddd, J=11.03, 7.28, 3.53 Hz, 1H), 4.08 (dd, J=19.40, 8.82 Hz, 1H), 3.27-3.41 (m, 1H), 2.04-2.42 (m, 4H), 1.99 (br d, J=11.03 Hz, 1H), 1.82 (br d, J=13.01 Hz, 1H), 1.36-1.45 (m, 1H).

Compound Int-29c-3: $^1$H NMR (400 MHz, CDCl$_3$): δ 10.88 (br t, J=5.73 Hz, 1H), 7.62 (d, J=7.06 Hz, 2H), 7.27-7.41 (m, 4H), 6.75-6.85 (m, 2H), 5.36 (br s, 1H), 5.25-5.31 (m, 1H), 5.17 (d, J=9.70 Hz, 1H), 4.90 (d, J=8.60 Hz, 1H), 4.55-4.64 (m, 3H), 4.01-4.18 (m, 2H), 3.35 (dt, J=19.46, 9.78 Hz, 1H), 2.50-2.64 (m, 1H), 1.95-2.03 (m, 4H), 1.75 (br d, J=10.14 Hz, 1H), 1.56 (br dd, J=12.24, 3.42 Hz, 1H).

Compound Int-29c-4: $^1$H NMR (400 MHz, CDCl$_3$): δ 10.88 (br t, J=5.40 Hz, 1H), 7.63 (d, J=6.84 Hz, 2H), 7.27-7.42 (m, 4H), 6.71-6.88 (m, 2H), 5.36 (br s, 1H), 5.29 (d, J=9.92 Hz, 1H), 5.17 (d, J=9.70 Hz, 1H), 4.90 (d, J=8.60 Hz, 1H), 4.61 (br s, 3H), 4.05-4.20 (m, 2H), 3.26-3.40 (m, 1H), 2.48-2.65 (m, 1H), 1.92-2.02 (m, 4H), 1.76 (br d, J=10.58 Hz, 2H), 1.51-1.59 (m, 1H).

Step D—Synthesis of Compound 148

To a solution of compound Int-29c-1 (20 mg, 0.037 mmol) in acetonitrile (2 mL) was added magnesium bromide (13.45 mg, 0.073 mmol) at 20° C. The mixture was stirred at 20° C. for 3 h. The reaction mixture was filtered and the filtrate was purified using preparative reverse phase HPLC (Column Boston Green ODS 150 mm*30 mm, 5 μm Condition water (0.1% TFA)-MeCN Begin B 35 End B 65 Gradient Time (min) 8 100% B Hold Time (min) 2 Flow Rate (mL/min) 30 Injections 4) to afford compound 148. $^1$H NMR (400 MHz, CD$_3$OD): δ 7.36-7.48 (m, 1H), 6.85-7.04 (m, 2H), 5.59 (d, J=3.97 Hz, 1H), 5.13 (br s, 1H), 4.54-4.68 (m, 4H), 3.81-3.98 (m, 1H), 3.33-3.39 (m, 1H), 2.02-2.38 (m, 6H), 1.89 (br d, J=12.35 Hz, 1H), 1.55 (br d, J=12.57 Hz, 1H). MS (M+H)$^+$: 458.0

The following compounds of the present invention were made using the methodology described in Step D of Example 29, and substituting the appropriate reactants.

Compound 149 (from compound Int-29c-2): $^1$H NMR (400 MHz, CD$_3$OD): δ 7.39-7.48 (m, 1H), 6.86-7.02 (m, 2H), 5.58 (d, J=3.97 Hz, 1H), 5.12 (br s, 1H), 4.56-4.67 (m, 4H), 3.83-3.94 (m, 1H), 3.32-3.38 (m, 1H), 2.00-2.36 (m, 6H), 1.88 (br d, J=12.57 Hz, 1H), 1.49-1.57 (m, 1H). MS (M+H)$^+$: 458.0.

Compound 150 (from compound Int-29c-3): $^1$H NMR (400 MHz, CD$_3$OD): δ 7.35-7.51 (m, 1H), 6.87-7.04 (m, 2H), 5.21-5.29 (m, 2H), 4.54-4.70 (m, 3H), 4.26-4.38 (m, 1H), 3.90 (dd, J=18.85, 9.15 Hz, 1H), 3.34 (br s, 1H), 2.48-2.61 (m, 1H), 1.92-2.16 (m, 6H), 1.67 (dt, J=11.85, 3.67 Hz, 1H). MS (M+H)$^+$: 458.0

Compound 151 (from compound Int-29c-4): $^1$H NMR (400 MHz, CD$_3$OD): δ 7.34-7.51 (m, 1H), 6.86-7.03 (m, 2H), 5.20-5.31 (m, 2H), 4.65 (br s, 1H), 4.58 (s, 2H), 4.26-4.40 (m, 1H), 3.92 (dd, J=18.96, 8.82 Hz, 1H), 2.50-2.61 (m, 1H), 1.87-2.16 (m, 7H), 1.66 (br d, J=12.13 Hz, 1H). MS (M+H)$^+$: 458.0

Example 30

Preparation of Compounds 152-171

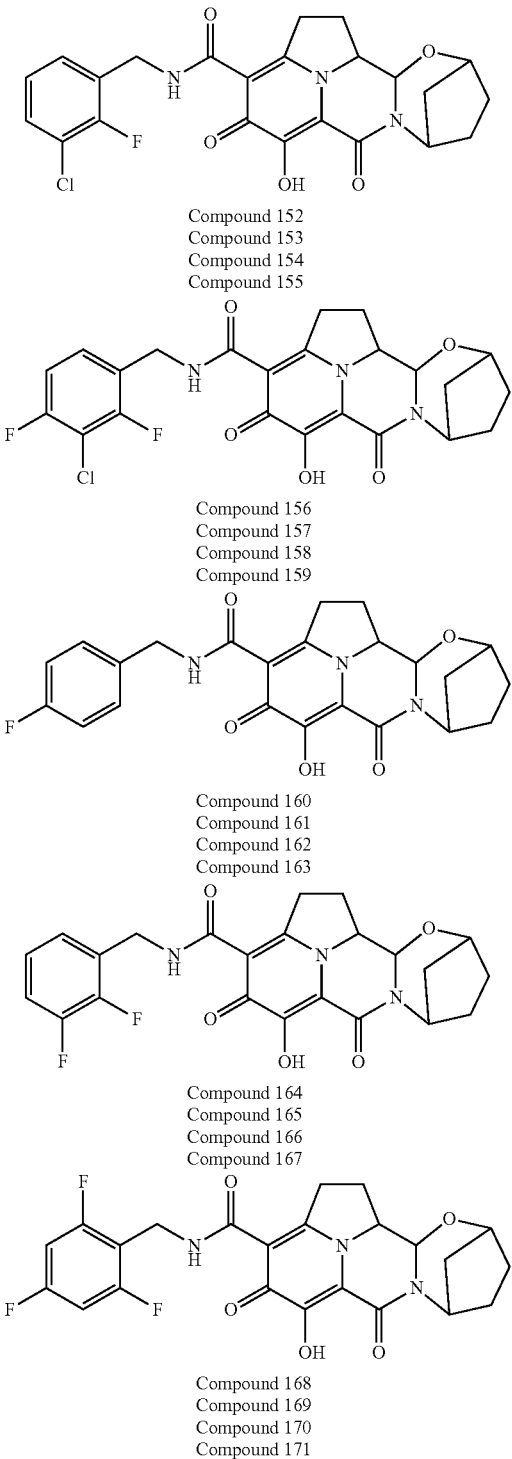

Compound 152
Compound 153
Compound 154
Compound 155

Compound 156
Compound 157
Compound 158
Compound 159

Compound 160
Compound 161
Compound 162
Compound 163

Compound 164
Compound 165
Compound 166
Compound 167

Compound 168
Compound 169
Compound 170
Compound 171

The following compounds of the present invention were made from compound Int-29b using the methodology described in Step C and Step D of Example 29, and substituting the appropriate reactants and/or reagents.

Compound 152: $^1$H NMR (400 MHz, CDCl$_3$): δ 10.84 (br s, 1H), 7.26-7.30 (m, 2H), 7.02 (t, J=7.83 Hz, 1H), 5.30 (s, 1H), 5.03 (d, J=8.60 Hz, 1H), 4.68 (br s, 3H), 4.02-4.22 (m, 2H), 3.30-3.43 (m, 1H), 2.54-2.64 (m, 1H), 1.87-2.16 (m, 6H), 1.56-1.65 (m, 1H). MS (M+H)$^+$: 474.1

Compound 153: $^1$H NMR (400 MHz, CDCl$_3$): δ 10.84 (br s, 1H), 7.26-7.33 (m, 2H), 6.98-7.06 (m, 1H), 5.30 (s, 1H), 5.04 (d, J=8.60 Hz, 1H), 4.68 (br s, 3H), 4.01-4.21 (m, 2H), 3.29-3.42 (m, 1H), 2.51-2.66 (m, 1H), 1.87-2.14 (m, 6H), 1.54-1.67 (m, 1H). MS (M+H)$^+$: 474.1

Compound 154: $^1$H NMR (400 MHz, CDCl$_3$): δ 10.90 (br s, 1H), 7.26-7.30 (m, 2H), 7.02 (t, J=7.72 Hz, 1H), 5.34 (d, J=3.97 Hz, 1H), 5.17 (br s, 1H), 4.67 (br s, 3H), 4.33-4.47 (m, 1H), 4.07 (br dd, J=18.96, 9.26 Hz, 1H), 3.38 (dt, J=19.90, 9.78 Hz, 1H), 2.01-2.44 (m, 6H), 1.94 (br d, J=12.35 Hz, 1H), 1.49 (br d, J=12.79 Hz, 1H). MS (M+H)$^+$: 474.1

Compound 155: $^1$H NMR (400 MHz, CDCl$_3$): δ 10.91 (br s, 1H), 7.26-7.31 (m, 2H), 7.02 (t, J=7.94 Hz, 1H), 5.34 (d, J=3.97 Hz, 1H), 5.17 (br s, 1H), 4.67 (br s, 3H), 4.40 (dt, J=7.33, 3.72 Hz, 1H), 4.07 (br dd, J=19.18, 8.82 Hz, 1H), 3.26-3.46 (m, 1H), 2.01-2.44 (m, 6H), 1.94 (br d, J=12.57 Hz, 1H), 1.49 (br d, J=12.79 Hz, 1H). MS (M+H)$^+$: 474.1

Compound 156: $^1$H NMR (400 MHz, CDCl$_3$): δ 10.84 (br s, 1H), 7.26-7.30 (m, 1H), 6.88-6.96 (m, 1H), 5.30 (s, 1H), 5.04 (d, J=8.82 Hz, 1H), 4.56-4.73 (m, 3H), 3.97-4.24 (m, 2H), 3.24-3.40 (m, 1H), 2.52-2.66 (m, 1H), 1.84-2.15 (m, 6H), 1.54-1.65 (m, 1H). MS (M+H)$^+$: 492.1

Compound 157: $^1$H NMR (400 MHz, CDCl$_3$): δ 10.86 (br s, 1H), 7.30 (s, 1H), 6.91 (t, J=8.38 Hz, 1H), 5.30 (br d, J=3.53 Hz, 1H), 4.97-5.05 (m, 1H), 4.60-4.72 (m, 3H), 4.00-4.24 (m, 2H), 3.28-3.41 (m, 1H), 2.56-2.66 (m, 1H), 1.86-2.09 (m, 6H), 1.61 (br d, J=11.03 Hz, 1H). MS (M+H)$^+$: 492.1

Compound 158: $^1$H NMR (400 MHz, CDCl$_3$): δ 10.82-11.03 (m, 1H), 7.29 (br s, 1H), 6.91 (td, J=8.54, 1.65 Hz, 1H), 5.29-5.40 (m, 1H), 5.17 (br d, J=3.53 Hz, 1H), 4.62-4.69 (m, 3H), 4.37-4.44 (m, 1H), 3.99-4.11 (m, 1H), 3.33-3.41 (m, 1H), 2.27-2.41 (m, 2H), 2.13-2.23 (m, 2H), 2.00-2.09 (m, 2H), 1.95 (br d, J=12.35 Hz, 1H), 1.49 (dt, J=12.35, 2.87 Hz, 1H). MS (M+H)$^+$: 482.1

Compound 159: $^1$H NMR (400 MHz, CDCl$_3$): δ 10.82-10.92 (m, 1H), 7.26-7.30 (m, 1H), 6.92 (td, J=8.49, 1.76 Hz, 1H), 5.34 (d, J=3.75 Hz, 1H), 5.17 (br d, J=3.09 Hz, 1H), 4.65 (br d, J=13.89 Hz, 3H), 4.42 (ddd, J=10.97, 7.00, 3.86 Hz, 1H), 4.05 (dd, J=19.29, 8.93 Hz, 1H), 3.37 (dt, J=19.51, 9.65 Hz, 1H), 2.28-2.43 (m, 2H), 2.13-2.26 (m, 2H), 1.99-2.10 (m, 2H), 1.94 (br d, J=12.57 Hz, 1H), 1.49 (dt, J=12.73, 2.89 Hz, 1H). MS (M+H)$^+$: 492.1

Compound 160: $^1$H NMR (400 MHz, CDCl$_3$) δ: 10.86 (s, 1H), 7.29 (dd, J=8.3, 5.4 Hz, 2H), 6.97 (s, 2H), 5.31 (d, J=3.9 Hz, 1H), 5.15 (s, 1H), 4.64 (s, 1H), 4.55 (s, 2H), 4.34-4.42 (m, 1H), 4.06 (dd, J=18.6, 9.0 Hz, 1H), 3.31-3.41 (m, 1H), 2.24-2.35 (m, 2H), 2.13-2.22 (m, 2H), 2.04 (dd, J=10.6, 3.7 Hz, 2H), 1.93 (d, J=12.9 Hz, 1H), 1.43-1.50 (m, 1H). MS (M+H)$^+$: 440.0

Compound 161: $^1$H NMR (400 MHz, CDCl$_3$) δ: 10.86 (s, 1H), 7.29-7.31 (m, 2H), 6.97 (m, 2H), 5.31 (d, J=3.7 Hz, 1H), 5.15 (s, 1H), 4.64 (s, 1H), 4.51-4.58 (m, 2H), 4.36-4.37 (m, 1H), 3.96-4.12 (m, 1H), 3.36 (m, 1H), 2.26-2.40 (m, 2H), 2.12-2.23 (m, 2H), 2.00-2.11 (m, 2H), 1.91-1.93 (m 1H), 1.43-1.58 (m, 1H). MS (M+H)$^+$: 440.0

Compound 162: $^1$H NMR (400 MHz, CDCl$_3$) δ: 10.72-10.98 (m, 1H), 7.30 (dd, J=8.6, 5.5 Hz, 2H), 6.92-7.04 (m, 2H), 5.28 (s, 1H), 5.01 (d, J=8.6 Hz, 1H), 4.67 (br s, 1H), 4.55 (d, J=3.7 Hz, 2H), 4.03-4.21 (m, 2H), 3.30-3.42 (m, 1H), 2.54-2.61 (m, 1H), 1.96-2.13 (m, 5H), 1.82 (s, 1H), 1.54-1.64 (m, 1H). MS (M+H)$^+$: 440.0

Compound 163: $^1$H NMR (400 MHz, CDCl$_3$) δ: 10.84 (s, 1H), 7.30 (dd, J=8.6, 5.5 Hz, 2H), 6.98 (t, J=8.8 Hz, 2H), 5.28 (s, 1H), 5.02 (d, J=8.6 Hz, 1H), 4.67 (s, 1H), 4.49-4.59 (m, 2H), 4.11-4.20 (m, 1H), 4.06 (dd, J=19.0, 9.2 Hz, 1H), 3.34 (m, 1H), 2.53-2.61 (m, 1H), 1.94-2.12 (m, 5H), 1.82-1.91 (m, 1H), 1.55-1.63 (m, 1H), MS (M+H)$^+$: 440.0

Compound 164: $^1$H NMR (400 MHz, CDCl$_3$): δ 10.84 (br s, 1H), 7.14 (br t, J=6.39 Hz, 1H), 6.97-7.08 (m, 2H), 5.30 (s, 1H), 5.03 (d, J=8.60 Hz, 1H), 4.68 (br s, 3H), 4.02-4.22 (m, 2H), 3.28-3.43 (m, 1H), 2.54-2.65 (m, 1H), 2.07 (br d, J=1.54 Hz, 6H), 1.57-1.65 (m, 1H). MS (M+H)$^+$: 458.0

Compound 165: $^1$H NMR (400 MHz, CDCl$_3$): δ 10.84 (br s, 1H), 7.14 (br t, J=6.50 Hz, 1H), 6.97-7.07 (m, 2H), 5.30 (s, 1H), 5.03 (d, J=8.60 Hz, 1H), 4.68 (br s, 3H), 4.03-4.20 (m, 2H), 3.29-3.43 (m, 1H), 2.56-2.62 (m, 1H), 2.07 (br s, 6H) 1.57-1.63 (m, 1H). MS (M+H)$^+$: 458.0

Compound 166: $^1$H NMR (400 MHz, CDCl$_3$): δ 10.89 (br s, 1H), 7.10-7.17 (m, 1H), 7.01 (s, 2H), 5.33 (d, J=3.97 Hz, 1H), 5.18 (br s, 1H), 4.69 (br d, J=6.17 Hz, 3H), 4.38 (s, 1H), 4.08 (dd, J=18.41, 8.93 Hz, 1H), 3.30-3.45 (m, 1H), 1.94-2.42 (m, 7H), 1.49 (br d, J=12.57 Hz, 1H). MS (M+H)$^+$: 458.0

Compound 167: $^1$H NMR (400 MHz, CDCl$_3$): δ 10.89 (br s, 1H), 7.13 (br t, J=6.95 Hz, 1H), 6.97-7.07 (m, 2H), 5.33 (d, J=3.75 Hz, 1H), 5.18 (br s, 1H), 4.68 (br d, J=5.51 Hz, 3H), 4.39 (br s, 1H), 4.08 (br dd, J=19.29, 9.37 Hz, 1H), 3.28-3.46 (m, 1H), 2.29-2.39 (m, 1H), 2.14-2.22 (m, 3H), 2.03-2.08 (m, 2H), 1.95 (br d, J=11.47 Hz, 1H), 1.48 (br d, J=12.57 Hz, 1H). MS (M+H)$^+$: 458.0

Compound 168: $^1$H NMR (400 MHz, CDCl$_3$): δ 10.74 (br t, J=5.2 Hz, 1H), 6.59-6.67 (m, 2H), 5.28 (t, J=3.2 Hz, 1H), 5.02 (d, J=8.4 Hz, 1H), 4.54-4.65 (m, 3H), 4.04-4.17 (m, 2H), 3.35 (ddd, J=8.4, 10.8, 19.2 Hz, 1H), 2.54-2.61 (m, 1H), 1.89-2.09 (m, 6H), 1.58-1.62 (m, 1H). MS (M+H)$^+$: 476.1

Compound 169: $^1$H NMR (400 MHz, CDCl$_3$): δ 10.75 (br t, J=5.2 Hz, 1H), 6.59-6.67 (m, 2H), 5.28 (t, J=3.2 Hz, 1H), 5.02 (d, J=8.4 Hz, 1H), 4.54-4.65 (m, 3H), 4.04-4.17 (m, 2H), 3.35 (ddd, J=8.4, 10.8, 19.2 Hz, 1H), 2.54-2.61 (m, 1H), 1.89-2.09 (m, 6H), 1.58-1.62 (m, 1H). MS (M+H)$^+$: 476.1

Compound 170: $^1$H NMR (400 MHz, CDCl$_3$): δ 10.80 (br t, J=5.2 Hz, 1H), 6.62-6.67 (m, 2H), 5.31 (d, J=4.0 Hz, 1H), 5.16 (br t, J=3.2 Hz, 1H), 4.62-4.65 (m, 3H), 4.35-4.40 (m, 1H), 4.08 (br dd, J=8.4, 18.8 Hz, 1H), 3.38 (dt, J=9.6, 9.6, 19.4 Hz, 1H), 2.29-2.35 (m, 2H), 2.12-2.21 (m, 2H), 2.01-2.08 (m, 2H), 1.93 (br d, J=12.4 Hz, 1H), 1.47 (dt, J=12.4, 2.8 Hz, 1H). MS (M+H)$^+$: 476.1

Compound 171: $^1$H NMR (400 MHz, CDCl$_3$): δ 10.80 (br t, J=5.2 Hz, 1H), 6.62-6.67 (m, 2H), 5.31 (d, J=4.0 Hz, 1H), 5.16 (br t, J=3.2 Hz, 1H), 4.62-4.65 (m, 3H), 4.35-4.40 (m, 1H), 4.08 (br dd, J=8.4, 18.8 Hz, 1H), 3.38 (dt, J=9.6, 9.6, 19.4 Hz, 1H), 2.29-2.35 (m, 2H), 2.12-2.21 (m, 2H), 2.01-2.08 (m, 2H), 1.93 (br d, J=12.4 Hz, 1H), 1.47 (dt, J=12.4, 2.8 Hz, 1H). MS (M+H)$^+$: 476.1

Example 31

Preparation of Compound Int-29-Cis-A/B and Compound Int-29-Trans-A/B

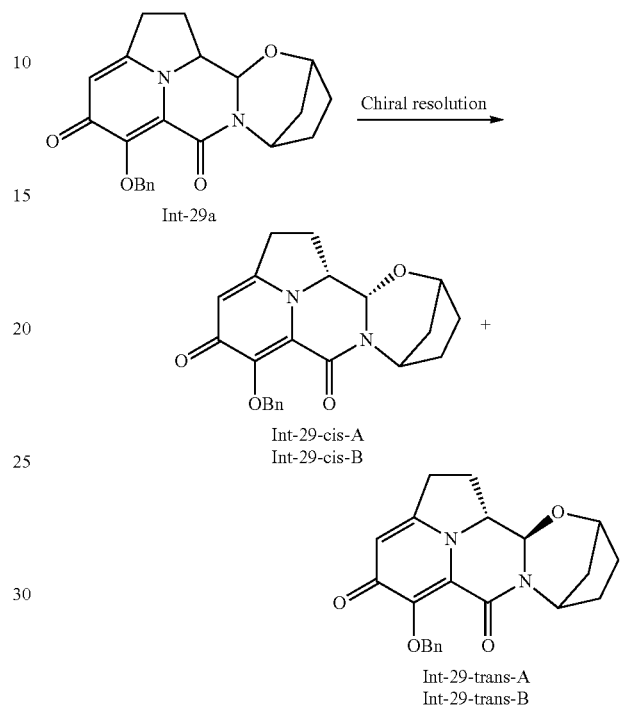

Chiral separation of each individual stereoisomer was accomplished with SFC (Column: OD (250 mm*50 mm, 10 μm) Mobile phase: 40% Base-EtOH (contained 0.1% NH$_3$H$_2$O) in CO$_2$ Flow rate: 200 mL/min Wavelength: 220 nm) to give compound Int-29-cis-A (first eluted peak), compound Int-29-cis-B (the second eluted peak), compound Int-29-trans-A (the third eluted peak), and Int-29-trans-B (the fourth eluted peak).

Compound Int-29-cis-A: $^1$H NMR (400 MHz, CDCl$_3$): δ 7.57 (d, J=7.2 Hz, 2H), 7.22-7.28 (m, 3H), 6.38 (s, 1H), 5.23-5.31 (m, 2H), 5.04-5.12 (m, 2H), 4.51 (s, 1H), 4.24-4.29 (m, 1H), 2.89-2.98 (m, 2H), 2.28 (m, 1H), 1.89-2.10 (m, 6H), 1.73 (m, 1H).

Compound Int-29-cis-B: $^1$H NMR (400 MHz, CDCl$_3$): δ 7.57 (d, J=7.2 Hz, 2H), 7.22-7.28 (m, 3H), 6.37 (s, 1H), 5.25-5.32 (m, 2H), 5.09-5.12 (m, 2H), 4.51 (s, 1H), 4.23-4.27 (m, 1H), 2.89-2.99 (m, 2H), 2.28 (m, 1H), 1.89-2.10 (m, 6H), 1.74 (m, 1H).

Compound Int-29-trans-A: $^1$H NMR (400 MHz, CDCl$_3$): δ 7.64 (d, J=6.8 Hz, 2H), 7.27-7.35 (m, 3H), 6.41 (s, 1H), 5.38-5.40 (m, 2H), 5.22-5.25 (m, 1H), 4.88 (d, J=8.0 Hz, 1H), 4.60 (s, 1H), 4.09-4.14 (m, 1H), 3.01-3.07 (m, 2H), 2.51-2.54 (m, 1H), 1.98-2.06 (m, 5H), 1.74-1.76 (m, 1H), 1.53-1.57 (m, 1H).

Compound Int-29-trans-B: $^1$H NMR (400 MHz, CDCl$_3$): δ 7.64 (d, J=6.8 Hz, 2H), 7.27-7.35 (m, 3H), 6.41 (s, 1H), 5.38-5.40 (m, 2H), 5.22-5.25 (m, 1H), 4.88 (d, J=8.0 Hz, 1H), 4.60 (s, 1H), 4.09-4.14 (m, 1H), 3.01-3.07 (m, 2H), 2.51-2.54 (m, 1H), 1.98-2.06 (m, 5H), 1.74-1.76 (m, 1H), 1.53-1.57 (m, 1H).

Example 32

Preparation of Compound 172 and Compound 173

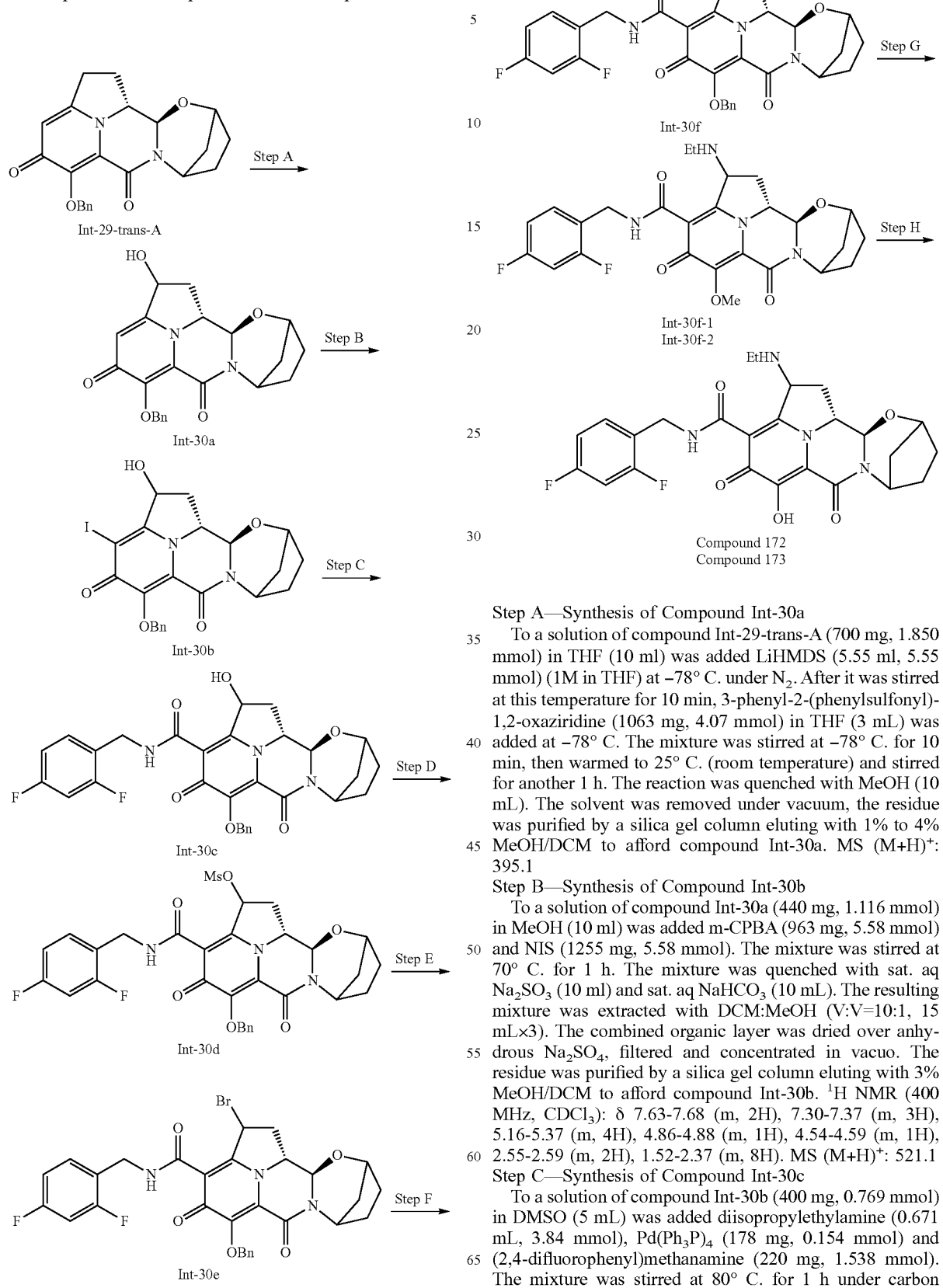

Step A—Synthesis of Compound Int-30a

To a solution of compound Int-29-trans-A (700 mg, 1.850 mmol) in THF (10 ml) was added LiHMDS (5.55 ml, 5.55 mmol) (1M in THF) at −78° C. under $N_2$. After it was stirred at this temperature for 10 min, 3-phenyl-2-(phenylsulfonyl)-1,2-oxaziridine (1063 mg, 4.07 mmol) in THF (3 mL) was added at −78° C. The mixture was stirred at −78° C. for 10 min, then warmed to 25° C. (room temperature) and stirred for another 1 h. The reaction was quenched with MeOH (10 mL). The solvent was removed under vacuum, the residue was purified by a silica gel column eluting with 1% to 4% MeOH/DCM to afford compound Int-30a. MS $(M+H)^+$: 395.1

Step B—Synthesis of Compound Int-30b

To a solution of compound Int-30a (440 mg, 1.116 mmol) in MeOH (10 ml) was added m-CPBA (963 mg, 5.58 mmol) and NIS (1255 mg, 5.58 mmol). The mixture was stirred at 70° C. for 1 h. The mixture was quenched with sat. aq $Na_2SO_3$ (10 ml) and sat. aq $NaHCO_3$ (10 mL). The resulting mixture was extracted with DCM:MeOH (V:V=10:1, 15 mL×3). The combined organic layer was dried over anhydrous $Na_2SO_4$, filtered and concentrated in vacuo. The residue was purified by a silica gel column eluting with 3% MeOH/DCM to afford compound Int-30b. $^1$H NMR (400 MHz, $CDCl_3$): δ 7.63-7.68 (m, 2H), 7.30-7.37 (m, 3H), 5.16-5.37 (m, 4H), 4.86-4.88 (m, 1H), 4.54-4.59 (m, 1H), 2.55-2.59 (m, 2H), 1.52-2.37 (m, 8H). MS $(M+H)^+$: 521.1

Step C—Synthesis of Compound Int-30c

To a solution of compound Int-30b (400 mg, 0.769 mmol) in DMSO (5 mL) was added diisopropylethylamine (0.671 mL, 3.84 mmol), $Pd(Ph_3P)_4$ (178 mg, 0.154 mmol) and (2,4-difluorophenyl)methanamine (220 mg, 1.538 mmol). The mixture was stirred at 80° C. for 1 h under carbon monoxide (1 atm). The mixture was filtered and diluted with 20 mL of EtOAc. The organic layer was washed with 0.5 M HCl (aq.) (10 mL×2) and brine (10 mL), dried over anhydrous $Na_2SO_4$, filtered and evaporated to dryness. The residue was purified by preparative-TLC (DCM:EtOAc=2:1) to afford compound Int-30c. MS $(M+H)^+$: 564.2

Step D—Synthesis of Compound Int-30d

To an ice-cooled solution of compound Int-30c (200 mg, 0.355 mmol) and $Et_3N$ (0.495 ml, 3.55 mmol) in DCM (3 mL), was added MsCl (0.138 mL, 1.774 mmol). The mixture was stirred at 0° C. for 30 min and then at 25 C for another 30 min. It was quenched by adding 10 mL of water, and the resulting mixture was extracted with DCM (10 mL×3). The combined organic layers were dried over $Na_2SO_4$, filtered, and the filtrate was concentrated under vacuum. The residue was purified by a preparative TLC (DCM:EtOAc=3:1) to give compound Int-30d. $^1$H NMR (400 MHz, $CDCl_3$): δ 10.46-10.85 (m, 1H), 7.62 (d, J=6.4 Hz, 2H), 7.31-7.38 (m, 3H), 7.05 (d, J=5.2 Hz, 1H), 6.81-6.83 (m, 2H), 5.21-5.37 (m, 3H), 4.43-4.86 (m, 4H), 3.02-3.18 (m, 4H), 2.24 (m, 1H), 2.00 (m, 3H), 1.24-1.75 (m, 5H). MS $(M+H)^+$: 642.1

Step E—Synthesis of Compound Int-30e

The mixture of compound Int-30d (200 mg, 0.312 mmol) and sodium bromide (321 mg, 3.12 mmol) in DMF (3 mL) was heated to 50° C. for 1 h. To the reaction mixture was added 10 mL of water. The resulting mixture was extracted with EtOAc (3×10 mL). The combined organic layers were washed with brine (3×10 mL), dried over anhydrous $Na_2SO_4$, filtered and evaporated to dryness. The residue was purified by preparative TLC (DCM:EtOAc=3:1) to give compound int-30e. MS $(M+H)^+$: 626.1

Step F—Synthesis of Compound Int-30f

In a sealed tube, a mixture of ethanamine (0.276 mL, 1.796 mmol, 6.5M in EtOH) and compound Int-30e (150 mg, 0.239 mmol) in EtOH (20 mL) was heated at 80° C. for 2 h and 85° C. for another 30 min. The solvent was removed under vacuum, the residue was purified by a preparative TLC (EtOAc:MeOH=15:1) to give compound int-30f. MS $(M+H)^+$: 591.2

Step G—Synthesis of Compound Int-30f-1 and Compound Int-30f-2

A mixture of compound Int-30f (38 mg, 0.064 mmol) and potassium carbonate (133 mg, 0.965 mmol) in MeOH (3 mL) was heated to 50° C. for 10 h. The reaction solution was filtered, the filtrate was concentrated under vacuum. The residue was purified by SFC ("Column: AS (250 mm*30 mm, 5 μm) Mobile phase: 25% Base-MeOH (contained 0.1% $NH_3H_2O$) in $CO_2$ Flow rate: 60 mL/min Wavelength: 220 nm") to give Compound Int-30f-1 (the first eluting peak) and Compound Int-30f-2 (the second eluting peak).

Compound Int-30f-1: $^1$H NMR (400 MHz, $CDCl_3$): δ 10.94 (m, 1H), 7.31-7.37 (m, 1H), 6.77-6.84 (m, 2H), 5.37 (m, 1H), 5.09 (d, J=7.2 Hz, 1H), 4.91 (d, J=8.4 Hz, 1H), 4.44-4.66 (m, 4H), 4.00 (s, 3H), 2.71-2.73 (m, 1H), 2.58-2.63 (m, 2H), 1.97-2.03 (m, 5H), 1.78 (m, 2H), 1.13 (t, J=6.8 Hz, 3H). MS $(M+H)^+$: 515.2

Compound Int-30f-2: $^1$H NMR (400 MHz, $CDCl_3$): δ 10.97 (m, 1H), 7.31-7.37 (m, 1H), 6.77-6.84 (m, 2H), 5.37 (m, 1H), 4.96-5.06 (m, 2H), 4.59-4.65 (m, 3H), 4.01-4.07 (m, 4H), 2.80-2.83 (m, 1H), 2.55-2.57 (m, 2H), 1.99-2.10 (m, 7H), 1.07 (t, J=6.8 Hz, 3H). MS $(M+H)^+$: 515.2

Step H—Synthesis of Compound 172 and Compound 173

A mixture of Compound Int-30f-1 (3 mg, 5.83 μmol) and magnesium bromide (10.74 mg, 0.058 mmol) in acetonitrile (1 mL) was stirred at 25° C. for 1 h. The mixture was purified using Gilson reverse phase column eluting with MeCN/0.1% TFA in water (20 to 50%) to afford compound 172. $^1$H NMR (400 MHz, $CDCl_3$): δ 11.54 (m, 1H), 10.37 (br, 1H), 7.32-7.38 (m, 1H), 6.83-6.90 (m, 2H), 5.29-5.43 (m, 2H), 4.99 (m, 1H), 4.60-4.67 (m, 3H), 4.19-4.21 (m, 1H), 3.40 (m, 1H), 2.94-3.11 (m, 3H), 2.15 (m, 1H), 1.95-2.06 (m, 4H), 1.60-1.62 (m, 2H), 1.50 (t, J=7.6 Hz, 3H). MS $(M+H)^+$: 501.0

Compound 173 was prepared from compound Int-30f-2 using similar procedure. $^1$H NMR (400 MHz, $CDCl_3$): δ 11.04 (m, 1H), 7.33-7.36 (m, 1H), 6.84-6.91 (m, 2H), 5.29 (m, 1H), 5.04-5.08 (m, 2H), 4.61-4.81 (m, 4H), 3.39 (m, 1H), 3.12-3.21 (m, 2H), 2.37-2.41 (m, 1H), 2.08-2.11 (m, 5H), 1.87 (m, 1H), 1.61-1.64 (m, 1H), 1.46 (t, J=7.2 Hz, 3H). MS $(M+H)^+$: 501.0

The following compounds of the present invention were made using the methodology described in Example 32, and substituting the appropriate reactants and/or reagents.

| Compound | Structure | derived from | Exact Mass $[M + H]^+$ |
|---|---|---|---|
| 174 | (structure shown) | Int-29-trans-B | Calc'd 501.2, found 501.0 |
| 175 | (structure shown) | Int-29-trans-B | Calc'd 501.2, found 501.0 |

-continued

| Compound | Structure | derived from | Exact Mass [M + H]+ |
|---|---|---|---|
| 176 | 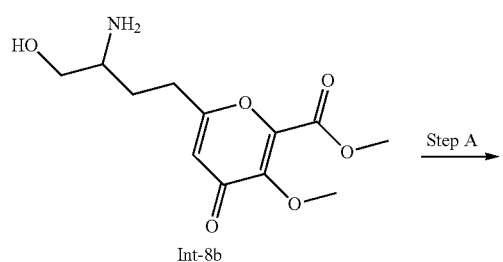 | Int-29-cis-A | Calc'd 501.2, found 501.1 |
| 177 | 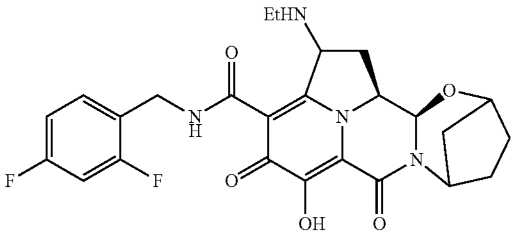 | Int-29-cis-B | Calc'd 501.2, found 501.1 |

| Compound | ¹H NMR |
|---|---|
| 174 | ¹H NMR (400 MHz, CDCl₃) δ 11.53 (m, 1H), 10.36 (m, 1H), 7.30-7.34 (m, 1H), 6.81-6.87 (m, 2H), 5.28-5.40 (m, 2H), 4.97 (m, 1H), 4.55-4.69 (m, 3H), 4.16-4.18 (m, 1H), 3.37 (m, 1H), 2.92-3.08 (m, 3H), 2.17-2.19 (m, 1H), 1.95-2.03 (m, 3H), 1.58-1.62 (m, 3H), 1.48 (t, J = 7.2 Hz, 3H). |
| 175 | ¹H NMR (400 MHz, CDCl₃) δ 11.09 (m, 1H), 7.32-7.34 (m, 1H), 6.81-6.85 (m, 2H), 5.28 (m, 1H), 5.07-5.09 (m, 1H), 4.96-4.98 (m, 1H), 4.79-4.81 (m, 1H), 4.70 (m, 1H), 4.60-4.62 (m, 2H), 3.37 (m, 1H), 3.13-3.21 (m, 2H), 2.32-2.35 (m, 1H), 2.07-2.10 (m, 4H), 1.79 (m, 1H), 1.65 (m, 2H), 1.44 (t, J = 7.2 Hz, 3H). |
| 176 | ¹H NMR (400 MHz, CDCl₃) δ 11.41 (m, 1H), 7.30-7.36 (m, 1H), 6.80-6.86 (m, 2H), 5.16-5.33 (m, 3H), 4.44-4.71 (m, 4H), 2.85-3.09 (m, 4H), 1.93-2.19 (m, 5H), 1.49 (d, J = 10.0 Hz, 1H), 1.33 (t, J = 7.2 Hz, 3H). |
| 177 | ¹H NMR (400 MHz, CDCl₃) δ 11.42 (m, 1H), 7.32 (m, 1H), 6.82-6.84 (m, 2H), 5.16-5.32 (m, 3H), 4.43-4.72 (m, 4H), 2.86-3.11 (m, 4H), 1.96-2.19 (m, 5H), 1.49 (d, J = 13.2 Hz, 1H), 1.33 (m, 3H). |

Example 33

Preparation of Compounds Int-31c-Cis-A/B and Int-31c-Trans-A/B

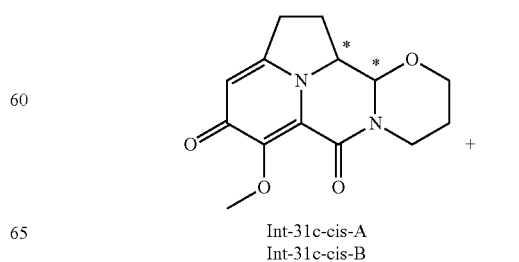

Int-8b

Step A

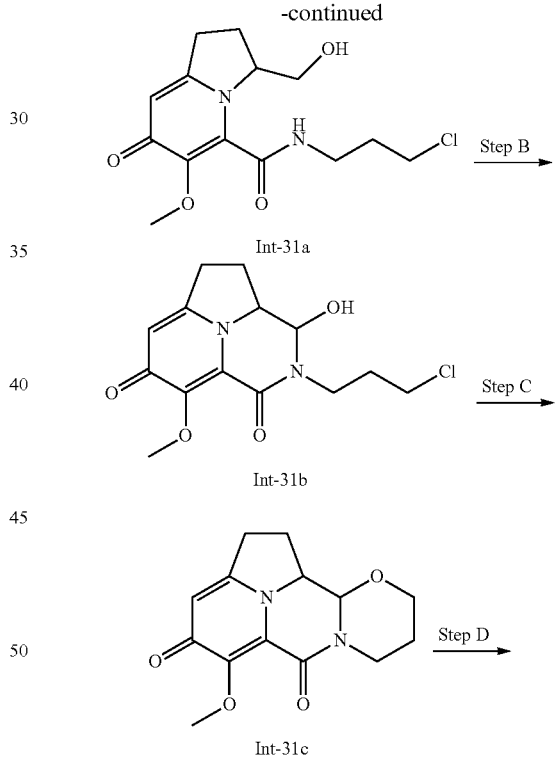

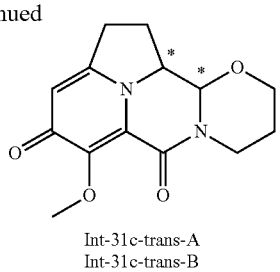

Int-31c-trans-A
Int-31c-trans-B

Step A—Synthesis of Compound Int-31a

A stirred solution of compound Int-8b (60 g, 221 mmol) in ethanol (600 mL) was stirred at 80° C. for 4 h. The solvent was removed under reduced pressure to give a crude residue, 20 g of which was dissolved in ethanol (300 mL). To the resulting solution, was added triethylamine (28 mL, 74.5 mmol) and 3-chloropropan-1-amine (13.95 g, 149 mmol). The mixture was stirred at 80° C. for 2 h. The solvent was removed under vacuum, the residue was purified by a silica gel column eluting with 10% MeOH/dichloromethane to afford compound Int-31a MS (M+H)$^+$: 315.0

Step B—Synthesis of Compound Int-31b

To a solution of oxalyl dichloride (33.4 mL, 381 mmol) in DCM (500 mL) stirred at −78° C., was added a solution of (methylsulfinyl)methane (44.0 mL, 620 mmol) in DCM (50 mL) dropwise under nitrogen atmosphere. After the addition was completed (about 20 min), the mixture was stirred at −78° C. for 30 min before a solution of compound Int-31a (30 g, 95 mmol) in DCM (50 mL) was added dropwise to the above mixture (about 20 min). The resulting mixture was stirred at −78° C. for another 1 h. The reaction mixture was quenched by addition of N-ethyl-N-isopropylpropan-2-amine (108 mL, 620 mmol) and the mixture was stirred at 20° C. for 0.5 h. The mixture was concentrated under vacuum and the residue was purified by preparative HPLC (Column: Phenomenex Synergi Max-RP 250 mm*80 mm*10 μm; Condition: water (0.1% TFA)-MeCN Begin B 30 End B 35; Gradient Time (min): 9; 100% B Hold Time (min): 4, FlowRate (ml/min): 150; Injections: 5) to afford compound Int-31b. $^1$H NMR (400 MHz, CD$_3$OD) δ 7.11 (s, 1H), 5.32 (s, 1H), 4.98-4.92 (m, 1H), 3.98-3.3.97 (m, 3H), 3.68-3.58 (m, 6H), 2.48-2.45 (m, 2H), 2.22-2.20 (m, 2H). MS (M+H)$^+$: 313.1

Step C—Synthesis of Compound Int-31c

To a solution of compound Int-31b (0.5 g, 1.599 mmol) in DMF (5 mL), was added sodium hydride (0.192 g, 4.80 mmol) at 0° C. The mixture was stirred at 0° C. for 2 h. The mixture was quenched with 1N HCl (1.5 mL). The solvent was removed under vacuum, the residue was purified with a silica gel column eluting with 10% MeOH/dichloromethane to afford compound Int-31c. MS (M+H)$^+$: 277.1

Step D—Synthesis of Compounds Int-31c-Cis-A/B and Int-31e-Trans-A/B

To a solution of compound Int-31c (13 g, 47.1 mmol) in THF (1300 mL) and MeOH (130 mL) was added trifluoromethanesulfonic acid (62.7 ml, 706 mmol) in dropwise at 20° C. The mixture was stirred at 80° C. for 6 h for effective isomerization. The reaction was cooled to room temperature, and basified with 2 N aqueous NaOH and saturated aqueous sodium dicarbonate to achieve pH=6. After majority of THF was evaporated, the mixture was purified by preparative HPLC (Column: Phenomenex Synergi Max-RP 250 mm*80 mm*10 μm; Condition: water (0.1% TFA)-ACN, Begin B 30 End B 35; Gradient Time (min): 9; 100% B Hold Time (min): 30; FlowRate (ml/min): 120; Injections: 120) to afford compound int-31c as a mixture of cis/trans isomers. MS (M+H)$^+$: 277.1. Chiral separation of each of the stereoisomers of this material was accomplished with SFC ("Column: AS (250 mm*50 mm, 10 μm); Mobile phase: Condition 0.1% NH$_3$H$_2$O MeOH Begin B 40% End B 40%; Flow rate: 200 mL/min") to give compound Int-31c-cis-A (the first eluting isomer), compound Int-31c-trans-A (the second eluting isomer), compound Int-31c-cis-B (the third eluting isomer), compound Int-31c-trans-B (the fourth eluting isomer).

Example 34

Preparation of Compound 178 and Compound 179

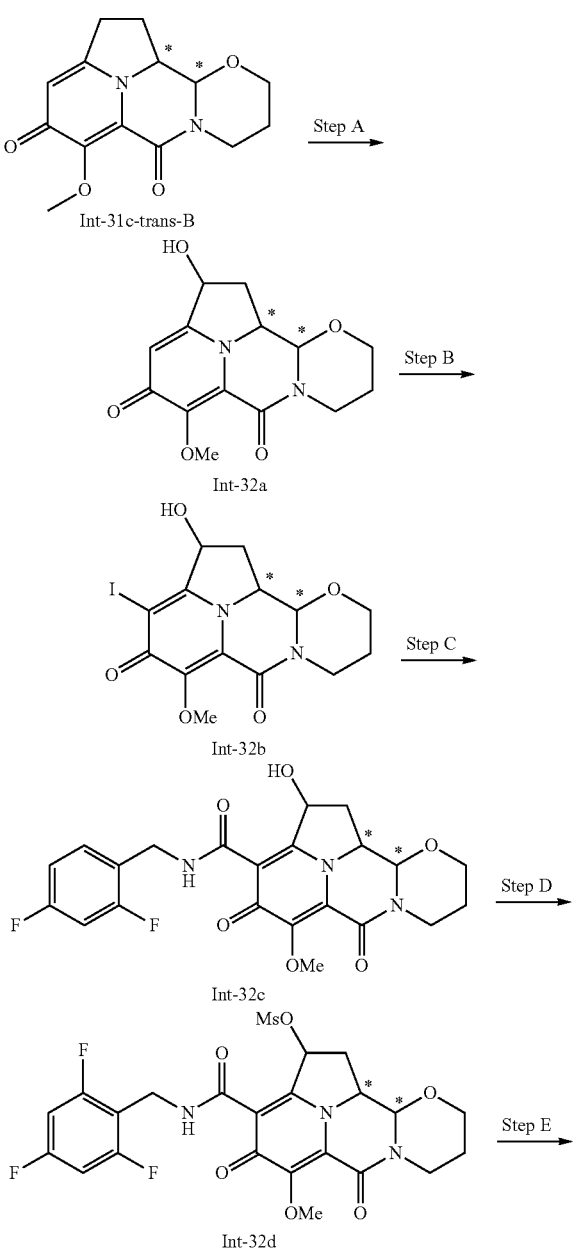

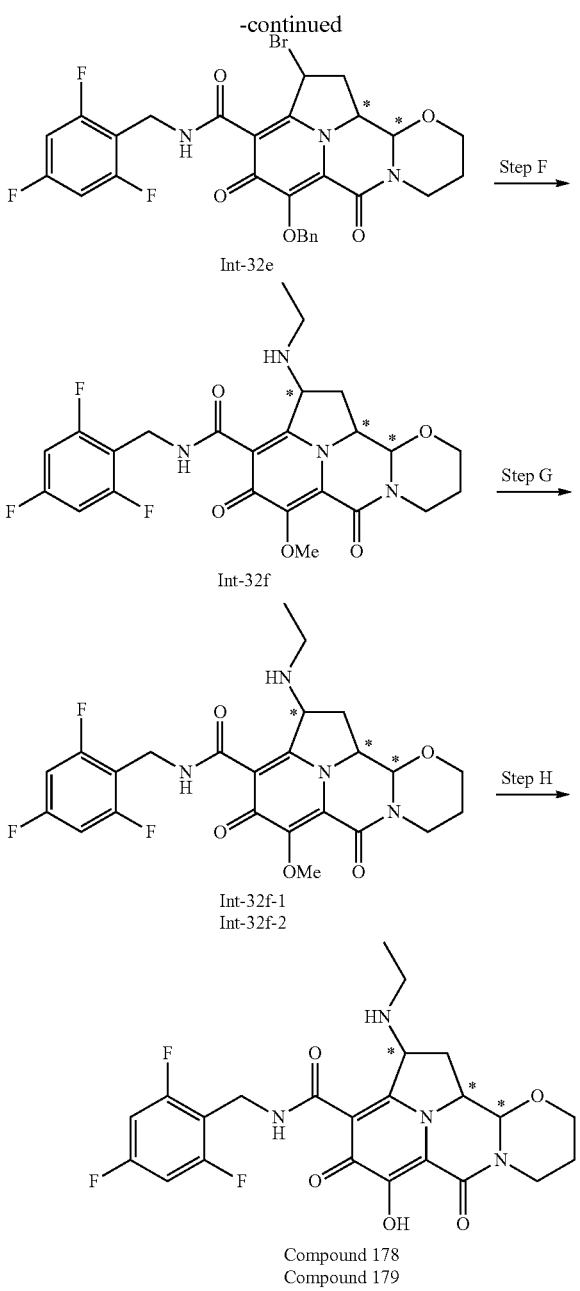

Int-32e

Int-32f

Int-32f-1
Int-32f-2

Compound 178
Compound 179

Step A—Synthesis of Compound Int-32a

To a solution of compound Int-31c-trans-B (1.5 g, 5.43 mmol) in THF (150 mL) was added a solution of 1 M lithium bis(trimethylsilyl)amide in THF (16.29 mL, 16.29 mmol) at −78° C. After stirring for 0.5 h, a solution of 3-phenyl-2-(phenylsulfonyl)-1,2-oxaziridine (3.12 g, 11.94 mmol) in THF (10 mL) was added at −78° C. The mixture was stirred at 20° C. for 12 min. The solvent was removed under vacuum, the residue was purified by a silica gel column eluting with 10% methanol/dichloromethane to afford compound Int-32a. $^1$H NMR (400 MHz, CD$_3$OD) δ 6.70-6.60 (m, 1H), 5.26-5.10 (m, 1H), 5.05-4.92 (m, 1H), 4.61-4.45 (m, 2H), 4.29-4.09 (m, 1H), 3.90-3.85 (d, J=4.39 Hz, 3H), 3.77-3.66 (m, 1H), 3.15-2.88 (m, 1H), 2.53-2.27 (m, 2H), 2.02-1.82 (m, 2H). MS (M+H)$^+$: 293.1

Step B—Synthesis of Compound Int-32b

To a solution of compound Int-32a (1.2 g, 4.11 mmol) in MeOH (15 mL) was added m-CPBA (1.328 g, 6.16 mmol) and NIS (1.847 g, 8.21 mmol). The mixture was stirred at 70° C. for 0.5 h. The reaction was quenched with sat. aq Na$_2$SO$_3$ (5 mL). The resulting mixture was adjusted to pH=7 with 10% aqueous NaHCO$_3$ and then extracted with DCM (50 mL×3). The organic phase was dried over anhydrous Na$_2$SO$_4$, filtered, and concentrated under vacuum. The residue was purified by a silica gel column eluting with 10% methanol in dichloromethane to afford compound Int-32b. $^1$H NMR (400 MHz, CD$_3$OD) δ 5.24-5.15 (m, 1H), 5.03-4.95 (m, 1H), 4.64 (d, J=9.3 Hz, 1H), 4.45 (br d, J=11.9 Hz, 1H), 4.25-4.03 (m, 1H), 3.82 (s, 3H), 3.74-3.62 (m, 1H), 3.10-2.95 (m, 1H), 2.51-2.31 (m, 2H), 2.06-1.87 (m, 1H), 1.83-1.74 (m, 1H). MS (M+H)$^+$: 419.0

Step C—Synthesis of Compound Int-32c

To a solution of compound Int-32b (60 mg, 0.143 mmol) in DMSO (2 mL) was added (2,4-difluorophenyl)methanamine (41.1 mg, 0.287 mmol), Pd(Ph$_3$P)$_4$ (33.2 mg, 0.029 mmol) and diisopropylethylamine (0.125 mL, 0.717 mmol). The mixture was stirred at 80° C. for 1 h under carbon monoxide (1 atm). The mixture was filtered and the filtrate was diluted with 15 mL of EtOAc. The resulting solution was washed with dilute HCl(aq.) (3 mL), dried over anhydrous Na$_2$SO$_4$, filtered, and concentrated under vacuum. The residue was purified by preparative TLC plate eluting with EtOAc to afford compound Int-32c. MS (M+H)$^+$: 462.1

Step D—Synthesis of Compound Int-32d

To a solution of compound Int-32c (160 mg, 0.334 mmol) in CH$_2$C$_{12}$ (3 mL) was added triethylamine (0.558 mL, 4.00 mmol) and MsCl (0.156 mL, 2.002 mmol) at 0° C. The mixture was stirred at 0° C. for 10 min. It was diluted with H$_2$O (5 mL), extracted with EtOAc (10 mL×3). The combined organic layer was washed with brine (3 mL). The solvent was removed under vacuum, the residue was purified using a silica gel column eluting with 5% MeOH/dichloromethane to afford compound Int-32d. MS (M+H)$^+$: 558.1

Step E—Synthesis of Compound Int-32e

To a mixture of compound Int-32d (134 mg, 0.240 mmol) in DMF (3 mL) was added sodium bromide (124 mg, 1.202 mmol). The mixture was stirred at 45° C. for 1 h. It was diluted with water (5 mL), extracted with EtOAc (5 mL×3), and the organic layers were concentrated to give crude compound Int-32e. This material was used in next step without further purification. MS (M+H)$^+$: 463.9.

Step F—Synthesis of Compound Int-32f

To a mixture of compound Int-32e (134 mg, 0.247 mmol) in EtOH (10 mL) was added ethylamine (0.353 mL, 2.471 mmol). The mixture was stirred in a sealed tube at 80° C. for 30 min. The solvent was removed under vacuum, the residue was purified by a silica gel column eluting with 10% MeOH/dichloromethane to give compound Int-32f. $^1$H NMR (400 MHz, CDCl$_3$) δ 11.10 (br s, 1H), 6.68 (t, J=8.0 Hz, 2H), 5.26-5.10 (m, 1H), 5.02 (t, J=8.4 Hz, 1H), 4.80-4.53 (m, 3H), 4.24-4.09 (m, 2H), 4.01 (s, 3H), 3.76-3.64 (m, 1H), 3.04 (dt, J=3.6, 13.1 Hz, 1H), 2.88 (td, J=8.4, 13.3 Hz, 1H), 2.77 (s, 2H), 2.11-1.93 (m, 2H), 1.82 (d, J=13.7 Hz, 1H), 1.34-1.22 (m, 3H). MS (M+H)$^+$: 507.2.

Step G—Synthesis of Compound Int-32f-1 and Compound Int-32f-2

To a stirred solution of compound Int-32f (60 mg, 0.118 mmol) in MeOH (5 mL) was added K$_2$CO$_3$ (82 mg, 0.592 mmol), and the resulting mixture was stirred at 55° C. for 12 h. The mixture was purified by SFC (AD(250 mm*30 mm, 5 μm) Condition 0.1% NH$_3$H$_2$O EtOH Begin B 55% End B 45% Gradient Time (min) 100% B Hold Time (min) Flow-Rate (ml/min) 80 Injections 60) to afford compound Int- 32f-1 (the first eluting isomer) and compound Int-32f-2 (the second eluting isomer). MS (M+H)⁺: 507.2

Step H—Synthesis of Compound 178 and Compound 179

To a solution of compound Int-32f-1 (23 mg, 0.045 mmol) in acetonitrile (2 mL) was added magnesium bromide (25.08 mg, 0.136 mmol). The mixture was stirred at 10° C. for 4 h. It was diluted by MeOH (1 mL) and purified by HPLC (Column Boston Green ODS 150*30 5 μm Condition water (0.1% TFA)-MeCN Begin B 23 End B 33 Gradient Time (min) 8 100% B Hold Time (min) 2 FlowRate (ml/min) 30 Injections 7) to afford compound 178.

$^1$H NMR (400 MHz, CDCl$_3$) δ 10.96 (br s, 1H), 6.77 (t, J=8.0 Hz, 2H), 5.15 (d, J=9.0 Hz, 1H), 5.07-5.00 (m, 1H), 4.95-4.86 (m, 1H), 4.78 (br d, J=13.5 Hz, 1H), 4.57 (br t, J=14.3 Hz, 2H), 4.27 (d, J=9.5 Hz, 1H), 3.75 (t, J=11.8 Hz, 1H), 3.48 (dd, J=6.7, 11.6 Hz, 1H), 3.28-3.08 (m, 3H), 2.58 (br d, J=5.3 Hz, 1H), 2.23-2.08 (m, 2H), 1.89 (brd, J=13.9 Hz, 1H), 1.52 (t, J=6.9 Hz, 3H). MS (M+H)⁺: 493.2

Compound 179 was prepared from compound Int-32f-2 using similar procedures: $^1$H NMR (400 MHz, CDCl$_3$) δ 12.28 (br s, 1H), 11.45 (br s, 1H), 10.39 (br s, 1H), 6.70 (t, J=7.9 Hz, 2H), 5.23 (d, J=8.4 Hz, 1H), 4.99 (t, J=7.8 Hz, 1H), 4.68-4.52 (m, 3H), 4.25 (q, J=8.3 Hz, 1H), 4.16 (d, J=8.2 Hz, 1H), 3.76 (t, J=11.7 Hz, 1H), 3.37 (s, 1H), 3.17-3.05 (m, 3H), 3.02-2.88 (m, 1H), 2.10-1.95 (m, 1H), 1.84 (d, J=12.6 Hz, 1H), 1.50 (t, J=7.2 Hz, 3H). MS (M+H)⁺: 493.2

The following compounds of the present invention were made using the methodology described in Example 34, starting from the appropriate Intermediate prepared in Example 33.

| Compound | Structure | derived from | Exact Mass [M + H]⁺ |
|---|---|---|---|
| 180 | 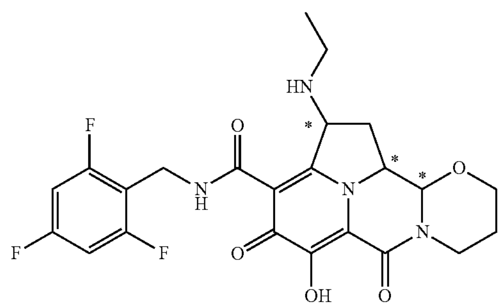 [SMILES: CCNC1CC2C3OCCCN3C(=O)c3c(O)c(=O)c(C(=O)NCc4c(F)cc(F)cc4F)c1n32] | Int-31c-trans-A | Calc'd 493.2, found 493.2 |
| 181 | 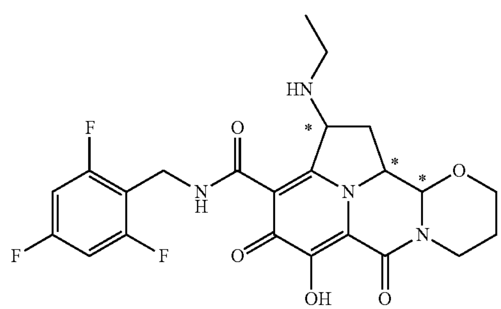 [SMILES: CCNC1CC2C3OCCCN3C(=O)c3c(O)c(=O)c(C(=O)NCc4c(F)cc(F)cc4F)c1n32] | Int-31c-cis-A | Calc'd 493.2, found 493.0 |
| 182 | 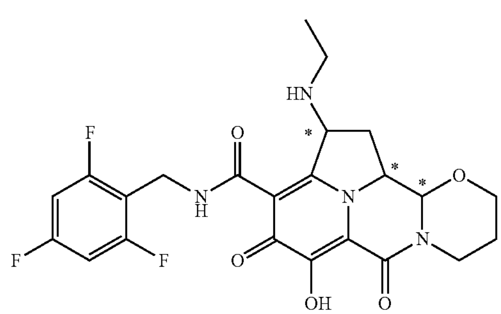 [SMILES: CCNC1CC2C3OCCCN3C(=O)c3c(O)c(=O)c(C(=O)NCc4c(F)cc(F)cc4F)c1n32] | Int-31c-cis-A | Calc'd 493.2, found 493.0 |

| Compound | Structure | derived from | Exact Mass [M + H]+ |
|---|---|---|---|
| 183 | 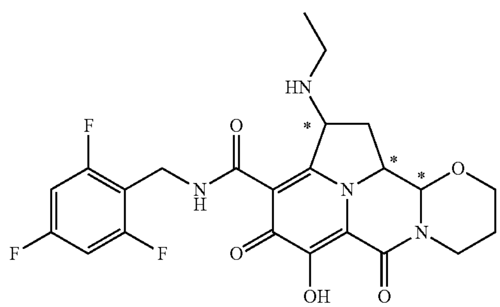 [SMILES: CCNC1CC2C3OCCCN3C(=O)c3c(O)c(=O)c(C(=O)NCc4c(F)cc(F)cc4F)c1n32] | Int-31c-cis-B | Calc'd 493.2, found 493.2 |
| 184 | 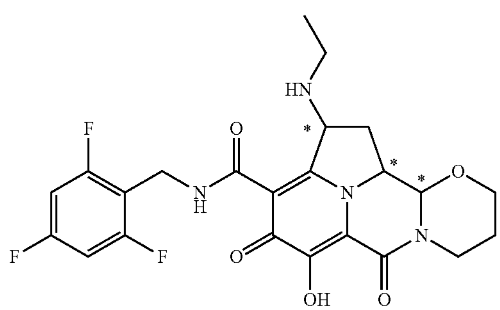 [SMILES: CCNC1CC2C3OCCCN3C(=O)c3c(O)c(=O)c(C(=O)NCc4c(F)cc(F)cc4F)c1n32] | Int-31c-cis-B | Calc'd 493.2, found 493.2 |

| Compound | 1H NMR |
|---|---|
| 180 | 1H NMR (400 MHz, CDCl3) δ 10.84 (m, 1H), 6.68-6.72 (t, J = 8.0 Hz, 2H), 5.01-5.06 (m, 2H), 4.70-4.82 (m, 2H), 4.44-4.48 (m, 2H), 4.17-4.20 (m, 1H), 3.69 (m, 1H), 3.30-3.40 (m, 1H), 3.06-3.15 (m, 3H), 2.53-2.56 (m, 1H), 2.04-2.07 (m, 1H), 1.80-1.83 (m, 1H), 1.42-1.46 (t, J = 7.2 Hz, 3H). |
| 181 | 1H NMR (400 MHz, CDCl3) δ 11.03-11.04 (m, 1H), 6.65-6.69 (m, 2H), 5.19-5.22 (m, 1H), 5.04-5.09 (m, 2H), 4.72-4.76 (m, 1H), 4.61-4.63 (m, 2H), 4.17-4.21 (m, 1H), 3.92-3.98 (m, 1H), 3.43-3.48 (m, 1H), 3.17-3.23 (m, 2H), 2.99-3.04 (m, 1H), 2.66-2.75 (m, 1H), 1.95-2.03 (m, 1H), 1.60-1.63 (m, 1H), 1.45 (t, J = 7.0 Hz, 3H). |
| 182 | 1H NMR (400 MHz, CDCl3) δ 11.34 (s, 1H), 6.66-6.70 (m, 2H), 5.22-5.25 (m, 1H), 5.03 (s, 1H), 4.66-4.77 (m, 2H), 4.52-4.60 (m, 2H), 4.24-4.28 (m, 1H), 3.94-3.99 (m, 1H), 2.85-3.20 (m, 5H), 1.96-2.08 (m, 1H), 1.62-1.66 (m, 1H), 1.33 (t, J = 7.2 Hz, 3H). |
| 183 | 1H NMR (400 MHz, CD3OD) δ: 6.92 (t, J = 8.4 Hz, 2H), 5.48 (br d, J = 8.6 Hz, 1H), 5.33 (br s, 1H), 4.99 (br s, 1H), 4.60-4.79 (m, 2H), 4.25-4.64 (m, 1H), 4.19 (brdd, J = 11.6, 4.5 Hz, 1H), 3.99-4.09 (m, 1H), 3.32-3.41 (m, 3H), 2.63-2.88 (m, 2H), 1.87-2.06 (m, 1H), 1.62 (br d, J = 13.7 Hz, 1H), 1.42 (br s, 3H) |
| 184 | 1H NMR (400 MHz, CD3OD) δ: 6.92 (t, J = 8.4 Hz, 2H), 5.28-5.39 (m, 2H), 4.62-4.81 (m, 4H), 4.24 (br dd, J = 11.6, 5.0 Hz, 1H), 4.04-4.12 (m, 1H), 3.34-3.42 (m, 1H), 3.16-3.25 (m, 2H), 2.92-3.05 (m, 1H), 2.48-2.65 (m, 1H), 1.90-2.03 (m, 1H), 1.67 (br d, J = 13.5 Hz, 1H), 1.39 (t, J = 7.2 Hz, 3H) |

Example 35

Preparation of Compounds 185-207

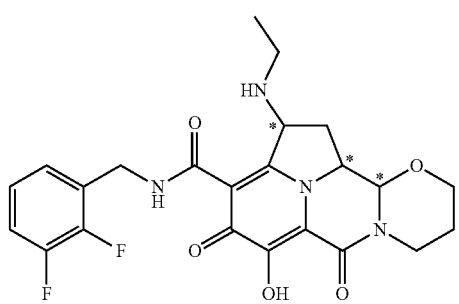

Compound 185
Compound 186
Compound 187
Compound 188
Compound 189
Compound 190
Compound 191
Compound 192

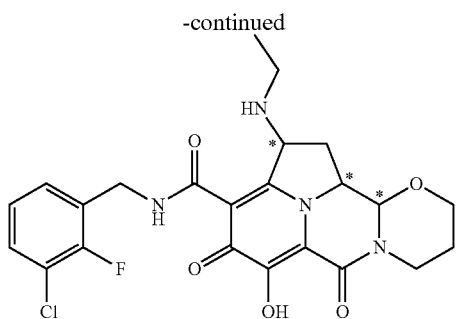

Compound 193
Compound 194
Compound 195
Compound 196
Compound 197
Compound 198
Compound 199
Compound 200

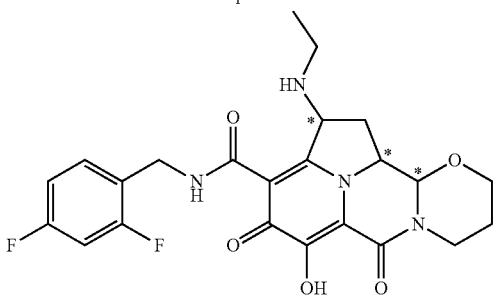

Compound 201
Compound 202
Compound 203
Compound 204
Compound 205
Compound 206
Compound 207

Starting from the corresponding intermediate prepared in Example 33, the following compounds of the present invention were made using the methodology described in Example 34, and substituting the appropriate benzylamine in Step C of Example 34.

Compound 185 (derived from compound Int-31c-trans-B): $^1$H NMR (400 MHz, CD$_3$OD) δ: 7.08-7.24 (m, 3H), 5.43 (d, J=8.6 Hz, 1H), 5.02 (d, J=8.8 Hz, 1H), 4.79-4.83 (m, 1H), 4.64-4.78 (m, 2H), 4.51 (d, J=13.0 Hz, 1H), 4.16 (d, J=7.3 Hz, 1H), 4.10-4.25 (m, 1H), 3.34 (d, J=6.8 Hz, 2H), 3.10 (td, J=13.2, 4.0 Hz, 1H), 2.91 (dd, J=15.0, 6.0 Hz, 1H), 2.54-2.67 (m, 1H), 1.93-2.05 (m, 1H), 1.84 (d, J=12.3 Hz, 1H), 1.39 (s, 3H). MS (M+H)$^+$: 475.0

Compound 186 (derived from compound Int-31c-trans-B): $^1$H NMR (400 MHz, CD$_3$OD) δ: 7.10-7.24 (m, 3H), 5.34 (t, J=8.6 Hz, 1H), 5.11 (d, J=9.0 Hz, 1H), 4.68-4.79 (m, 2H), 4.56 (d, J=11.7 Hz, 1H), 4.39-4.47 (m, 1H), 4.19 (d, J=11.3 Hz, 1H), 3.79 (t, J=10.6 Hz, 1H), 3.24 (q, J=7.0 Hz, 2H), 3.09-3.19 (m, 2H), 2.34-2.45 (m, 1H), 1.94-2.07 (m, 1H), 1.85 (d, J=12.1 Hz, 1H), 1.40 (t, J=7.2 Hz, 3H). MS (M+H)$^+$: 475.0

Compound 187 (derived from compound Int-31c-trans-A): $^1$H NMR (400 MHz, CDCl$_3$) δ: 7.12-7.23 (m, 3H), 5.42-5.45 (m, 1H), 5.05-5.07 (br d, J=8.8 Hz, 1H), 4.71-4.74 (m, 3H), 4.64-4.78 (m, 1H), 4.51 (m, 1H), 4.16 (m, 1H), 4.10-4.25 (m, 2H), 3.34 (m, 1H), 3.10 (m, 1H), 2.91 (m, 1H), 2.54-2.67 (m, 1H), 1.93-2.05 (m, 1H), 1.83-1.86 (m, 1H), 1.41 (br s, 3H). MS (M+H)$^+$: 475.2

Compound 188 (derived from compound Int-31c-trans-A): $^1$H NMR (400 MHz, CDCl$_3$) δ: 7.12-7.20 (m, 3H), 5.34 (br t, J=8.6 Hz, 1H), 5.11 (d, J=9.0 Hz, 1H), 4.68-4.79 (m, 2H), 4.56 (br d, J=11.7 Hz, 1H), 4.39-4.47 (m, 1H), 4.19 (br d, J=11.3 Hz, 1H), 3.79 (br t, J=10.6 Hz, 1H), 3.24 (q, J=7.0 Hz, 2H), 3.09-3.19 (m, 2H), 2.34-2.45 (m, 1H), 1.94-2.07 (m, 1H), 1.85 (br d, J=12.1 Hz, 1H), 1.40 (t, J=7.2 Hz, 3H). MS (M+H)$^+$: 475.1

Compound 189 (derived from compound Int-31c-cis-B): $^1$H NMR (400 MHz, CDCl$_3$) δ: 11.17 (br s, 1H), 9.04 (br s, 1H), 6.96-7.16 (m, 3H), 5.35 (br s, 1H), 4.98-5.16 (m, 2H), 4.60-4.81 (m, 3H), 4.20 (br dd, J=11.7, 4.0 Hz, 1H), 3.97 (br t, J=11.5 Hz, 1H), 3.44-3.54 (m, 1H), 3.12-3.28 (m, 2H), 3.00 (br dd, J=14.2, 6.7 Hz, 1H), 2.67-2.79 (m, 1H), 2.05 (br s, 1H), 1.65 (br s, 1H), 1.46 (br t, J=7.1 Hz, 3H) MS (M+H)$^+$: 475.2

Compound 190 (derived from compound Int-31c-cis-B): $^1$H NMR (400 MHz, CDCl$_3$) δ: 11.39 (br s, 1H), 6.88-7.14 (m, 3H), 5.18 (brs, 1H), 4.98 (br s, 1H), 4.71 (br d, J=11.2 Hz, 1H), 4.60 (brd, J=5.1 Hz, 2H), 4.46 (br s, 1H), 4.21 (br d, J=7.9 Hz, 1H), 3.92 (br t, J=11.8 Hz, 1H), 2.66-3.26 (m, 5H), 1.91-2.00 (m, 1H), 1.59 (br d, J=14.3 Hz, 1H), 1.26 (br t, J=7.1 Hz, 3H) MS (M+H)$^+$: 475.2

Compound 191 (derived from compound Int-31c-cis-A): $^1$H NMR (400 MHz, CDCl$_3$) δ: 11.11 (s, 1H), 7.01-7.12 (m, 3H), 5.18-5.23 (m, 1H), 5.05-5.11 (m, 2H), 4.62-4.75 (m, 3H), 4.17-4.21 (m, 1H), 3.93-3.99 (m, 1H), 3.42-3.46 (m, 1H), 3.14-3.24 (m, 2H), 2.97-3.03 (m, 1H), 2.68-2.77 (m, 1H), 1.93-2.03 (m, 1H), 1.61-1.64 (m, 1H), 1.43 (t, J=7.0 Hz, 3H); MS (M+H)$^+$: 475.2

Compound 192 (derived from compound Int-31c-cis-A): $^1$H NMR (400 MHz, CDCl$_3$) δ: 11.41 (s, 1H), 7.05-7.13 (m, 3H), 5.20-5.22 (m, 1H), 5.04 (s, 1H), 4.74-4.78 (m, 1H), 4.57-4.65 (m, 3H), 4.24-4.27 (m, 1H), 3.94-3.99 (m, 1H), 3.18-3.24 (m, 1H), 2.82-3.12 (m, 4H), 1.96-2.00 (m, 1H), 1.62-1.66 (m, 1H), 1.31 (t, J=7.0 Hz, 3H); MS (M+H)$^+$: 475.2

Compound 193 (derived from compound Int-31c-trans-B): $^1$H NMR (400 MHz, CDCl$_3$) δ 10.86-10.77 (br s, 1H), 7.30 (t, J=7.4 Hz, 2H), 7.08-7.00 (m, 1H), 5.93 (d, J=5.0 Hz, 1H), 4.87-4.74 (m, 2H), 4.70-4.56 (m, 2H), 4.47 (dt, J=5.5, 9.3 Hz, 1H), 4.26-4.16 (m, 1H), 3.72 (dt, J=2.1, 11.9 Hz, 1H), 3.47 (s, 3H), 3.07 (dt, J=3.9, 13.2 Hz, 1H), 2.69 (dd, J=5.5, 13.4 Hz, 1H), 2.14-1.97 (m, 2H), 1.94-1.69 (m, 1H). MS (M+H)$^+$: 491.0

Compound 194 (derived from compound Int-31c-trans-B): $^1$H NMR (400 MHz, CDCl$_3$) δ 10.22 (br s, 1H), 7.37-7.29 (m, 2H), 7.12-6.96 (m, 1H), 5.67 (t, J=6.6 Hz, 1H), 4.94 (d, J=8.8 Hz, 1H), 4.80 (dd, J=6.1, 16.0 Hz, 1H), 4.64 (d, J=12.1 Hz, 2H), 4.22 (d, J=8.2 Hz, 1H), 4.13 (q, J=8.5 Hz, 1H), 3.73 (t, J=11.1 Hz, 1H), 3.50 (s, 3H), 3.13-3.00 (m, 2H), 2.18-2.00 (m, 2H), 1.85 (d, J=13.0 Hz, 1H). MS (M+H)$^+$: 491.0

Compound 195 (derived from compound Int-31c-trans-A): $^1$H NMR (400 MHz, CDCl$_3$) δ 10.88 (s, 1H), 7.33-7.37 (m, 1H), 7.26-7.27 (m, 1H), 7.06-7.10 (m, 1H), 5.98-5.04 (m, 2H), 4.83-4.84 (m, 1H), 4.49-4.56 (m, 3H), 4.17-4.20 (m, 1H), 3.70-3.72 (m, 1H), 3.35-3.38 (m, 1H), 3.07-3.10 (m, 3H), 2.50-2.53 (m, 1H), 2.04-2.08 (m, 1H), 1.80-1.83 (m, 1H), 1.40-1.44 (t, J=7.2 Hz, 1H); MS (M+H)$^+$: 491.0

Compound 196 (derived from compound Int-31c-trans-A): $^1$H NMR (400 MHz, CDCl$_3$) δ 11.48 (s, 1H), 10.33 (m, 1H), 7.31-7.35 (m, 1H), 7.23 (m, 1H), 7.04-7.08 (m, 1H), 5.21-5.24 (m, 1H), 4.96 (m, 1H), 4.62-4.67 (m, 1H), 4.57-4.61 (m, 2H), 4.47-4.30 (m, 1H), 4.13-4.16 (m, 1H), 3.74

(m, 1H), 3.20-3.30 (m, 1H), 3.06-3.12 (m, 3H), 2.93-2.97 (m, 1H), 1.81-2.00 (m, 2H), 1.45-1.48 (t, J=7.2 Hz, 1H); MS (M+H)+: 491.2

Compound 197 (derived from compound Int-31c-cis-B): $^1$H NMR (400 MHz, CD$_3$OD) δ: 7.31-7.45 (m, 2H), 7.14 (t, J=7.6 Hz, 1H), 5.47 (br d, J=8.2 Hz, 1H), 5.34 (br s, 1H), 5.00 (br s, 1H), 4.66-4.80 (m, 3H), 4.03-4.25 (m, 2H), 3.33-3.41 (m, 3H), 2.64-2.92 (m, 2H), 1.86-2.03 (m, 1H), 1.63 (br d, J=13.0 Hz, 1H), 1.41 (br s, 3H) MS (M+H)+: 491.0

Compound 198 (derived from compound Int-31c-cis-B): $^1$H NMR (400 MHz, CDCl$_3$) δ: 11.46 (br s, 1H), 7.33 (br t, J=7.5 Hz, 2H), 7.02-7.12 (m, 1H), 5.25 (brs, 1H), 5.04 (br s, 1H), 4.42-4.81 (m, 4H), 4.28 (br d, J=8.4 Hz, 1H), 3.98 (br t, J=11.6 Hz, 1H), 2.72-3.36 (m, 5H), 2.01 (brs, 1H), 1.67 (br s, 1H), 1.27-1.39 (m, 3H) MS (M+H)+: 491.0

Compound 199 (derived from compound Int-31c-cis-A): $^1$H NMR (400 MHz, CDCl$_3$) δ: 11.18 (s, 1H), 7.31-7.34 (m, 2H), 7.01-7.08 (m, 1H), 5.22-5.23 (m, 1H), 5.01-5.09 (m, 2H), 4.68-4.78 (m, 3H), 4.20-4.21 (m, 1H), 3.96-3.97 (m, 1H), 3.45-3.46 (m, 1H), 3.04-3.21 (m, 3H), 2.71-2.77 (m, 1H), 1.99-2.01 (m, 1H), 1.64-1.65 (m, 1H), 1.43 (t, J=7.0 Hz, 3H); MS (M+H)+: 491.2

Compound 200 (derived from compound Int-31c-cis-A): $^1$H NMR (400 MHz, CDCl$_3$) δ: 11.48 (s, 1H), 7.27-7.35 (m, 2H), 7.03-7.07 (m, 1H), 5.27-5.29 (m, 2H), 4.63-4.76 (m, 3H), 4.26-4.28 (m, 1H), 3.98-3.99 (m, 1H), 3.46-3.48 (m, 1H), 2.77-3.12 (m, 5H), 2.01-2.03 (m, 1H), 1.62-1.65 (m, 1H), 1.43 (t, J=7.0 Hz, 3H); MS (M+H)+: 491.2

Compound 201 (derived from compound Int-31c-trans-B): $^1$H NMR (400 MHz, CD$_3$OD): δ 10.89 (br s, 1H), 7.30-7.38 (m, 1H), 6.80-6.91 (m, 2H), 4.95-5.11 (m, 2H), 4.79-4.87 (m, 1H), 4.48-4.63 (m, 3H), 4.19 (br d, J=9.4 Hz, 1H), 3.69 (t, J=11.3 Hz, 1H), 3.37 (dd, J=11.7, 7.0 Hz, 1H), 3.03-3.15 (m, 3H), 2.49 (dt, J=14.8, 9.4 Hz, 1H), 2.00-2.12 (m, 1H), 1.82 (br d, J=14.1 Hz, 1H), 1.43 (t, J=7.0 Hz, 3H). MS (M+H)+: 475.2

Compound 202 (derived from compound Int-31c-trans-B): $^1$H NMR (400 MHz, CD$_3$OD): δ 11.81 (br s, 1H), 11.42 (br s, 1H), 10.53 (br s, 1H), 7.28-7.36 (m, 1H), 6.79-6.89 (m, 2H), 5.21 (d, J=8.6 Hz, 1H), 4.98 (br t, J=8.0 Hz, 1H), 4.53-4.65 (m, 3H), 4.29 (q, J=8.2 Hz, 1H), 4.15 (d, J=9.0 Hz, 1H), 3.75 (t, J=11.5 Hz, 1H), 3.34 (dd, J=11.2, 7.2 Hz, 1H), 2.96-3.13 (m, 4H), 1.94-2.09 (m, 1H), 1.82 (d, J=14.1 Hz, 1H), 1.47 (t, J=7.2 Hz, 3H). MS (M+H)+: 475.2

Compound 203 (derived from compound Int-31c-trans-A): $^1$H NMR (400 MHz, CDCl$_3$) δ 10.89 (m, 1H), 7.30-7.36 (m, 1H), 6.82-6.88 (m, 2H), 5.04-5.07 (m, 2H), 4.96-4.98 (m, 1H), 4.51-4.59 (m, 3H), 4.10 (m, 1H), 3.69 (m, 1H), 3.36 (m, 1H), 3.06-3.12 (m, 3H), 2.47-2.51 (m, 1H), 2.05 (m, 1H), 1.80-1.83 (m, 1H), 1.41-1.44 (t, J=7.2 Hz, 3H); MS (M+H)+: 475.2

Compound 204 (derived from compound Int-31c-cis-B): $^1$H NMR (400 MHz, CDCl$_3$) δ 11.06 (br s, 1H), 8.98 (br s, 1H), 7.23-7.28 (m, 1H), 6.73-6.80 (m, 2H), 5.0-25.15 (m, 1H), 4.94-4.96 (m, 2H), 4.55-4.69 (m, 3H), 4.13-4.16 (m, 1H), 3.89-3.96 (m, 1H), 3.42-3.46 (m, 1H), 3.00-3.11 (m, 3H), 2.64-2.673 (m, 1H), 1.91-1.95 (m, 1H), 1.40-1.59 (m, 1H), 1.36-1.38 (m, 3H). MS (M+H)+: 475.2

Compound 205 (derived from compound Int-31c-cis-A): $^1$H NMR (400 MHz, CDCl$_3$) δ: 11.08-11.11 (m, 1H), 7.29-7.35 (m, 1H), 6.79-6.86 (m, 2H), 5.19-5.23 (m, 1H), 5.03-5.10 (m, 2H), 4.73-4.78 (m, 1H), 4.59-4.64 (m, 2H), 4.18-4.22 (m, 1H), 3.93-3.99 (m, 1H), 3.43-3.48 (m, 1H), 3.14-3.24 (m, 2H), 2.99-3.04 (m, 1H), 2.70-2.74 (m, 1H), 1.94-2.04 (m, 1H), 1.61-1.64 (m, 1H), 1.44 (t, J=7.2 Hz, 3H); MS (M+H)+: 475.0

Compound 206 (derived from compound Int-31c-cis-A): $^1$H NMR (400 MHz, CDCl$_3$) δ: 11.08-11.11 (m, 1H), 7.29-7.35 (m, 1H), 6.79-6.86 (m, 2H), 5.19-5.23 (m, 1H), 5.03-5.10 (m, 2H), 4.73-4.78 (m, 1H), 4.59-4.64 (m, 2H), 4.18-4.22 (m, 1H), 3.93-3.99 (m, 1H), 3.43-3.48 (m, 1H), 3.14-3.24 (m, 2H), 2.99-3.04 (m, 1H), 2.70-2.74 (m, 1H), 1.94-2.04 (m, 1H), 1.61-1.64 (m, 1H), 1.44 (t, J=7.2 Hz, 3H); MS (M+H)+: 475.2

Compound 207 (derived from compound Int-31c-cis-B): $^1$H NMR (400 MHz, CDCl$_3$) δ 11.34-11.37 (m, 1H), 11.08 (s, 1H), 10.63 (s, 1H), 7.31-7.36 (m, 1H), 6.79-6.86 (m, 2H), 5.07-5.22 (m, 1H), 5.07 (m, 1H), 4.73-4.75 (m, 1H), 4.60-4.61 (m, 3H), 4.22-4.26 (m, 1H), 3.96-3.99 (m, 1H), 3.14-3.21 (m, 2H), 2.89-2.97 (m, 3H), 1.99-2.02 (m, 1H), 1.62-1.65 (m, 1H), 1.33-1.37 (m, 3H); MS (M+H)+: 475.2

Assay for Inhibition of HIV Replication

This assay is a kinetic assay that employs a reporter cell line (MT4-gag-GFP) to quantify the number of new cells infected in each round of replication.

MT4-GFP cells (250,000 cells/ml) were bulk-infected with HIV-1 (NL4-3 strain) at low multiplicity of infection (MOI) in RPMI cell culture medium+10% FBS for 24 hours. Cells were then washed once in RPMI cell culture medium+10% FBS and resuspended in RPMI cell culture medium+0% or 10% or 100% normal human serum (NHS). Test compounds were serial-diluted in DMSO on an ECHO® liquid handler. The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen eX3. Viral reproductive ratio ($R_0$) was determined using the number of infected cells at 48 hours divided by the number of infected cells at 24 hours. Percent viral growth inhibition was calculated by [1−(R−R$_{tripledrug}$)/(R$_{DMSO}$−R$_{tripledrug}$)]*100. Compound potency IP or IC$_{50}$ was determined by a 4-parameter dose response curve analysis. In vitro potency in the cell-based assay in the absence of normal human serum (NHS) and the presence of 100% NHS.

Illustrative compounds of the present invention were tested using this assay protocol and results are presented in the Table below.

| Compound | VIKING IP$_{50}$ (nM) with 0% NHS | VIKING IP$_{50}$ (nM) with 100% NHS |
|---|---|---|
| 2 | 0.283 | 2172 |
| 3 | 0.478 | 371.8 |
| 4 | 0.4386 | 93.59 |
| 5 | 0.4093 | 2246 |
| 6 | 0.825 | 7913 |
| 7 | 2.145 | 1410 |
| 8 | 1.002 | 244.7 |
| 9 | 0.7 | 1134 |
| 10 | 0.813 | 226 |
| 11 | 1.088 | 589.2 |
| 12 | 1.39 | 892.1 |
| 13 | 0.8273 | 5524 |
| 14 | 0.8271 | 193.8 |
| 15 | 0.6089 | 372.8 |
| 16 | 6.283 | 8000 |
| 17 | 7.093 | 7940 |
| 18 | 0.4831 | 8000 |
| 19 | 0.5392 | 1229 |

| Compound | VIKING IP$_{50}$ (nM) with 0% NHS | VIKING IP$_{50}$ (nM) with 100% NHS |
|---|---|---|
| 20 | 0.7267 | 601.7 |
| 21 | 0.6054 | 157.5 |
| 22 | 0.8948 | 502.9 |
| 23 | 1.064 | 2187 |
| 24 | 0.6215 | 8000 |
| 25 | 0.8094 | 2541 |
| 26 | 0.3331 | 346.9 |
| 27 | 0.3133 | 955.9 |
| 28 | 0.4012 | 257.3 |
| 29 | 0.4117 | 3413 |
| 30 | 0.536 | 837.8 |
| 31 | 0.4176 | 197.2 |
| 32 | 0.6713 | 100.6 |
| 33 | 0.5435 | 1941 |
| 34 | 0.6352 | 1564 |
| 35 | 0.7328 | 88.65 |
| 36 | 0.8258 | 1059 |
| 37 | 0.5461 | 1694 |
| 38 | 0.5432 | 46.44 |
| 39 | 0.5751 | 8000 |
| 40 | 1.842 | 8000 |
| 41 | 0.8536 | 2382 |
| 42 | 1.38 | 1570 |
| 43 | 1.059 | 18.22 |
| 44 | 0.8794 | 378.5 |
| 45 | 5.81 | 486 |
| 46 | 34.49 | 221.7 |
| 47 | 2.39115 | 2679.5 |
| 48 | 1.308 | 27.34 |
| 49 | 0.9596 | 1192 |
| 50 | 0.9013 | 1068 |
| 51 | 1.247 | 32.61 |
| 52 | 1.286 | 3375 |
| 53 | 0.9628 | 392.7 |
| 54 | 0.654 | 904.2 |
| 55 | 1.0295 | 39.45 |
| 56 | 0.7012 | 1804 |
| 57 | 0.9195 | 870.65 |
| 58 | 0.84505 | 1521 |
| 59 | 3.079 | 8403 |
| 60 | 0.9339 | 27.58 |
| 61 | 22.05 | 8000 |
| 62 | 0.8304 | 528.5 |
| 63 | 3.093 | 127.4 |
| 64 | 0.8558 | 29.62 |
| 65 | 0.9388 | 6685 |
| 66 | 1.48 | 834.4 |
| 67 | 0.5769 | 1474 |
| 68 | 1.6725 | 223.35 |
| 69 | 1.3645 | 349.1 |
| 70 | 1.1245 | 3920.5 |
| 71 | 1.255 | 30.73 |
| 72 | 0.7543 | 8000 |
| 73 | 0.6788 | 49.41 |
| 74 | 2.192 | 180.9 |
| 75 | 4.985 | 6181 |
| 76 | 1.012 | 17.78 |
| 77 | 1.556 | 2163 |
| 78 | 2.121 | 534.5 |
| 79 | 1.787 | 135.2 |
| 80 | 0.6624 | 13.75 |
| 81 | 1.147 | 24.19 |
| 82 | 1.17 | 550.1 |
| 83 | 0.8571 | 16.81 |
| 84 | 0.7625 | 37.48 |
| 85 | 0.7028 | 17.8 |
| 86 | 0.4265 | 9.174 |
| 87 | 0.8746 | 1003 |
| 88 | 0.7051 | 13.71 |
| 89 | 0.7091 | 119.9 |
| 90 | 0.3968 | 24.59 |
| 91 | 1.004 | 464.3 |
| 92 | 0.6696 | 8.125 |
| 93 | 1.135 | 49 |
| 94 | 0.5033 | 14.49 |
| 95 | 2.593 | 123.7 |
| 96 | 2.045 | 13.84 |
| 97 | 4.296 | 48.31 |
| 98 | 1.479 | 16.01 |
| 99 | 2.277 | 19.22 |
| 100 | 1.939 | 56.54 |
| 101 | 1.992 | 23.37 |
| 102 | 1.05 | 579.1 |
| 103 | 1.449 | 15.42 |
| 104 | 0.3969 | 71.4 |
| 105 | 0.4955 | 32.64 |
| 106 | 3.676 | 88.92 |
| 107 | 2.818 | 272.3 |
| 108 | 1.169 | 80.14 |
| 109 | 1.166 | 479.7 |
| 110 | 0.7327 | 67.82 |
| 111 | 1.189 | 259.5 |
| 112 | 0.806 | 40.36 |
| 113 | 3.578 | 291.3 |
| 114 | 6.36 | 174.9 |
| 115 | 7.401 | 112.8 |
| 116 | 4.571 | 195.2 |
| 117 | 3.778 | 130.5 |
| 118 | 8.735 | 1285 |
| 119 | 8.772 | 445 |
| 120 | 1.19 | 24.48 |
| 121 | 1.452 | 308.4 |
| 122 | 2.168 | 30.13 |
| 123 | 2.555 | 58.59 |
| 124 | 7.405 | 28.02 |
| 125 | 10.35 | 57.72 |
| 126 | 2.415 | 210.7 |
| 127 | 1.195 | 11.68 |
| 128 | 6.692 | 360.7 |
| 129 | 15.3 | 282.8 |
| 130 | 3.532 | 92.83 |
| 131 | 2.333 | 36.15 |
| 132 | 1.292 | 212.4 |
| 133 | 0.9298 | 617.2 |
| 134 | 1.291 | 20.52 |
| 135 | 0.7909 | 1284 |
| 136 | 0.825 | 89.39 |
| 137 | 1.7366 | 1082.15 |
| 138 | 2.407 | 26.99 |
| 139 | 4.049 | 143.3 |
| 140 | 0.5568 | 11.3 |
| 141 | 0.3794 | 6.167 |
| 142 | 0.5045 | 9.409 |
| 143 | 0.6617 | 5.266 |
| 144 | 5.242 | 352.2 |
| 145 | 4.281 | 41.7 |
| 146 | 2.645 | 4723 |
| 147 | 3.255 | 42.48 |
| 148 | 3.084 | 7249 |
| 149 | 4.404 | 48.79 |
| 150 | 4.068 | 1478 |
| 151 | 5.7 | 45.76 |
| 152 | 5.52 | 2097 |
| 153 | 4.529 | 95.46 |
| 154 | 4.143 | 79.16 |
| 155 | 2.774 | 7456 |
| 156 | 11.85 | 5273 |
| 157 | 12.87 | 733.4 |
| 158 | 3.997 | 16090 |
| 159 | 5.846 | 89.35 |
| 160 | 4.145 | 73.13 |
| 161 | 2.668 | 5513 |
| 162 | 3.902 | 50.43 |
| 163 | 4.316 | 1663 |
| 164 | 4.894 | 1387 |
| 165 | 6.419 | 56.1 |
| 166 | 5.387 | 50.58 |
| 167 | 3.783 | 3392 |
| 168 | 3.717 | 1623 |
| 169 | 2.705 | 42.86 |

-continued

| Compound | VIKING IP$_{50}$ (nM) with 0% NHS | VIKING IP$_{50}$ (nM) with 100% NHS |
|---|---|---|
| 170 | 2.588 | 5362 |
| 171 | 2.821 | 74.63 |
| 172 | 13.54 | 91.46 |
| 173 | 13.19 | 4267 |
| 174 | 30.18 | 114.4 |
| 175 | 20.82 | 78.75 |
| 176 | 16.75 | 128.6 |
| 177 | 11.21 | 191.2 |
| 178 | 16.03 | 6088 |
| 179 | 12.7 | 39.07 |
| 180 | 3.574 | 20.12 |
| 181 | 6.406 | 29.88 |
| 182 | 6.63 | 44.92 |
| 183 | 13.35 | 3571 |
| 184 | 5.001 | 166.7 |
| 185 | 11.69 | 1156 |
| 186 | 9.855 | 36.47 |
| 187 | 3.511 | 49.09 |
| 188 | 16.31 | 461.6 |
| 189 | 11 | 3870 |
| 190 | 5.257 | 66.38 |
| 191 | 12.61 | 63.6 |
| 192 | 8.76 | 92.29 |
| 193 | 7.889 | 2908 |
| 194 | 15.7 | 35.08 |
| 195 | 12.39 | 25.69 |
| 196 | 15.29 | 882.6 |
| 197 | 14.01 | 15120 |
| 198 | 5.287 | 96.86 |
| 199 | 7.116 | 42.89 |
| 200 | 10.05 | 67.26 |
| 201 | 8.983 | 2059 |
| 202 | 7.733 | 39.35 |
| 203 | 6.466 | 25.83 |
| 204 | 15.72 | 4829 |
| 205 | 11.26 | 116.5 |
| 206 | 7.114 | 51.61 |
| 207 | 5.215 | 140 |

Treatment or Prevention of HIV Infection

The Tetracyclic Heterocycle Compounds may be useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Tetracyclic Heterocycle Compounds may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Tetracyclic Heterocycle Compound or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Tetracyclic Heterocycle Compounds are also useful in the preparation and execution of screening assays for antiviral compounds. For example the Tetracyclic Heterocycle Compounds may be useful for identifying resistant HIV cell lines harboring mutations, which are excellent screening tools for more powerful antiviral compounds. Furthermore, the Tetracyclic Heterocycle Compounds may be useful in establishing or determining the binding site of other antivirals to the HIV Integrase.

The compositions and combinations of the present invention can be useful for treating a subject suffering from infection related to any HIV genotype.

Combination Therapy

In another embodiment, the present methods for treating or preventing HIV infection can further comprise the administration of one or more additional therapeutic agents which are not Tetracyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Tetracyclic Heterocycle Compound (which may include two or more different Tetracyclic Heterocycle Compounds), or a pharmaceutically acceptable salt or prodrug thereof, and (ii) at least one additional therapeutic agent that is other than a Tetracyclic Heterocycle Compound, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tetracyclic Heterocycle Compound and an additional therapeutic agent may be present in fixed amounts (dosage amounts) in a single dosage unit (e.g., a capsule, a tablet and the like).

In one embodiment, at least one Tetracyclic Heterocycle Compound is administered during a time when the additional therapeutic agent(s) exert their prophylactic or therapeutic effect, or vice versa.

In another embodiment, at least one Tetracyclic Heterocycle Compound and the additional therapeutic agent(s) are administered in doses commonly employed when such agents are used as monotherapy for treating a viral infection.

In another embodiment, at least one Tetracyclic Heterocycle Compound and the additional therapeutic agent(s) are administered in doses lower than the doses commonly employed when such agents are used as monotherapy for treating a viral infection.

In still another embodiment, at least one Tetracyclic Heterocycle Compound and the additional therapeutic agent(s) act synergistically and are administered in doses lower than the doses commonly employed when such agents are used as monotherapy for treating a viral infection.

In one embodiment, at least one Tetracyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one Tetracyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tetracyclic Heterocycle Compound and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Rey ataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | II |
| doravirine | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirti de, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |

TABLE A-continued

| Name | Type |
|---|---|
| lamivudine + zidovudine, Combivir ® | nRTI |
| lopinavir | PI |
| lopinavir + ritonavir, Katetra ® | PI |
| maraviroc, Selzentry ® | EI |
| nelfinavir, Viracept ® | PI |
| nevirapine, NVP, Viramune ® | nnRTI |
| rilpivirine, TMC-278 | nnRTI |
| ritonavir, Norvir ® | PI |
| saquinavir, Invirase ®, Fortovase ® | PI |
| stavudine, d4T,didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; PI = protease inhibitor; nRTI = nucleoside reverse transcriptase inhibitor; II = integrase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine and lopinavir.

In another embodiment, the compound of formula (I) is used in combination with lamivudine.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In one embodiment, the compound of formula (I) is used in combination with lamivudine and abacavir.

In another embodiment, the compound of formula (I) is used in combination with darunavir.

In another embodiment, the compound of formula (I) is used in combination with emtricitabine and tenofovir.

In still another embodiment, the compound of formula (I) is used in combination atazanavir.

In another embodiment, the compound of formula (I) is used in combination with ritonavir and lopinavir.

In one embodiment, the compound of formula (I) is used in combination with abacavir and lamivudine.

In another embodiment, the compound of formula (I) is used in combination with lopinavir and ritonavir.

In another embodiment, the compound of formula (I) is used in combination with doravirine.

In another embodiment, the compound of formula (I) is used in combination with EFdA (4'-ethynyl-2-fluoro-2'-deoxyadenosine).

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, such as the 70th edition (2016) and earlier editions. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Tetracyclic Heterocycle Compound(s) and the other agent(s) can be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Tetracyclic Heterocycle Compounds can be administered as a component of a composition that comprises a pharmaceutically acceptable carrier or vehicle. The present invention provides pharmaceutical compositions comprising an effective amount of at least one Tetracyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tetracyclic Heterocycle Compounds are administered orally.

In another embodiment, the one or more Tetracyclic Heterocycle Compounds are administered intravenously.

In one embodiment, a pharmaceutical preparation comprising at least one Tetracyclic Heterocycle Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Tetracyclic Heterocycle Compound(s) by weight or volume. In various embodiments, the present compositions can contain, in one embodiment, from about 1% to about 70% or from about 5% to about 60% of the Tetracyclic Heterocycle Compound(s) by weight or volume.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Tetracyclic Heterocycle Compounds may be administered at varying frequencies. In one embodiment, a unit dosage of a Tetracyclic Heterocycle Compound can be administered once daily. In another embodiment, a unit dosage of a Tetracyclic Heterocycle Compound can be administered twice weekly. In another embodiment, a unit dosage of a Tetracyclic Heterocycle Compound can be administered once weekly. In still another embodiment, a unit dosage of a Tetracyclic Heterocycle Compound can be administered once biweekly. In another embodiment, a unit dosage of a Tetracyclic Heterocycle Compound can be administered once monthly. In yet another embodiment, a unit dosage of a Tetracyclic Heterocycle Compound can be administered once bimonthly. In another embodiment, a unit dosage of a Tetracyclic Heterocycle Compound can be administered once every 3 months. In a further embodiment, a unit dosage of a Tetracyclic Heterocycle Compound can be administered once every 6 months. In another embodiment, a unit dosage of a Tetracyclic Heterocycle Compound can be administered once yearly.

The amount and frequency of administration of the Tetracyclic Heterocycle Compounds will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Tetracyclic Heterocycle Compound, or a pharmaceutically acceptable salt or prodrug of said compound and a pharmaceutically acceptable carrier, vehicle or diluent.

In another aspect the present invention provides a kit comprising an amount of at least one Tetracyclic Heterocycle Compound, or a pharmaceutically acceptable salt or prodrug of said compound and an amount of at least one additional therapeutic agent listed above, wherein the amounts of the two or more active ingredients result in a desired therapeutic effect. In one embodiment, the one or more Tetracyclic Heterocycle Compounds and the one or more additional therapeutic agents are provided in the same container. In one embodiment, the one or more Tetracyclic Heterocycle Compounds and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A method for the treatment of infection by HIV or for the treatment, or delay in the onset or progression of AIDS in a subject in need thereof, which comprises administering to the subject an effective amount of a compound having the structure:

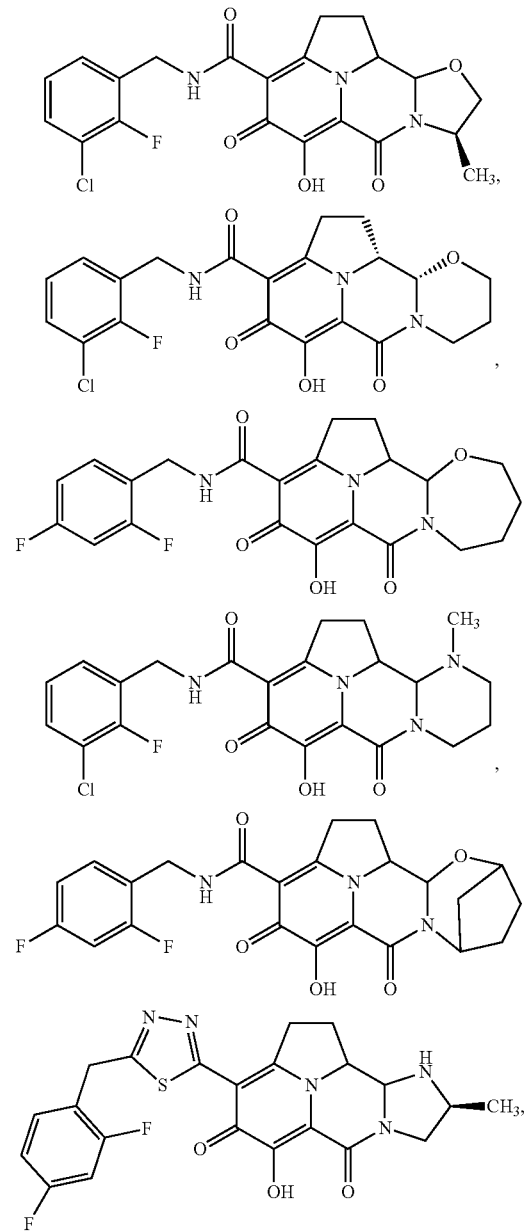

or a pharmaceutically acceptable salt thereof, and doravirine, or a pharmaceutically acceptable salt thereof.

2. The method of claim 1 comprising

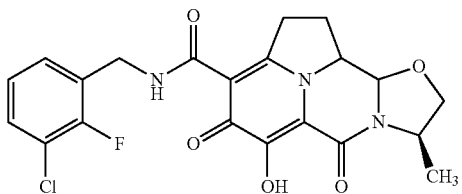 [SMILES: C[C@@H]1COC2C3CCc4c(C(=O)NCc5cccc(Cl)c5F)c(=O)c(O)c(n43)C(=O)N21]

or a pharmaceutically acceptable salt thereof, and doravirine, or a pharmaceutically acceptable salt thereof.

3. The method of claim 1 comprising

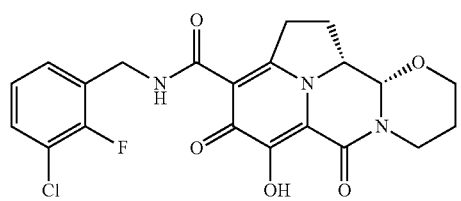 [SMILES: O=C(NCc1cccc(Cl)c1F)c1c2n3c(c(O)c1=O)C(=O)N1CCCO[C@H]1[C@H]3CC2]

or a pharmaceutically acceptable salt thereof, and doravirine, or a pharmaceutically acceptable salt thereof.

4. The method of claim 1 comprising

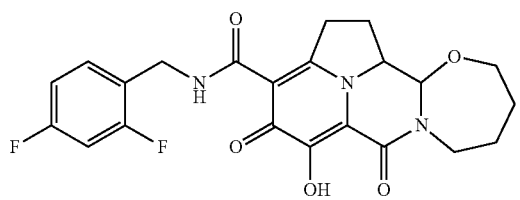 [SMILES: O=C(NCc1ccc(F)cc1F)c1c2n3c(c(O)c1=O)C(=O)N1CCCCOC1C3CC2]

or a pharmaceutically acceptable salt thereof, and doravirine, or a pharmaceutically acceptable salt thereof.

5. The method of claim 1 comprising

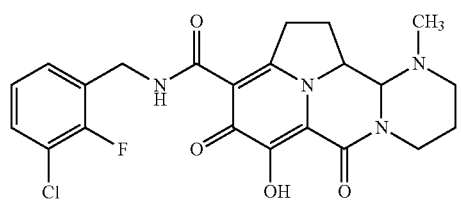 [SMILES: CN1CCCN2C(=O)c3c(O)c(=O)c(C(=O)NCc4cccc(Cl)c4F)c4n3C(CC4)C12]

or a pharmaceutically acceptable salt thereof, and doravirine, or a pharmaceutically acceptable salt thereof.

6. The method of claim 1 comprising

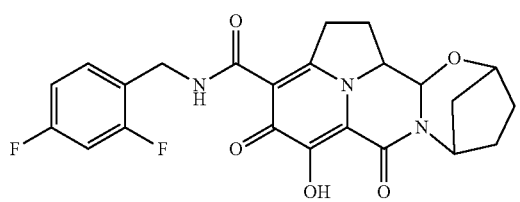 [SMILES: O=C(NCc1ccc(F)cc1F)c1c2n3c(c(O)c1=O)C(=O)N1C4CCC(C4)OC1C3CC2]

or a pharmaceutically acceptable salt thereof, and doravirine, or a pharmaceutically acceptable salt thereof.

7. The method of claim 1 comprising

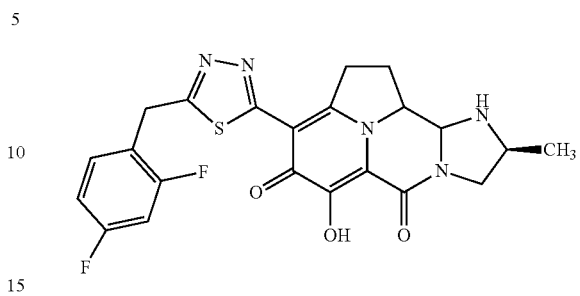

or a pharmaceutically acceptable salt thereof, and doravirine, or a pharmaceutically acceptable salt thereof.

8. A method for the treatment of infection by HIV or for the treatment, or delay in the onset or progression of AIDS in a subject in need thereof, which comprises administering to the subject an effective amount of a compound having the structure:

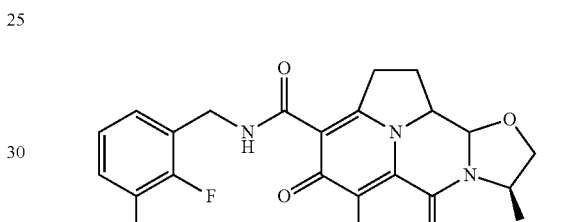

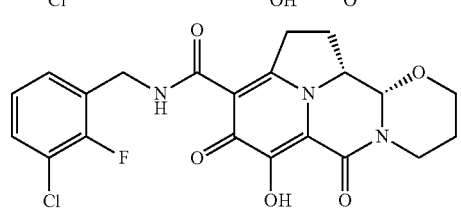

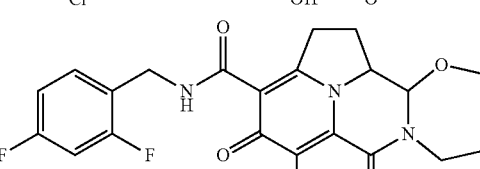

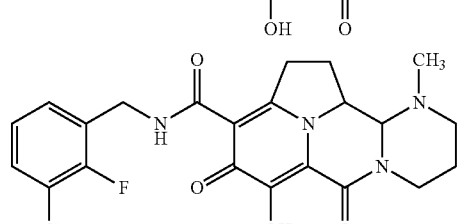

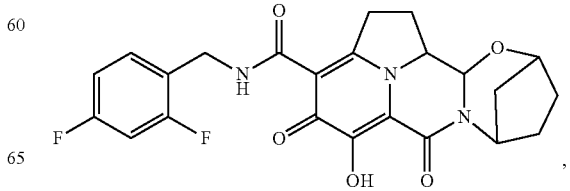

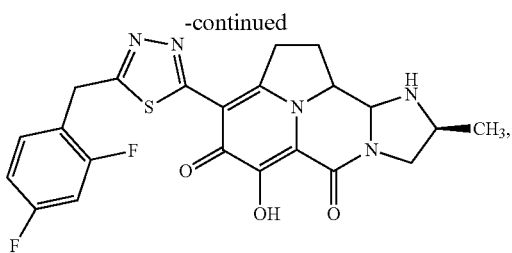

or a pharmaceutically acceptable salt thereof, and 4'-ethynyl-2-fluoro-2'-deoxyadenosine, or a pharmaceutically acceptable salt thereof.

9. The method of claim 8 comprising

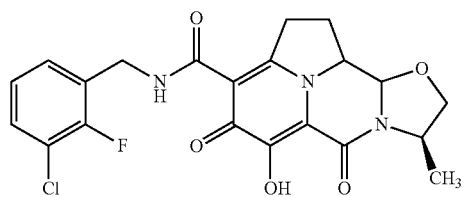 [SMILES: C[C@@H]1COC2C3CCc4c(C(=O)NCc5cccc(Cl)c5F)c(=O)c(O)c(n43)C(=O)N21]

or a pharmaceutically acceptable salt thereof, and 4'-ethynyl-2-fluoro-2'-deoxyadenosine, or a pharmaceutically acceptable salt thereof.

10. The method of claim 8 comprising

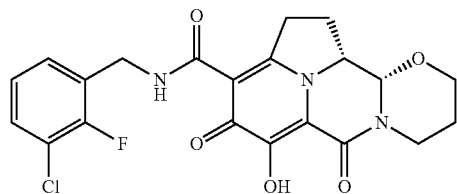 [SMILES: O=C(NCc1cccc(Cl)c1F)c1c2n3c(c(O)c1=O)C(=O)N1CCCO[C@H]1[C@H]3CC2]

or a pharmaceutically acceptable salt thereof, and 4'-ethynyl-2-fluoro-2'-deoxyadenosine, or a pharmaceutically acceptable salt thereof.

11. The method of claim 8 comprising

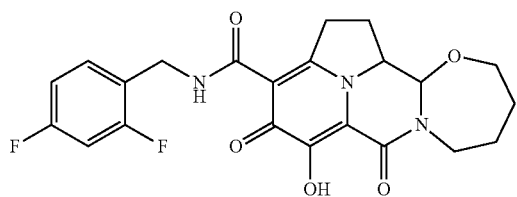 [SMILES: O=C(NCc1ccc(F)cc1F)c1c2n3c(c(O)c1=O)C(=O)N1CCCCOC1C3CC2]

or a pharmaceutically acceptable salt thereof, and 4'-ethynyl-2-fluoro-2'-deoxyadenosine, or a pharmaceutically acceptable salt thereof.

12. The method of claim 8 comprising

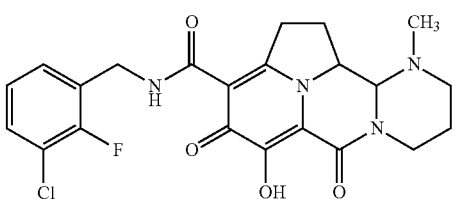 [SMILES: CN1CCCN2C(=O)c3c(O)c(=O)c(C(=O)NCc4cccc(Cl)c4F)c4n3C(CC4)C12]

or a pharmaceutically acceptable salt thereof, and 4'-ethynyl-2-fluoro-2'-deoxyadenosine, or a pharmaceutically acceptable salt thereof.

13. The method of claim 8 comprising

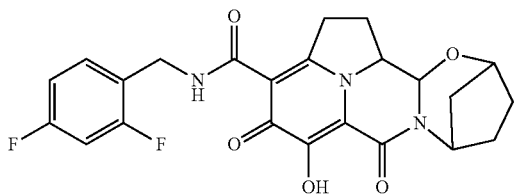 [SMILES: O=C(NCc1ccc(F)cc1F)c1c2n3c(c(O)c1=O)C(=O)N1C4CCC(C4)OC1C3CC2]

or a pharmaceutically acceptable salt thereof, and 4'-ethynyl-2-fluoro-2'-deoxyadenosine, or a pharmaceutically acceptable salt thereof.

14. The method of claim 8 comprising

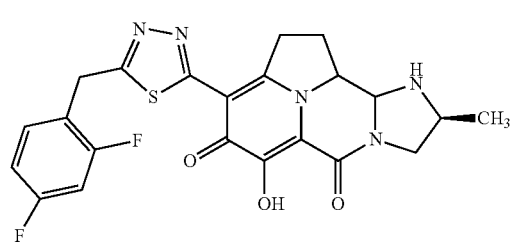 [SMILES: C[C@H]1CN2C(=O)c3c(O)c(=O)c(-c4nnc(Cc5ccc(F)cc5F)s4)c4n3C(CC4)C2N1]

or a pharmaceutically acceptable salt thereof, and 4'-ethynyl-2-fluoro-2'-deoxyadenosine, or a pharmaceutically acceptable salt thereof.

* * * * *